US007067251B2

(12) United States Patent
Zauderer et al.

(10) Patent No.: US 7,067,251 B2
(45) Date of Patent: Jun. 27, 2006

(54) METHODS OF DIRECTLY SELECTING CELLS EXPRESSING INSERTS OF INTEREST

(75) Inventors: Maurice Zauderer, Pittsford, NY (US); Ernest S. Smith, Ontario, NY (US)

(73) Assignee: University of Rochester, Rochester, NY (US)

( * ) Notice: Subject to any disclaimer, the term of this patent is extended or adjusted under 35 U.S.C. 154(b) by 188 days.

(21) Appl. No.: 09/818,991

(22) Filed: Mar. 28, 2001

(65) Prior Publication Data

US 2003/0022157 A1 Jan. 30, 2003

Related U.S. Application Data

(60) Provisional application No. 60/271,426, filed on Feb. 27, 2001, provisional application No. 60/263,226, filed on Jan. 23, 2001, provisional application No. 60/203,343, filed on May 10, 2000, provisional application No. 60/192,586, filed on Mar. 28, 2000.

(51) Int. Cl.
*C12Q 1/68* (2006.01)
*C12N 15/86* (2006.01)
*C12N 15/87* (2006.01)
*C07H 21/04* (2006.01)

(52) U.S. Cl. .................. 435/6; 435/5; 435/320.1; 435/69.1; 435/DIG. 1; 435/DIG. 4; 435/DIG. 14; 435/DIG. 17; 536/23.1; 536/23.5

(58) Field of Classification Search ............... 435/6, 435/5, 456, 69.1, 320.1, DIG. 1, DIG. 4, 435/DIG. 14, DIG. 17, 69.7, 457, 463, 325; 536/23.1, 23.5, 24.1, 24.2; 424/93.2, 93.21, 424/93.1
See application file for complete search history.

(56) References Cited

U.S. PATENT DOCUMENTS

| | | | |
|---|---|---|---|
| 4,690,915 | A | 9/1987 | Rosenberg |
| 5,166,057 | A | 11/1992 | Palese et al. |
| 5,494,807 | A | 2/1996 | Paoletti et al. |
| 5,530,096 | A | 6/1996 | Wölfel et al. |
| 5,578,473 | A | 11/1996 | Palese et al. |
| 5,712,115 | A * | 1/1998 | Hawkins et al. ........... 435/69.1 |
| 5,804,382 | A | 9/1998 | Sytkowski et al. |
| 5,843,648 | A | 12/1998 | Robbins et al. |
| 5,866,383 | A | 2/1999 | Moss et al. |
| 5,874,560 | A | 2/1999 | Kawakami et al. |
| 6,706,477 | B1 | 3/2004 | Zauderer |
| 6,800,442 | B1 | 10/2004 | Zauderer |
| 6,872,518 | B1 | 3/2005 | Zauderer |
| 2002/0110543 | A1 | 8/2002 | Chiocca et al. |
| 2003/0124128 | A1 | 7/2003 | Lillie et al. |
| 2003/0133917 | A1* | 7/2003 | Zauderer ............ 424/93.21 |
| 2003/0194696 | A1 | 10/2003 | Zauderer et al. |

FOREIGN PATENT DOCUMENTS

| | | |
|---|---|---|
| DE | 19950385 A1 | 8/2000 |
| WO | WO 95/33835 A1 | 12/1995 |
| WO | WO 97/24438 A1 | 7/1997 |
| WO | WO 97/26328 A1 | 7/1997 |
| WO | WO 97/34143 A1 | 9/1997 |
| WO | WO 99/30151 A1 | 6/1999 |
| WO | WO 99/47643 A1 | 9/1999 |
| WO | WO 99/55910 A1 | 11/1999 |
| WO | WO 00/28016 A1 | 5/2000 |
| WO | WO 01/72995 A2 | 10/2001 |
| WO | WO 01/72995 A3 | 10/2001 |
| WO | WO 02/053576 | 7/2002 |
| WO | WO 2004/037993 | 5/2004 |

OTHER PUBLICATIONS

Aota, S-i., et al., "Nucleotide sequence and molecular evolution of mouse retrovirus-like IAP elements," *Gene* 56:1-12, Elsevier Science Publishers B.V. (1987).

Bennink, J.R., and Yewdell, J.W., "Recombinant Vaccinia Viruses as Vectors for Studying T Lymphocyte Specificity and Function," *Curr. Top. Microbiol. Immunol.* 163:153-184, Springer-Verlag (1990).

Boël, P., et al., "*BAGE*: a New Gene Encoding an Antigen Recognized on Human Melanomas by Cytolytic T Lymphocytes," *Immunity* 2:167-175, Cell Press (1995).

Brichard, V., et al., "The Tyrosinase Gene Codes for an Antigen Recognized by Autologous Cytolytic T Lymphocytes on HLA-A2 Melanomas," *J. Exp. Med.* 178:489-495, Rockefeller University Press (1993).

de Bergeyck, V., et al., "An intracisternal A-particle sequence codes for an antigen recognized by syngeneic cytolytic T lymphocytes on a mouse spontaneous leukemia," *Eur. J. Immunol.* 24:2203-2212, VCH Verlagsgesellschaft mbH (1994).

Huang, A.Y.C., et al., "Role of Bone Marrow-Derived Cells in Presenting MHC Class I-Restricted Tumor Antigens," *Science* 264:961-965, American Association for the Advancement of Science (1994).

Inaba, K., et al., "Dendritic Cell Progenitors Phagocytose Particulates, Including Bacillus Calmette-Guerin Organisms, and Sensitize Mice to Mycobacterial Antigens In Vivo," *J. Exp. Med.* 178:479-488, Rockefeller University Press (1993).

(Continued)

*Primary Examiner*—Padmashri Ponnaluri
(74) *Attorney, Agent, or Firm*—Sterne, Kessler, Goldstein & Fox P.L.L.C.

(57) ABSTRACT

The present invention relates to a high efficiency method of introducing DNA into linear DNA viruses such as poxvirus, a method of producing libraries in linear DNA viruses such as poxvirus, and methods of selecting polynucleotides of interest based on cell nonviability or other phenotypes.

51 Claims, 31 Drawing Sheets

OTHER PUBLICATIONS

Figure 1:
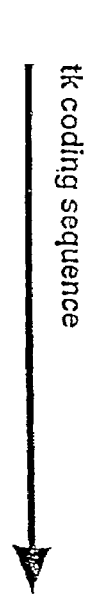

Inaba, K., et al., "Generation of Large Numbers of Dendritic Cells from Mouse Bone Marrow Cultures Supplemented with Granulocyte/Macrophage Colony-stimulating Factor," *J. Exp. Med.* 176:1693-1702, Rockefeller University Press (1992).

Janeway, Jr., C.A., and Travers, P., "The generation of T-cell ligands," and "The two classes of MHC molecule have distinct subunit structure but a similar three-dimensional structure," in *Immunobiology. The Immune System in Health and Disease*, Robertson, M. et al., eds., Current Biology, Ltd./Garland Publishing, Inc., pp. 4:2-4:5 (1994).

Kawakami, Y., et al., "Cloning of the gene coding for a shared human melanoma antigen recognized by autologous T cells infiltrating into tumor," *Proc. Natl. Acad. Sci. USA* 91:3515-3519, National Academy of Sciences (1994).

Kitts, P.A., et al., "Linearization of baculovirus DNA enhances the recovery of recombinant virus expression vectors," *Nucleic Acids Res.* 18:5667-5672, IRL Press (1990).

Kitts, P.A., and Possee, R.D., "A Method for Producing Recombinant Baculovirus Expression Vectors at High Frequency," *Biotechniques* 14:810-812, 814, and 816-817, Eaton Publishing Company (1993).

Kuff, E.L., and Lueders, K.K., "The Intracisternal A-Particle Gene Family: Structure and Functional Aspects," *Adv. Cancer Res.* 51:183-276, Academic Press, Inc. (1988).

LaFace, D.M., et al., "Human CD8 Transgene Regulation of HLA Recognition by Murine T Cells," *J. Exp. Med.* 182:1315-1325, Rockefeller University Press (1995).

Liang, P., and Pardee, A.B., "Differential Display of Eukaryotic Messenger RNA by Means of the Polymerase Chain Reaction," *Science* 257:967-971, American Association for the Advancement of Science (1992).

Lisitsyn, N., et al., "Cloning the Differences Between Two Complex Genomes," *Science* 259:946-951, American Association for the Advancement of Science (1993).

Mackett, M., et al., "Vaccinia virus: A selectable eukaryotic cloning and expression vector," *Proc. Natl. Acad. Sci. USA* 79:7415-7419, National Academy of Sciences (1982).

Mackett M., et al., "General Method for Production and Selection of Infectious Vaccinia Virus Recombinants Expressing Foreign Genes," *J. Virol.* 49:857-864, American Society for Microbiology (1984).

Merchlinsky, M., and Moss, B., "Introduction of Foreign DNA into the Vaccinia Virus Genome by *in Vitro* Ligation: Recombination-Independent Selectable Cloning Vectors," *Virology* 190:522-526, Academic Press, Inc. (1992).

Merchlinsky, M., et al., "Construction and Characterization of Vaccinia Direct Ligation Vectors," *Virology* 238:444-451, Academic Press, Inc. (1997).

Meyer H., et al., "Mapping of deletions in the genome of the highly attenuated vaccinia virus MVA and their influence on virulence," *J. Gen. Virol.* 72:1031-1038, Society for General Microbiology (1991).

Miyake, S., et al., "Efficient generation of recombinant adenoviruses using adenovirus DNA-terminal protein complex and a cosmid bearing the full-length virus genome," *Proc. Natl. Acad. Sci. USA* 93:1320-1324, National Academy of Sciences (1996).

Moss, B., "Vaccinia Virus: A Tool for Research and Vaccine Development," *Science* 252:1662-1667, American Association for the Advancement of Science (1991).

Palese, P., et al., "Negative-strand RNA viruses: Genetic engineering and applications," *Proc. Natl. Acad. Sci. USA* 93:11354-11358, National Academy of Sciences (1996).

Panicali, D., and Paoletti, E., "Construction of poxviruses as cloning vectors: Insertion of the thymidine kinase gene from herpes simplex virus into the DNA of infectious vaccinia virus," *Proc. Natl. Acad. Sci. USA* 79:4927-4931, National Academy of Sciences (1982).

Pfleiderer, M., et al., "A novel vaccina virus expression system allowing construction of recombinants without the need for selection markers, plasmids and bacterial hosts," *J. Gen. Virol.* 76:2957-2962, Society for General Microbiology (1995).

Quill, H., "Anergy as a Mechanism of Peripheral T Cell Tolerance," *J. Immunol.* 156:1325-1327, American Association of Immunologists (1996).

Ralph, D., et al., "RNA fingerprinting using arbitrarily primed PCR identifies differently regulated RNAs in milk lung (My1Lu) cells growth arrested by transforming growth factor β1," *Proc. Natl. Acad. Sci. USA* 90:10710-10714, National Academy of Sciences (1993).

Sahasrabudhe, D.M., et al., "Shared T Cell-Defined Antigens on Independently Derived Tumors," *J. Immunol.* 151:6302-6310, American Association of Immunologists (1993).

Sambrook, J., et al., "Identification of cDNA clones of interest," in *Molecular Cloning. A Laboratory Manual*, 2nd ed., Sambrook, J., et al., eds., Cold Spring Harbor Laboratory Press, Plainview, NY, pp. 8.46-8.52 (1989).

Scheiflinger, F., et al., "Construction of chimeric vaccinia viruses by molecular cloning and packaging," *Proc. Natl. Acad. Sci. USA* 89:9977-9981, National Academy of Sciences (1992).

Shirai, M., et al., "CTL Responses of HLA-A2.1-Transgenic Mice Specific for Hepatitis C Viral Peptides Predict Epitopes for CTL of Humans Carrying HLA-A2.1," *J. Immunol.* 154:2733-2742, American Association of Immunologists (1995).

Sidney, J., et al., "Practical, biochemical and evolutionary implications of the discovery of HLA class I supermotifs," *Immunol. Today* 17:261-266, Elsevier Science, Ltd.(1996).

Takahashi, H., et al., "Induction of CD8$^+$cytotoxic T cells by immunization with purified HIV-1 envelope protein in ISCOMs," *Nature* 344:873-875, Macmillan Journals Ltd. (1990).

Torigoe, T., et al., "Tumor Rejection Antigens on BALB3T3 Cells Transformed by Activated Oncogenes," *J. Immunol.* 147:3251-3258, American Association of Immunologists (1991).

van der Bruggen, P., et al., "A Gene Encoding an Antigen Recognized by Cytolytic T Lymphocytes on a Human Melanoma," *Science* 254:1643-1647, American Association for the Advancement of Science (1991).

Van den Eynde, B., et al. "A New Family of Genes Coding for an Antigen Recognized by Autologous Cytolytic T Lymphocytes on a Human Melanoma," *J. Exp. Med.* 182:689-698, Rockefeller University Press (1995).

Vitiello, A., et al., "Analysis of the HLA-restricted Influenza-specific Cytotoxic T Lymphocyte Response in Transgenic Mice Carrying a Chimeric Human-Mouse Class I Major Histocompatibility Complex," *J. Exp. Med.* 173:1007-1015, Rockefeller University Press (1991).

Wang, R-F., et al., "Development of a Retrovirus-based Complementary DNA Expression System for the Cloning of Tumor Antigens," *Cancer Res.* 58:3519-3525, American Association of Cancer Research (1998).

Welsh, J., et al., "Arbitrarily primed PCR fingerprinting of RNA," *Nucleic Acids Res.* 20:4965-4970, Oxford University Press (1992).

Wentworth, P.A., et al., "Differences and similarities in the A2.1-restricted cytotoxic T cell repertoire in humans and human leukocyte antigen-transgenic mice," *Eur. J. Immunol.* 26:97-101, VCH Verlagsgellschaft mbH (1996).

Wilson, S.H., and Kuff, E.L., "A Novel DNA Polymerase Activity Found in Association with Intracisternal A-Type Particles," *Proc. Natl. Acad. Sci. USA* 69:1531-1536, National Academy of Sciences (1972).

Wölfel, T., et al., "Immunogenic (tum) variants obtained by mutagenesis of mouse mastocytoma P815," *Immunogenetics* 26:178-187, Springer-Verlag (1987).

Clontech Catalog 1998/1999, "CLONTECH PCR-Select Subtraction," p. 24 (Clontech Laboratories, Inc., Palo Alto, CA) (1998).

Smith, E.S., et al., "Lethality-based selection of recombinant genes in mammalian cells: Application to identifying tumor antigens," *Nat. Med.* 7:967-972, Nature America Inc. (Aug. 2001).

Traversari, C., et al., "Transfection and expression of a gene coding for a human melanoma antigen recognized by autologous cytolytic T lymphocytes," *Immunogenetics* 35:145-152, Springer-Verlag (1992).

Pending Non-Provisional U. S. Appl. No. 10/901,415, Zauderer, M., filed Jul. 29, 2004 (Not Published).

Buller, R.M.L., et al., "Deletion of the Vaccinia Virus Growth Factor Gene Reduces Virus Virulence," *J. Virol.* 62: 866-874, American Society for Microbiology (1988).

Greenhalf, W., et al., "A Selection System for Human Apoptosis Inhibitors Using Yeast," *Yeast* 15: 1307-1321, John Wiley & Sons, Ltd. (Sep. 1999).

Moss, B., et al., "Deletion of a 9,000-Base-Pair Segment of the Vaccinia Genome that Encodes Nonessential Polypeptides," *J. Virol.* 40: 387-395, American Society for Microbiology (1981).

Panicali, D., et al., "Two Major DNA Variants Present in Serially Propagated Stocks of the WR Strain of Vaccinia Virus," *J. Virol.* 37: 1000-1010, American Society for Microbiology (1981).

Smith, et al., "Identification and Characterization of a Shared Murine Tumor Antigen," transcript of Ph.D. Thesis Seminar, Sep. 18, 1998.

Smith, E.S., "Identification and Characterization of a Shared Murine Tumor Antigen," Ph.D. Thesis, University of Rochester, Jun. 30, 1999.

Vidović, D., and Toral, J.I., "Selective Apoptosis of Neoplastic Cells by the HLA-DR-Specific Monoclonal Antibody," *Cancer Lett.* 128: 127-135. Elsevier Science Ireland Ltd. (1998).

Database esp@cenet, English language Abstract of WO 00/44894, available online at http://v3/espacenet.com/textdoc?DB=EPODOC&IDX=WO0044894&F=8 &QPN=WO0044894.

Faber, L.M., et al., "Generation of CD4+ cytotoxic T-lymphocyte clones from a patient with severe graft-versus-host disease after allogenic bone marrow transplantation: implications for graft-versus-leukemia reactivity," *Blood* 86:2821-2828, American Society of Hematology (1995) (PubMed Abstract Only).

International Search Report for International Appl. No. PCT/US03/33557, mailed on Jun. 7, 2005.

EST Database, Accession No. AA010615, Hillier, L., et al., entry date Jul. 29, 1996.

* cited by examiner

A 1. p7.5tk

5'- GGCCAAAAATTGAAAAACTAGATCTATTTATTGCACGGCCGCCATGGGCCCCGGCC -3'

7.5K PROMOTER        NOTI        APAI 2. p7.5/ATG0/tk

5'- GGCCAAAAATTGAAAAACTAGATCTATTTATTGCACGGCCGCCGTGGATCCCCGGGCTGCAGGAA 7.5K PROMOTER       NOTI     BAMHI  SMAI    PSTI

TTCGATATCAAGCTTATCGATACCGTCGACCTCGAGGGGGGGCCTAACTAACTAATTTTGTTTTTGT

SALI                   TRANSLATION    TRANSCRIPTION
                                                            STOP CODONS    STOP SIGNAL

APAI

GGGCCCGGGCC -3'

Figure 3:
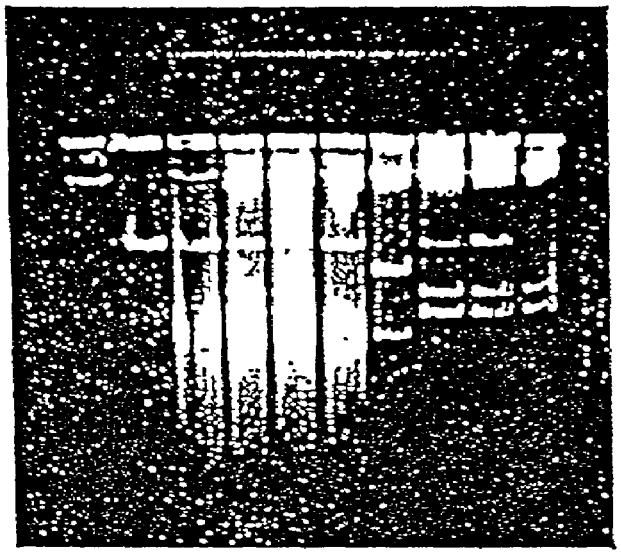
Figure 3:
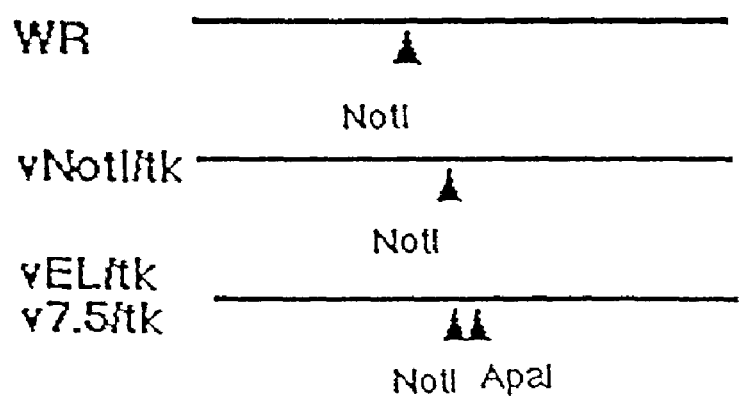

FIGURE 8A 3. p7.5/ATG1/tk

5'- GGCCAAAAATTGAAAAACTAGATCTATTTATTGCACGGCCGCCATGGGATCCCCGGGGCTGCAGGAA 7.5K PROMOTER          NOTI   START CODON  BAMHI  SMAI  PSTI

TTCGATATCAAGCTTATCGATACCGTCGACCTCGAGGGGGGGCCTAACTAACTAATTTGTTTTTGT

SALI           TRANSLATION   TRANSCRIPTION
                                    STOP CODONS   STOP SIGNAL

APAI
GGGCCCGGCC -3'

Figure 4:
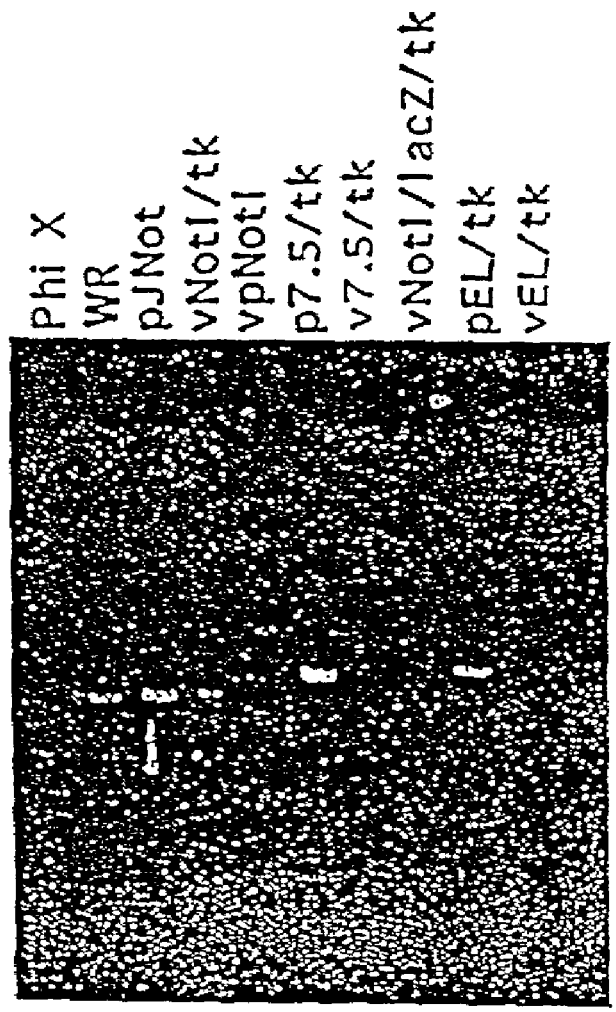

FIGURE 8B 4. p7.5/ATG2/tk

```
                                    START
              7.5K PROMOTER         CODON   BAMHI  SMAI    PSTI
                                NOTI
5'-GGCCAAAAATTGAAAAACTAGATCTATTTATTGCACGGCCGCCATGAGTGGATCCCCCGGGGCTGCAGGA

TRANSLATION    TRANSCRIPTION
                         SALI           STOP CODONS    STOP SIGNAL
TTCGATATCAAGCTTATCGATACCGTCGACCTCGAGGGGGGGCCCTAACTAACTAATTTTGTTTTTGT

APAI
GGGCCCGGCC -3'
```

Figure 5:
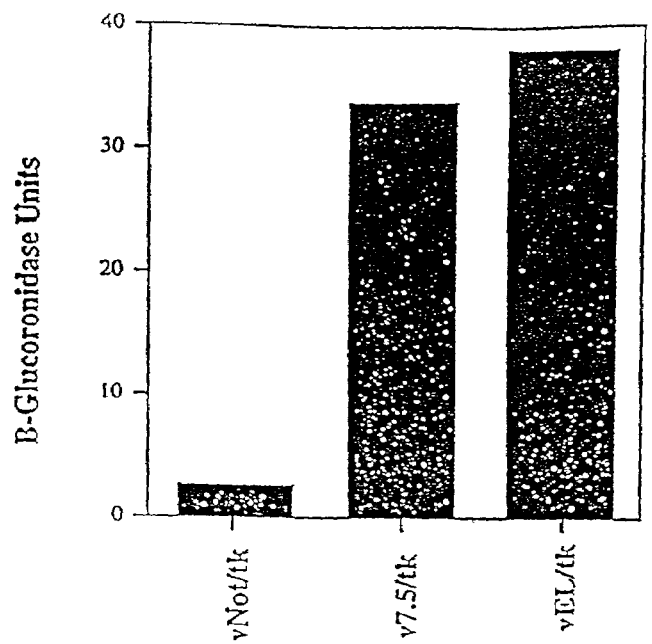

FIGURE 8C 5. p7.5/ATG3/tk 7.5K PROMOTER    START CODON    NOTI    BAMHI    SMAI    PSTI

5'- GGCCAAAAATTGAAAAACTAGATCTATTTATTGCACGCGGCCGCCATGACGTGGATCCCCCGGGGCTGCAGGAA

SALI    TRANSLATION    TRANSCRIPTION
STOP CODONS    STOP SIGNAL

TTCGATATCAAGCTTATCGATACCGTCGACCTCGAGGGGGGCCTAACTAACTAATTTTGTTTTTGT

APAI
GGGCCCGGGCC -3'

FIGURE 8D

|  | Percent Specific Lysis | |
|---|---|---|
|  | Effector : Target | |
| Target | 10:1 | 2:1 |
| BCA 34 | 68.4 | 54.8 |
| BCA 39 | 36.6 | 23.4 |
| B/C.N | 0.2 | 0.3 |
| B/C.N + vF5.8 | 47.5 | 34.6 |
| B/C.N + vH2.16 | 67.8 | 56.2 |
| B/C.N + vaccinia vector | 0 | 0.2 |

FIGURE 11B

A. L3

| Amino Acid Position | 45 | 46 | 47 | 48 | 49 | 50 | 51 | 52 | 53 | 54 | 55 | 56 |
|---|---|---|---|---|---|---|---|---|---|---|---|---|
| Sequence | A | F | L | G | Y | K | A | G | M | T | H | I |
| Nucleotide | GCC | TTT | CTG | GGT | TAC | AAG | GCT | GGC | ATG | ACC | CAC | ATC |

B. H2.16

| Amino Acid Position | 45 | 46 | 47 | 48 | 49 | 50 | 51 | 52 | 53 | 54 | 55 | 56 |
|---|---|---|---|---|---|---|---|---|---|---|---|---|
| Sequence | A | F | L | G | Y | K | A | G | M | I | H | I |
| Nucleotide | --- | --- | --- | --- | --- | --- | --- | --- | --- | -T- | --- | --- |

FIGURE 12

|                              | Percent Specific Lysis |       |
|                              | Effector: Target       |       |
| Target                       | 10:1                   | 2:1   |
| BCA 34                       | 62.4                   | 32.1  |
| BCA 39                       | 49.7                   | 23.6  |
| B/C.N                        | 3.3                    | 0.2   |
| B/C.N + L3 peptide 48-56(I54)| 46.0                   | 16.1  |
| B/C.N + L3 peptide 48-56(T54)| 2.0                    | 0     |
| B/C.N + L3 peptide 45-54(I54)| 0                      | 0     |

FIGURE 13A

Published L3 (1276 bp)

168-171 = GACC

H2.16 (1276 bp)

168-171 = GATC

| Target | Percent Specific Lysis Immunogen | | | |
|---|---|---|---|---|
| | vH2.16 | | v7.5/tk | |
| | 40:1 | 10:1 | 40:1 | 10:1 |
| BCA 34 | 33.6 | 12.9 | 5.7 | 4.0 |
| BCA 39 | 22.1 | 9.0 | 5.3 | 3.1 |
| B/C.N + L3 48-56 (I54) | 48.2 | 20.2 | 3.9 | 1.5 |
| B/C.N + L3 48-56 (T54) | 6.4 | 1.4 | 1.8 | 2.9 |
| B/C.N | 7.1 | 5.7 | 6.1 | 2.8 |
| YAC | 1.2 | 2.5 | 0 | 1.8 |

FIGURE 15 A

A.

Influenza Specific Cytolytic Activity of CD4+ CD45RA+ Human T Cells Stimulated in the Presence of IL-12 and IL-18.

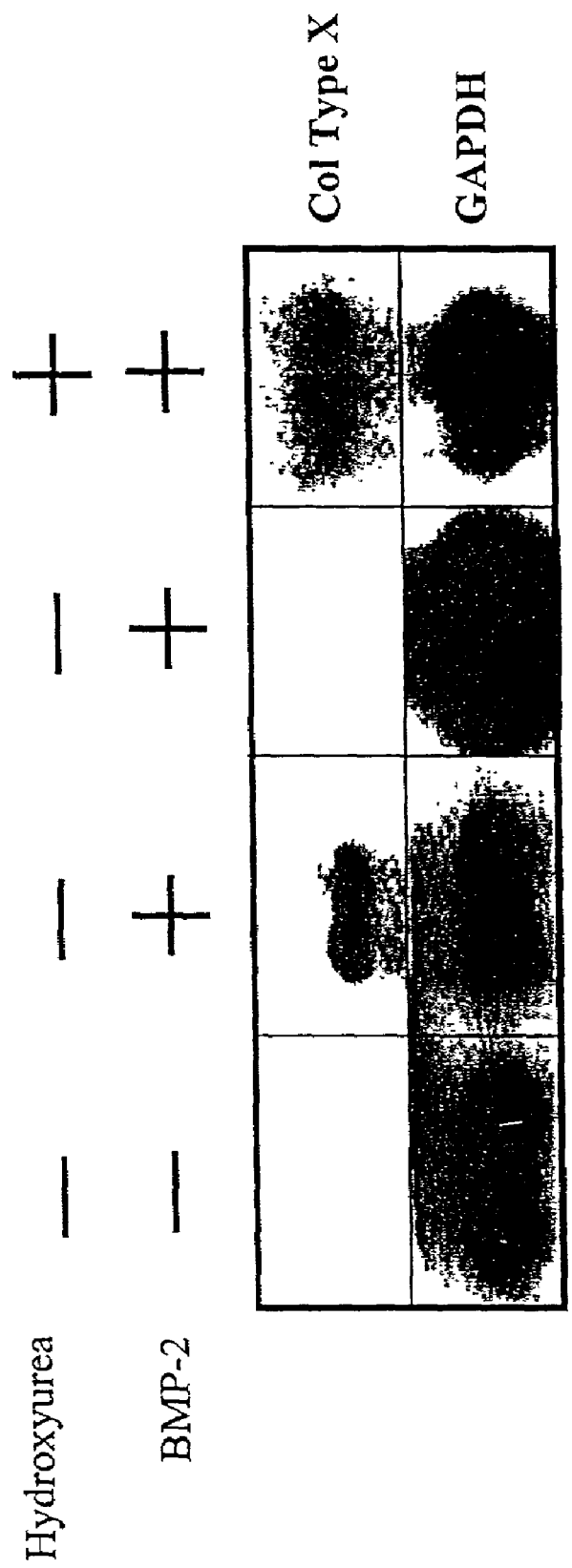

SEQUENCE LISTING

```
<160> NUMBER OF SEQ ID NOS: 65

<210> SEQ ID NO 1
<211> LENGTH: 69
<212> TYPE: DNA
<213> ORGANISM: Artificial Sequence
<220> FEATURE:
<221> NAME/KEY: misc_feature
<223> OTHER INFORMATION: Nucleotide Sequence of p7.5/tk

<400> SEQUENCE: 1
ggccaaaaat tgaaaacta gatctattta ttgcacgcgg ccgccatggg cccggccgcc      60
aacggcgga                                                             69

<210> SEQ ID NO 2
<211> LENGTH: 8
<212> TYPE: PRT
<213> ORGANISM: Artificial Sequence
<220> FEATURE:
<221> NAME/KEY: misc_feature
<223> OTHER INFORMATION: tk coding sequence

<400> SEQUENCE: 2

Met Gly Pro Ala Ala Asn Gly Gly
1               5

<210> SEQ ID NO 3
<211> LENGTH: 75
<212> TYPE: DNA
<213> ORGANISM: Artificial Sequence
<220> FEATURE:
<221> NAME/KEY: misc_feature
<223> OTHER INFORMATION: Nucleotide Sequence of pEL/tk

<400> SEQUENCE: 3
ggccaaaaat tgaaatttta ttttttttt ttggaatata aagcggccgc catgggcccg      60
gccgccaacg gcgga                                                      75

<210> SEQ ID NO 4
<211> LENGTH: 145
<212> TYPE: DNA
<213> ORGANISM: Artificial Sequence
<220> FEATURE:
<221> NAME/KEY: misc_feature
<223> OTHER INFORMATION: Nucleotide Sequence of p7.5/ATG0/tk

<400> SEQUENCE: 4
ggccaaaaat tgaaaacta gatctattta ttgcacgcgg ccgccgtgga tccccgggc       60 tgcaggaatt cgatatcaag cttatcgata ccgtcgacct cgagggggg cctaactaac    120 taattttgtt tttgtgggcc cggcc                                          145

<210> SEQ ID NO 5
<211> LENGTH: 148
<212> TYPE: DNA
<213> ORGANISM: Artificial Sequence
<220> FEATURE:
<221> NAME/KEY: misc_feature
<223> OTHER INFORMATION: Nucleotide Sequence of p7.5/ATG1/tk
```

```
<400> SEQUENCE: 5
ggccaaaaat tgaaaaacta gatctattta ttgcacgcgg ccgccatggt ggatcccccg      60
ggctgcagga attcgatatc aagcttatcg ataccgtcga cctcgagggg gggcctaact     120 aactaattttt gttttttgtgg gcccggcc                                      148

<210> SEQ ID NO 6
<211> LENGTH: 149
<212> TYPE: DNA
<213> ORGANISM: Artificial Sequence
<220> FEATURE:
<221> NAME/KEY: misc_feature
<223> OTHER INFORMATION: Nucleotide Sequence of p7.5/ATG2/tk

<400> SEQUENCE: 6
ggccaaaaat tgaaaaacta gatctattta ttgcacgcgg ccgccatgag tggatcccc       60 gggctgcagg aattcgatat caagcttatc gataccgtcg acctcgaggg ggggcctaac    120
taactaattt tgttttttgtg ggcccggcc                                      149

<210> SEQ ID NO 7
<211> LENGTH: 150
<212> TYPE: DNA
<213> ORGANISM: Artificial Sequence
<220> FEATURE:
<221> NAME/KEY: misc_feature
<223> OTHER INFORMATION: Nucleotide Sequence of p7.5/ATG3/tk

<400> SEQUENCE: 7
ggccaaaaat tgaaaaacta gatctattta ttgcacgcgg ccgccatgac gtggatcccc      60
cgggctgcag gaattcgata tcaagcttat cgataccgtc gacctcgagg ggggcctaa     120 ctaactaatt ttgttttttgt gggcccggcc                                     150

<210> SEQ ID NO 8
<211> LENGTH: 36
<212> TYPE: DNA
<213> ORGANISM: Artificial Sequence
<220> FEATURE:
<221> NAME/KEY: CDS
<222> LOCATION: (1)..(36)
<221> NAME/KEY: misc_feature
<223> OTHER INFORMATION: rpL3

<400> SEQUENCE: 8 gcc ttt ctg ggt tac aag gct ggc atg acc cac atc                        36
Ala Phe Leu Gly Tyr Lys Ala Gly Met Thr His Ile
1               5                   10

<210> SEQ ID NO 9
<211> LENGTH: 12
<212> TYPE: PRT
<213> ORGANISM: Artificial Sequence
<220> FEATURE:
<221> NAME/KEY: misc_feature
<223> OTHER INFORMATION: rpL3

<400> SEQUENCE: 9

Ala Phe Leu Gly Tyr Lys Ala Gly Met Thr His Ile
1               5                   10

<210> SEQ ID NO 10
<211> LENGTH: 36
<212> TYPE: DNA
<213> ORGANISM: Artificial Sequence
<220> FEATURE:
```

```
<221> NAME/KEY: CDS
<222> LOCATION: (1)..(36)
<221> NAME/KEY: misc_feature
<223> OTHER INFORMATION: H2.16

<400> SEQUENCE: 10 gcc ttt ctg ggt tac aag gct ggc atg atc cac atc                      36
Ala Phe Leu Gly Tyr Lys Ala Gly Met Ile His Ile
1               5                   10

<210> SEQ ID NO 11
<211> LENGTH: 12
<212> TYPE: PRT
<213> ORGANISM: Artificial Sequence
<220> FEATURE:
<221> NAME/KEY: misc_feature
<223> OTHER INFORMATION: H2.16

<400> SEQUENCE: 11

Ala Phe Leu Gly Tyr Lys Ala Gly Met Ile His Ile
1               5                   10

<210> SEQ ID NO 12
<211> LENGTH: 9
<212> TYPE: PRT
<213> ORGANISM: Unknown
<220> FEATURE:
<223> OTHER INFORMATION: cyclin A destruction box of unknown origin
<221> NAME/KEY: misc_feature
<223> OTHER INFORMATION: Destruction box of cyclin A

<400> SEQUENCE: 12

Arg Thr Val Leu Gly Val Ile Gly Asp
1               5

<210> SEQ ID NO 13
<211> LENGTH: 9
<212> TYPE: PRT
<213> ORGANISM: Unknown
<220> FEATURE:
<223> OTHER INFORMATION: cyclin B1 destruction box of unknown origin
<221> NAME/KEY: misc_feature
<223> OTHER INFORMATION: Destruction box of cyclin B1

<400> SEQUENCE: 13

Arg Thr Ala Leu Gly Asp Ile Gly Asn
1               5

<210> SEQ ID NO 14
<211> LENGTH: 27
<212> TYPE: PRT
<213> ORGANISM: Rattus sp.
<220> FEATURE:
<221> NAME/KEY: misc_feature
<223> OTHER INFORMATION: Destruction box of rat cyclin B

<400> SEQUENCE: 14

Tyr Met Thr Val Ser Ile Ile Asp Arg Phe Met Gln Asp Ser Cys Val
1               5                   10                  15

Pro Lys Lys Met Leu Gln Leu Val Gly Val Thr
            20                  25

<210> SEQ ID NO 15
<211> LENGTH: 28
<212> TYPE: PRT
<213> ORGANISM: Mus sp.
<220> FEATURE:
<221> NAME/KEY: misc_feature
```

```
<223> OTHER INFORMATION: Destruction box of mouse cyclin B

<400> SEQUENCE: 15

Lys Phe Arg Leu Leu Gln Glu Thr Met Tyr Met Thr Val Ser Ile Ile
 1               5                  10                  15

Asp Arg Phe Met Gln Asn Ser Cys Val Pro Lys Lys
            20                  25

<210> SEQ ID NO 16
<211> LENGTH: 27
<212> TYPE: PRT
<213> ORGANISM: Mus sp.
<220> FEATURE:
<221> NAME/KEY: misc_feature
<223> OTHER INFORMATION: Destruction box of mouse cyclin 131

<400> SEQUENCE: 16

Arg Ala Ile Leu Ile Asp Trp Leu Ile Gln Val Gln Met Lys Phe Arg
 1               5                  10                  15

Leu Leu Gln Glu Thr Met Tyr Met Thr Val Ser
            20                  25

<210> SEQ ID NO 17
<211> LENGTH: 26
<212> TYPE: PRT
<213> ORGANISM: Mus sp.
<220> FEATURE:
<221> NAME/KEY: misc_feature
<223> OTHER INFORMATION: Destruction box of mouse cyclin 132

<400> SEQUENCE: 17

Asp Arg Phe Leu Gln Ala Gln Leu Val Cys Arg Lys Lys Leu Gln Trp
 1               5                  10                  15

Gly Ile Thr Ala Leu Leu Leu Ala Ser Lys
            20                  25

<210> SEQ ID NO 18
<211> LENGTH: 18
<212> TYPE: PRT
<213> ORGANISM: Mus sp.
<220> FEATURE:
<221> NAME/KEY: misc_feature
<223> OTHER INFORMATION: Destruction box of mouse cyclin A2

<400> SEQUENCE: 18

Met Ser Val Leu Arg Gly Lys Leu Gln Leu Val Gly Thr Ala Ala Met
 1               5                  10                  15

Leu Leu

<210> SEQ ID NO 19
<211> LENGTH: 53
<212> TYPE: DNA
<213> ORGANISM: Artificial Sequence
<220> FEATURE:
<221> NAME/KEY: misc_feature
<223> OTHER INFORMATION: 7.5k gene promoter MM436

<400> SEQUENCE: 19
ggccaaaaat tgaaaaacta gatctatttta ttgcacgcgg ccgccatggg ccc        53

<210> SEQ ID NO 20
<211> LENGTH: 53
<212> TYPE: DNA
<213> ORGANISM: Artificial Sequence
<220> FEATURE:
```

```
<221> NAME/KEY: misc_feature
<223> OTHER INFORMATION: 7.5k gene promoter MM437

<400> SEQUENCE: 20
ggccgggccc atggcggccg cgtgcaataa atagatctag tttttcaatt ttt          53

<210> SEQ ID NO 21
<211> LENGTH: 59
<212> TYPE: DNA
<213> ORGANISM: Artificial Sequence
<220> FEATURE:
<221> NAME/KEY: misc_feature
<223> OTHER INFORMATION: Synthetic EL promoter MM438

<400> SEQUENCE: 21
ggccaaaaat tgaaatttta tttttttttt ttggaatata aagcggccgc catgggccc    59

<210> SEQ ID NO 22
<211> LENGTH: 59
<212> TYPE: DNA
<213> ORGANISM: Artificial Sequence
<220> FEATURE:
<221> NAME/KEY: misc_feature
<223> OTHER INFORMATION: Synthetic EL promoter MM439

<400> SEQUENCE: 22
ggccgggccc atggcggccg ctttatattc caaaaaaaaa aataaaatt tcaattttt     59

<210> SEQ ID NO 23
<211> LENGTH: 39
<212> TYPE: DNA
<213> ORGANISM: Artificial Sequence
<220> FEATURE:
<221> NAME/KEY: misc_feature
<223> OTHER INFORMATION: Primer MM440

<400> SEQUENCE: 23
gggaaagggg cggccgccat gttacgtcct gtagaaacc                          39

<210> SEQ ID NO 24
<211> LENGTH: 36
<212> TYPE: DNA
<213> ORGANISM: Artificial Sequence
<220> FEATURE:
<221> NAME/KEY: misc_feature
<223> OTHER INFORMATION: Primer MM441

<400> SEQUENCE: 24
gggaaagggg ggccctcatt gtttgcctcc ctgctg                             36

<210> SEQ ID NO 25
<211> LENGTH: 39
<212> TYPE: DNA
<213> ORGANISM: Artificial Sequence
<220> FEATURE:
<221> NAME/KEY: misc_feature
<223> OTHER INFORMATION: Primer MM442

<400> SEQUENCE: 25
gggaaagggg cggccgcctc attgtttgcc tccctgctg                          39

<210> SEQ ID NO 26
<211> LENGTH: 8
<212> TYPE: PRT
<213> ORGANISM: Artificial Sequence
<220> FEATURE:
<221> NAME/KEY: misc_feature
```

<223> OTHER INFORMATION: Cytotoxic T-cell epitope for ovalbumin (11)

<400> SEQUENCE: 26

Ser Ile Ile Asn Phe Glu Lys Leu
1               5

<210> SEQ ID NO 27
<211> LENGTH: 70
<212> TYPE: DNA
<213> ORGANISM: Artificial Sequence
<220> FEATURE:
<221> NAME/KEY: misc_feature
<223> OTHER INFORMATION: 75ova

<400> SEQUENCE: 27
ggccaaaaat tgaaaaacta gatctattta ttgcaccatg agtataatca actttgaaaa      60
actgtagtga                                                            70

<210> SEQ ID NO 28
<211> LENGTH: 71
<212> TYPE: DNA
<213> ORGANISM: Artificial Sequence
<220> FEATURE:
<221> NAME/KEY: misc_feature
<223> OTHER INFORMATION: 75ovarv

<400> SEQUENCE: 28
ggcctcacta cagtttttca aagttgatta atactcatgg tgcaataaat agatctagtt      60 tttcaattttt t                                                         71

<210> SEQ ID NO 29
<211> LENGTH: 77
<212> TYPE: DNA
<213> ORGANISM: Artificial Sequence
<220> FEATURE:
<221> NAME/KEY: misc_feature
<223> OTHER INFORMATION: ELova

<400> SEQUENCE: 29
ggccaaaaat tgaaatttta ttttttttttt ttggaatata aaccatgagt ataatcaact      60
ttgaaaaact gtagtga                                                    77

<210> SEQ ID NO 30
<211> LENGTH: 77
<212> TYPE: DNA
<213> ORGANISM: Artificial Sequence
<220> FEATURE:
<221> NAME/KEY: misc_feature
<223> OTHER INFORMATION: ELovarv

<400> SEQUENCE: 30
ggcctcacta cagtttttca aagttgatta tactcatggt ttatattcca aaaaaaaaa       60 ataaaatttc aattttt                                                    77

<210> SEQ ID NO 31
<211> LENGTH: 36
<212> TYPE: DNA
<213> ORGANISM: Artificial Sequence
<220> FEATURE:
<221> NAME/KEY: misc_feature
<223> OTHER INFORMATION: Primer V V 0 L Z 5

<400> SEQUENCE: 31
gcaggtgcgg ccgccgtgga tccccgggc tgcagg                                 36

<210> SEQ ID NO 32
<211> LENGTH: 47
<212> TYPE: DNA
<213> ORGANISM: Artificial Sequence
<220> FEATURE:
<221> NAME/KEY: misc_feature
<223> OTHER INFORMATION: Primer V V T L Z 3

<400> SEQUENCE: 32
gtaccgggcc cacaaaaaca aaattagtta gttaggcccc ccctcga        47

<210> SEQ ID NO 33
<211> LENGTH: 27
<212> TYPE: DNA
<213> ORGANISM: Artificial Sequence
<220> FEATURE:
<221> NAME/KEY: misc_feature
<223> OTHER INFORMATION: Primer MM407

<400> SEQUENCE: 33
ggtccctatt gttacagatg gaagggt        27

<210> SEQ ID NO 34
<211> LENGTH: 24
<212> TYPE: DNA
<213> ORGANISM: Artificial Sequence
<220> FEATURE:
<221> NAME/KEY: misc_feature
<223> OTHER INFORMATION: Primer MM408

<400> SEQUENCE: 34
ccttcgtttg ccatacgctc acag        24

<210> SEQ ID NO 35
<211> LENGTH: 7
<212> TYPE: PRT
<213> ORGANISM: Artificial sequence
<220> FEATURE:
<221> NAME/KEY: misc_feature
<223> OTHER INFORMATION: Partial sequence of tk gene at N terminus

<400> SEQUENCE: 35

Met Gly Pro Ala Ala Asn Gly
1               5

<210> SEQ ID NO 36
<211> LENGTH: 20
<212> TYPE: DNA
<213> ORGANISM: Artificial Sequence
<220> FEATURE:
<221> NAME/KEY: misc_feature
<223> OTHER INFORMATION: L3 specific primer L3.Fl.S

<400> SEQUENCE: 36
cggcgagatg tctcacagga        20

<210> SEQ ID NO 37
<211> LENGTH: 20
<212> TYPE: DNA
<213> ORGANISM: Artificial Sequence
<220> FEATURE:
<221> NAME/KEY: misc_feature
<223> OTHER INFORMATION: L3 specific primer L3.Fl.AS

<400> SEQUENCE: 37
accccaccat ctgcacaaag        20

<210> SEQ ID NO 38
<211> LENGTH: 15
<212> TYPE: DNA
<213> ORGANISM: Artificial Sequence
<220> FEATURE:
<221> NAME/KEY: misc_feature
<223> OTHER INFORMATION: BglII-NcoI Sense

<400> SEQUENCE: 38
gatctcggta accgc                                                        15

<210> SEQ ID NO 39
<211> LENGTH: 15
<212> TYPE: DNA
<213> ORGANISM: Artificial Sequence
<220> FEATURE:
<221> NAME/KEY: misc_feature
<223> OTHER INFORMATION: BglII-NcoI Antisense

<400> SEQUENCE: 39
catggcggtt accga                                                        15

<210> SEQ ID NO 40
<211> LENGTH: 15
<212> TYPE: DNA
<213> ORGANISM: Artificial Sequence
<220> FEATURE:
<221> NAME/KEY: misc_feature
<223> OTHER INFORMATION: Xho-I-XmaIII sense

<400> SEQUENCE: 40
ggccgaaata accgc                                                        15

<210> SEQ ID NO 41
<211> LENGTH: 15
<212> TYPE: DNA
<213> ORGANISM: Artificial Sequence
<220> FEATURE:
<221> NAME/KEY: misc_feature
<223> OTHER INFORMATION: Xho-I-XmaIII antisense

<400> SEQUENCE: 41
tcgagcggtt atttc                                                        15

<210> SEQ ID NO 42
<211> LENGTH: 15
<212> TYPE: DNA
<213> ORGANISM: Artificial Sequence
<220> FEATURE:
<221> NAME/KEY: misc_feature
<223> OTHER INFORMATION: H3-NcoI sense

<400> SEQUENCE: 42
agcttcggta accgc                                                        15

<210> SEQ ID NO 43
<211> LENGTH: 15
<212> TYPE: DNA
<213> ORGANISM: Artificial Sequence
<220> FEATURE:
<221> NAME/KEY: misc_feature
<223> OTHER INFORMATION: H3-NcoI antisense

<400> SEQUENCE: 43
catggcggtt accga                                                        15

```
<210> SEQ ID NO 44
<211> LENGTH: 20
<212> TYPE: DNA
<213> ORGANISM: Artificial Sequence
<220> FEATURE:
<221> NAME/KEY: misc_feature
<223> OTHER INFORMATION: PstI-XmaIII sense

<400> SEQUENCE: 44
ggccggaaat aaccgctgca                                              20

<210> SEQ ID NO 45
<211> LENGTH: 12
<212> TYPE: DNA
<213> ORGANISM: Artificial Sequence
<220> FEATURE:
<221> NAME/KEY: misc_feature
<223> OTHER INFORMATION: PstI-XmaIII antisense

<400> SEQUENCE: 45
gcggttattt cc                                                      12

<210> SEQ ID NO 46
<211> LENGTH: 16
<212> TYPE: DNA
<213> ORGANISM: Artificial Sequence
<220> FEATURE:
<221> NAME/KEY: misc_feature
<223> OTHER INFORMATION: SalI-NcoI sense

<400> SEQUENCE: 46
ctgaggaaat aaccgc                                                  16

<210> SEQ ID NO 47
<211> LENGTH: 16
<212> TYPE: DNA
<213> ORGANISM: Artificial Sequence
<220> FEATURE:
<221> NAME/KEY: misc_feature
<223> OTHER INFORMATION: SalI-NcoI antisense

<400> SEQUENCE: 47
catggcggtt atttcc                                                  16

<210> SEQ ID NO 48
<211> LENGTH: 21
<212> TYPE: DNA
<213> ORGANISM: Artificial Sequence
<220> FEATURE:
<221> NAME/KEY: misc_feature
<223> OTHER INFORMATION: Gus sense

<400> SEQUENCE: 48
atgttacgtc ctgtagaaac c                                            21

<210> SEQ ID NO 49
<211> LENGTH: 21
<212> TYPE: DNA
<213> ORGANISM: Artificial Sequence
<220> FEATURE:
<221> NAME/KEY: misc_feature
<223> OTHER INFORMATION: Gus antisense

<400> SEQUENCE: 49
tcattgtttg cctccctgct g                                            21
```

```
<210> SEQ ID NO 50
<211> LENGTH: 28
<212> TYPE: DNA
<213> ORGANISM: Artificial Sequence
<220> FEATURE:
<221> NAME/KEY: misc_feature
<223> OTHER INFORMATION: NX-Gus sense

<400> SEQUENCE: 50
aaagcggccg ccccgggatg ttacgtcc                                28

<210> SEQ ID NO 51
<211> LENGTH: 29
<212> TYPE: DNA
<213> ORGANISM: Artificial Sequence
<220> FEATURE:
<221> NAME/KEY: misc_feature
<223> OTHER INFORMATION: AA-Gus antisense

<400> SEQUENCE: 51
aaagggcccg gcgcgcctca ttgtttgcc                               29

<210> SEQ ID NO 52
<211> LENGTH: 37
<212> TYPE: DNA
<213> ORGANISM: Artificial Sequence
<220> FEATURE:
<221> NAME/KEY: misc_feature
<223> OTHER INFORMATION: D4R Sense

<400> SEQUENCE: 52
aaaggatcca taatgaattc agtgactgta tcacacg                      37

<210> SEQ ID NO 53
<211> LENGTH: 34
<212> TYPE: DNA
<213> ORGANISM: Artificial Sequence
<220> FEATURE:
<221> NAME/KEY: misc_feature
<223> OTHER INFORMATION: D4R antisense

<400> SEQUENCE: 53
cttgcggccg cttaataaat aaacccttga gccc                         34

<210> SEQ ID NO 54
<211> LENGTH: 34
<212> TYPE: DNA
<213> ORGANISM: Artificial Sequence
<220> FEATURE:
<221> NAME/KEY: misc_feature
<223> OTHER INFORMATION: D4R Flank sense

<400> SEQUENCE: 54
attgagctct taatactttt gtcgggtaac agag                         34

<210> SEQ ID NO 55
<211> LENGTH: 29
<212> TYPE: DNA
<213> ORGANISM: Artificial Sequence
<220> FEATURE:
<221> NAME/KEY: misc_feature
<223> OTHER INFORMATION: D4R Flank antisense

<400> SEQUENCE: 55
ttactcgaga gtgtcgcaat ttggattttt                              29

<210> SEQ ID NO 56
```

```
<211> LENGTH: 29
<212> TYPE: DNA
<213> ORGANISM: Artificial Sequence
<220> FEATURE:
<221> NAME/KEY: misc_feature
<223> OTHER INFORMATION: 7.5Gus sense

<400> SEQUENCE: 56
aaagaattcc tttattgtca tcggccaaa                              29

<210> SEQ ID NO 57
<211> LENGTH: 30
<212> TYPE: DNA
<213> ORGANISM: Artificial Sequence
<220> FEATURE:
<221> NAME/KEY: misc_feature
<223> OTHER INFORMATION: 7.5Gus antisense

<400> SEQUENCE: 57
aatctgcagt cattgtttgc ctccctgctg                             30

<210> SEQ ID NO 58
<211> LENGTH: 37
<212> TYPE: DNA
<213> ORGANISM: Artificial Sequence
<220> FEATURE:
<221> NAME/KEY: misc_feature
<223> OTHER INFORMATION: Modified D4R sense primer with EcoRI site

<400> SEQUENCE: 58
aaagaattca taatgaattc agtgactgta tcacacg                     37

<210> SEQ ID NO 59
<211> LENGTH: 32
<212> TYPE: DNA
<213> ORGANISM: Artificial Sequence
<220> FEATURE:
<221> NAME/KEY: misc_feature
<223> OTHER INFORMATION: Modified D4R antisense primer with BamHI site

<400> SEQUENCE: 59
cttggatcct taataaataa acccttgagc cc                          32

<210> SEQ ID NO 60
<211> LENGTH: 29
<212> TYPE: DNA
<213> ORGANISM: Artificial Sequence
<220> FEATURE:
<221> NAME/KEY: misc_feature
<223> OTHER INFORMATION: D4R left flank sense

<400> SEQUENCE: 60
aataagcttt gactccagat acatatgga                              29

<210> SEQ ID NO 61
<211> LENGTH: 25
<212> TYPE: DNA
<213> ORGANISM: Artificial Sequence
<220> FEATURE:
<221> NAME/KEY: misc_feature
<223> OTHER INFORMATION: D4R left flank antisense

<400> SEQUENCE: 61
aatctgcagc accagttcca tcttt                                  25

<210> SEQ ID NO 62
<211> LENGTH: 23
```

```
<212> TYPE: DNA
<213> ORGANISM: Artificial Sequence
<220> FEATURE:
<221> NAME/KEY: misc_feature
<223> OTHER INFORMATION: D4R right flank sense

<400> SEQUENCE: 62
aatggatcct catccagcgg cta                                    23

<210> SEQ ID NO 63
<211> LENGTH: 27
<212> TYPE: DNA
<213> ORGANISM: Artificial Sequence
<220> FEATURE:
<221> NAME/KEY: misc_feature
<223> OTHER INFORMATION: D4R right flank antisense

<400> SEQUENCE: 63
aatgagctct agtacctaca acccgaa                                27

<210> SEQ ID NO 64
<211> LENGTH: 28
<212> TYPE: DNA
<213> ORGANISM: Artificial Sequence
<220> FEATURE:
<221> NAME/KEY: misc_feature
<223> OTHER INFORMATION: EL-Gus sense

<400> SEQUENCE: 64
aaagtcgacg gccaaaaatt gaaatttt                               28

<210> SEQ ID NO 65
<211> LENGTH: 25
<212> TYPE: DNA
<213> ORGANISM: Artificial Sequence
<220> FEATURE:
<221> NAME/KEY: misc_feature
<223> OTHER INFORMATION: EL-Gus antisense

<400> SEQUENCE: 65
aatggatcct cattgtttgc ctccc                                  25
```

METHODS OF DIRECTLY SELECTING CELLS EXPRESSING INSERTS OF INTEREST

CROSS-REFERENCE TO RELATED APPLICATIONS

The present application claims the benefit of U.S. Provisional Appl. No. 60/192,586, filed Mar. 28, 2000; U.S. Provisional Appl. No. 60/203,343, filed May 10, 2000; U.S. Provisional Appl. No. 60/263,226, filed Jan. 23, 2001; and U.S. Provisional Appl. No. 60/271,426, filed Feb. 27, 2001; each disclosure of which is herein incorporated by reference in its entirety.

BACKGROUND OF THE INVENTION

1. Field of the Invention

The present invention relates to a high efficiency method of introducing DNA into poxvirus, a method of producing libraries in poxvirus, and methods of isolating polynucleotides of interest based on cell nonviability or screening methods.

2. Background Art

Identification of Disease Genes. In the past decade it has become apparent that many diseases result from genetic alterations in signaling pathways. These include diseases related to unregulated cell proliferation such as cancers, atherosclerosis and psoriasis, as well as inflammatory conditions such as sepsis, rheumatoid arthritis and tissue rejection. The finding that these proliferative diseases are based on genetic defects is the basis of new approaches for disease management by designing drugs which modulate cell signaling. In order to develop highly specific drugs, i.e., drugs which potently interfere with uncontrolled cell proliferation but which have low toxicity or side effects, it is important to identify the genes encoding polypeptides involved in the cellular signal transduction pathways whose aberrant function may result in the loss of growth control.

Although tremendous progress in understanding relevant signal transduction pathways has been made in recent years, it is clear that many of the genes involved in the development of proliferative disorders remain to be discovered.

Toxic Sequences. Several approaches have been employed for the identification and isolation of cell proliferation genes such as oncogenes and tumor suppressor genes. Traditional approaches include detection of cytogenetic abnormalities in tumor cells, kindred analysis of familial forms of cancer, and loss of heterozygosity analysis in tumor cells. Each of these classical genetic approaches is limited in the type of gene which can be isolated or in the extensive time and labor required. A faster approach would be to identify disease genes using in vitro techniques. However, a major technical limitation to the cloning of many disease genes is their negative or toxic effect on cell proliferation when present in multiple copies, such as when carried on a vector.

One approach for identifying toxic sequences involves the selection of variants that have lost certain malignancy traits, namely "revertants." In this method, cells transformed by a variety of oncogenes are subsequently treated with a cytotoxic agent which kills dividing cells. "Revertants" that have lost the ability to rapidly divide are thus selected. However, revertant lines typically are difficult to identify and separate from the majority of rapidly growing transformed parental cells. In addition, the method may preclude the isolation of certain classes of revertants. The selection procedure may itself induce epigenetic or cytogenetic changes, thus further complicating the identification of genes responsible for the revertant phenotype.

Zarbl et al. developed an alternative assay for the selection of revertant tumor cells (Zarbl et al., 1991, Environmental Health Perspectives 93:83–89). This selection protocol is based on the prolonged retention of a fluorescent molecule within the mitochondria of a number of transformed cells relative to non-transformed cells. However, the approach is limited to particular transformation mechanisms because the prolonged dye retention phenotype is neither essential nor sufficient for cell transformation.

Other methods used to identify cell proliferation genes involve biochemical approaches for analyzing cell cycle regulators (Serrano et al., 1993, Nature 366:704–707; Xiong et al., 1993, Nature 366:701–704), random sequencing of expressed sequence tags (ESTs) and homology comparison (Lennon et al., 1996, Genomics 33:151–152), and methods for identifying differentially expressed genes, such as differential display (Liang et al., 1995, Methods Enzymol. 254:304–321). None of these approaches, however, offers a way to directly assess gene function as a method of identifying genes of interest, especially negative regulators of proliferation. Instead, candidates are identified based on a presumed (or identifiable) biochemical function or an abnormal pattern of expression. These candidates are then tested further for involvement in cancer. Such tests include mutation detection in primary cancers or cell lines, experiments using somatic cells (for example, to determine the effect of ectopic expression), or experiments in transgenic mice or knockout mice containing inactivated genes.

A more recent method for identifying cell proliferation genes involves the isolation of variants of transformed cells to identify a cell proliferation promoting activity. See U.S. Pat. No. 5,998,136. This selection system comprises the creation of growth arrested tumor cell lines or cells which undergo apoptosis by, for example, the expression of a gene encoding a growth suppressor or apoptosis-inducing gene product under the control of an inducible promoter, and selection of revertants that allow the cells to survive. Induction of the suppressor or apoptosis-inducing product causes suppression of tumor cell growth and/or cell death. Growth-proficient revertants cells are identified by virtue of their continued proliferation.

The identification of toxic molecules such as tumor suppressor genes and other inhibitors of cell proliferation to screen for potential new drugs is difficult using current technology. For example, it would be of great value to identify dominant negative mutations of signaling molecules that might be used to inhibit the unregulated growth of transformed cells. Those negative or toxic mutations that result in inhibition of cell growth or in cell death may be masked in a library or other population of cells due to the low efficiency of transfection. Additionally, such negative or toxic mutations cannot be selected for or screened using current technology because cells expressing such variants are lost from the population of transformants. These limitations may have been addressed to a limited extent by the use of inducible promoter systems, see, for example, those described in Levinson, A. D., "Gene Expression Technology," In D. V. Goeddel (Ed.), *Methods in Enzymology*, Academic Press, p. 497 (1991). However, this approach is labor-intensive, is not applicable to certain situations, and has met with varied success depending on the cell type and origin of the promoter utilized.

As alluded to above, there are methods to identify positive regulators of cell growth such as oncogenes, but approaches to isolate toxic genes such as tumor suppressor genes are limited. In addition to those described above, methods for isolating negative regulators include genetic analysis based on anti-sense RNA technologies.

Another approach is a method of selection subtraction by tagging a clone in an expression library, cloning the tagged clone into a vector, delivering the tagged clone to a target cell, and comparing tags before and after selection whereby toxic genes and the attached tags disappear. See WO 99/47643.

Yet another approach selects all transformants in a population of cells before those transformants expressing negative or toxic variants are lost from the population. See WO 97/08186. This method comprises use of a cloning vector encoding a recombinant immunoglobulin molecule (rAb) that is specific for a particular hapten and expressed on the cell surface. Cells receiving the vector express the rAb early after transfection, and are separated from the non-recipient cells by the ability to bind the cognate hapten conjugated to a solid surface, such as beads. This method does not distinguish recipients expressing a gene or cDNA of interest, e.g., a negative or toxic variant, from the remaining recipients.

Differentially Expressed Sequences. Cloning, sequencing, and identification of function of mammalian genes is a first priority in a genomic based drug discovery. In particular, it is important to identify and make use of genes which are spatially and/or temporally regulated in an organism, for example, genes involved in differentiation and growth regulation.

Animal model systems such as the fruit fly and the worm are often used in gene identification because of ease of manipulation of the genome and ability to screen for mutants. While these systems have their limitations, large numbers of developmental mutations have been identified in those organisms either by monitoring the phenotypic effects of mutations or by screening for expression of reporter genes incorporated into developmentally regulated genes.

Many features of the mouse make it the best animal model system to study gene function. However, the mouse has not been used for large scale classical genetic mutational analysis because random mutational screening and analysis is very cumbersome and expensive due to long generation times and maintenance costs.

A disadvantage in using animal models for the identification of genes is the need to establish a transgenic animal line for each mutational event. This disadvantage is alleviated in part by using embryonic stem (ES) cell lines because mutational events may be screened in vitro prior to generating an animal. ES cells are totipotent cells isolated from the inner cell mass of the blastocyst. Methods are well known for obtaining ES cells, incorporating genetic material into ES cells, and promotion of differentiation of ES cells. ES cells may be caused to differentiate in vitro or the cells may be incorporated into a developing blastocyst in which the ES cells will contribute to all differentiated tissues of the resulting animal. Vectors for transforming ES cells and suitable genes for use as reporters and selectors are also well known.

Gene entrapment strategies also have been employed to identify developmentally regulated genes. One type of entrapment vector is called a "promoter trap," which consists of a reporter gene sequence lacking a promoter. Its integration is detected when the reporter is integrated "in-frame" into an exon. In contrast, a "gene trap" vector targets the more prevalent introns of the eucaryotic genome. The latter vector consists of a splice-acceptor site upstream from a reporter gene. Integration of the reporter into an intron results in a fusion transcript containing RNA from the endogenous gene and from the reporter gene sequence.

Gene trap vectors may be made more efficient by incorporation of an internal ribosomal entry site (IRES) such as that derived from the 5' non-translated region of encephalomyocarditis virus (EMCV). Placement of a IRES site between the splice acceptor and the reporter gene of a gene trap vector means the reporter gene product need not be translated as a fusion product with the endogenous gene product, thereby increasing the likelihood that integration of the vector will result in expression of the reporter gene product.

Gossler, A., et al. *Science* 244:463–465 (1989) describe the use of enhancer trap gene trap vectors for use in identifying developmentally regulated genes. The gene trap vector consists of the mouse En-2 splice acceptor upstream from lacZ (reporter) and a selector gene (hBa-neo). This and other current methods requires elaborate screening procedures for linking a mutation to a particular spacial/temporal scheme or event whereby the mutation is detected in the relevant tissue.

A more recently developed method is complementation trapping. See WO 99/02719. This method makes use of known genes whose expression is restricted to specific tissue, tissues or specialized cells ("restricted expression") to facilitate identification and manipulation of new genes and their associated transcription control elements which have similar patterns of expression. The method comprises (i) transforming a eucaryotic cell with a DNA sequence encoding a first indicator component under the control of a promoter having restricted expression; (ii) transforming the cell of (i) or a descendent of the cell of step (i), by operably integrating into the cell's genome DNA lacking a promoter but which comprises a sequence encoding a second indicator component; (iii) producing tissue or specialized cells from the cell of (ii); and (iv) monitoring the tissue or specialized cells of (iii) for a detectable indicator resulting from both the first and second indicator components.

Expression Libraries. A basic tool in the field of recombinant genetics is the conversion of poly(A)$^+$ mRNA to double-stranded (ds) cDNA, which then can be inserted into a cloning vector and expressed in an appropriate host cell. A substantial number of variables affect the successful cloning of a gene of interest and cDNA cloning strategy thus must be chosen with care. A method common to many cDNA cloning strategies involves the construction of a "cDNA library" which is a collection of cDNA clones derived from the poly(A)$^+$ mRNA derived from a cell of the organism of interest.

A mammalian cell may contain up to 30,000 different mRNA sequences, and the number of clones required to obtain low-abundance mRNAs, for example, may be much greater. Methods of constructing genomic eukaryotic DNA libraries in different expression vectors, including bacteriophage lambda, cosmids, and viral vectors, are known. Some commonly used methods are described, for example, in Maniatis et al., Molecular Cloning: A Laboratory Manual, Cold Spring Harbor Laboratory, publisher, Cold Spring Harbor, N.Y. (1982).

Once a genomic cDNA library has been constructed and expressed in host cells, it is necessary to isolate from the thousands of host cells the particular cell or cells which contain the particular gene of interest. Many different methods of isolating target genes from cDNA libraries have been utilized, with varying success. These include, for example, the use of nucleic acid probes, which are labeled mRNA fragments having nucleic acid sequences complementary to the DNA sequence of the target gene. When this method is applied to cDNA clones of abundant mRNAs in transformed bacterial hosts, colonies hybridizing strongly to the probe are likely to contain the target DNA sequences. The identity of the clone then may be proven, for example, by in situ hybridization/selection (Goldberg et al., Methods Enzymol., 68:206 (1979)) hybrid-arrested translation (Paterson et al., Proceedings of the National Academy of Sciences, 74:4370 (1977)), or direct DNA sequencing (Maxam and Gilbert, Proceedings of the National Academy of Sciences, 74:560 (1977); Maat and Smith, Nucleic Acids Res., 5:4537 (1978)).

Such methods, however, have major drawbacks when the object is to clone mRNAs of relatively low abundance from cDNA libraries. For example, using direct in situ colony hybridization, it is very difficult to detect clones containing cDNA complementary to mRNA species present in the initial library population at less than one part in 200. As a result, various methods for enriching mRNA in the total population (e.g. size fractionation, use of synthetic oligodeoxynucleotides, differential hybridization, or immunopurification) have been developed and are often used when low abundance mRNAs are cloned. Such methods are described, for example, in Maniatis et al., Molecular Cloning: A Laboratory Manual, supra.

Use of mammalian expression libraries to isolate cDNAs encoding mammalian proteins such as those described above would offer several advantages. For example, the protein expressed in a mammalian host cell should be functional and should undergo any normal posttranslational modification. A protein ordinarily transported through the intracellular membrane system to the cell surface should undergo the complete transport process. A mammalian expression system also would allow the study of intracellular transport mechanisms and of the mechanism that insert and anchor cell surface proteins to membranes. Further, use of a mammalian system would make it possible to isolate polynucleotides based on functional expression of mammalian RNA or protein.

One common mammalian host cell, called a "COS" cell, is formed by infecting monkey kidney cells with a mutant viral vector, designated simian virus strain 40 (SV40), which has functional early and late genes, but lacks a functional origin of replication. In COS cells, any foreign DNA cloned on a vector containing the SV40 origin of replication will replicate because SV40 T antigen is present in COS cells. The foreign DNA will replicate transiently, independently of the cellular DNA.

With the exception of some recent lymphokine cDNAs isolated by expression in COS cells (Wong, G. G., et al., Science 228:810–815 (1985); Lee, F. et al., Proc. Natl. Acad. Sci. USA 83.2061–2065 (1986); Yokota, T., et al., Proc. Natl. Acad. Sci. USA 83:5894–5898 (1986); Yang, Y., et al., Cell 47:3–10 (1986)), however, few cDNAs in general are isolated from mammalian expression libraries. There appear to be two principal reasons for this: First, the existing technology (Okayama, H. et al., Mol. Cell. Biol. 2:161–170 (1982)) for construction of large plasmid libraries is difficult to master, and library size rarely approaches that accessible by phage cloning techniques. (Huynh, T. et al., In: DNA Cloning Vol. I, A Practical Approach, Glover, D. M. (ed.), IRL Press, Oxford (1985), pp. 49–78). Second, the existing vectors are, with one exception (Wong, G. G., et al., Science 228:810–815 (1985)), poorly adapted for high level expression, particularly in COS cells. The reported successes with lymphokine cDNAs do not imply a general fitness of the methods used, since these cDNAs are particularly easy to isolate from expression libraries: Lymphokine bioassays are very sensitive ((Wong, G. G., et al., Science 228:810–815 (1985); Lee, F. et al., Proc. Natl. Acad. Sci. USA 83:2061–2065 (1986); Yokota, T. et al., Proc. Natl. Acad. Sci. USA 83:5894–5898 (1986); Yang, Y. et al., Cell 47:3–10 (1986)) and the mRNAs are typically both abundant and short (Wong, G. G. et al., Science 228:810–815 (1985); Lee, F., et al., Proc. Natl. Acad. Sci. USA 83:2061–2065 (1986); Yokota, T., et al., Proc. Natl. Acad. Sci. USA 83:5894–5898 (1986); Yang, Y., et al., Cell 47:3–10 (1986)).

Thus, expression in mammalian hosts previously has been most frequently employed solely as a means of verifying the identity of the protein encoded by a gene isolated by more traditional cloning methods. For example, Stuve et al., J. Virol. 61(2):327–335 (1987), cloned the gene for glycoprotein gB2 of herpes simplex type II strain 333 by plaque hybridization of M13-based recombinant phage vectors used to transform competent E. coli JM101. The identity of the protein encoded by the clone thus isolated was verified by transfection of mammalian COS and Chinese hamster ovary (CHO) cells. Expression was demonstrated by immunofluorescence and radioimmunoprecipitation.

Oshima et al. used plaque hybridization to screen a phage lambda gt11 cDNA library for the gene encoding human placental beta-glucuronidase. Oshima et al., Proceedings of the National Academy of Sciences, U.S.A. 84:685–689 (1987). The identity of isolated cDNA clones was verified by immunoprecipitation of the protein expressed by COS-7 cells transfected with cloned inserts using the SV40 late promoter.

Transient expression in mammalian cells has been employed as a means of confirming the identity of genes previously isolated by other screening methods. Gerald et al., Journal of General Virology 67:2695–2703(1986). Mackenzie, Journal of Biological Chemistry 261:14112–14117 (1986); Seif et al., Gene 43:1111–1121 (1986); Orkin et al., Molecular and Cellular Biology 5(4): 762–767 (1985). These methods often are inefficient and tedious and require multiple rounds of screening to identify full-length or overlapping clones. Prior screening methods based upon expression of fusion proteins are inefficient and require large quantities of monoclonal antibodies. Such drawbacks are compounded by use of inefficient expression vectors, which result in protein expression levels that are inadequate to enable efficient selection.

Seed et al., U.S. Pat. No. 5,506,126 developed a cloning technique based upon transient expression of antigen in eukaryotic cells and physical selection of cells expressing the antigen by adhesion to an antibody-coated substrate, such as a culture dish. This method for cloning cDNA encoding a cell surface antigen comprises preparing a cDNA library; introducing this cDNA library into eukaryotic mammalian cells; culturing the cells under conditions allowing expression of the cell surface antigen; exposing the cells to a first antibody or antibodies directed against the cell surface antigen, thereby allowing the formation of a cell surface antigen-first antibody complex; subsequently exposing the cells to a substrate coated with a second antibody directed against the first antibody, thereby causing cells expressing the cell surface antigen to adhere to the substrate via the formation of a cell surface antigen-first antibody-second antibody complex; and separating adherent from non-adherent cells. However, this method is limited to the isolation and cloning of proteins which are expressed and transported to the cell surface, whose expression does not adversely affect cell viability, and for which specific antibody has been isolated.

Poxvirus Vectors. Poxvirus vectors are used extensively as expression vehicles for protein and antigen expression in eukaryotic cells. The ease of cloning and propagating vaccinia in a variety of host cells has led to the widespread use of poxvirus vectors for expression of foreign protein and as vaccine delivery vehicles (Moss, B. 1991, Science 252: 1662–7).

Customarily, a foreign protein coding sequence is introduced into the poxvirus genome by homologous recombination. In this method, a previously isolated foreign DNA is cloned in a transfer plasmid behind a vaccinia promoter flanked by sequences homologous to a region in vaccinia which is non-essential for viral replication. The transfer plasmid is introduced into vaccinia virus-infected cells to allow the transfer plasmid and vaccinia virus genome to recombine in vivo via homologous recombination. As a result of the homologous recombination, the foreign DNA is transferred to the viral genome.

Although homologous recombination is efficient for transferring previously isolated foreign DNA of relatively small size into vaccinia virus, the method is much less efficient for transferring large inserts, for constructing libraries, and for transferring foreign DNA which is deleterious to bacteria.

Alternative methods using direct ligation vectors have been developed to efficiently construct chimeric genomes in situations not readily amenable for homologous recombination (Merchlinsky, M. et al., 1992, Virology 190:522–526; Scheiflinger, F. et al., 1992, Proc. Natl. Acad. Sci. USA. 89:9977–9981). In such protocols, the DNA from the genome is digested, ligated to insert DNA in vitro, and transfected into cells infected with a helper virus (Merchlinsky, M. et al., 1992, Virology 190:522–526, Scheiflinger, F. et al., 1992, Proc. Natl. Acad. Sci. USA 89:9977–9981). In one protocol, the genome was digested at a unique NotI site and a DNA insert containing elements for selection or detection of the chimeric genome was ligated to the genomic arms (Scheiflinger, F. et al., 1992, Proc. Natl. Acad. Sci. USA. 89:9977–9981). This direct ligation method was described for the insertion of foreign DNA into the vaccinia virus genome (Pfleiderer et al., 1995, J. General Virology 76:2957–2962). Alternatively, the vaccinia WR genome was modified by removing the NotI site in the HindIII F fragment and reintroducing a NotI site proximal to the thymidine kinase gene such that insertion of a sequence at this locus disrupts the thymidine kinase gene, allowing isolation of chimeric genomes via use of drug selection (Merchlinsky, M. et al., 1992, Virology 190:522–526).

The direct ligation vector vNotI/tk allows one to efficiently clone and propagate previously isolated DNA inserts at least 26 kilobase pairs in length (Merchlinsky, M. et al., 1992, Virology, 190:522–526). Although large DNA fragments are efficiently cloned into the genome, proteins encoded by the DNA insert will only be expressed at the low level corresponding to the thymidine kinase gene, a relatively weakly expressed early class gene in vaccinia. In addition, the DNA will be inserted in both orientations at the NotI site.

The cloning methods and the selection methods above have a number of drawbacks and limitations. Therefore it is desirable, and the objective of the present invention, to develop cloning and selection methods that would permit the identification and isolation of novel genes based on functional analysis.

BRIEF SUMMARY OF THE INVENTION

In accordance with one aspect of the present invention, there is provided a method of high efficiency cloning using a linear DNA virus vector such as vaccinia virus vector, comprising tri-molecular recombination.

In accordance with another aspect of the present invention, there is provided a method of producing a library using a linear DNA virus vector such as vaccinia virus vector.

In accordance with yet another aspect of the present invention, there is provided a method of cloning a polynucleotide which negatively affects cell viability.

In accordance with yet another aspect of the present invention, there is provided a method of cloning a polynucleotide in a nondividing cell.

In accordance with yet another aspect of the present invention, there is provided a method of directly or indirectly selecting a polynucleotide which negatively affects cell viability from a plurality of polynucleotides.

In accordance with yet another aspect of the present invention, there is provided a method of directly or indirectly selecting a polynucleotide which encodes an epitope from a plurality of polynucleotides.

In accordance with another aspect of the present invention, there is provided a method of directly or indirectly selecting a polynucleotide which alters a phenotype of a cell.

In accordance with yet another aspect of the present invention, there is provided a method of modifying a linear DNA virus vector such as vaccinia virus.

In accordance with a further aspect of the present invention, there is provided a kit for producing a library using tri-molecular recombination. In one embodiment, the invention provides a kit for producing an antisense expression library comprising a linear DNA viral genome such as vaccinia virus or two fragments thereof, and two vectors for producing a transfer plasmid containing a polynucleotide insert in each of two orientations. In another embodiment, the invention provides a kit for producing a protein expression library comprising a linear DNA genome such as vaccinia virus or two fragments thereof, and three vectors for producing a transfer plasmid containing a polynucleotide insert in each of three translation reading frames.

BRIEF DESCRIPTION OF THE DRAWINGS/FIGURES

FIG. 1. Nucleotide Sequence of p7.5/tk (SEQ ID NO:1) and pEL/tk (SEQ ID NO:3). The nucleotide sequence of the promoter and beginning of the thymidine kinase gene for v7.5/tk and vEL/tk. The partial thymidine kinase amino acid sequence is also shown (SEQ ID NO:2).

Figure 2:
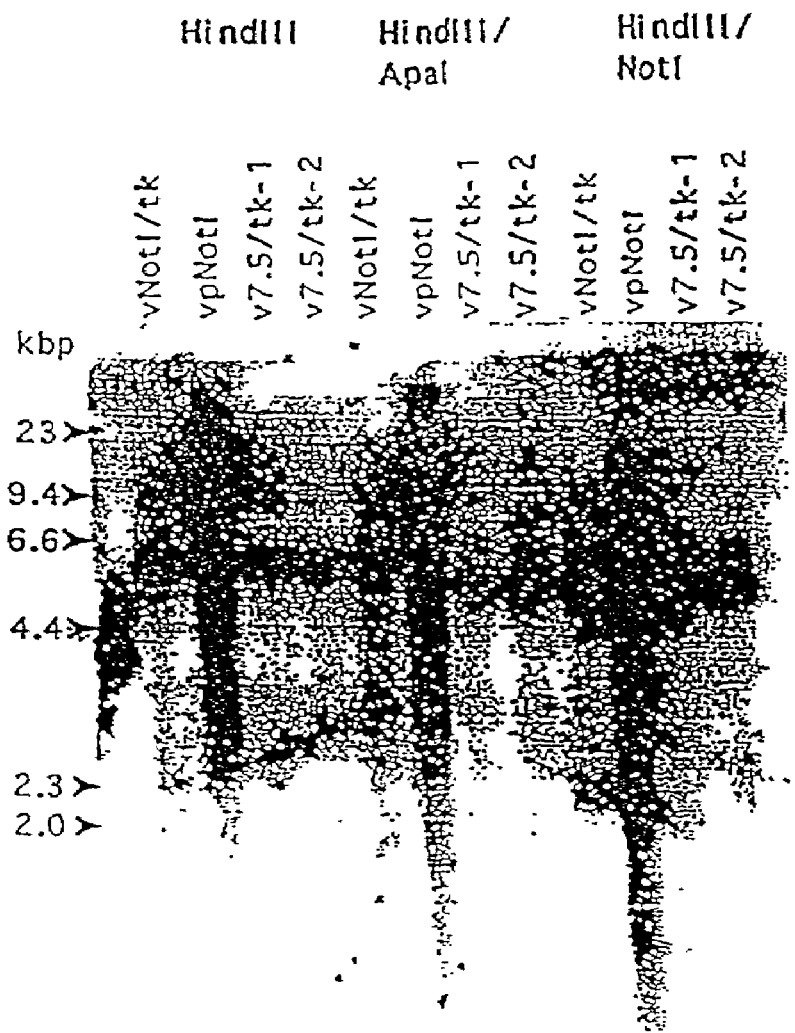
Figure 2:
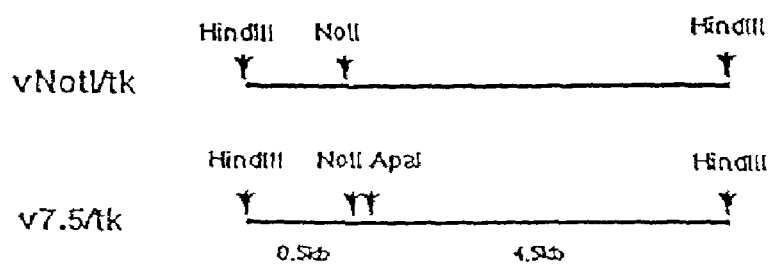

FIG. 2. Southern Blot Analysis of Viral Genomes p7.5/tk and pEL/tk. The viruses v7.5/tk and vEL/tk were used to infect a well of a 6 well dish of BSC-1 cells at high multiplicity of infection (moi) and after 48 hours the cells were harvested and the DNA was isolated using DNAzol (Gibco). The final DNA product was resuspended in 50 microliters of TE 8.0 and 2.5 microliters were digested with HindIII, HindIII and ApaI, or HindIII and NotI, electrophoresed through a 1.0% agarose gel, and transferred to Nytran (Schleicher and Schuell) using a Turboblotter (Schleicher and Schuell). The samples were probed with p7.5/tk (A) or pEL/tk (B) labeled with $^{32}P$ using Random Primer DNA Labeling Kit (Bio-Rad) in QuickHyb (Stratagene). The lower portion of the figure denotes a map of the HindIII J fragment with the positions of the HindIII, NotI, and ApaI sites illustrated. The leftmost 0.5 kilobase fragment has electrophoresed off the bottom of the gel.

FIG. 3. Restriction Enzyme Analysis of Virus Genomes Using CHEF Gel. BSC-1 cells were infected at high multiplicity of infection (moi) by vaccinia WR, vEL/tk, v7.5/tk, or vNotI/tk. After 24 hours the cells were harvested and formed into agarose plugs. The plugs were equilibrated in the appropriate restriction enzyme buffer and 1 mM PMSF for 16 hours at room temperature, incubated with restriction enzyme buffer, 100 ng/ml Bovine Serum Albumin and 50 units NotI or ApaI for two hours at 37° C. (NotI) or room temperature (ApaI) and electrophoresed in a 1.0% agarose gel on a Bio-Rad CHEFII apparatus for 15 hours at 6 V/cm with a switching time of 15 seconds. The leftmost sample contains lambda DNA, the second sample contains undigested vaccinia DNA, and the remainder of the samples contain the DNA samples described above each well digested with ApaI or NotI where vEL refers to vEL/tk and v7.5 refers to v7.5/tk. The lower portion of the figure is a schematic map showing the location of the NotI and ApaI sites in each virus.

FIG. 4. Analysis of v7.5/tk and vEL/tk by PCR. One well of a 6 well dish of BSC-1 cells was infected with v7.5/tk, vEL/tk, vNotI/tk, vpNotI, vNotI/lacZ/tk, or wild type vaccinia WR at high multiplicity of infection (moi) and after 48 hours the cells were harvested, and the DNA was isolated using DNAzol (Gibco). The final DNA product was resuspended in 50 microliters of TE (10 mM TrisHCl, pH8.0. 1 mM EDTA) and used in a PCR with primers MM407 and MM408. The primers are separated by 518 nucleotides in vaccinia WR and yield a fragment containing the N terminus of the thymidine kinase gene. The products were electrophoresed through a 2% agarose gel. The leftmost sample contains phiX 174 HaeIII digestion products; all others contain the PCR product using primers MM407 and MM408 with the DNA sample indicated above the well.

FIG. 5. Promoter strength of recombinant viruses. The units of β-glu activity were determined as described by Miller (10) as adapted for 96-well plates.

The $A_{405}$ values were determined on a microplate reader (Dynatech MR3000) and the β-glu activity was determined by comparison to β-glu (Clontech) standards analyzed in the same assay.

Figure 6:
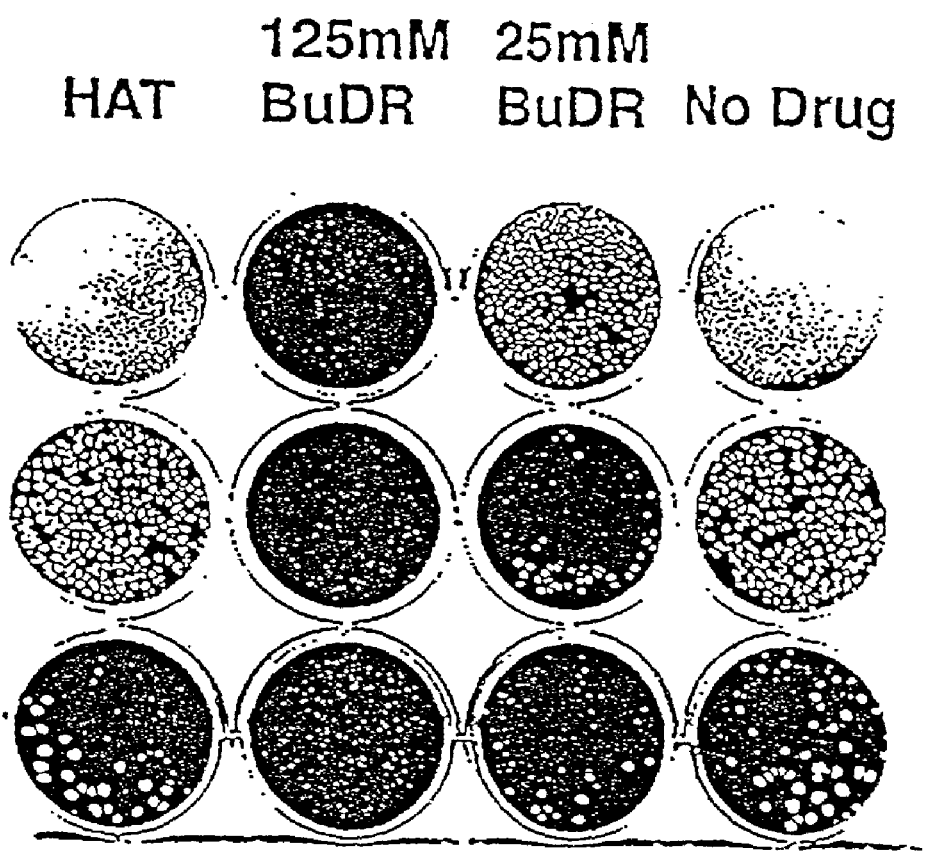

FIG. 6. Plaque assay on vEL/tk. Ten-fold dilutions of vEL/tk were incubated with Hutk⁻ cells (top to bottom) for one hour at 37° C. in 1 ml of E-MEM (Gibco) with 10% Fetal Bovine Serum for one hour, the media was replaced with 3 ml of E-MEM with 5% methyl cellulose (Sigma M-0387), 5% Fetal Bovine Serum and HAT supplement (Gibco), 25 or 125 mM bromodeoxyuridine, or no drug, incubated for 48 hours at 37° C., and stained with 0.5% Crystal Violet (Sigma C 0775), 20% ethanol, 7.5% formaldehyde.

Figure 7:
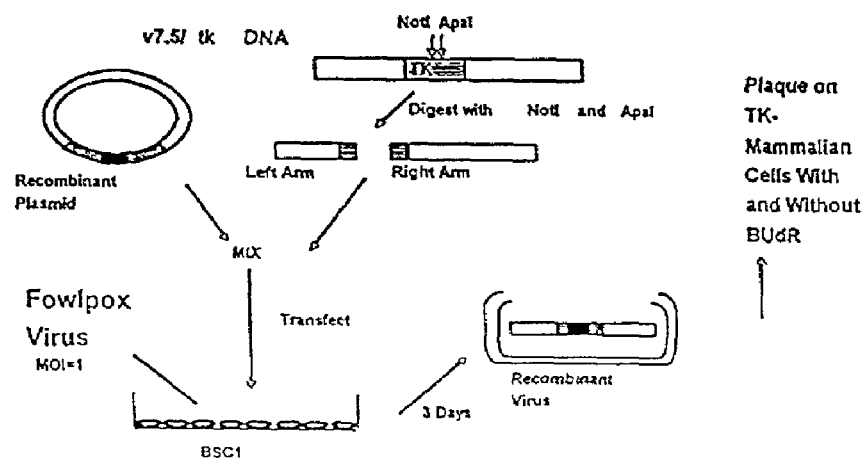

FIG. 7. Schematic of the Tri-Molecular Recombination Method.

FIG. 8. Modifications in the nucleotide sequence of the p7.5/tk vaccinia transfer plasmid. Four new vectors, p7.5/ATG0/tk (SEQ ID NO:4), p7.5/ATG1/tk (SEQ ID NO:5), p7.5/ATG2/tk (SEQ ID NO:6), and p7.5/ATG3/tk (SEQ ID NO:7) have been derived as described in the text from the p7.5/tk vaccinia transfer plasmid. Each vector includes unique BamHI, SmaI, PstI, and SalI sites for cloning DNA inserts that employ either their own endogenous translation initiation site (in vector p7.5/ATG0 /tk) or make use of a vector translation initiation site in any one of the three possible reading frames (p7.5/ATG1/tk, p7.5/ATG3/tk, and p7.5/ATG4/tk).

Figure 9:
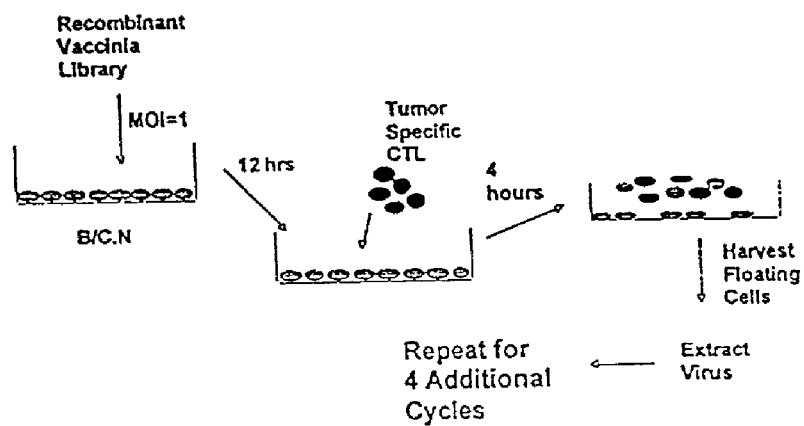

FIG. 9. Schematic of a direct selection method using CTL.

Figure 10:
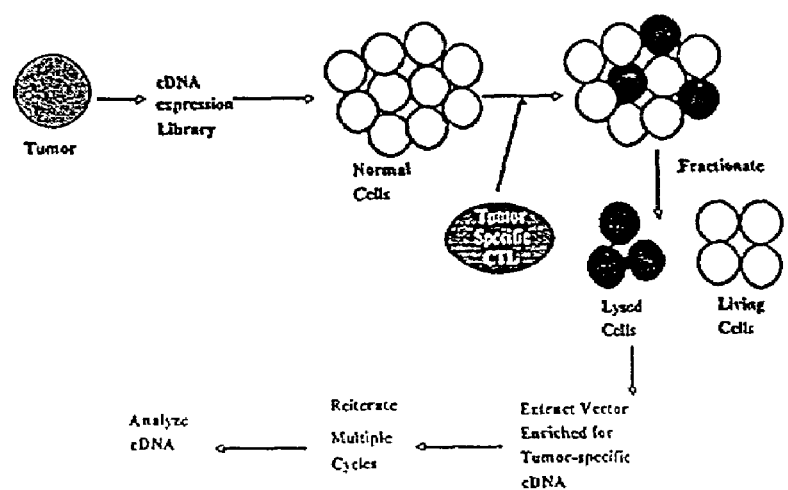

FIG. 10. Schematic of the strategy to identify shared tumor antigen.

FIG. 11. CML selected recombinant vaccinia cDNA clones stimulate tumor specific CTL. (A) CML Selected vaccinia clones were assayed for the ability, following infection of B/C.N, to stimulate tumor specific CTL to secrete interferon gamma (IFNγ). The amount of cytokine was measured by ELISA, and is represented as OD490 (14). An OD490 of 1.4 is approximately equal to 4 ng/ml of IFNγ, and an OD490 of 0.65 is approximately equal to 1 ng/ml of IFNγ. (B) CML selected clones sensitize host cells to lysis by tumor specific CTL. Monolayers of B/C.N in wells of a 6 well plate were infected with moi=1 of the indicated vaccinia virus clones. After 14 hours of infection the infected cells were harvested and along with the indicated control targets labeled with $^{51}$Cr. Target cells were incubated with the indicated ratios of tumor specific Cytotoxic T Lymphocytes for 4 hours at 37° C. and percentage specific lysis was determined (15). This experiment was repeated at least three times with similar results.

FIG. 12. The tumor antigen is encoded by a ribosomal protein L3 gene. Sequence of H2.16 and rpL3 from amino acid position 45 to 56. (A) The amino acid (in single letter code) (SEQ ID NO:8) and nucleotide sequence (SEQ ID NO:9) of cDNA clone rpL3 (GenBank Accession no. Y00225). (B) A single nucleotide substitution at C170T of the H2.16 tumor cDNA (SEQ ID NO:10) is the only sequence change relative to the published L3 ribosomal allele. This substitution results in a T54I amino acid substitution in the protein (SEQ ID NO:11).

FIG. 13. Identification of the peptide epitope recognized by the tumor specific CTL. (A) CML assay to identify the peptide recognized by tumor specific CTL. Target cells were labeled with $^{51}$Cr (15). During the $^{51}$Cr incubation samples of B/C.N cells were incubated with 1 µM peptide $L3_{48-56}$ (I54), 100 µM $L3_{48-56}$(T54) or 100 µM peptide $L3_{45-54}$(I54). Target cells were incubated with the indicated ratios of tumor specific Cytotoxic T Lymphocytes for 4 hours at 37° C. and percentage specific lysis was determined. This experiment was repeated at least three times with similar results. (B) Titration of peptide $L3_{48-56}$ (I54). Target cells were labeled with $^{51}$Cr. During the $^{51}$Cr incubation samples of B/C.N cells were incubated either with no peptide addition (D) or with the indicated concentrations (1 µM, 10 nM, 1 nM) of $L3_{48-56}$(I54) (■), BCA 39 cells were included as a positive control (▲). Target cells were incubated with the indicated ratios of Tumor Specific Cytotoxic T Lymphocytes for 4 hours at 37° C. and percentage specific lysis was determined. The experiment was repeated twice with similar results.

FIG. 14. Analysis of L3 expressed by each cell line. (A) Sau3AI map of published rpL3 and H2.16. Shown above is the Sau3AI restriction map for the published ribosomal protein L3 gene (Top), and for H2.16 (Bottom). Digestion of cDNA for the published L3 sequence generates fragments of 200, 355, 348, 289, and 84 bp. The pattern for H2.16 is identical except for an extra Sau3AI site at position 168 caused by the C170T. This results in a 168 bp digestion product in place of the 200 bp fragment. (B) The BCA tumors express both L3 alleles. RT-PCR products generated from each cell line or from vH2.16 were generated using L3 specific primers and then digested with Sau3AI, and resolved on a 3% agarose gel for 2 hours at 80 volts. (C) The Immunogenic L3 allele is expressed at greatly reduced levels in B/C.N, BCB13, and Thymus. L3 specific RT-PCR products from each indicated sample were generated using a $^{32}$P end labeled 5 prime PCR primer. No PCR product was observed when RNA for each sample was used as template for PCR without cDNA synthesis, indicating that no sample was contaminated with genomic DNA. The PCR products were gel purified to ensure purity, digested with Sau3AI, and resolved on a 3% agarose gel for 15 hours at 60 volts. No PCR product was observed in a control PCR sample that had no template added to it. This result has been reproduced a total of 3 times.

FIG. 15. Immunization with iL3 is immunoprotective. (A) Immunization with H2.16 induces tumor specific CTL. Balb/c mice (2/group) were immunized by subcutaneous injection with $5\times10^6$ pfu of vH2.16, or control vector v7.5/tk. Seven days later splenocytes were harvested and restimulated with peptide L3$_{48-56}$(I54) (26). Five days following the second restimulation the lymphocytes were tested in a chromium release assay as described in FIG. 11. The L3$_{48-56}$(I54) peptide was used at a 1 micromolar concentration, and the L3$_{48-56}$(T54) peptide was used at a 100 micromolar concentration. Similar results were obtained when the immunization experiment was repeated. (B) Female Balb/cByJ mice were immunized as indicated (27). The mice were challenged by SC injection with 200,000 viable BCA 34 tumor cells into the abdominal wall. Data are from day 35 post challenge. These data are representative of 4 independent experiments.

Figure 16:
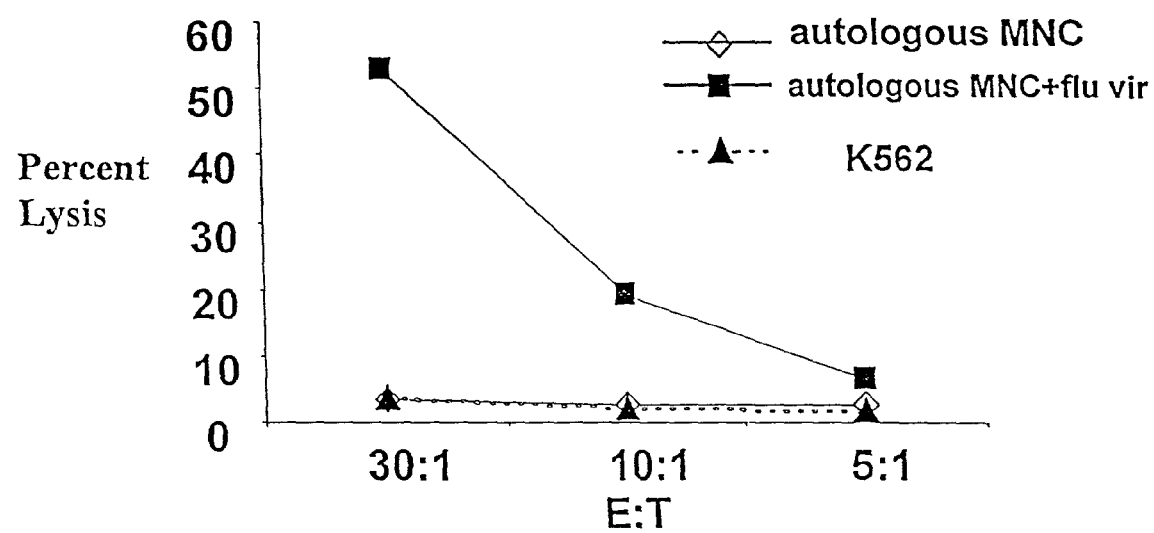

FIG. 16. Influenza-specific cytolytic activity of CD4+ CD45RA+ human T cells stimulated in the presence of IL12 and IL18. Naïve human CD4+ CD45RA+ T cells were isolated from PBL of an HLA-A2+ normal donor and stimulated in vitro with autologous dendritic cells pulsed with heat-inactivated influenza virus. The dendritic cells were derived from PBMC by culture with GM-CSF+IL-4 (1000 U/ml each) for 7 days. DC were pulsed with heat-inactivated influenza virus (1000 HAU) and transferred to monocyte conditioned medium for 3 more days to induce maturation prior to T cell stimulation. Cultures of naive T cells and antigen-pulsed dendritic cells received rhIL-2 (20 U/ml), rhIL-12 (20 U/ml, R&D Systems), rhIL-18 (10 ng/ml, R&D Systems), rhIFN-γ (1 ng/ml), and mouse anti-human IL-4 (50 mg/ml, Pharmingen). Cells were restimulated after 7 days using identical conditions with fresh autologous DC pulsed with virus. Cytotoxic activity was assayed at day 14 in a 4 hr $^{51}$Cr release assay using autologous monocytes+/−heat-inactivated virus or K562 control targets.

Figure 17:
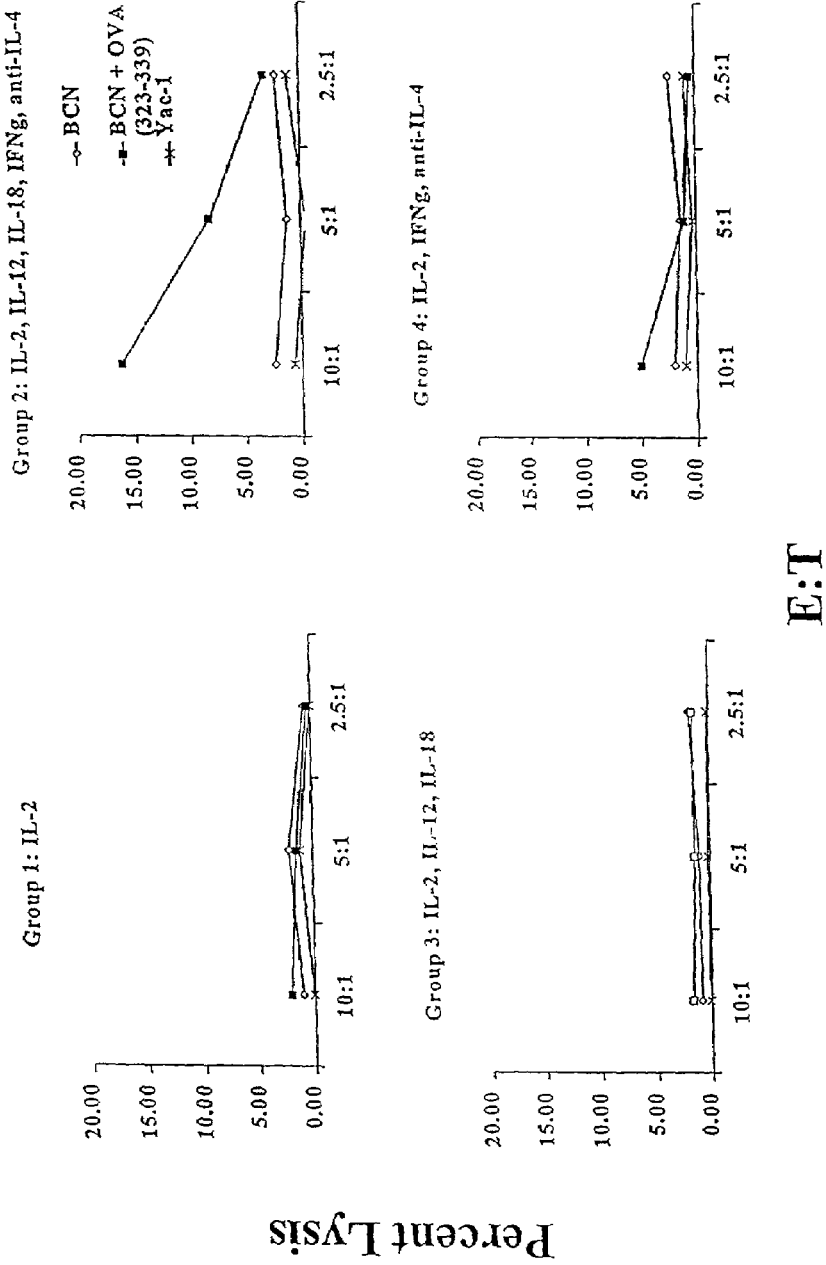

FIG. 17. CD4+ cytotoxic T cell response. Naïve CD4+ mouse T lymphocytes from heterozygous DO11.10 transgenic females were cultured for 9 days in the presence of BALB/c bone marrow-derived mature dendritic cells pulsed with OVA 323–339 (10 mM). Recombinant murine cytokines were purchased from R&D Systems and used at the same concentrations as indicated above for the human cytokines. Rat ant-mouse IL-4 (11B11, Pharmingen) was used at 50 mg/ml. B/c.N (H-2$^d$) targets were incubated 72 hours with rmIFN-γ (1000 U/ml) to induce expression of class II MHC molecules prior to a 4 hr $^{51}$Cr release assay. The four panels demonstrate that OVA (323–339) specific cytotoxic cells are efficiently induced only in the presence of all 4 cytokines and anti-IL-4 antibody. As expected for this OVA (323–339) class II MHC restricted response, all the T cells recovered were CD4 positive.

Figure 18:
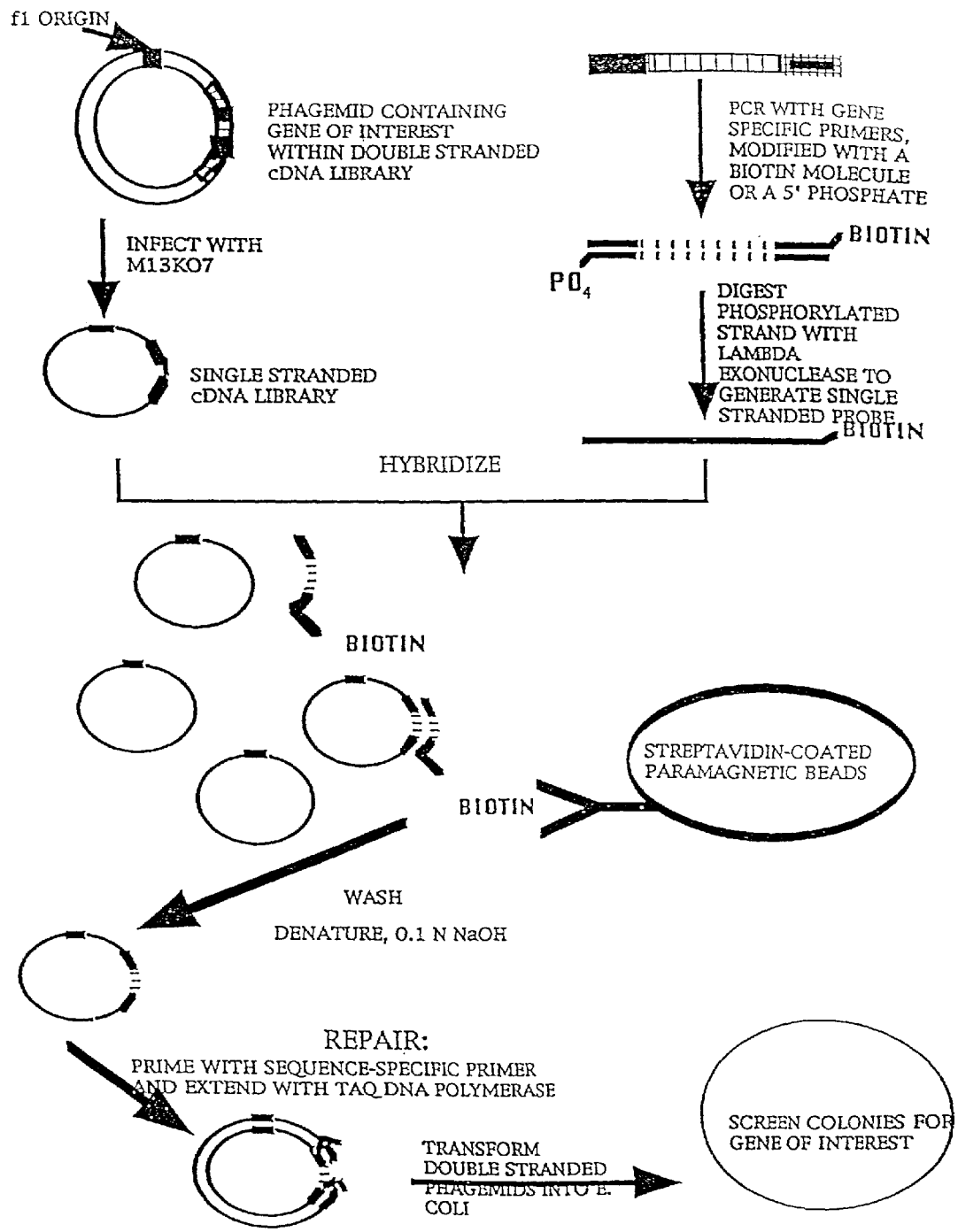

FIG. 18. Gene isolation in solution. Schematic of a method for selection of longer length cDNA from single strand circles rescued from a phagemid library. DNA fragments identified through RDA or Modified Differential Display are employed to select more full length cDNA.

Figure 19:
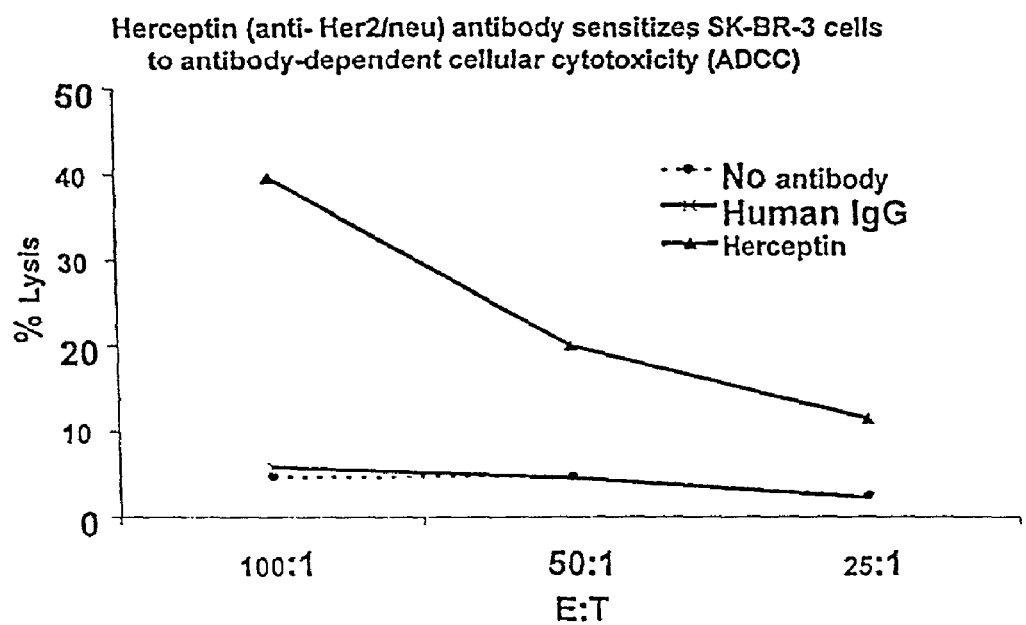

FIG. 19. An example of ADCC during a 4 hour incubation of normal PBL derived monocytes with human breast cancer SK-BR-3 cells sensitized with 1 mg/ml Herceptin (humanized anti-Her2/neu antibody) at different ADCC Effector to Target ratios.

Figure 20:
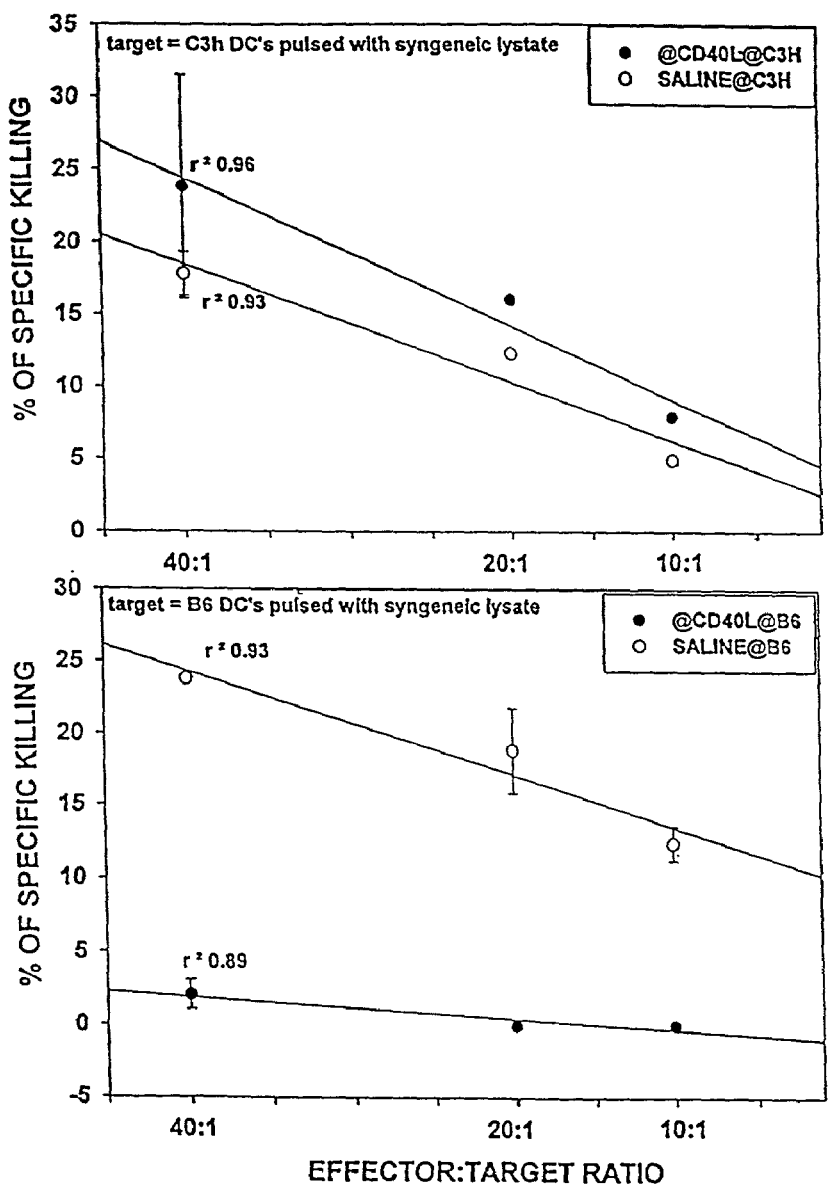

FIG. 20. Tolerance Induction. DBA/2 (H-2$^d$) mice were immunized with $10^7$ C57B1/6 (H-2$^b$) spleen cells intraperitoneally and, in addition, were injected with either saline or 0.5 mg monoclonal anti-CD40 ligand antibody (MR1B, anti-CD154) administered both at the time of immunization and two days later. On day 10 following immunization, spleen cells from these mice were removed and stimulated in vitro with either C57B1/6 or control allogeneic C3H (H-2$^k$) spleen cells that had been irradiated (20 Gy). After 5 days in vitro stimulation, C57B1/6 and C3H specific cytolytic responses were assayed at various effector:target ratios by $^{51}$Cr release assay from specific labeled targets, in this case, either C3H or C57B1/6 dendritic cells pulsed with syngeneic spleen cell lysates.

FIG. 21. Attenuation of poxvirus-mediated cytopathic effects.

DETAILED DESCRIPTION OF THE INVENTION

In one embodiment, the invention provides a method of selecting a target polynucleotide, comprising: (a) introducing into a population of host cells a library of insert polynucleotides; wherein at least one of the insert polynucleotides comprises the target polynucleotide; and wherein expression of the target polynucleotide directly or indirectly promotes host cell death; (b) culturing said host cells; and (c) collecting insert polynucleotides from those host cells which undergo cell death.

In a further embodiment, the method further comprises: (d) introducing the collected polynucleotides into a population of host cells, wherein expression of the target polynucleotide directly or indirectly promotes host cell death; (e) culturing said host cells; and (f) collecting insert polynucleotides from those host cells which undergo cell death.

In a further embodiment, the method further comprises repeating steps (d)–(f) one or more times, thereby enriching for the target polynucleotide.

In a further embodiment, the method further comprises purifying the collected polynucleotides.

In a further embodiment, the host cells are adherent to a solid support.

In a further embodiment, expression of the target polynucleotide indirectly promotes cell death upon exposure of the host cells to an agent.

In a further embodiment, the agent comprises a member selected from the group consisting of: a physical agent, a chemical agent, and a biological agent.

In a further embodiment, the physical agent is selected from the group consisting of: radiation, UV radiation, gamma radiation, infrared radiation, visible light, increased temperature, and decreased temperature.

In a further embodiment, the chemical agent is selected from the group consisting of: a chemotherapeutic agent, a cytotoxic agent, and a DNA damaging agent.

In a further embodiment, the biological agent is selected from the group consisting of an antisense construct, an infectious agent, a therapeutic agent, an antibody, a cytotoxic T-lymphocyte (CTL), a ligand, a hapten, an epitope, and a receptor.

In a further embodiment, the biological agent is conjugated to a toxin.

In another embodiment, the biological agent effects cell death by a process selected from the group consisting of: CTL-induced cytotoxicity, antibody-dependent cellular cytotoxicity and complement-dependent cytotoxicity.

In a further embodiment, the biological agent comprises a cytotoxic T lymphocyte (CTL), wherein said CTL expresses surface CD4, wherein said target polynucleotide encodes a polypeptide, and wherein said polypeptide is processed and presented in association with a class II major histocompatibility molecule (MHC).

In a further embodiment, expression of said target polynucleotide effects a cellular process selected from the group consisting of cellular differentiation, growth regulation, cellular proliferation, apoptosis, and hormonal response.

In a further embodiment, cell death is the result of apoptosis.

In a further embodiment, apoptosis is induced through expression of a apoptosis-related gene product which directly promotes apoptosis.

In a further embodiment, apoptosis is induced through expression of an apoptosis-related gene product which indirectly promotes apoptosis.

In a further embodiment, the apoptosis-related gene product comprises a death domain containing receptor expressed on the surface of said host cells, and wherein said host cells are contacted with a ligand for said death domain containing receptor.

In a further embodiment, those cells which have undergone apoptosis are released from said substrate.

In a further embodiment, the released host cells, or contents thereof, are collected by removing the liquid medium in which said host cells are cultured.

In a further embodiment, those host cells which have undergone apoptosis are fully or partially lysed, thereby releasing their cytoplasmic contents into the liquid medium in which said host cells are cultured.

In a further embodiment, the released host cell contents are collected by removing the liquid medium in which said host cells are cultured.

In a further embodiment, the cell death is the result of a cytotoxic T-lymphocyte induced lytic event.

In a further embodiment, the target polynucleotide encodes a target epitope for a cytotoxic T lymphocyte (CTL).

In a further embodiment, the CTL is a CD4+ CTL.

In a further embodiment, the target epitope is expressed on the surface of said host cells in the context of a native MHC molecule expressed on said host cell, and wherein said host cells are contacted with CTLs which are restricted for said MHC molecule and specific for said target epitope.

In a further embodiment, the MHC molecule is selected from the group consisting of a class I MHC molecule and a class II MHC molecule.

In a further embodiment, the MHC molecule is a class II MHC molecule.

In a further embodiment, the target polynucleotide is fused to a polynucleotide encoding Ii-80 fragment of the class II MHC molecule invariant chain.

In a further embodiment, those cells which have undergone a CTL-mediated lytic event are released from said substrate.

In a further embodiment, the released host cells, or contents thereof, are collected by removing the liquid medium in which said host cells are cultured.

In a further embodiment, those host cells which have undergone a CTL-mediated lytic event are fully or partially lysed, thereby releasing their cytoplasmic contents into the liquid medium in which said host cells are cultured.

In a further embodiment, the released host cell contents are collected by removing the liquid medium in which said host cells are cultured.

In a further embodiment, the cell death is the result of expression of a suicide gene product.

In a further embodiment, the suicide gene product is selected from the group consisting of a diphtheria toxin A chain polypeptide, a *Pseudomonas* exotoxin A chain polypeptide, a ricin A chain polypeptide, an abrin A chain polypeptide, a modeccin A chain polypeptide, and an alpha-sarcin polypeptide.

In a further embodiment, the host cells are progenitor cells comprising a suicide gene operably associated with a tissue-restricted promoter; wherein expression of said target polynucleotide directly or indirectly induces transcription of said tissue-restricted promoter, resulting in expression of said suicide gene; and wherein expression of said suicide gene promotes death of those progenitor cells harboring said target polynucleotide.

In a further embodiment, the host cell is a RAW cell, and wherein said suicide gene is operably associated with the TRAP promoter.

In a further embodiment, the target polynucleotide directly or indirectly regulates osteoclast differentiation.

In a further embodiment, the suicide gene encodes the Diphtheria toxin A subunit.

In a further embodiment, the tissue-restricted promoter is identified by gene expression profiling of said host cells under different conditions in microarrays of ordered cDNA libraries.

In a further embodiment, those host cells expressing said suicide gene product are released from said substrate.

In a further embodiment, the released host cells, or contents thereof, are collected by removing the liquid medium in which said host cells are cultured.

In a further embodiment, those host cells expressing said suicide gene product are fully or partially lysed, thereby releasing their cytoplasmic contents into the liquid medium in which said host cells are cultured.

In a further embodiment, the released host cell contents are collected by removing the liquid medium in which said host cells are cultured.

In a further embodiment, cell death occurs within a period selected from the group consisting of: 48 hours after expression of said insert polynucleotide, 24 hours after expression of said insert polynucleotide, and 12 hours after expression of said insert polynucleotide.

In a further embodiment, said library of polynucleotides is constructed in a eukaryotic virus vector.

In a further embodiment, the eukaryotic virus vector is an animal virus vector.

In a further embodiment, the eukaryotic virus vector is a plant virus vector.

In a further embodiment, the eukaryotic virus vector is capable of producing infectious viral particles in cells selected from the group consisting of insect cells, plant cells, and mammalian cells.

In a further embodiment, the eukaryotic virus vector is attenuated.

In a further embodiment, the eukaryotic virus vector is capable of producing infectious viral particles in mammalian cells.

In a further embodiment, the attenuation is by genetic mutation.

In a further embodiment, the attenuation is by reversible inhibition of virus replication.

In a further embodiment, the naturally-occurring genome of said eukaryotic virus vector is DNA.

In a further embodiment, the naturally-occurring genome of said eukaryotic virus vector is linear, double-stranded DNA.

In a further embodiment, the eukaryotic virus vector is selected from the group consisting of an adenovirus vector, a herpesvirus vector and a poxvirus vector.

In a further embodiment, the eukaryotic virus vector is a poxvirus vector.

In a further embodiment, the poxvirus vector is selected from the group consisting of an orthopoxvirus vector, an avipoxvirus vector, a capripoxvirus vector, a leporipoxvirus vector, and a suipoxvirus vector.

In a further embodiment, the poxvirus vector is an orthopoxvirus vector selected from the group consisting of a vaccinia virus vector and a raccoon poxvirus vector.

In a further embodiment, the orthopoxvirus vector is a vaccinia virus vector.

In another embodiment, the invention provides a method of selecting a target polynucleotide, comprising: (a) introducing into a population of host cells a library of insert polynucleotides; wherein said library is constructed in a linear DNA virus vector; wherein at least one of said insert polynucleotides comprises said target polynucleotide; and wherein expression of said target polynucleotide directly or indirectly prevents death of a host cell comprising said target polynucleotide; (b) culturing said host cells; and (c) collecting insert polynucleotides from those host cells which do not undergo cell death.

In a further embodiment, the method further comprises: (d) introducing said collected polynucleotides into a population of host cells, and wherein expression of said target polynucleotide directly or indirectly prevents death of a host cell comprising said target polynucleotide; (e) culturing said host cells; and (f) collecting insert polynucleotides from those host cells which do not undergo cell death.

In a further embodiment, the method further comprises repeating steps (d)–(f) one or more times, thereby enriching for said target polynucleotide.

In a further embodiment, the method further comprises purifying said collected polynucleotides.

In another embodiment, the invention provides a method of selecting a target polynucleotide, comprising: (a) introducing into a population of host cells a library of insert polynucleotides; wherein said library is constructed in a linear DNA virus vector; wherein at least one of said insert polynucleotides comprises said target polynucleotide; wherein exposure of said host cells to an agent promotes cell death; and wherein expression of said target polynucleotide directly or indirectly prevents death of a host cell comprising said target polynucleotide; (b) culturing said host cells; (e) exposing said host cells to said agent; and (d) collecting insert polynucleotides from those host cells which do not undergo cell death.

In a further embodiment, the method further comprises: (e) introducing said collected polynucleotides into a population of host cells, wherein exposure of said host cells to an agent promotes cell death; and wherein expression of said target polynucleotide directly or indirectly prevents death of a host cell comprising said target polynucleotide; (f) culturing said host cells; (g) exposing said host cells to said agent; and (h) collecting insert polynucleotides from those host cells which do not undergo cell death.

In a further embodiment, the method further comprised repeating steps (e)–(h) one or more times, thereby enriching for said target polynucleotide.

In a further embodiment, the method further comprises purifying said collected polynucleotides.

In a further embodiment, said cell death is the result of a cellular effect selected from the group consisting of cell lysis, expression of a suicide gene product, a cytotoxic T-lymphocyte induced lytic event, apoptosis, loss of viability, loss of membrane integrity, loss of structural stability, cell disruption, disruption of cytoskeletal elements, inability to maintain membrane potential, arrest of cell cycle, inability to generate energy, growth arrest, cytotoxic effects, cytostatic effects, genotoxic effects, and growth suppressive effects.

In a further embodiment, cell death occurs within a period selected from the group consisting of: 48 hours after expression of said insert polynucleotide, 24 hours after expression of said insert polynucleotide, and 12 hours after expression of said insert polynucleotide.

In a further embodiment, the host cells are adherent to a solid support.

In a further embodiment, the agent is a member selected from the group consisting of: a physical agent, a chemical agent, and a biological agent.

In a further embodiment, the physical agent is selected from the group consisting of: radiation, UV radiation, gamma radiation, infrared radiation, visible light, increased temperature, and decreased temperature.

In a further embodiment, the chemical agent is selected from the group consisting of: a chemotherapeutic agent, a cytotoxic agent, and a DNA damaging agent.

In a further embodiment, the biological agent is selected from the group consisting of an antisense construct, an infectious agent, a therapeutic agent, an antibody, a cytotoxic T-lymphocyte (CTL), a ligand, a hapten, an epitope, and a receptor.

In a further embodiment, the biological agent is selected from the group consisting of: an infectious agent, a therapeutic agent, an antibody, a ligand, a hapten, an epitope, and a receptor; and wherein said biological agent is conjugated to a toxin.

In a further embodiment, the biological agent effects cell death by a process selected from the group consisting of: CTL-induced cytotoxicity, antibody-dependent cellular cytotoxicity and complement-dependent cytotoxicity.

In a further embodiment, the biological agent comprises a cytotoxic T lymphocyte (CTL), wherein said CTL expresses surface CD4, wherein said target polynucleotide encodes a polypeptide, and wherein said polypeptide is processed and presented in association with a class II major histocompatibility molecule (MHC).

In a further embodiment, expression of said target polynucleotide effects a cellular process selected from the group consisting of cellular differentiation, growth regulation, cellular proliferation, apoptosis, and hormonal response.

In a further embodiment, the cell death is the result of apoptosis.

In a further embodiment, apoptosis is induced through expression of an apoptosis-related gene product which directly promotes apoptosis.

In a further embodiment, apoptosis is induced through expression of an apoptosis-related gene product which indirectly promotes apoptosis.

In a further embodiment, the apoptosis-related gene product comprises a death domain containing receptor expressed on the surface of said host cells, and wherein said host cells are contacted with a ligand for said death domain containing receptor.

In a further embodiment, those cells which have undergone apoptosis are released from said support.

In a further embodiment, the released host cells, or contents thereof, are removed from said cells which do not undergo cell death.

In a further embodiment, those host cells which have undergone apoptosis are fully or partially lysed, thereby releasing their cytoplasmic contents into the liquid medium in which said host cells are cultured.

In a further embodiment, the released host cell contents are removed from said cells which do not undergo cell death.

In a further embodiment, cell death is the result of expression of a suicide gene product.

In a further embodiment, expression of said target polynucleotide directly or indirectly inhibits expression of a suicide gene encoding said suicide gene product.

In a further embodiment, the suicide gene product is selected from the group consisting of a diphtheria toxin A chain polypeptide, a *Pseudomonas* exotoxin A chain polypeptide, a ricin A chain polypeptide, an abrin A chain polypeptide, a modeccin A chain polypeptide, and an alpha-sarcin polypeptide.

In a further embodiment, the host cells are progenitor cells comprising a suicide gene operably associated with a tissue-restricted promoter; wherein exposure to said agent induces transcription from said tissue-restricted promoter, resulting in expression of said suicide gene; and wherein expression of said target polynucleotide directly or indirectly inhibits expression of said suicide gene, thereby preventing death of said progenitor cells comprising said target polynucleotide.

In a further embodiment, the host cell is a RAW cell, wherein said agent is the RANK ligand (RANKL), and wherein said tissue-restricted promoter is the TRAP promoter.

In a further embodiment, the target polynucleotide directly or indirectly regulates osteoclast differentiation.

In a further embodiment, the suicide gene encodes the Diphtheria toxin A subunit.

In a further embodiment, the tissue-restricted promoter is identified by gene expression profiling of said host cells under different conditions in microarrays of ordered cDNA libraries.

In a further embodiment, the expression profiling compares gene expression under different conditions in host cells infected with a eukaryotic virus expression vector, wherein said eukaryotic virus expression vector is the vector used to construct said library of polynucleotides.

In a further embodiment, the host cells are non-dividing cells comprising a suicide gene operably associated with a proliferation-specific promoter; wherein exposure to said agent induces transcription from said proliferation-specific promoter, resulting in expression of said suicide gene; and wherein expression of said target polynucleotide directly or indirectly inhibit sexpression of said suicide gene, thereby preventing death of said non-dividing cells comprising said target polynucleotide.

In a further embodiment, the proliferation-specific promoter is identified by gene expression profiling of said host cells under different conditions in microarrays of ordered cDNA libraries.

In a further embodiment, the expression profiling compares gene expression under different conditions in host cells infected with a eukaryotic virus expression vector, wherein said eukaryotic virus expression vector is the vector used to construct said library of polynucleotides.

In a further embodiment, those host cells expressing said suicide gene product are released from said support.

In a further embodiment, the released host cells, or contents thereof, are removed from said cells which do not undergo cell death.

In a further embodiment, those host cells expressing said suicide gene product are fully or partially lysed, thereby releasing their cytoplasmic contents into the liquid medium in which said host cells are cultured.

In a further embodiment, the released host cell contents are removed from said cells which do not undergo cell death.

In a further embodiment, cell death occurs within a period selected from the group consisting of: 48 hours after expression of said insert polynucleotide, 24 hours after expression of said insert polynucleotide, and 12 hours after expression of said insert polynucleotide.

In another embodiment, the invention provides a method of selecting a target polynucleotide, comprising: (a) introducing into a population of host cells a library of insert polynucleotides; wherein said library is constructed in a linear DNA virus vector; wherein at least one of said insert polynucleotides comprises the target polynucleotide; and wherein expression of said target polynucleotide directly or indirectly alters a phenotype in a cell comprising said target polynucleotide; (b) culturing said host cells; and (c) collecting insert polynucleotides from those host cells which exhibit said altered phenotype.

In a further embodiment, the method further comprises: (d) introducing said collected polynucleotides into a population of host cells, and wherein expression of said target polynucleotide directly or indirectly alters a phenotype of a host cell comprising said target polynucleotide; (e) culturing said host cells; and (f) collecting insert polynucleotides from those host cells which exhibit said altered phenotype.

In a further embodiment, the method further comprises repeating steps (d)–(f) one or more times, thereby enriching for said target polynucleotide.

In a further embodiment, method further comprises purifying said collected polynucleotides.

In a further embodiment, the altered phenotype is the expression of a reporter gene product.

In a further embodiment, the reporter gene product is selected from the group consisting of an epitope, chloramphenicol acetyl transferase (CAT), green fluorescent protein (GFP), blue fluorescent protein (BFP), yellow fluorescent protein (YFP), red fluorescent protein (RFP), luciferase and β-galactosidase.

In a further embodiment, expression of said target polynucleotide indirectly promotes expression of said selectable gene product in said host cells upon exposure of said host cells to an agent.

In a further embodiment, the agent is a member selected from the group consisting of: a physical agent, a chemical agent, and a biological agent.

In a further embodiment, the physical agent is selected from the group consisting of: radiation, UV radiation, gamma radiation, infrared radiation, visible light, increased temperature, and decreased temperature.

In a further embodiment, the chemical agent is selected from the group consisting of: a chemotherapeutic agent, a cytotoxic agent, and a DNA damaging agent.

In a further embodiment, the biological agent is selected from the group consisting of an antisense construct, an infectious agent, a therapeutic agent, an antibody, a cytotoxic T-lymphocyte (CTL), a ligand, a hapten, an epitope, and a receptor.

In a further embodiment, the biological agent is selected from the group consisting of: an infectious agent, a therapeutic agent, an antibody, a ligand, a hapten, an epitope, and a receptor; and wherein said biological agent is conjugated to a toxin.

In a further embodiment, the biological agent is selected from the group consisting of: an infectious agent, a therapeutic agent, an antibody, a ligand, a hapten, an epitope, and a receptor; and wherein said biological agent is labeled.

In a further embodiment, the biological agent effects cell death by a process selected from the group consisting of: CTL-induced cytotoxicity, antibody-dependent cellular cytotoxicity and complement-dependent cytotoxicity.

In a further embodiment, the biological agent comprises a cytotoxic T lymphocyte (CTL), wherein said CTL expresses surface CD4, wherein said target polynucleotide encodes a polypeptide, and wherein said polypeptide is processed and presented in association with a class II major histocompatibility molecule (MHC).

In a further embodiment, expression of said target polynucleotide effects a cellular process selected from the group consisting of cellular differentiation, growth regulation, cellular proliferation, apoptosis, and hormonal response.

In a further embodiment, the host cells are progenitor cells comprising a selectable gene product operably associated with a tissue-restricted promoter; wherein expression and secretion of a product encoded by said target polynucleotide directly or indirectly induces transcription of said tissue restricted promoter, resulting in expression of said selectable gene product.

In a further embodiment, the host cell is a RAW cell, and wherein said selectable gene product is operably associated with the TRAP promoter.

In a further embodiment, the target polynucleotide directly or indirectly regulates osteoclast differentiation.

In a further embodiment, the tissue-restricted promoter is identified by gene expression profiling of said host cells under different conditions in microarrays of ordered cDNA libraries.

In a further embodiment, the host cells are non-dividing cells comprising a selectable gene product operably associated with a proliferation-specific promoter; wherein expression and secretion of a product encoded by said target polynucleotide directly or indirectly induces transcription of said proliferation-specific promoter, resulting in expression of said selectable gene product.

In a further embodiment, the proliferation-specific promoter is identified by gene expression profiling of said host cells under different conditions in microarrays of ordered cDNA libraries.

In another embodiment, the invention provides a method of selecting a target polynucleotide, comprising: (a) dividing host cells comprising a library of insert polynucleotides into pools; wherein said library is constructed in a linear DNA virus vector; wherein at least one of said insert polynucleotides comprises the target polynucleotide; and wherein expression of said target polynucleotide and secretion of the product of said target polynucleotide directly or indirectly alters a phenotype of an indicator cell; (b) culturing said host cell pools in the presence of indicator cells; (c) collecting insert polynucleotides from those host cell pools in which said indicator cells exhibit an altered phenotype.

In a further embodiment, the method further comprises: (d) introducing said collected polynucleotides into host cells; (e) dividing the host cells of (d) into pools; wherein expression of said target polynucleotide directly or indirectly alters a phenotype of said indicator cells; (f) culturing said host cell pools in the presence of indicator cells; (g) collecting insert polynucleotides from those host cell pools in which said indicator cells exhibit an altered phenotype.

In a further embodiment, the method further comprises repeating steps (d)–(g) one or more times, thereby enriching for said target polynucleotide.

In a further embodiment, the method further comprises purifying said collected polynucleotides.

In a further embodiment, the altered phenotype is the expression of a reporter gene product.

In a further embodiment, the reporter gene product is selected from the group consisting of an epitope, chloramphenicol acetyl transferase (CAT), green fluorescent protein (GFP), blue fluorescent protein (BFP), yellow fluorescent protein (YFP), red fluorescent protein (RFP), luciferase and β-galactosidase.

In a further embodiment, the indicator cells are selected from the group consisting of: tumor cells, metastatic tumor cells, primary cells, transformed primary cells, immortalized primary cells, dividing cells, non dividing cells, terminally differentiated cells, pluripotent stem cells, committed progenitor cells, uncommitted stem cells, progenitor cells, muscle cells, epithelial cells, nervous system cells, circulatory system cells, respiratory system cells, endocrine cells, endocrine-associated cells, skeletal system cells, connective tissue cells, musculoskeletal cells, chondrocytes, osteoblasts, osteoclasts, myocytes, fully differentiated blood cells, fully differentiated epidermal cells, neurons, glial cells, kidney cells, liver cells, muscle cell progenitors, epithelial cell progenitors, nervous system cell progenitors, circulatory system cell progenitors, respiratory system cell progenitors, endocrine cell progenitors, endocrine-associated cell progenitors, skeletal system cell progenitors, connective tissue cell progenitors, musculoskeletal cell progenitors, chondrocyte progenitors, osteoblast progenitors, osteoclast progenitors, myocyte progenitors, blood cell progenitors, epidermal cell progenitors, neuron progenitors, glial cell progenitors, kidney cell progenitors, liver cell progenitors and any combination thereof.

In a further embodiment, the target polynucleotide alters a phenotype of said indicator cells upon exposure of said host cells to an agent.

In a further embodiment, the agent is selected from the group consisting of: a physical agent, a chemical agent, and a biological agent.

In a further embodiment, the physical agent is selected from the group consisting of: radiation, UV radiation, gamma radiation, infrared radiation, visible light, increased temperature, and decreased temperature.

In a further embodiment, the chemical agent is selected from the group consisting of: a chemotherapeutic agent, a cytotoxic agent, and a DNA damaging agent.

In a further embodiment, the biological agent is selected from the group consisting of an antisense construct, an infectious agent, a therapeutic agent, an antibody, a cytotoxic T-lymphocyte (CTL), a ligand, a hapten, an epitope, and a receptor.

In a further embodiment, the biological agent is selected from the group consisting of: an infectious agent, a therapeutic agent, an antibody, a ligand, a hapten, an epitope, and a receptor; and wherein said biological agent is conjugated to a toxin.

In a further embodiment, the biological agent is selected from the group consisting of: an infectious agent, a therapeutic agent, an antibody, a ligand, a hapten, an epitope, and a receptor; and wherein said biological agent is labeled.

In a further embodiment, the biological agent effects cell death by a process selected from the group consisting of: CTL-induced cytotoxicity, antibody-dependent cellular cytotoxicity and complement-dependent cytotoxicity.

In a further embodiment, the biological agent comprises a cytotoxic T lymphocyte (CTL), wherein said CTL expresses surface CD4, wherein said target polynucleotide encodes a polypeptide, and wherein said polypeptide is processed and presented in association with a class II major histocompatibility molecule (MHC).

In a further embodiment, expression of said target polynucleotide effects a cellular process selected from the group consisting of cellular differentiation, growth regulation, cellular proliferation, apoptosis, and hormonal response.

In a further embodiment, the indicator cells are progenitor cells comprising a selectable gene product operably associated with a tissue-restricted promoter; wherein expression of said target polynucleotide directly or indirectly induces transcription of said tissue-restricted promoter, resulting in expression of said selectable gene product.

In a further embodiment, the indicator cell is a RAW cell, and wherein the marker gene is operably associated with the TRAP promoter.

In a further embodiment, the target polynucleotide directly or indirectly regulates osteoclast differentiation in said indicator cells.

In a further embodiment, the indicator cells are non-dividing cells comprising a marker gene operably associated with a proliferation-specific promoter; wherein expression of said target polynucleotide in said host cells directly or indirectly induces transcription of said proliferation-specific promoter, resulting in expression of said marker gene.

In another embodiment, the invention provides a method of selecting a target polynucleotide encoding a secreted product, comprising: (a) introducing into a population of host cells a library of insert polynucleotides; wherein at least one of said insert polynucleotides comprises said target polynucleotide; and wherein expression of said target polynucleotide directly or indirectly alters a phenotype in a population of indicator cells; (b) culturing said pools of host cells in the presence of said indicator cells; and (c) collecting insert polynucleotides from those host cell pools in the presence of which said selectable gene product is expressed.

In a further embodiment, the method further comprises: (d) dividing said collected insert polynucleotides into sub-pools; (e) introducing said polynucleotide sub-pools into sub-pools of host cells, wherein expression of said target polynucleotide and secretion of said product directly or indirectly promotes expression of a selectable gene product in a population of indicator cells; (f) culturing said host cell sub-pools in the presence of said indicator cells; and (g) collecting insert polynucleotides from those sub-pools of host cells in the presence of which said selectable gene product is expressed.

In another embodiment, the invention provides a method of selecting a target polynucleotide encoding a secreted product, comprising: (a) introducing into a population of host cells a library of insert polynucleotides; wherein at least one of said insert polynucleotides comprises the target polynucleotide; and wherein expression of said target polynucleotide and secretion of said product directly or indirectly inhibits expression of a selectable gene product in a population of indicator cells, said indicator cells expressing said selectable gene product upon exposure to an agent; (b) culturing said host cell subpools in the presence of said indicator cells; (c) exposing said indicator cells to said agent; and (d) collecting insert polynucleotides from those host cell pools in the presence of which said selectable gene product is not expressed.

In a further embodiment, the method further comprises: (e) dividing said collected insert polynucleotides into sub-pools; (f) introducing said polynucleotide sub-pools into sub-pools of host cells, wherein expression of said target polynucleotide and secretion of said product directly or indirectly inhibits expression of a selectable gene product in a population of indicator cells, said indicator cells expressing said selectable gene product upon exposure to an agent; (g) culturing said host cell sub-pools in the presence of said indicator cells; (h) exposing said indicator cells to said agent; and (i) collecting insert polynucleotides from those sub-pools of host cells in the presence of which said selectable gene product is not expressed.

In a further embodiment, the method further comprised repeating steps (e)–(i) one or more times, thereby enriching for said target polynucleotide.

In a further embodiment, the method further comprises purifying said collected polynucleotides.

In a further embodiment, the library of insert polynucleotides is an antisense library.

In a further embodiment, the agent is a member selected from the group consisting of: a physical agent, a chemical agent, and a biological agent.

In a further embodiment, the physical agent is selected from the group consisting of: radiation, UV radiation, gamma radiation, infrared radiation, visible light, increased temperature, and decreased temperature.

In a further embodiment, the chemical agent is selected from the group consisting of: a chemotherapeutic agent, a cytotoxic agent, and a DNA damaging agent.

In a further embodiment, the biological agent is selected from the group consisting of an antisense construct, an infectious agent, a therapeutic agent, an antibody, a cytotoxic T-lymphocyte (CTL), a ligand, a hapten, an epitope, and a receptor.

In a further embodiment, the biological agent is selected from the group consisting of: an infectious agent, a therapeutic agent, an antibody, a ligand, a hapten, an epitope, and a receptor; and wherein said biological agent is conjugated to a toxin.

In a further embodiment, the biological agent effects cell death by a process selected from the group consisting of: CTL-induced cytotoxicity, antibody-dependent cellular cytotoxicity and complement-dependent cytotoxicity.

In a further embodiment, the biological agent comprises a cytotoxic T lymphocyte (CTL), wherein said CTL expresses surface CD4, wherein said target polynucleotide encodes a polypeptide, and wherein said polypeptide is processed and presented in association with a class II major histocompatibility molecule (MHC).

In a further embodiment, expression of said target polynucleotide effects a cellular process selected from the group consisting of cellular differentiation, growth regulation, cellular proliferation, apoptosis, and hormonal response.

In a further embodiment, the indicator cells are progenitor cells comprising a selectable gene product operably associated with a tissue-restricted promoter; wherein expression and secretion of a product encoded by said target polynucleotide directly or indirectly inhibits transcription of said tissue-restricted promoter, thereby blocking expression of said selectable gene product.

In a further embodiment, the indicator cell is a RAW cell, wherein said agent is the RANK Ligand (RANKL), and wherein said tissue-restricted promoter is the TRAP promoter.

In a further embodiment, the target polynucleotides expressing a secreted product which directly or indirectly regulates osteoclast differentiation in indicator cells.

In a further embodiment, the tissue-restricted promoter is identified by gene expression profiling of said indicator cells under different conditions in microarrays of ordered cDNA libraries.

In a further embodiment, the indicator cells are non-dividing cells comprising a selectable gene product operably associated with a proliferation-specific promoter; and wherein expression and secretion of a product encoded by said target polynucleotide directly or indirectly inhibits transcription of said proliferation-specific promoter, thereby blocking expression of said selectable gene product.

In a further embodiment, the proliferation-specific promoter is identified by gene expression profiling of said indicator cells under different conditions in microarrays of ordered cDNA libraries.

In a further embodiment of each of methods above and herein, the cell death may be the result of a cellular effect selected from the group consisting of cell lysis, expression of a suicide gene product, a cytotoxic T-lymphocyte induced lytic event, apoptosis, loss of viability, loss of membrane integrity, loss of structural stability, cell disruption, disruption of cytoskeletal elements, inability to maintain membrane potential, arrest of cell cycle, inability to generate energy, growth arrest, cytotoxic effects, cytostatic effects, genotoxic effects, and growth suppressive effects.

In a further embodiment of each of methods above and herein, the population of host cells is selected from the group consisting of: tumor cells, metastatic tumor cells, primary cells, transformed primary cells, immortalized primary cells, dividing cells, non dividing cells, terminally differentiated cells, pluripotent stem cells, committed progenitor cells, uncommitted stem cells, progenitor cells, muscle cells, epithelial cells, nervous system cells, circulatory system cells, respiratory system cells, endocrine cells, endocrine-associated cells, skeletal system cells, connective tissue cells, musculoskeletal cells, chondrocytes, osteoblasts, osteoclasts, myocytes, fully differentiated blood cells, fully differentiated epidermal cells, neurons, glial cells, kidney cells, liver cells, muscle cell progenitors, epithelial cell progenitors, nervous system cell progenitors, circulatory system cell progenitors, respiratory system cell progenitors, endocrine cell progenitors, endocrine-associated cell progenitors, skeletal system cell progenitors, connective tissue cell progenitors, musculoskeletal cell progenitors, chondrocyte progenitors, osteoblast progenitors, osteoclast progenitors, myocyte progenitors, blood cell progenitors, epidermal cell progenitors, neuron progenitors, glial cell progenitors, kidney cell progenitors, liver cell progenitors and any combination thereof.

In a further embodiment of each of methods above and herein, the solid support is selected from the group consisting of: tissue culture plastic, glass, polystyrene, polypropylene, polyethylene, dextran, nylon, amylases, natural and modified celluloses, polyacrylamides, gabbros, magnetite, soluble material, partially soluble material, insoluble material, magnetic material, and nonmagnetic material.

In a further embodiment of each of methods above and herein, the solid support has a structure selected from the group consisting of: spherical, bead-like, bead, cylindrical, test tube-like, tube-like, tube, rod-like, rod, flat, sheet-like, sheet, test strip, strip-like, strip, bead, microbead, well, plate, tissue culture plate, petri plate, microplate, microtiter plate, flask, stick, vial, and paddle.

In a further embodiment of each of methods above and herein, the library of insert polynucleotides is selected from the group consisting of: a cDNA library, a genomic library, a combinatorial polynucleotide library, a library of natural polynucleotides, a library of artificial polynucleotides, a library of polynucleotides endogenous to the host cells, a library of polynucleotides exogenous to the host cells, an antisense library, and any combination thereof.

In a further embodiment of each of methods above and herein, the library of insert polynucleotides is constructed in said eukaryotic virus vector by a method comprising: (a) providing host cells comprising a linear DNA virus genome which has been cleaved to produce a first viral fragment and a second viral fragment, wherein said first fragment is nonhomologous with said second fragment; (b) providing a population of transfer plasmids comprising said insert polynucleotides in operable association with a vector transcriptional control region, a 5' flanking region, and a 3' flanking region; wherein said 5' flanking region is homologous to said first viral fragment and said 3' flanking region is homologous to said second viral fragment; and wherein said transfer plasmids are capable of homologous recombination with said first and second viral fragments such that a viable virus genome is formed; (c) introducing said transfer plasmids into said host cells under conditions wherein a transfer plasmid and said first and second viral fragments undergo in vivo homologous recombination, thereby producing a viable modified virus genome comprising an insert polynucleotide; and (d) collecting said modified virus genome.

In a further embodiment of each of methods above and herein, the first and second viral fragments are produced by infecting said host cells with a virus comprising said linear DNA virus genome, and wherein said virus genome is cleaved in vivo.

In a further embodiment of each of methods above and herein, the first and second viral fragments are produced by cleaving an isolated linear DNA virus genome in vitro, and wherein said first and second viral fragments are introduced into said host cells.

In a further embodiment of each of methods above and herein, the virus genome comprises a first recognition site for a first restriction endonuclease; and wherein said first and second viral fragments are produced by digesting said viral genome with said first restriction endonuclease, and isolating said first and second viral fragments.

In a further embodiment of each of methods above and herein, the virus genome further comprises a second recognition site for a second restriction endonuclease; and wherein said first and second viral fragments are produced by digesting said viral genome with said first restriction endonuclease and said second restriction endonuclease, and isolating said first and second viral fragments.

In a further embodiment of each of methods above and herein, the first and second recognition sites are physically arranged in said genome such that the region extending between said first and second viral fragments is not essential for virus infectivity.

In a further embodiment of each of methods above and herein, the modified virus genome is packaged in an infectious viral particle.

In a further embodiment of each of methods above and herein, the modified virus genome is defective in an essential gene and said host cell comprises a complementing copy of said essential gene.

In a further embodiment of each of methods above and herein, the complementing copy of said essential gene is operably associated with an inducible promoter.

In a further embodiment of each of methods above and herein, the inducible promoter is selected from the group consisting of: a differentiation-induced promoter, a cell type-restricted promoter, a tissue-restricted promoter, a temporally-regulated promoter, a spatially-regulated promoter, a proliferation-induced promoter, a cell-cycle specific promoter.

In a further embodiment of each of methods above and herein, the linear DNA virus genome is a herpes virus genome.

In a further embodiment of each of methods above and herein, the linear DNA virus genome is an adenovirus genome.

In a further embodiment of each of methods above and herein, the linear DNA virus genome is a poxvirus genome.

In a further embodiment of each of methods above and herein, the poxvirus genome is a vaccinia virus genome.

In a further embodiment of each of methods above and herein, the transfer plasmid and said first and second viral fragments are introduced into a host cell comprising a helper virus, wherein said host cell is non-permissive for the production of infectious virus particles of said helper virus.

In a further embodiment of each of methods above and herein, the helper virus is an avipoxvirus.

In a further embodiment of each of methods above and herein, the helper virus is a fowlpox virus.

In a further embodiment of each of methods above and herein, the 5' and 3' flanking regions of said transfer plasmids are capable of homologous recombination with a vaccinia virus thymidine kinase gene.

In a further embodiment of each of methods above and herein, the 5' and 3' flanking regions of said transfer plasmids are capable of homologous recombination with a vaccinia virus HindIII J fragment.

In a further embodiment of each of methods above and herein, the transfer plasmid comprises an insert polynucleotide operably associated with a promoter selected from the group consisting of a vaccinia virus p7.5 promoter, a synthetic early/late promoter, and a vaccinia virus MH5 early/late promoter.

In a further embodiment of each of methods above and herein, the transfer plasmid comprises the sequence shown in SEQ ID NO: 4.

In a further embodiment of each of methods above and herein, the library of polynucleotides is constructed in a eukaryotic virus vector.

In a further embodiment of each of methods above and herein, the host cells are infected with said library at an MOI selected from the group consisting of: from about 1 to about 10, about 1 to about 5, and about 1.

In a further embodiment of each of methods above and herein, the eukaryotic virus vector is an animal virus vector.

In a further embodiment of each of methods above and herein, wherein said eukaryotic virus vector is a plant virus vector.

In a further embodiment of each of methods above and herein, the eukaryotic virus vector is capable of producing infectious viral particles in cells selected from the group consisting of insect cells, plant cells, and mammalian cells.

In a further embodiment of each of methods above and herein, the eukaryotic virus vector is attenuated.

In a further embodiment of each of methods above and herein, the eukaryotic virus vector is capable of producing infectious viral particles in mammalian cells.

In a further embodiment of each of methods above and herein, the attenuation is by genetic mutation.

In a further embodiment of each of methods above and herein, the attenuation is by reversible inhibition of virus replication.

In a further embodiment of each of methods above and herein, the naturally-occurring genome of said eukaryotic virus vector is DNA.

In a further embodiment of each of methods above and herein, the naturally-occurring genome of said eukaryotic virus vector is linear, double-stranded DNA.

In a further embodiment of each of methods above and herein, the eukaryotic virus vector is selected from the group consisting of an adenovirus vector, a herpesvirus vector and a poxvirus vector.

In a further embodiment of each of methods above and herein, the eukaryotic virus vector is a poxvirus vector.

In a further embodiment of each of methods above and herein, the poxvirus vector is selected from the group consisting of an orthopoxvirus vector, an avipoxvirus vector, a capripoxvirus vector, a leporipoxvirus vector, and a suipoxvirus vector.

In a further embodiment of each of methods above and herein, the poxvirus vector is an orthopoxvirus vector selected from the group consisting of a vaccinia virus vector and a raccoon poxvirus vector.

In a further embodiment of each of methods above and herein, the orthopoxvirus vector is a vaccinia virus vector.

In a further embodiment of each of methods above and herein, the host cells are permissive for the production of infectious viral particles of said virus.

In a further embodiment of each of methods above and herein, the vaccinia virus is attenuated.

In a further embodiment of each of methods above and herein, the attenuation is by genetic mutation.

In a further embodiment of each of methods above and herein, the attenuation is by reversible inhibition of virus replication.

In a further embodiment of each of methods above and herein, the vaccinia virus vector is derived from strain MVA.

In a further embodiment of each of methods above and herein, the vaccinia virus vector is derived from strain D4R.

In a further embodiment of each of methods above and herein, the insert polynucleotide is in operable associated with a transcriptional control sequence.

In a further embodiment of each of methods above and herein, the transcriptional control sequence functions in the cytoplasm of a poxvirus-infected cell.

In a further embodiment of each of methods above and herein, the transcriptional control sequence comprises a promoter.

In a further embodiment of each of methods above and herein, the promoter is constitutive.

In a further embodiment of each of methods above and herein, the promoter is a vaccinia virus p7.5 promoter.

In a further embodiment of each of methods above and herein, the vector comprises the sequence shown in SEQ ID NO: 1.

In a further embodiment of each of methods above and herein, the promoter is a synthetic early/late promoter.

In a further embodiment of each of methods above and herein, the vector comprises the sequence shown in SEQ ID NO: 3.

In a further embodiment of each of methods above and herein, the transcriptional control sequence comprises a transcriptional termination region.

Vaccinia Virus and Other Poxviruses

"Poxvirus" includes any member of the family Poxviridae, including the subfamililes Chordopoxviridae (vertebrate poxviruses) and Entomopoxviridae (insect poxviruses). See, for example, B. Moss in: *Virology*, B. N. Fields, D. M. Knipe et al., Eds., Raven Press, p. 2080 (1990). The chordopoxviruses comprise, inter alia, the following genera: Orthopoxvirus (e.g., vaccinia); Avipoxvirus (e.g., fowlpox); Capripoxvirus (e.g, sheeppox) Leporipoxvirus (e.g., rabbit (Shope) fibroma, and myxoma); and Suipoxvirus (e.g., swinepox). The entomopoxviruses comprise three genera: A, B and C.

In the present invention, orthopoxviruses are preferred. Vaccinia virus is the prototype orthopoxvirus, and has been developed and is well-characterized as a vector for the expression of heterologous proteins. In the present invention, vaccinia virus vectors, particularly those that have been developed to perform trimolecular recombination, are preferred. However, other orthopoxviruses, in particular, raccoon poxvirus have also been developed as vectors and in some applications, have superior qualities.

Vaccinia virus, like other members of the pox virus group, is distinguished by its large size and complexity. The DNA of vaccinia virus is similarly large and complex. Vaccinia DNA is about 180 kilodaltons in size, for instance, compared with a DNA size of only 3.6 megadaltons for simian virus 40 (SV40). The DNA molecule of vaccinia is double-stranded and terminally crosslinked so that a single stranded circle is formed upon denaturation of the DNA. Vaccinia DNA has been physically mapped using a number of different restriction enzymes and a number of such maps are presented in an article by Panicali et al., J. Virol. 37, 1000–1010 (1981) which reports the existence of two major DNA variants of the WR strain of vaccinia virus (ATCC No. VR 119), which strain has been most widely used for the investigation and characterization of pox viruses. The two variants differ in that the S ("small") variant (ATCC No. VR 2034) has a 6.3 megadalton deletion not occurring in the DNA of the L ("large") variant (ATCC No. VR 2035). Maps obtained by treatment of the variants with the restriction enzymes Hind III, Ava I, Xho I, Sst I, and Sma I are presented in the aforementioned article.

Vaccinia, a eukaryotic virus, reproduces entirely within the cytoplasm of a host cell. It is a lytic virus, i.e. a virus, the replication of which in a cell results in lysis of the cell. The virus is considered non-oncogenic. The virus has been used for approximately 200 years in vaccines for inoculation against smallpox and the medical profession is well acquainted with the properties of the virus when used in a vaccine.

Concerning the structure of the vaccinia genome, the cross-linked double strands of the DNA are characterized by inverted terminal repeats each approximately 8.6 megadaltons in length, representing about 10 kilobasepairs (kbp). Since the central portions of the DNA of all pox viruses are similar, while the terminal portions of the viruses differ more strongly, the responsibility of the central portion for functions common to all the viruses, such as replication, is suggested, whereas the terminal portions appear responsible for other characteristics such as pathogenicity, host range, etc. If such a genome is to be modified by the rearrangement or removal of DNA fragments therefrom or the introduction of exogenous DNA fragments thereinto, while producing a stable viable mutant, the portion of the naturally-occurring DNA which is rearranged, removed, or disrupted by the introduction of exogenous DNA thereinto must be non-essential to the viability and stability of the vaccinia virus. Such non-essential portions of the genome have been found to be present in the WR strain of vaccinia virus, for instance within the region present within the L-variant but deleted from the S-variant or within the Hind III F-fragment of the genome. See, for example, Paoletti et al., U.S. Pat. No. 5,972,597.

Attenuated and Defective Viral Vectors Such As Vaccinia Virus. A limitation of wild type vaccinia virus as an expression vector for lethality based selection is that the virus has cytopathic effects in many mammalian cells. The kinetics of these effects is very dependent on the host cells. For many tissue culture lines, cytopathic effects that result in release from a monolayer are not significant until well after 48 to 72 hours infection. This allows a 2 to 3 day time frame for high level expression of recombinant genes and selection of a non-viable or non-adherent phenotype independent of the intrinsic cytopathic effects of the vector. This has been shown to be adequate for immunoselection, and, because of the toxicity of suicide gene constructs, is expected to be adequate for studies of genes that regulate differentiation in many but not necessarily all cell types. There is, therefore, a need for a pox virus vector with attenuated cytopathic effects so that, wherever necessary, the time frame of selection can be extended.

For example, certain attenuations are achieved through genetic mutation. Many vaccinia virus mutants have been characterized. These may be fully defective mutants, i.e., the production of infectious virus particles requires helper virus, or they may be conditional mutants, e.g., temperature sensitive mutants. Conditional mutants are particularly preferred, in that the virus-infected host cells can be maintained in a non-permissive environment, e.g., at a non-permissive temperature, during the period where host gene expression is required, and then shifted to a permissive environment, e.g., a permissive temperature, to allow virus particles to be produced. Alternatively, a fully infectious virus may be "attenuated" by chemical inhibitors which reversibly block virus replication at defined points in the infection cycle. Chemical inhibitors include, but are not limited to hydroxyurea and 5-fluorodeoxyuridine. Virus-infected host cells are maintained in the chemical inhibitor during the period where host gene expression is required, and then the chemical inhibitor is removed to allow virus particles to be produced.

Modified Vaccinia Ankara (MVA) is a highly attenuated strain of vaccinia virus that was derived during over 570 passages in primary chick embryo fibroblasts (Mayr, A. et al., *Infection* 3:6–14 (1975)). The recovered virus deleted approximately 15% of the wild type vaccinia DNA which profoundly affects the host range restriction of the virus. MVA cannot replicate or replicates very inefficiently in most mammalian cell lines. A unique feature of the host range restriction is that the block in non-permissive cells occurs at a relatively late stage of the replication cycle. Expression of viral late genes is relatively unimpaired but virion morphogenesis is interrupted (Suter, G. and Moss, B., *Proc Natl Acad Sci USA* 89:10847–51 (1992); Carroll, M. W. and Moss, B., Virology 238:198–211 (1997)). The high levels of viral protein synthesis even in non-permissive host cells make MVA an especially safe and efficient expression vector. However, because MVA cannot complete the infectious cycle in most mammalian cells, in order to recover infectious virus for multiple cycles of selection it will be necessary to complement the MVA deficiency by coinfection or superinfection with a helper virus that is itself deficient and that can be subsequently separated from infectious MVA recombinants by differential expansion at low MOI in MVA permissive host cells.

As an alternative to MVA, some strains of vaccinia virus that are deficient in an essential early gene have been shown to have greatly reduced inhibitory effects on host cell protein synthesis. Attenuated poxviruses which lack defined essential early genes have also been described. See, e.g., U.S. Pat. No. 5,766,882, by Falkner, et al. Examples of essential early genes which may be rendered defective include, but are not limited to the vaccinia virus 17L, F18R, D13L, D6R, A8L, J1R, E7L, F11L, E4L, I1L, J3R, J4R, H7R, and A6R genes. A preferred essential early gene to render defective is the D4R gene, which encodes a uracil DNA glycosylase enzyme.

Vaccinia viruses defective in defined essential genes are easily propagated in complementing cell lines which provides the essential gene product. As used herein, the term "complementation" refers to a restoration of a lost function in trans by another source, such as a host cell, transgenic animal or helper virus. The loss of function is caused by loss by the defective virus of the gene product responsible for the function. Thus, a defective poxvirus is a non-viable form of a parental poxvirus, and is a form that can become viable in the presence of complementation. The host cell, transgenic animal or helper virus contains the sequence encoding the lost gene product, or "complementation element." The complementation element should be expressible and stably integrated in the host cell, transgenic animal or helper virus, and preferably would be subject to little or no risk for recombination with the genome of the defective poxvirus.

Viruses produced in the complementing cell line are capable of infecting non-complementing cells, and further are capable of high-level expression of early gene products. However, in the absence of the essential gene product, host shut-off, DNA replication, packaging, and production of infectious virus particles do not take place.

In particularly preferred embodiments described herein, selection of desired insert polynucleotides expressed in a complex library constructed in vaccinia virus is accomplished through coupling induction of expression of the complementation element to expression of the insert polynucleotide. Since the complementation element is only expressed in those host cells expressing the insert polynucleotide, only those host cells will produce infectious virus which is easily recovered.

In another preferred aspect, inactivation of the library constructed in a virus vector is carried out by treating a sample of the library constructed in a virus vector with 4'-aminomethyl-trioxsalen (psoralen) and then exposing the virus vector to ultraviolet (UV) light. Psoralen and UV inactivation of viruses is well known to those of ordinary skill in the art. See, e.g., Tsung, K., et al., *J. Virol.* 70:165–171 (1996), which is incorporated herein by reference in its entirety.

Psoralen treatment typically comprises incubating a cell-free sample of the virus vector with a concentration of psoralen ranging from about 0.1 µg/ml to about 20 µg/ml, preferably about 1 µg/ml to about 17.5 µg/ml, about 2.5 µg/ml to about 15 µg/ml, about 5 µg/ml to about 12.5 µg/ml, about 7.5 µg/ml to about 12.5 µg/ml, or about 9 µg/ml to about 11 µg/ml. Accordingly, the concentration of psoralen may be about 0.1 µg/ml, 0.5 µg/ml, 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 11 µg/ml, 12 µg/ml, 13 µg/ml, 14 µg/ml, 15 µg/ml, 16 µg/ml, 17 µg/ml, 18 µg/ml, 19 µg/ml, or 20 µg/ml. Preferably, the concentration of psoralen is about 10 µg/ml.

As used herein, the term "about" takes into account that measurements of time, chemical concentration, temperature, pH, and other factors typically measured in a laboratory or production facility are never exact, and may vary by a given amount based on the type of measurement and the instrumentation used to make the measurement.

The incubation with psoralen is typically carried out for a period of time prior to UV exposure. This time period preferably ranges from about one minute to about 20 minutes prior to the UV exposure. Preferably, the time period ranges from about 2 minutes to about 19 minutes, from about 3 minutes to about 18 minutes, from about 4 minutes to about 17 minutes, from about 5 minutes to about 16 minutes, from about 6 minutes to about 15 minutes, from about 7 minutes to about 14 minutes, from about 8 minutes to about 13 minutes, or from about 9 minutes to about 12 minutes. Accordingly, the incubation time may be about 1 minute, about 2 minutes, about three minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, or about 20 minutes. More preferably, the incubation is carried out for 10 minutes prior to the UV exposure.

The psoralen-treated viruses are then exposed to UV light. The UV may be of any wavelength, but is preferably long-wave UV light, e.g., about 365 nm. Exposure to UV is carried out for a time period ranging from about 0.1 minute to about 20 minutes. Preferably, the time period ranges from about 0.2 minute to about 19 minutes, from about 0.3 minute to about 18 minutes, from about 0.4 minute to about 17 minutes, from about 0.5 minute to about 16 minutes, from about 0.6 minute to about 15 minutes, from about 0.7 minute to about 14 minutes, from about 0.8 minute to about 13 minutes, from about 0.9 minute to about 12 minutes from about 1 minute to about 11 minutes, from about 2 minutes to about 10 minutes, from about 2.5 minutes to about 9 minutes, from about 3 minutes to about 8 minutes, from about 4 minutes to about 7 minutes, or from about 4.5 minutes to about 6 minutes. Accordingly, the incubation time may be about 0.1 minute, about 0.5 minute, about 1 minute, about 2 minutes, about three minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, or about 20 minutes. More preferably, the virus vector is exposed to UV light for a period of about 5 minutes.

The terms "vacciniavirus" and "poxvirus" are used interchangeably herein. The preferred embodiments relating to vaccinia virus may be modified in ways apparent to one of ordinary skill in the art for use with any poxvirus vector. In the direct selection method, vectors other than poxvirus or vaccinia virus may be used.

The Tri-Molecular Recombination Method

Vaccinia virus vectors are not currently used to identify previously unknown genes of interest from a complex population of clones, such as a cDNA or other library, because a high efficiency, high titer-producing method of cloning does not exist for vaccinia. The standard methods of cloning in vaccinia virus are in vivo homologous recombination and in vitro direct ligation. Using homologous recombination, the cloning efficiency is in the range of approximately 0.1% or less, and although the cloning efficiency using direct ligation is higher, the resulting titer is relatively low. Thus, the use of vaccinia virus vector has been limited to the cloning of previously isolated DNA for the purposes of protein expression and vaccine development.

Tri-molecular recombination is a novel, high efficiency, high titer-producing method for cloning in vaccinia virus. Using the tri-molecular recombination method, the present inventor has achieved cloning efficiencies of at least 90%, and titers at least 30-fold, at 100-fold, i.e., at least 2 orders of magnitude higher, than those obtained by direct ligation.

Thus, in one embodiment, the invention provides a method of high efficiency cloning using a vaccinia virus vector, comprising tri-molecular recombination.

By "tri-molecular recombination" or a "tri-molecular recombination method" is meant a method of producing a vaccinia virus genome which contains insert polynucleotide (e.g. insert DNA), comprising introducing two nonhomologous fragments of a vaccinia virus genome and a transfer vector or transfer polynucleotide (e.g. transfer DNA) containing insert polynucleotide (e.g. DNA) into a recipient cell, and allowing the three polynucleotide (e.g. DNA) molecules to recombine in vivo. As a result of the recombination, a single vaccinia virus genome molecule is produced which comprises each of the two vaccinia genome fragments and the insert polynucleotide (e.g. DNA).

Thus, the tri-molecular recombination method comprises: (a) providing a recipient cell which comprises packaging function; (b) introducing into the cell (i) transfer vector or transfer polynucleotide (e.g. DNA), and (ii) two fragments of vaccinia virus genome; and (c) culturing the cells under conditions such that the transfer polynucleotide (e.g. DNA) and the two fragments undergo trimolecular recombination.

By "cloning" is meant the use of in vitro and in vivo recombination techniques to insert one or a plurality of polynucleotide sequences into a vector. In order to successfully clone a polynucleotide, it is often necessary to employ methods for generating polynucleotide fragments, for joining the fragments to vector molecules, for introducing the composite polynucleotide molecule into a host cell in which it can replicate, and for selecting the clone having a polynucleotide insert, for example by virtue of a resistance marker such as thymidine kinase⁻ (tk⁻), from among the cells containing either no vector or vector alone without an insert. Such methods are well known in the art, and include the methods described herein.

By "cloning efficiency" or "efficiency of cloning" is meant the ratio of recombinant virus to total virus produced during tri-molecular recombination. As shown in Example 2, the efficiency may be calculated by dividing the titer of recombinant virus by the titer of total virus and multiplying by 100%. For example, the titer is determined by plaque assay of crude virus stock on appropriate cells either with selection (e.g., for recombinant virus) or without selection (e.g., for recombinant virus plus wild type virus). Methods of selection are well-known in the art and include BrdU resistance due to disruption of the tk gene as described herein and other well-known methods. See Examples 1 and 2.

By "high efficiency cloning" is meant a cloning efficiency of at least 1%, and more preferably a cloning efficiency of at least 2%, 2.264%, 3%, 3.5%, 3.571%, 5%, 10%, 20%, 30%, 40%, 50%, 60%, 70%, 75%, 80%, 85%, 90%, 95%, or 99%.

A number of selection systems may be used, including but not limited to the thymidine kinase such as herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes which can be employed in tk⁻, hgprt⁻ or aprt⁻ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Together, the two fragments or arms of the vaccinia virus genome contain all the genes necessary for viral replication and for production of infectious viral particles. See the Examples for examples of structures of vaccinia virus vector useful in the trimolecular recombination method. Preferred structures are presented in Examples 1 and 2. See Falkner et al., U.S. Pat. No. 5,770,212 for guidance concerning essential regions for vaccinia replication.

However, naked vaccinia genomic DNA cannot produce infectious progeny without virus-encoded protein protein(s)/function(s) associated with the incoming viral particle. The virus-encoded function, also referred to as "packaging function," includes an RNA polymerase that recognizes the transfected vaccinia DNA as a template and initiates transcription and, ultimately, replication of the transfected DNA. See Dorner, et al. U.S. Pat. No. 5,445,953.

Thus, to produce infectious progeny virus, the recipient cell preferably contains packaging function. The packaging function may be provided by helper virus, i.e., a virus that, together with the transfected naked genomic DNA, provides appropriate proteins and factors necessary for replication and assembly of progeny virus.

The helper virus may be a closely related virus, for instance, a poxvirus of the same poxvirus subfamily as vaccinia, whether from the same or a different genus. In such a case it is advantageous to select a helper virus which provides an RNA polymerase that recognizes the transfected DNA as a template and thereby serves to initiate transcription and, ultimately, replication of the transfected DNA. The use of a heterologous virus to package the modified DNA molecule, such as the use of temperature sensitive (ts) vaccinia, fowlpox, or ectromelia (mouse pox) virus as a helper for vaccinia virus constructs, minimizes recombination events between the helper virus genome and the transfected genome which take place when homologous sequences of closely related viruses are present in one cell. See Fenner & Comben, *Virology* 5:530 (1958); Fenner, *Virology* 8:499 (1959).

Alternatively, the necessary packaging function in the recipient cell is supplied by a genetic element other than a helper virus, such as a plasmid or retrovirus or other expression vector suitable for expressing the required helper virus function. See Dorner, et al. U.S. Pat. No. 5,445,953.

The two vaccinia genomic fragments are unable to ligate with each other, i.e., they do not contain compatible cohesive ends or alternatively, they have been treated with a dephosphorylating enzyme. Further, the two fragments are nonhomologous, such that they are unable to recombine with one another.

By "insert polynucleotide" (e.g. "insert DNA") is meant one or more polynucleotide segments. Polynucleotides are also referred to herein as nucleic acid. An insert polynucleotide may be DNA. A polynucleotide (e.g. DNA) segment may be naturally occurring, non naturally occurring, synthetic, or a combination thereof. A polynucleotide (e.g. DNA) segment may be any length. It may be endogenous or exogenous to the vector, such as vaccinia virus, or it may be endogenous or exogenous to the host cell, it may be a previously known sequence or an unknown sequence. It may be a gene, a cDNA, a combinatorial sequence, etc. Insert polynucleotides may also be referred to herein by the term "candidate polynucleotides" or "test polynucleotides" or other equivalents, especially in reference to selection methods of the invention.

By "transfer plasmid" is meant a vector containing insert polynucleotide (e.g. DNA) positioned between a 5' flanking region and a 3' flanking region. The 5' flanking region shares homology with one of the vaccinia genome fragments, and the 3' flanking region shares homology with the other of the vaccinia genome fragments. Preferably, the transfer plasmid contains a suitable promoter, such as a strong, constitutive vaccinia promoter, upstream of the insert DNA. The term "vector" means a polynucleotide (e.g. DNA) construct containing a polynucleotide (e.g. DNA) sequence which is operably linked to a suitable control sequence capable of effecting the expression of the polynucleotide (e.g. DNA) in a suitable host. Such control sequences include a promoter to effect transcription, an optional operator sequence to control such transcription, a sequence encoding suitable mRNA ribosome binding sites, sequences which control the termination of transcription and translation, and other control sequences as are well known in the art. The vector may be a plasmid, a phage particle, or simply a potential genomic insert. Once transformed into a suitable host, the vector may replicate and function independently of the host genome, or may in some instances, integrate into the genome itself. In the present specification, "plasmid" and "vector" are sometimes used interchangeably. However, the invention is intended to include such other form of vector which serves equivalent function as and which are, or become, known in the art. Typical expression vectors for mammalian cell culture expression, for example, are based on pRK5 (EP 307,247), pSV16B (WO 91/08291) and pVL1392 (Pharmingen).

However, transfer plasmid is not limited to a vector or a plasmid. Any polynucleotide (e.g. DNA) segment in circular or linear or other suitable form may act as a vehicle for transferring the polynucleotide (e.g. DNA) insert to the vaccinia vector in the tri-molecular recombination method. Other suitable "plasmids" include lambda phage, polynucleotide (e.g. DNA) fragments, etc., as described herein or otherwise known in the art. A plurality of plasmids may be a "primary library" such as those described herein for lambda.

Preferably, the insert polynucleotides are operably associated with poxvirus expression control sequences, more preferably, strong constitutive poxvirus promoters.

Nucleic acid is "operably associated" when it is placed into a functional relationship with another nucleic acid sequence. This can be a gene and a regulatory sequence(s) which are connected in such a way as to permit gene expression when the appropriate molecules (e.g., transcriptional activator proteins) are bound to the regulatory sequences(s). For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it affects the transcription of the sequence; or a ribosome binding site is operably linked to a coding sequence if it is positioned so as to facilitate translation. Generally, "operably associated" means that the polynucleotide (e.g. DNA) sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

By "control sequences" is meant polynucleotide (e.g. DNA) sequences necessary for the expression of an operably associated coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. For a library cloned in apoxvirus vector, preferably, if the control sequence is a transcriptional control sequence, it is one which functions in the cytoplasm of a poxvirus-infected cell.

Poxvirus transcriptional control sequences comprise a promoter and a transcription termination signal. Gene expression in poxviruses is temporally regulated, and promoters for early, intermediate, and late genes possess different structures. Certain poxvirus genes are expressed constitutively (i.e., early to late), and promoters for these "early-late" genes bear hybrid structures. Synthetic early-late promoters have also been developed. See Hammond J. M., et al., *J. Virol. Methods* 66:135–8 (1997); Chakrabarti S., et al., *Biotechniques* 23:1094–7 (1997). In the present invention, any poxvirus promoter may be used, but use of early, late, or constitutive promoters may be desirable based on the host cell and/or selection scheme chosen. Typically, the use of constitutive promoters is preferred.

Examples of early promoters include the 7.5-kD promoter (also a late promoter), the DNA pol promoter, the tk promoter, the RNA pol promoter, the 19-kD promoter, the 22-kD promoter, the 42-kD promoter, the 37-kD promoter, the 87-kD promoter, the H3' promoter, the H6 promoter, the D1 promoter, the D4 promoter, the D5 promoter, the D9 promoter, the D12 promoter, the I3 promoter, the M1 promoter, and the N2 promoter. See, e.g., Moss, B., "Poxviridae and their Replication" IN *Virology*, 2d Edition, B. N. Fields, D. M. Knipe et al., Eds., Raven Press, p. 2088 (1990). Early genes transcribed in vaccinia virus and other poxviruses recognize the transcription termination signal TTTTTNT, where N can be any nucleotide. Transcription normally terminates approximately 50 bp upstream of this signal. Accordingly, if heterologous genes are to be expressed from poxvirus early promoters, care must be taken to eliminate occurrences of this signal in the coding regions for those genes. See, e.g., Earl, P. L., et al., *J. Virol.* 64:2448–51 (1990).

Example of late promoters include the 7.5-kD promoter, the MIL promoter, the 37-kD promoter, the 11-kD promotor, the 11L promoter, the 12L promoter, the 13L promoter, the 15L promoter, the 17L promoter, the 28-kD promoter, the H1L promoter, the H3L promoter, the H5L promoter, the H6L promoter, the H8L promoter, the D11L promoter, the D12L promotor, the D13L promoter, the A1L promoter, the A2L promoter, the A3L promoter, and the P4b promoter. See, e.g., Moss, B., "Poxviridae and their Replication" IN *Virology*, 2d Edition, B. N. Fields, D. M. Knipe et al., Eds., Raven Press, p. 2090 (1990). The late promoters apparently do not recognize the transcription termination signal recognized by early promoters.

Preferred constitutive promoters for use in the present invention include the synthetic early-late promoters described by Hammond and Chakrabarti, the MH-5 early-late promoter, and the 7.5-kD or "p 7.5" promoter. Examples utilizing these promoters are disclosed herein.

As discussed above, certain selection and screening methods based on host cell death require that the mechanisms leading to cell death occur prior to any cytopathic effect (CPE) caused by virus infection. The kinetics of the onset of CPE in virus-infected cells is dependent on the virus used, the multiplicity of infection, and the type of host cell. For example, in many tissue culture lines infected with vaccinia virus at an MOI of about 1, CPE is not significant until well after 48 to 72 hours post-infection. This allows a 2 to 3 day time frame for high level expression of immunoglobulin molecules, and antigen-based selection independent of CPE caused by the vector. However, this time frame may not be sufficient for certain selection methods, especially where higher MOIs are used, and further, the time before the onset of CPE may be shorter in a desired cell line. There is, therefore, a need for virus vectors, particularly poxvirus vectors such as vaccinia virus, with attenuated cytopathic effects so that, wherever necessary, the time frame of selection can be extended.

By "recipient cell" or "host cell" or "cell" is meant a cell or plurality of cells into which polynucleotides (e.g. DNA) is introduced for the tri-molecular recombination method or a direct or indirect selection method described below, preferably a eukaryotic cell or cell line, preferably an animal, vertebrate, mammalian, rodent, mouse, primate, or human cell or cell line. Additional examples of host cells are disclosed herein. The host cells may also comprise packaging function.

Polynucleotides (e.g. DNA) may be introduced into host cells by any method known to those of skill, for example, by lipofection (such as with anionic liposomes (see, e.g., Felgner et al., 1987 *Proc. Natl. Acad Sci. U.S.A.* 84:7413 or cationic liposomes (see, e.g., Brigham, K. L. et al. *Am. J Med Sci.* 298(4):278–2821(1989); U.S. Pat. No. 4,897,355 (Eppstein, et al.)), by electroporation, by calcium phosphate precipitation (see generally, Sambrook et al., *Molecular Cloning: A Laboratory Manual*, 2nd Ed., Cold Spring Harbor Laboratory, Cold Spring Harbor, N.Y., 1989), by protoplast fusion, by spheroplast fusion, or by the DEAE dextran method (Sussman et al., Cell. Biol. 4:1641–1643 (1984)). When the selected method is lipofection, the nucleic acid can be complexed with a cationic liposome, such as DOTMA:DOPE, DOTMA, DOPE, DC-cholesterol, DOTAP, Transfectam® (Promega), Tfx® (Promega), LipoTAXI™ (Stratagene), PerFect Lipid™ (Invitrogen), SuperFect™ (Qiagen). When the nucleic acid is transected via an anionic liposome, the anionic liposome can encapsulate the nucleic acid. Preferably, polynucleotide (e.g. DNA) is introduced by liposome-mediated transfection using the manufacturer's protocol (such as for Lipofectamine; Life Technologies Incorporated).

Modifications of Trimolecular Recombination

Trimolecular recombination has been used by the present inventors to construct cDNA libraries in vaccinia virus with titers of the order of $10^7$ pfu. There are several factors that limit the complexity of these cDNA or other libraries. These include: the size of the primary cDNA library or other library that can be constructed in a plasmid vector, and the labor involved in the purification of large quantities (hundreds of micrograms) of vaccinia virus, poxvirus, or other vector DNA. Modifications of trimolecular recombination that would allow for vector (e.g. vaccinia or other poxvirus DNA) recombination with transfer polynucleotides (e.g. primary cDNA libraries or other libraries constructed in bacteriophage lambda or DNA or phagemids derived therefrom), or that would allow separate vector (e.g. vaccinia virus) DNA arms to be generated in vivo following infection with a modified viral vector could greatly increase the quality and titer of the libraries (e.g. vaccinia virus cDNA or other libraries) that are constructed using these methods.

Transfer of cDNA Inserts from a Bacteriophage Lambda Library to Vaccinia Virus. Lambda phage vectors have several advantages over plasmid vectors for construction of cDNA libraries or other libraries. Plasmid libraries (e.g. cDNA or other DNA insert) or linear polynucleotide (e.g. DNA) libraries are introduced into bacterial cells by chemical/heat shock transformation, or by electroporation. Bacterial cells are often transformed preferentially by smaller plasmids, resulting in a potential loss of representation of longer polynucleotides (e.g., cDNA or other insert DNA) in a library. In addition, transformation is a relatively inefficient process for introducing foreign polynucleotides (e.g., cDNA or other insert DNA) into a cell requiring the use of expensive commercially prepared competent bacteria in order to construct a library (e.g. a cDNA library).

In contrast, lambda phage vectors can tolerate polynucleotide inserts (e.g., cDNA or other insert DNA) of 12 kilobases or more without any size bias. Lambda vectors are packaged into virions in vitro using high efficiency commercially available packaging extracts so that the recombinant viral (lambda) genomes can be introduced into bacterial cells by infection. This results in primary libraries with higher titers and better representation of large polynucleotide (e.g. cDNA or DNA) inserts than is commonly obtained in plasmid libraries.

To enable transfer of polynucleotide inserts (e.g. cDNA inserts or other inserts) from a library constructed in a lambda vector to vaccinia virus, the lambda vector must be modified to include vaccinia virus DNA sequences that allow for homologous recombination with the vaccinia virus DNA. For example, the vaccinia virus HindIII J fragment (vaccinia tk gene) contained in plasmid p7.5/ATG0/tk can be excised using HindIII and SnaBI (3 kb of vaccinia DNA sequence), and subcloned into the HindIII/SnaBI sites of pT7Blue3 (Novagen cat no. 70025–3) creating pT7B3.Vtk. The vaccinia tk gene can be excised from this vector with SacI and SnaBI and inserted into the SacI/SmaI sites of Lambda Zap Express (Stratagene) to create lambda.Vtk. The lambda.Vtk vector will contain unique NotI, BamHI, SmaI, and SalI sites for insertion of EDNA downstream of the vaccinia 7.5 k promoter. Libraries (e.g., cDNA or other DNA libraries) can be constructed in lambda.Vtk employing methods that are well known in the art.

DNA from a library (e.g. cDNA or other library) constructed in lambda. Vtk, or any similar bacteriophage that includes polynucleotide (e.g. cDNA inserts or other insert DNA) with flanking vaccinia DNA sequences to promote homologous recombination, can be employed to generate cDNA (or other insert DNA or polynucleotide) recombinant vaccinia virus. Methods are well known in the art for excising a plasmid from the lambda genome by coinfection with a helper phage (ExAssist phage, Stratagene cat no. 211203). Mass excision from a lambda based library creates an equivalent library (e.g. cDNA or other library) in a plasmid vector. Plasmids excised from, for example, the lambda.Vtk polynucleotide (e.g. cDNA) library will contain the vaccinia tk sequences flanking the polynucleotide (e.g.

cDNA or other DNA) inserts. This plasmid DNA can then be used to construct vaccinia recombinants by trimolecular recombination.

Another embodiment of this method is to purify the lambda DNA directly from the initial lambda.Vtk library, and to transfect this recombinant viral (lambda) DNA or fragments thereof together with the two large vaccinia virus DNA fragments for trimolecular recombination.

Generation of vaccinia arms in vivo. Purification and transfection of vaccinia DNA "arms" or fragments are a limiting factor in the construction of vaccinia libraries (e.g. cDNA or other libraries) by trimolecular recombination. Modifications to the method to allow for the requisite generation of vaccinia arms in vivo would allow for more efficient construction of larger libraries (e.g. cDNA or other libraries) in vaccinia virus.

Cells (e.g. packaging or host cells) can be modified to express a restriction endonuclease that recognizes a unique site introduced into the vaccinia virus genome. When vaccinia virus infects these cells (e.g. packaging or host cells) the restriction endonuclease will digest the vaccinia DNA, generating "arms" that can only be repaired, i.e., rejoined, by trimolecular recombination. Examples of restriction endonucleases include the bacterial enzymes NotI and ApaI, the Yeast endonuclease VDE (R. Hirata, Y. Ohsumi, A. Nakano, H. Kawasaki, K. Suzuki, Y. Anraku. 1990 *J. Biological Chemistry* 265: 6726–6733), the *Chlamydomonas eugametos* endonuclease I-CeuI and others well-known in the art. For example, a vaccinia strain containing unique NotI and ApaI sites in the tk gene has already been constructed, and a strain containing unique VDE and/or I-CeuI sites in the tk gene could be readily constructed by methods known in the art.

Constitutive expression of a restriction endonuclease would be lethal to a cell, due to the fragmentation of the chromosomal DNA by that enzyme. To avoid this complication, in one embodiment cells (e.g. packaging or host cells) are modified to express the gene(s) for the restriction endonuclease(s) under the control of an inducible promoter. A preferred method for inducible expression would utilize the Tet-On Gene Expression System (Clontech). In this system expression of the gene encoding the endonuclease is silent in the absence of an inducer (tetracycline). This makes it possible to isolate a stably transfected cell line that can be induced to express a toxic gene, i.e., the endonuclease (Gossen, M. et al., *Science* 268: 1766–1769 (1995)). The addition of the tetracycline derivative doxycycline induces expression of the endonuclease. In a preferred embodiment, BSC1 cells (e.g. packaging or host cells) will be stably transfected with the Tet-On vector controlling expression of the NotI gene. Confluent monolayers of these cells will be induced with doxycycline and then infected with v7.5/tk (unique NotI site in tk gene), and transfected with polynucleotide (e.g. cDNA or DNA) recombinant transfer plasmid or transfer polynucleotide (e.g. transfer DNA) or lambda phage or phagemid DNA. Digestion of exposed vaccinia DNA at the unique NotI site, for example in the tk gene or other sequence, by the NotI endonuclease encoded in the host cells produces two large vaccinia DNA fragments which can give rise to full-length viral DNA only by undergoing trimolecular recombination with the transfer polynucleotide, transfer plasmid or phage DNA. Digestion of host cell chromosomal DNA by NotI is not expected to prevent production of infectious viral recombinants because the host cells are not required to proliferate during viral replication and virion assembly.

In another embodiment of this method to generate vaccinia arms in vivo, a vaccinia strain is constructed that contains a unique endonuclease site in the tk gene or other sequence and the cDNA encoding the endonuclease under the control of the T7 bacteriophage promoter at another site in the vaccinia genome. Infection of cells that express the T7 RNA polymerase would result in expression of the endonuclease, and subsequent digestion of the vaccinia DNA by the endonuclease.

In a preferred embodiment, the endonuclease is NotI. In another preferred embodiment, the v7.5/tk strain of vaccinia is modified by insertion of a cassette containing the cDNA encoding NotI with expression controlled by the T7 promoter into the HindIII C or F region (Coupar, E. H. B. et al., *Gene* 68: 1–10 (1988); Flexner, C. et al., *Nature* 330: 259–262 (1987)), generating v7.5/tk/T7NotI. A cell line is stably transfected with the cDNA encoding the T7 RNA polymerase under the control of a mammalian promoter as described (O. Elroy-Stein, B. Moss. 1990 *Proc. Natl. Acad. Sci. USA* 87: 6743–6747). Infection of this cell line (e.g. packaging cell line) with v7.5/tk/T7NotI will result in T7 RNA polymerase dependent expression of NotI, and subsequent digestion of the vaccinia DNA into arms. Infectious full-length viral DNA can only be reconstituted and packaged from the digested vaccinia DNA arms following trimolecular recombination with a transfer plasmid or phage DNA.

In yet another embodiment of this method, the T7 RNA polymerase can be provided by co-infection with a T7 RNA polymerase recombinant helper virus, such as fowlpox virus (P. Britton, P. Green, S. Kottier, K. L. Mawditt, Z. Penzes, D. Cavanagh, M. A. Skinner. 1996 *J. General Virology* 77: 963–967).

A unique feature of trimolecular recombination employing these various strategies for generation of large vaccinia DNA fragments in vivo is that digestion of the vaccinia DNA may but does not need to precede recombination. It suffices that only recombinant virus escapes destruction by digestion. This contrasts with trimolecular recombination employing transfection of vaccinia DNA digested in vitro where, of necessity, vaccinia DNA fragments are created prior to recombination. It is possible that the opportunity for bimolecular recombination prior to digestion will yield a greater frequency of recombinants than can be obtained through trimolecular recombination following digestion.

Production of a Library Using a Poxvirus Vector Such as Vaccinia Virus

In one embodiment, the trimolecular recombination method is used in the production of a library, preferably an expression library. In this embodiment, a cDNA library is prepared by extracting total RNA, mRNA, size-fractionated RNA, etc. from a cell, synthesizing a series of complementary double-stranded cDNA fragments from the RNA and introducing these cDNA fragments into cells in tissue culture, by, for example, first cloning the fragments into a vector, preferably a poxvirus vector. The cells are maintained under conditions which allow them to express the protein, or alternatively only the transcript, encoded by the cDNA.

Alternatively, the tri-molecular recombination method is used to produce a genomic library or a combinatorial library The methods of the invention are applicable to a wide variety of libraries including mixtures of cDNAs cloned in sense or anti-sense orientation, mixtures of fragments of genomic DNA or cDNA, fragments of individual cDNAs and mixtures of artificial sequences. Libraries include combinatorial libraries made up of natural and/or artificial sequences. In a preferred embodiment, the library is an expression library. Libraries may comprise a plurality of insert polynucleotides (e.g. DNAs). The insert polynucleotides (e.g. DNAs) may comprise any DNA or other polynucleotide segment as described above.

By "cDNA" is meant complementary or copy DNA produced from an RNA template by the action of RNA-dependent DNA polymerase (reverse transcriptase). Thus a "cDNA clone" means a duplex DNA sequence complementary to an RNA molecule of interest, carried in a cloning vector. The cDNA may be from mRNA, a portion of a mRNA, a pre-mRNA including introns, or an intron. Alternatively, the cDNA may be from viral RNA. Molecular cloning methods for ds cDNA have been reviewed, for example, by Williams, "The Preparation and Screening of a cDNA Clone Bank," in Williamson, ed., Genetic Engineering, Vol. 1, p. 2, Academic Press, New York (1981); Maniatis, "Recombinant DNA", in Prescott, ed., Cell Biology, Academic Press, New York (1980); and Efstratiadis et al., "Cloning of Double-Stranded DNA," in Stelo et al., Genetic Engineering, Vol. 1, p. 15, Plenum Press, New York (1979).

By "cDNA library" is meant a collection of recombinant DNA molecules containing cDNA inserts which together comprise all or a portion of the genome of an organism. Such a cDNA library may be prepared by art-recognized methods described, for example, in Maniatis et al., *Molecular Cloning: A Laboratory Manual*, supra. Generally, RNA is first isolated from the cells of an organism from whose genome it is desired to clone a particular gene. Preferred for the purposes of the present invention are animal cells, including insect cells, mammalian cells, and particularly human cells, or cell lines derived from these organisms. Alternatively, RNA can be isolated from a tumor cell derived from an animal tumor, and preferably from a human tumor. Thus, a library may be prepared from, for example, a human adrenal tumor, but any tumor may be used.

By "expression library" is meant a recombinant vector in which insert polynucleotide (e.g. DNA) is cloned and which allows expression of at least RNA, and preferably also expression of protein encoded by the insert polynucleotide (e.g. DNA).

The insert polynucleotide (e.g. DNA) may be cloned in two vectors for producing a transfer plasmid containing a polynucleotide (e.g. DNA) insert in each of two orientations. The invention also provides a kit for producing a transcription expression library comprising poxvirus and two transfer plasmids for inserting polynucleotide (e.g. DNA) in each orientation. In another embodiment, the invention provides a kit for producing a protein expression library comprising a vaccinia virus genome or two fragments thereof, and three vectors for producing a transfer plasmid containing a polynucleotide (e.g. DNA) insert in each of three translation reading frames.

The tri-molecular recombination method allows the use of vaccinia virus as a high efficiency cloning vector suitable for producing libraries. As such, vaccinia virus now may be used to identify previously unknown genes of interest from a complex population of clones, such as a cDNA or other library. Further, its ability to replicate in nondividing cells and its potential to express proteins at a high level in nondividing cells allows vaccinia virus to be used for cloning and isolating sequences that positively or negatively affect growth, differentiation, or cell viability.

Thus, in one embodiment, the invention provides a method of producing a library in nondividing cells comprising the trimolecular recombination method. Nondividing cells include terminally differentiated cells. Nondividing cells include musculoskeletal cells such as, for example, chondrocytes, osteoblast, osteoclasts, and myocytes. Other examples of nondividing cells are fully differentiated blood and epidermal cells, neurons, glial cells, kidney and liver cells.

In a preferred embodiment, the library is produced in a cell line which efficiently produces recombinant vector, such as BSC-1 or HeLa cells for libraries cloned in vaccinia virus, and the progeny recombinant vector population is transferred to a second population of cells in which the direct or indirect selection method is used. The library may be amplified by several passages in the efficient cell line before the direct or indirect selection method is used in the cell line in which the insert polynucleotide is functionally selected.

In another embodiment, the invention provides a method of isolating an insert polynucleotide in a cell which is dead or which has ceased dividing. For example, the present inventor has used the tri-molecular recombination method to select polynucleotides encoding a target epitope recognized by particular cytotoxic T lymphocytes (CTLs). (See Examples 3 and 4.) In this experiment, monolayer of calls was infected with a complex library produced using tri-molecular recombination, the monolayer was incubated under conditions allowing expression of the target epitope, and epitope-specific CTLs were added to the cell monolayer. After CTL-mediated induction of lysis in cells expressing the target epitope, vaccinia virus DNA was recovered from cells that had become nonadherent or that had lysed.

Selection of Non-Viable Cells Infected with a cDNA Library Constructed in Adenovirus, Herpesvirus or Other Vectors Herpesvirus. A method has been described for the generation of helper virus free stocks of recombinant, infectious Herpes Simplex Virus amplicons (T. A. Stavropoulos, and C. A. Strathdee. *J. Virology* 72:7137–7143 (1998)). A polynucleotide library (e.g. cDNA or other library) constructed in such a plasmid amplicon vector could be packaged into a library of infectious amplicon particles using this method. Such a library could be employed in the indirect or direct selection methods (e.g. lethality/adherence based selection methods) of this invention. For example, a library (e.g. cDNA or other library) constructed in a herpes amplicon vector could be used to infect a monolayer of target cells. Then, for example, tumor specific CTL added to this infected monolayer would induce lysis of cells that express polynucleotides (e.g. cDNA or other DNA) encoding the target antigen. Amplicons recombinant for such polynucleotides (e.g. cDNA or other DNA) might then be recovered from non-viable cells released from the monolayer. However, since in the absence of helper virus the amplicons are replication defective and are not packaged into infectious particles, the amplicon vector recovered from these selected cells could not be employed directly to infect fresh target cells for another cycle of selection. It would be necessary to recover the amplicon vector DNA for transformation into bacteria. Amplicon plasmid DNA could then be re-extracted from bacteria following antibiotic selection and packaged into infectious viral particles by cotransfection of amplicon DNA and packaging defective HSV genomic DNA into packaging cells. The infectious amplicon particles harvested could then be used to infect a fresh population of target cells for another round of selection. A more rapid means of recovering infectious amplicons would be, for example, to transfect cells employed as targets for CTL selection with the packaging defective HSV genomic DNA. This would, however, severely restrict the functional host range for selection to a few highly transfectable cell lines, i.e. Cos 7 and 293 cells.

Adenovirus. Methods have been described for the production of recombinant Adenovirus (Miyake, S. et al., *Proc. Natl. Acad. Sci. USA* 93: 1320–1324 (1996); He, T. C. et al., *Proc. Natl. Acad. Sci. USA* 95: 2509–2514 (1998)). Although current methods yield relatively low viral titers and construction of a representative (e.g. cDNA) library in adenovirus has not been reported, it is possible that a cDNA library or other library could be constructed in an Adenovirus vector using either of these methods. Insertion of cDNA or other insert polynucleotide (e.g. DNA) into the E4 region of Adenovirus results in a replication competent recombinant virus. Such a library could be employed in the direct (e.g. lethality/adherence based) and indirect selection methods of this invention.

For example, a tumor cDNA library constructed in an adenovirus vector could be used to infect a monolayer of target (e.g. host) cells. Tumor specific CTL added to this infected monolayer would induce lysis of cells that express cDNA recombinants encoding the target antigen. Adenovirus recombinants for the cDNA encoding the target antigen recognized by CTL could then be recovered from cells released from the monolayer as described for selection from a vaccinia virus cDNA library. The virus recovered from the selected cells is infectious and could be employed for additional cycles of selection.

Advantages of Vaccinia Virus. In comparison with either herpesvirus or adenovirus, there are significant advantages to vaccinia virus based vectors for the construction and manipulation of libraries, preferably representative and other cDNA libraries. Employing current technology, the titers that have been reported for primary adenoviral constructs are relatively low compared to what can be achieved through trimolecular recombination with vaccinia virus. Although not being bound by any theories, there are a number of factors that may contribute to the high titers obtained for recombinant vaccinia virus using the tri-molecular recombination method. Vaccinia virus, because it replicates in the cytoplasm of the host cell, may undergo more frequent recombination events with transfer DNA than other mammalian DNA viruses like adenovirus and herpesvirus, which replicate in the nucleus and are presumed to require translocation of transfer plasmids to the nucleus for recombination. The frequency of transfer plasmid recombination events in vaccinia virus infected cells may be further enhanced because vaccinia virus, but not adenovirus or herpesvirus, replicates plasmids in the cytoplasm in a sequence independent manner (M. Merchlinsky, B. Moss. *Cancer Cells* 6: 87–93 (1988). Although higher titer libraries can be constructed in the herpes amplicon vector than in adenovirus, manipulation of these libraries is, as described above, hampered by the complexity of packaging infectious amplicons. These technical issues no doubt account for the fact that there has to date been no reported use of the current methods to construct a cDNA library in either adenovirus or herpesvirus based vectors.

Method of Selecting a Target Polynucleotide from a Population

In addition to selecting a target epitope, the invention provides a method of selecting target polynucleotides, directly or indirectly, based on a phenotype such as nonadherence or nonviability. Thus, in one embodiment, the invention provides a method of directly selecting a target polynucleotide comprising: (a) providing a plurality of cells which comprise vector comprising insert polynucleotides, and (b) culturing the cells under conditions such that the insert polynucleotides are expressed and wherein a cell expressing a target polynucleotide becomes nonadherent, (c) collecting or removing the nonadherent cell or cell contents, thereby directly selecting the target polynucleotide.

Alternatively, polynucleotides may be selected based on a phenotype such as adherence or viability, or another phenotype, as is further described herein.

In further embodiments, the invention provides a method of selecting target polynucleotides based on any altered phenotype. By "altered phenotype" or "changed physiology" or other grammatical equivalents herein is meant that the phenotype of the cell is altered in some way, preferably in some detectable and/or measurable way. As will be appreciated in the art, a strength of the present invention is the wide variety of cell types and potential phenotypic changes which may be tested using the present methods. Accordingly, as described above, any phenotypic change which may be observed, detected, or measured may be the basis of the screening methods herein.

Suitable phenotypic changes include, but are not limited to: gross physical changes such as changes in cell morphology, cell growth, cell viability, adhesion to substrates or other cells, and cellular density; changes in the expression of one or more RNAs, proteins, lipids, hormones, cytokines, or other molecules; changes in the equilibrium state (i.e. half-life) or one or more RNAs, proteins, lipids, hormones, cytokines, or other molecules; changes in the localization of one or more RNAs, proteins, lipids, hormones, cytokines, or other molecules; changes in the bioactivity or specific activity of one or more RNAs, proteins, lipids, hormones, cytokines, receptors, or other molecules; changes in the secretion of ions, cytokines, hormones, growth factors, or other molecules; alterations in cellular membrane potentials, polarization, integrity or transport; changes in infectivity, susceptibility, latency, adhesion, and uptake of viruses and bacterial pathogens; etc. By "capable of altering the phenotype" herein is meant that the target polynucleotide can change the phenotype of the cell in some detectable and/or measurable way. See, e.g., below, and Example 24.

An altered phenotype may be detected by any method known in the art, such as expression of a marker (e.g. indicator) gene. An indicator/marker gene includes an epitope, sometimes called an antigen TAG, an enzyme (such as one that generates a novel or chromogenic product), a selectable marker, or a fluorescent molecule, such as green fluorescent protein (GFP), blue fluorescent protein (BFP), yellow fluorescent protein (YFP), red fluorescent protein (RFP), luciferase, β-galactosidase, and CAT, and others disclosed herein or known in the art. When antigen TAGs are used, preferred embodiments utilize cell surface antigens. The epitope is preferably any detectable peptide which is not generally found on the cytoplasmic membrane, although in some instances, if the epitope is one normally found on the cells, increases may be detected, although this is generally not preferred.

An altered phenotype may also be detected by FACS as described herein, by optical properties, such as inherent optical properties, or those resulting from dyes, etc., and other detection methods, such as binding of an antibody, ligand, etc., as described herein. Such an antibody, ligand, etc., may be labeled or may be conjugated to a toxin. Many other methods for detecting an altered phenotype are well known in the art, and may also be described herein.

A target polynucleotide may alter a phenotype of a cell comprising said target polynucleotide. Alternatively, a target polynucleotide may alter a phenotype of a second cell (i.e. an indicator cell) as described elsewhere herein. When the phenotype of a second cell is altered, it may be preferable to divide the host cells into pools which also comprise the indicator cells. Then insert polynucleotides are collected from those pools in which an altered phenotype of an indicator cell is detected.

The selection methods include one or a combination of the modifications, uses, and other embodiments described herein and also provide for the exclusion of any one or more modifications, uses and other embodiments. For example, the invention provides a method for selection based on immunological methods which include antibody-based methods, but which exclude CD8+ CTL-based methods. As another example, the method may include selection of DNA inserts in dividing cells, but exclude selection in tumor cells. As yet another example, the selection method may include mechanisms based on nonadherence, but exclude nonadherence due to lysis. As a further example, the selection method may include direct selection, but exclude CTL-mediated selection.

Preferably, the plurality of cells comprise a library. Thus, the "vector comprising insert polynucleotides" is preferably a plurality of insert polynucleotides which represent a library, and which is cloned in a vector. Alternatively, the plurality of cells may contain a single type of insert polynucleotide cloned in a vector, i.e., the plurality of cells represents a single "clone." Preferably, at least one of the insert polynucleotides is a target polynucleotide, i.e., a polynucleotide of interest, which is selectable by at least one direct selection method of the invention. As mentioned above, "insert polynucleotides" may also be referred to herein as "candidate polynucleotides" or other grammatical equivalents.

In the embodiment wherein the plurality of cells comprise a library, the library may be any type of library such as cDNA, genomic DNA, combinatorial, etc., as described elsewhere herein or otherwise known in the art. The insert polynucleotides may be natural or synthetic or a mixture of natural and synthetic products. They may be generated, for example, in vivo or in vitro, enzymatically, or chemically. The insert polynucleotides may be from any source such as a cell line, a biological sample, a patient sample, etc. Preferably, the insert polynucleotides are cloned in vaccinia virus. Preferably, the insert polynucleotide is one or a plurality of products of tri-molecular recombination, including progeny thereof, preferably infectious progeny.

The methods herein are applicable to a wide variety of expression libraries including mixtures of cDNAs cloned in sense or anti-sense orientation, mixtures of fragments of genomic DNA or cDNA or both, fragments of individual cDNAs and mixtures of artificial sequences. The insert polynucleotide (e.g. DNA) may be cloned in each of two orientations or may be cloned in each of three translation reading frames. Preferably, the insert polynucleotides are operably associated with strong constitutive expression control sequences, preferably strong constitutive poxvirus promoters such as the 7.5K vaccinia virus promoter or a strong synthetic early/late (E/L) promoter.

By "host cell" or "recipient cell" or "library cell" is meant a cell or plurality of cells into which DNA is introduced for the tri-molecular recombination method or a direct or indirect selection method described below. Preferably, the host cells adhere to a solid support. However, normally nonadherent cells and cell types may be made to adhere to a solid support by use of a molecule such as a protein, an antibody, or poly L-lysine on the surface of the solid support. Other means for attaching cells to a solid support are well known in the art. The host cells may also comprise packaging function. Host cells are eukaryotic cells or cell lines, preferably animal, vertebrate, mammalian, or human cells or cell lines. Host cells may be cells derived from primary tumors, cells derived from metastatic tumors, primary cells, cells which have lost contact inhibition, transformed primary cells, immortalized primary cells, cells which may undergo apoptosis, and cell lines derived therefrom.

Cells and cells lines for use as host or recipient or library cells according to the present invention include those disclosed in scientific literature such as American Type Culture Collection publications including American Type Culture Collection Catalogue of Cell Lines and Hybridomas, 7th ed., ATCC, Rockville, Md. (1992) and subsequent editions, which list deposited cell lines as well as culture conditions and additional references.

For example, host cells according to the present invention include the monkey kidney cell line, designated "COS," including COS cell clone M6. COS cells are those that have been transformed by SV40 DNA containing a functional early gene region but a defective origin of viral DNA replication. Also preferred are murine "WOP" cells, which are NIH 3T3 cells transfected with polyoma origin deletion DNA.

Other examples of host cells for use in the disclosed methods are monkey kidney CVI line transformed by SV40 (COS-7, ATCC CRL 165 1); human embryonic kidney line (293, Graham et al. J. Gen Virol. 36:59 (1977)); baby hamster kidney cells (BHK, ATCC CCL 10); chinese hamster ovary-cells-DHFR (CHO, Urlaub and Chasin, *Proc. Natl. Acad. Sci.* (*USA*) 77:4216, (1980); mouse sertoli cells (TM4, Mather, *Biol. Reprod.* 23:243–251 (1980)); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells (Mather et al., Annals N.Y. Acad. Sci 383:44–68 (1982)); human B cells (Daudi, ATCC CCL 213); human T cells (MOLT-4, ATCC CRL 1582); and human macrophage cells (U-937, ATCC CRL 1593).

Preferred cell types for use in the invention will vary with the cellular phenotype to be modulated. Suitable cells include, but are not limited to, mammalian cells, including animal (rodents, including mice, rats, hamsters and gerbils), primates, and human cells, particularly including tumor cells of all types, including breast, skin, lung, cervix, colorectal, leukemia, brain, etc.

The murine stem cell line RAW (Hsu, H. et al., Proc Natl Acad Sci USA 96(7):3540–45 (1999); Owens, J. M. et al., *J Cell Physiol* 179:170 (1999)) and pluripotent stem cell line C3H10T1/2 (Denker, A. et al., *Differentiation* 64, 67–76 (1999)) are especially preferred for studies of osteoclast and chondrocyte or osteoblast differentiation.

However, the choice of cells or cell lines is not limited to those described herein, and may be any cell or cell line. As indicated below, the choice depends on the system under study, or the particular polynucleotide which is desired to be isolated. For example, to select or isolate an epitope recognized by a human $CD8^+$ CTL, it is preferable to use a host cell which expresses human class I MHC molecules, and to select or isolate an epitope recognized by a human $CD4^+$ CTL, it is preferable to use a host cell which expresses or can be induced to express human class II MHC molecules, to allow the CTL to recognize the encoded epitope in association with the appropriate MHC molecules. As another example, to select or isolate a polynucleotide which is growth suppressive or toxic in breast cancer, it is preferable to use as host cells breast cancer cell lines such as 21NT, 21PT, 21MT-1, AND 21MT-2. Band et al., *Cancer Res.* 50:7351–7 (1990). Once a growth suppressive polynucleotide is isolated, it may be tested in non transformed controls, such as normal breast epithelial cell line H16N2, to determine whether its growth suppressive activity is specific for tumor cells.

Many cell types can be used in the selection method of the invention. Cells include dividing cells, non dividing cells, terminally differentiated cells, pluripotent stem cells, committed progenitor cells and uncommitted stem cells.

Cells and cell types also include muscle cells such as cardiac muscle cells, skeletal muscle cells and smooth muscle cells; epithelial cells such as squamous epithelial cells, including endothelial cells, cuboid epithelial cells and columnar epithelial cells; nervous tissue cells such as neurons and neuroglia. Also included are progenitor cells of each of these cells.

Cells that can be used in the selection method of the present invention also include nervous system cells such as neurons, including cortical neurons, inter neurons, central effector neurons, peripheral effector neurons and bipolar neurons;

and neuroglia, including Schwann cells, oligodendrocytes, astrocytes, microglia and ependyma. Also included are progenitor cells of each of these cells.

Additionally, endocrine and endocrine-associated cells may also be used such cells as pituitary gland cells including epithelial cells, pituicytes, neuroglia, agranular chromophobes, granular chromophils (acidophils and basophils); adrenal gland cells including epinephrine-secreting cells, non-epinephrine-secreting cells, medullary cells, cortical cells (cells of the glomerulosa, fasciculata and reticularis); thyroid gland cells including epithelial cells (principal and parafollicular); parathyroid gland cells including epithelial cells (chief cells and oxyphils); pancreas cells including cells of the islets of Langerhans (alpha, beta and delta cells); pineal gland cells including parenchymal cells and neuroglial cells; thymus cells including parafollulicular cells; cells of the testes including seminiferous tubule cells, interstitial cells ("Leydig cells"), spermatogonia, spermatocytes (primary and secondary), spermatids, spermatozoa, Sertoli cells and myoid cells; cells of the ovary including ova, oogonia, oocytes, granulosa cells, theca cells (internal and external), germinal epithelial cells and follicle cells (primordial, vesicular, mature and atretic). Also included are progenitor cells of each of these cells.

Also included are muscle cells such as myofibrils, intrafusal fibers and extrafusal fibers; skeletal system cells such as osteoblasts, osteocytes, osteoclasts and their progenitor cells. Also included are progenitor cells of each of these cells.

Circulatory system cells are also included such as heart cells (myocardial cells); cells of the blood and lymph including erythropoietin-sensitive stem cells, erythrocytes, leukocytes (such as eosinophils, basophils and neutrophils (granular cells) and lymphocytes and monocytes (agranular cells)), thrombocytes, tissue macrophages (histiocytes), organ-specific phagocytes (such as Kupffer cells, alveolar macrophages and microglia), B-lymphocytes, T-lymphocytes (such as cytotoxic T cells, helper T cells and suppressor T cells), megaloblasts, monoblasts, myeloblasts, lymphoblasts, proerythroblasts, megakaryoblasts, promonocytes, promyelocytes, prolymphocytes, early normoblasts, megakaryocytes, intermediate normoblasts, metamyelocytes (such as juvenile metamyelocytes, segmented metamyelocytes and polymorphonuclear granulocytes), late normoblasts, reticulocytes, bone marrow cells, and dendritic cells (such as mature, immature, etc). Also included are progenitor cells of each of these cells.

Respiratory system cells are also included such as capillary endothelial cells and alveolar cells; as are urinary system cells such as nephrons, capillary endothelial cells, granular cells, tubule endothelial cells and podocytes; digestive system such as simple columnar epithelial cells, mucosal cells, acinar cells, parietal cells, chief cells, zymogen cells, peptic cells, enterochromaffin cells, goblet cells, Argentaffen cells and G cells; and sensory cells such as auditory system cells (hair cells); olfactory system cells such as olfactory receptor cells and columnar epithelial cells; equilibrium/vestibular apparatus cells including hair cells and supporting cells; visual system cells including pigment cells, epithelial cells, photoreceptor neurons (rods and cones), ganglion cells, amacrine cells, bipolar cells and horizontal cells are also included. Also included are progenitor cells of each of these cells.

Additionally, mesenchymal cells, stromal cells, fibroblasts, hair cells/follicles, adipose (fat) cells, cells of simple epithelial tissues (squamous epithelium, cuboidal epithelium, columnar epithelium, ciliated columnar epithelium and pseudostratified ciliated columnar epithelium), cells of stratified epithelial tissues (stratified squamous epithelium (keratinized and non-keratinized), stratified cuboidal epithelium and transitional epithelium), goblet cells, endothelial cells of the mesentery, endothelial cells of the small intestine, endothelial cells of the large intestine, endothelial cells of the vasculature capillaries, endothelial cells of the microvasculature, endothelial cells of the arteries, endothelial cells of the arterioles, endothelial cells of the veins, endothelial cells of the venules, etc.;cells of the connective tissue include chondrocytes, adipose cells, periosteal cells, endosteal cells, odontoblasts, osteoblasts, osteoclasts and osteocytes; endothelial cells, hepatocytes, keratinocytes and basal keratinocytes, muscle cells, cells of the central and peripheral nervous systems, prostate cells, and lung cells, cells in the lung, breast, pancreas, stomach, small intestine, and large intestine; epithelial cells such as sebocytes, hair follicles, hepatocytes, type II pneumocytes, mucin-producing goblet cells, and other epithelial cells and their progenitors of the skin, lung, liver, and gastrointestinal tract may be used in the methods of the present invention, preferably the selection and screening methods. Also included are progenitor cells of each of these cells.

Cells useful in the inventions herein also include progenitor cells of all the cells above and elsewhere herein.

By a "plurality" or "population" or "library" of cells is meant at least two cells, with at least about $10^3$, $10^4$, $10^5$, $10^6$, $10^7$, $10^8$, $10^9$ being particularly preferred. The plurality or population can contain a mixture of different cell types from either primary or secondary cultures although samples containing only a single cell type are preferred, for example, the population can be from a cell line, including tumor cell lines. The cells may be in any cell phase, either synchronous or not, including M, G1, S, and G2. In a preferred embodiment, cells that are replicating or proliferating are used. Alternatively, non-replicating cells may be used.

By "solid support" is meant any support capable of binding a cell, which may be in any of various forms, as is known in the art. Well-known supports include tissue culture plastic, glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration as long as the coupled molecule is capable of binding to a cell. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. The support configuration may include a tube, bead, microbead, well, plate, tissue culture plate, petri plate, microplate, microtiter plate, flask, stick, strip, vial, paddle, etc., etc. A solid support may be magnetic or non-magnetic. Those skilled in the art will know many other suitable carriers for binding cells, or will be able to readily ascertain the same.

Cells may be directly or indirectly bound to a solid support, as is well known in the art. For example, cells may be indirectly attached via one or more molecules such as protein, antibody, receptor, ligand, poly L-lysine, or may be indirectly attached via other cells. In one embodiment, cells are attached to a solid support via antibody. In a preferred embodiment, the cells are attached to a magnetic solid support, such as magnetic beads, via antibody. (See, for example, Dynal Technical Handbook, "Biomagnetic Techniques in Molecular Biology", 1995.)

By "tissue culture" or "cell culture" or "culture" or "culturing" is meant the maintenance or growth of animal tissue or cells in vitro under conditions that allow preservation of cell architecture, preservation of cell function, further differentiation, or all three, as well as permitting expression of insert polynucleotides. "Primary tissue cells" are those taken directly from tissue, i.e., a population of cells of the same kind performing the same function in an organism. Treating such tissue cells with the proteolytic enzyme trypsin, for example, dissociates them into individual primary tissue cells that grow or maintain cell architecture when seeded onto culture plates. Cell cultures arising from multiplication of primary cells in tissue culture are called "secondary cell cultures." Most secondary cells divide a finite number of times and then die. A few secondary cells, however, may pass through this "crisis period," after which they are able to multiply indefinitely to form a continuous "cell line."

A recipient cell containing a target polynucleotide may become "nonadherent" or "nonviable" by any mechanism, which may include lysis, inability to adhere, loss of viability, loss of membrane integrity, loss of structural stability, disruption of cytoskeletal elements, inability to maintain membrane potential, arrest of cell cycle, inability to generate energy, etc. Thus, cells containing target polynucleotides may be collected, i.e., recovered or separated from remaining cells, by any physical means such as aspiration, washing, filtration, centrifugation, cell sorting, fluorescence activated cell sorting (FACS), etc. Collected cells or polynucleotides may also be referred to herein as "recovered" cells or polynucleotides, or as "isolated" cells or polynucleotides.

For example, cells containing target polynucleotides may lyse and thereby release recombinant vaccinia into the culture media or may become nonadherent and therefore lift away from the solid support. Thus, in a preferred embodiment, released recombinant vaccinia and/or nonadherent cells are separated from adherent cells by aspiration or washing of the liquid medium, e.g. culture medium.

In another embodiment, a recipient cell containing a target polynucleotide may become "adherent" or "viable" by any mechanism. In this embodiment, host cells which do not contain a target polynucleotide undergo lysis, are unable to adhere, are not viable in culture, lose membrane integrity, lose structural stability, become disrupted in their cytoskeletal elements, are unable to maintain membrane potential, are arrested in cell cycle, are unable to generate energy, etc. Cells containing a target polynucleotide fail to lyse, do adhere, remain viable, retain or gain membrane integrity, retain or gain structural stability, retain or gain cytoskeletal elements, maintain or gain membrane potential, are not growth cycle arrested, or generate energy, etc. Thus, cells not containing target polynucleotides, or their contents, may be removed from those containing target polynucleotides by any physical means of separation such as aspiration, washing, filtration, centrifugation, cell sorting, fluorescence activated cell sorting (FACS), etc. For example, cells which do not contain a target polynucleotide may be removed from the cells which do contain a target polynucleotide by washing or aspiration. The remaining cells containing target polynucleotides are then collected.

Method of Enriching for Target Polynucleotides

The methods of the invention are useful to enrich for target polynucleotides from a plurality of test polynucleotides, such as a complex library including cDNA and other libraries.

A single round of direct or indirect selection may not necessarily result in isolation of a pure set of target polynucleotides; the mixture obtained after a first round may be enriched for the desired polynucleotides but may also be contaminated with non-target insert sequences. For example, selection of cytotoxic and cytostatic target polynucleotides may require or benefit by several rounds of selection, which thus increase the proportion of cells containing target polynucleotides. To achieve increased purification, the material obtained after the first round is used to infect a second population of cells and the resulting sublibrary is subjected to a second round of selection.

Thus, in this embodiment, the invention provides a method of producing a subpopulation of target polynucleotides comprising the direct or indirect selection method, and further comprising: isolating target polynucleotides from the selected (e.g. nonviable) cells, introducing the target polynucleotides into a second plurality of host cells, and separating the selected cells (e.g. non-viable or contents thereof). In yet a further embodiment, the method comprises additional rounds of infection of new host cells and direct or indirect selection. Thus, the method provides multiple rounds of enrichment to produce subpopulations, or sublibraries, which comprise a progressively decreasing ratio of nontarget polynucleotides, i.e., decreased background.

Following collection of the target polynucleotides as described above and elsewhere herein, or following enrichment of the target polynucleotides from the library as described above, those polynucleotides which have been recovered are "isolated," i.e., they are substantially removed from their native environment and are largely separated from polynucleotides in the library which do not encode antigen-specific immunoglobulin subunit polypeptides. For example, cloned polynucleotides (i.e. insert polynucleotides) contained in a vector are considered isolated for the purposes of the present invention. It is understood that two or more different polynucleotides which effect the same or similar phenotype may be collected or recovered by the methods described herein. Accordingly, a mixture of target polynucleotides is also considered to be "isolated." Further examples of isolated polynucleotides include those maintained in heterologous host cells or purified (partially or substantially) DNA molecules in solution. For example, a polynucleotide contained in a virus vector is "isolated" after it has been recovered and plaque purified, and a polynucleotide contained in a plasmid vector is isolated after it has been expanded from a single bacterial colony. However, a polynucleotide contained in a clone that is a member of a mixed library and that has not been isolated from other clones of the library is not "isolated" for the purposes of this invention.

Given that a phenotype may be effected by more than one polynucleotide, it is contemplated that several suitable polynucleotides, e.g., two, three, four, five, ten, 100 or more polynucleotides, may be recovered from the first step of this embodiment, each of which may be a target a polynucleotide. It is contemplated that each different polynucleotide recovered from the library may be separately isolated. However, these polynucleotides may be isolated as a group of polynucleotides which effect the same or similar phenotypes and these polynucleotides may be "isolated" together. Such mixtures of polynucleotides, whether separately isolated or collectively isolated, may be introduced into host cells in the second step, as explained below, either individually, or with two, three, four, five, ten, 100 or more of the polynucleotides pooled together.

Following collection or recovery, target polynucleotides may be purified (partially or substantially) from protein such as viral and or cellular proteins and other components, using well-known techniques such as those described in the examples (see, e.g., Example 2).

Uses and Modifications of the Direct or Indirect Selection Methods

The present invention provides an alternative method of identification of polynucleotides (e.g. gene sequences) whose expression elicits growth suppression, apoptosis or any other phenotype selectable by the present invention. It is based on the isolation from an expression library of one or more cells expressing a target polynucleotide, such that expression of the target polynucleotide causes cell lysis or otherwise compromises cell integrity or cell viability. For example, the target polynucleotide may be toxic or may sensitize the cell to an agent. The target polynucleotide may inhibit the ability of a cell to remain adherent, such as due to a cytoskeletal effect or an effect on ATP production.

The direct or indirect selection method exploits various cell-disrupting mechanisms to isolate polynucleotides of interest from a library. Cell-disrupting mechanisms which may be used include the following: immune system-mediated disruption such as by CTLs, antibody-dependent cellular cytotoxicity (ADCC), and complement-dependent cytotoxicity (CDC); disruption by toxic sequences such as apoptosis-inducing polynucleotides, cell cycle arresters, tumor suppressor genes, dominant negative oncogene variants, cell proliferation inhibitors, and CDK inhibitors; negative regulation of essential genes by antisense expression; and induction of suicide gene expression. These and other cell disruption mechanisms are not mutually exclusive with one another and many overlap.

This method has many applications such as isolation of growth suppressive molecules (DNA, RNA, polypeptides, or peptides) with specificity against certain cell types, and identification of new genes involved in negative growth regulation (i.e., tumor suppressive genes, genes involved in control of apoptosis, cellular senescence, sensitivity to chemical, physical or biological treatments, etc.), drug susceptibility, cell cycle regulation, cell differentiation, or transformation.

Thus, examples of target polynucleotides are those that decrease growth rate or kill cells under normal conditions of growth or under specific conditions, including sensitization of cells to certain physical, chemical or biological treatments that have no or low effect on the majority of cells in, for example, a library-carrying cell population.

Alternatively, an indirect selection method may be used, wherein the host cells lyse or otherwise are compromised in cell integrity or cell viability, and wherein target polynucleotides are selected which allow such cells to remain intact.

Target polynucleotides may be cell proliferation genes which, when aberrantly expressed or regulated, may induce or otherwise be involved in the development of cell proliferative disorders. Such cell proliferative disorders include, but are not limited to cancers, arteriosclerosis, psoriasis, viral disease, as well as inflammatory conditions such as arthritis or sepsis. Cell proliferation genes include dominant transforming genes, such as oncogenes and other genes encoding products involved in the induction of cell growth and recessive cell proliferation genes, such as genes encoding tumor suppressors, genes involved in the induction of apoptosis or genes involved in viral growth.

Isolation of Growth-suppressive Genetic Elements with Cell-specific Activity. Target polynucleotides include those that are growth suppressive for certain cell types (for example, tumor cells, virus infected cells, cells of certain tissue, etc.) but that have no or low effect on other cell types, such as the parent cell type. Isolation of clones that are specifically toxic for certain cell type may require additional selection of the isolated mixture of clones in the cell type of different origin in order to define those clones that have selective biological activity against the cells of choice.

Selection of cytotoxic and cytostatic target polynucleotides may require or benefit by several rounds of selection, which thus increase the proportion of cells containing target polynucleotides. Isolation of target polynucleotides that are not cytotoxic or cytostatic by themselves, but which display growth suppressive activity under certain conditions of cell maintenance or treatment requires application of the appropriate selection. Such selection is preferably noncytotoxic or low-cytotoxic by itself and should not lead to significant cell death or growth arrest in host cells which do not contain a target polynucleotide. For example, polynucleotides restoring the activity of the p53 pathway by blocking p53 inhibitors (such as papilloma virus protein E6 or cellular p53 inhibitor MDM2) are expected to cause cell sensitization to DNA-damaging treatments since p53 plays a role of negative growth regulator that is activated under conditions of genotoxic stress.

The direct or indirect selection method is not limited to the isolation of cytotoxic or cytostatic elements. It can be used for isolation of genetic elements that induce any cell phenotype (i.e. expression of cell surface antigens, alterations in cell adhesion, cell size, etc.) that can be used as a selective trait to enrich or to exhaust a cell population.

In a preferred embodiment, the methods disclosed herein are used to select for modulators of cellular phenotypes. Cellular phenotypes that may be selected for include, but are not limited to, cellular apoptosis, including cell cycle regulation, toxicity to small molecules, the expression of any number of moieties including receptors (particularly cell surface receptors), adhesion molecules, cytokine secretion, protein-protein interactions, transcriptional activation of particular promoters, etc.

Additionally, cells containing such target polynucleotides may be collected or isolated, for example, by fluorescence-activated cell sorting (FACS). Fluorescence activated cell sorting (FACS), also called flow cytometry, is used to sort individual cells on the basis of optical properties, including fluorescence. It is useful for screening large populations of cells in a relatively short period of time.

Rapid and inexpensive screens or selections such as by FACS would be of particular interest for identifying drug candidates such as modulators of cell cycle regulation.

Further, cells containing target polynucleotides may be collected, for example, by magnetic beads. Such methods are described in more detail herein and are also well known in the art.

The hallmark of a malignant cell is uncontrolled proliferation. This phenotype is acquired through the accumulation of gene mutations, the majority of which promote passage through the cell cycle. Cancer cells ignore growth regulatory signals and remain committed to cell division. Classic oncogenes, such as ras, lead to inappropriate transition from G1 to S phase of the cell cycle, mimicking proliferative extracellular signals. Cell cycle checkpoint controls ensure faithful replication and segregation of the genome. The loss of cell cycle checkpoint control results in genomic instability, greatly accelerating the accumulation of mutations which drive malignant transformation. Hence, checkpoint regulators, such as p53 and ATM (ataxia telangiectasia mutated), also function as tumor suppressors. Thus, modulating cell cycle checkpoint pathways with therapeutic agents could exploit the differences between normal and tumor cells, both improving the selectivity of radio- and chemotherapy, and leading to novel cancer treatments.

Target polynucleotides may modulate cell cycle regulation, by, for example, suppressing or activating a cell cycle checkpoint pathway, or ameliorating or inducing checkpoint defects. Thus, in a preferred embodiment, host cells are sorted in a FACS machine by assaying cell parameters, including, but not limited to, cell viability, cell proliferation, and cell phase. In this embodiment, preferred cellular parameters or assays are cell viability assays, assays to determine whether cells are arrested at a particular cell cycle stage ("cell proliferation assays"), and assays to determine at which cell stage the cells have arrested ("cell phase assays"). By assaying or measuring one or more of these parameters, it is possible to detect not only alterations in cell cycle regulation, but alterations of different steps of the cell cycle regulation pathway. In this manner, rapid, accurate screening of insert polynucleotides may be performed to identify those that modulate cell cycle regulation, viability, growth, proliferation, etc. It may be possible to alter the activities of certain enzymes, for example kinases, phosphatases, proteases or ubiquitination enzymes, that contribute to initiating cell phase and/or other changes.

In a preferred embodiment, the methods are used to evaluate cell cycle regulation. Cells cycle through various stages of growth, starting with the M phase, where mitosis and cytoplasmic division (cytokinesis) occurs. The M phase is followed by the G1 phase, in which the cells resume a high rate of biosynthesis and growth. The S phase begins with DNA synthesis, and ends when the DNA content of the nucleus has doubled. The cell then enters G2 phase, which ends when mitosis starts, signaled by the appearance of condensed chromosomes. Terminally differentiated cells are arrested in the G1 phase, and no longer undergo cell division. In this embodiment, preferred cellular parameters or assays are cell viability assays, assays to determine whether cells are arrested at a particular cell cycle stage ("cell proliferation assays"), and assays to determine at which cell stage the cells have arrested ("cell phase assays"). By separating cells based on one or more of these parameters, it is possible to detect not only alterations in cell cycle regulation, but alterations of different steps of the cell cycle regulation pathway, and to isolate target polynucleotides which confer such alteration.

In one embodiment, an MVA vaccinia virus vector or other attenuated virus is used.

In a preferred embodiment, the methods outlined herein are performed on cells that are not arrested in the G1 phase; that is, they are rapidly or uncontrollably growing and replicating, such as tumor cells. In this manner, insert polynucleotides are evaluated to target polynucleotides that alter cell cycle regulation, i.e. cause cells to arrest at cell cycle checkpoints, such as G1, although arresting in other phases such as S, G2 or M are also desirable. Alternatively, insert polynucleotides are evaluated to find those that cause proliferation of a population of cells, i.e. that allow cells that are generally arrested in G1 to start proliferating again; for example, peripheral blood cells, terminally differentiated cells, stem cells in culture, etc.

Thus, the direct or indirect selection method is useful for isolating the following polynucleotides: polynucleotides encoding epitopes and antigens; any toxic sequence, for example, apoptosis-inducing genes, genes that arrest cell cycle, tumor suppressor genes, dominant negative oncogene variants, inhibitors of cell proliferation, and CDK inhibitors; essential genes; and genes that induce expression of a suicide gene construct (i.e., a suicide gene operably associated with a regulated promoter). Among genes that induce expression of a suicide gene include those that promote cell cycle progression and thereby induce a cell cycle specific suicide gene construct (i.e., operably associated with a cell-cycle specific promoter), those that promote differentiation and thereby induce a spatially or temporally regulated suicide gene construct (i.e., operably associated with a spatially-regulated or temporally-regulated promoter) or a tissue or cell specific suicide gene construct (i.e., operably associated with a tissue- or cell-specific promoter) (collectively, differentiation-specific promoters), those that interact with another protein in a two-hybrid transcription system and thereby induce expression of a suicide gene.

Thus, the invention provides a method of directly selecting a target polynucleotide comprising: (a) providing a plurality of cells which comprise (i) packaging function, (ii) transfer plasmid comprising a 5' flanking region, an insert polynucleotide, and a 3' flanking region, (iii) a first virus fragment comprising a sequence homologous to the 5' flanking region, and (iv) a second virus fragment comprising a sequence homologous to the 3' flanking region; (b) culturing the cells under conditions such that the transfer plasmid and virus fragments undergo trimolecular recombination, and the insert polynucleotides are expressed, and (c) removing the nonviable cell or the target polynucleotide, thereby directly selecting the target polynucleotide.

Prior to the direct or indirect selection in a cell line of choice, two or several rounds of replication in HeLa or another cell line favorable for vaccinia replication may be necessary to dilute out the helper virus from the tri-molecular recombination.

Thus, preferably, the method comprises contacting a plurality of cells with infectious progeny produced by trimolecular recombination, culturing said cells under conditions such that the insert polynucleotides are expressed, and removing a nonviable cell expressing the target.

Immune System-Mediated Selection. In one embodiment, antigen-specific cytotoxic mechanisms such as cell, antibody, and complement-mediated cytotoxicity, may be used to isolate host cells expressing a protein of interest. Thus, cytotoxic T cells (CTL), antibody-toxin conjugates, antibody-dependent cellular cytotoxicity (ADCC), and complement-dependent cytotoxicity (CDC) may be used to select any antigen capable of inducing CTL or antibody.

The immune-based direct selection method may be used to identify target antigens in tumor cells, target antigens in other cells against which it is desirable to induce cell-mediated or humoral immunity, or any target epitope which is capable of inducing specific CTL or antibody. For example, the differential immunogenicity methods of the invention can be applied to identify immunogenic molecules of cells infected with virus, fungus or mycobacteria by tolerization of mice with uninfected cells followed by immunization with infected cells at different times after infection. Isolated CTLs or antibodies can be employed to select polynucleotides (e.g. recombinants) that encode target antigens in a plasmid or viral expression library. For example, an expression library can be constructed with cDNA isolated from the infected cell in a vaccinia virus vector using tri-molecular recombination.

One use of this approach is to identify pathogen-encoded antigens and host cell antigens whose expression is altered during infection. Such antigens may be useful as a vaccine against infection by the pathogen.

Pathogens include all pathogenic agents known in the art. Pathogens include, but are not limited to: viral pathogens, such as human immunodeficiency virus (HIV), Epstein Barr virus, hepatitis virus, herpes virus, human papillomavirus, cytomegalovirus, respiratory syncytial virus; fungal pathogens, such as *Candida albicans, Pneumocystis carnii*; and mycobacterial pathogens, such as *M. tuberculosis, M avium*.

Pathogens also include the bacteria *Pseudomonas aeruginosa, Mycobacterium tuberculosis, Hemophilus influenzae, Staphylococcus aureus, Mycoplasma pneumoniae, Escherichia coli, Streptococcus pneumoniae, Neisseria gonorrhaea, Streptococcus viridans, Streptococcus pyogenes, Proteus mirabilis, Proteus vulgaris, Salmonella typhimurium, Shigella dysentereae, Clostridium difficile*, and *Kebsiella pneumoniae*, and the fungi *Candida albicans, Aspergillus flavus, Aspergillus fumagatus*, and *Histoplasmatus capsulatum*.

Pathogens also include those listed elsewhere herein and otherwise known in the art.

Cytotoxic T Lymphocytes. In this version of immune-system based selection, epitope-specific CTLs are used to select target polynucleotides expressing an epitope of interest.

The possibility that altered features of a tumor cell are recognized by the immune system as non-self and may induce protective immunity is the basis for attempts to develop cancer vaccines. Whether or not this is a viable strategy depends on how the features of a transformed cell are altered. Appreciation of the central role of mutation in tumor transformation gave rise to the hypothesis that tumor antigens arise as a result of random mutation in genetically unstable cells. Although random mutations might prove immunogenic, it would be predicted that these would induce specific immunity unique for each tumor. This would be unfavorable for development of broadly effective tumor vaccines.

An alternate hypothesis, however, is that a tumor antigen may arise as a result of systematic and reproducible tissue specific gene deregulation that is associated with the transformation process. This could give rise to qualitatively or quantitatively different expression of shared antigens in certain types of tumors that might be suitable targets for immunotherapy. Early results, demonstrating that the immunogenicity of some experimental tumors could be traced to random mutations (De Plaen, et al., 1988, Proc. Natl. Acad. Sci. USA 85: 2274–2278; Srivastava, & Old, 1989, Immunol. Today 9: 78), clearly supported the first hypothesis.

There is, however, no a priori reason why random mutation and systematic gene deregulation could not both give rise to new immunogenic expression in tumors. Indeed, more recent studies in both experimental tumors (Sahasrabudhe, et al., 1993, J. Immunology 151:6202–6310; Torigoe, et al., 1991, J. Immunol. 147:3251) and human melanoma (van Der Bruggen, et al., 1991, Science 254:1643–1647; Brichard, et al., 1993, J. Exp. Med. 178: 489–495; Kawakami, et al., 1994, Proc. Natl. Acad. Sci. USA 91:3515–3519; Boel, et al., 1995, Immunity 2:167–175; Van den Eynde, et al., 1995, J. Exp. Med. 182: 689–698) have clearly demonstrated expression of shared tumor antigens encoded by deregulated normal genes. The identification of MAGE-1 and other antigens common to different human melanoma holds great promise for the future development of multiple tumor vaccines.

The most widespread and to date most successful approach to identify immunogenic molecules uniquely expressed in tumor cells is to screen a cDNA library with tumor-specific CTLs (cytotoxic T lymphocytes). Application of this strategy has identified several gene families expressed predominantly in human melanoma. Two major limitations of this approach, however, are that (1) screening requires labor intensive transfection of numerous small pools of recombinant DNA into separate target populations in order to assay T cell stimulation by a minor component of some pool; and (2) target cells must be highly transfectable in order to take up cDNA for screening. Only two commonly employed cell lines have the requisite properties, Cos 7 and 293. However, since a fundamental property of T cells is that they are restricted to recognize peptide epitopes presented in association with MHC molecules, these African Green Monkey cells do not express the appropriate human MHC molecules. Although it is possible to co-transfect MHC genes, it is often unclear which of the six possible MHC class I or MHC class II alleles in a heterozygous individual are required for presentation of the target peptide epitope. By constructing cDNA libraries in an infectious vector with a very broad host range, it is possible to employ as the target cell autologous fibroblasts, epithelial cells or EBV transformed B cells that naturally express the full complement of relevant MHC molecules. In contrast, alternatives to screening cDNA libraries, such as the use of tandem HPLC/mass spectrometry to screen peptides eluted from tumor cells, have the limitation that very large numbers of tumor cells are required for peptide purification, quantities which are not normally available from patient samples.

In a preferred embodiment, human tumor-specific T cells are isolated by stimulation with either autologous tumor or autologous antigen presenting cells pulsed with tumor cell lysates and these T cells are employed to screen expression libraries generated from tumor cell DNA, RNA or cDNA to identify reactive target antigens.

Thus, in this embodiment of the invention, tumor-specific or infection-specific CTLs generated in animals are used to screen expression libraries generated from tumor cell or infected cell DNA, RNA or cDNA to identify reactive target antigens. To this end, animals tolerized with a non-tumorigenic or non-infected human cell line are immunized with tumor cells or infected cells derived from the non-tumorigenic or non-infected cell line. In an alternative embodiment, tumor-specific or infection-specific CTLs generated in vitro are used to screen expression libraries. The resulting CTLs, which are tumor-specific or infection-specific and not cross-reactive with normal cells, can be used to screen expression libraries constructed from tumor cell- or infected cell-derived DNA, RNA or cDNA. Clones so identified in the library encode target antigens which are candidates for the immunogenic compositions and vaccines of the invention. Improved and modified vaccinia virus vectors for efficient construction of such DNA libraries using a "trimolecular recombination" approach are described to improve screening efficiency.

Animals, such as normal or transgenic mice, may be tolerized with normal cells or lysates thereof prior to immunizing with tumor cells or cells infected with a pathogen, or a lysate thereof. Tolerance induction is preferred because the animal's immune response would otherwise be dominated by specificity for a large number of broadly expressed human proteins that are not specifically associated with tumor transformation or infection. In a particularly preferred embodiment, and to enhance the efficiency of this approach, it is convenient to work with human tumors that are derived from an immortalized, non-tumorigenic human cell line by in vitro carcinogenesis or oncogene transformation. This provides a ready source of the normal control cells for an extended tolerization protocol in both neonatal and adult mice. For example, CTLs generated by this approach (see Examples 15–18) can be employed in a selection procedure (such as that described in Examples 3–4) to isolate recombinant clones (i.e. target polynucleotides) that encode the target antigens from a tumor cDNA library, for example, such as that constructed in vaccina virus by tri-molecular recombination (see Example 2).

Antibody-based Selection. In other versions of immune-based selection, the host cells are exposed to an antibody or plurality of antibodies directed against an epitope of interest. This results in formation of an antigen-antibody complex at the cell surface. Alternatively, the complexes are contacted with a second antibody or plurality of antibodies directed against the first antibody. The second antibody may be conjugated with a toxin, or alternatively, the first antibody is conjugated with a toxin.

Alternatively, complement-dependent cytotoxicity (CDC) or antibody-dependent cellular cytotocity (ADCC) is used to select target polynucleotides. See U.S. Pat. No. 5,500,362 for ADCC and CDC assays. Such assays may be modified for use in the present selection method by, for example, omitting the $^{51}$Cr labeling of cells, as will be apparent to one of ordinary skill in the art. See, e.g. Hellstrom et al., *Proc. Natl. Acad. Sci. USA* 82:1499–1502 (1985). The complement or cell mediators of ADCC may be added to the antigen-antibody complexes. Alternatively, the antibody and cell mediators of ADCC may be combined prior to contacting the host cells.

Cells expressing the antigen are thus induced to undergo lysis or other mechanisms leading to nonadherence. Nonviable cells, and the cell contents of lysed cells are separated from viable cells. Alternatively, the antibody is labeled and the cells are separated by FACS. In another alternative, the cells adhere to a magnetic solid support, such as a magnetic bead, via antibody on the surface of the solid support and are separated from nonadherent cells by the use of a magnet.

As used herein, the term "antibody" (Ab) or "monoclonal antibody" (Mab) is meant to include intact molecules as well as antibody fragments (such as, for example, Fab and F(ab')$_2$ fragments) which are capable of specifically binding to the protein encoded by a target polynucleotide. If ADCC- or complement-mediated cell killing is utilized in the direct or indirect selection method, the antibodies preferably include an Fc portion. Mouse IgG$_{2a}$ and IgG$_3$ and human IgG$_1$ and IgG$_3$ isotypes are most commonly associated with antibody-dependent cellular cytotoxicity and complement-dependent cytotoxicity These antibodies can be, for example, polyclonal or monoclonal antibodies. The present invention also includes chimeric, single chain and humanized antibodies, as well as Fab fragments, or the product of an Fab expression library. Various procedures known in the art can be used for the production of such antibodies and fragments.

The antibodies used according to the present invention may be directed against the antigen of interest or against a family of related antigens. A single antibody or a group of antibodies may be used, the choice depending upon the nature of the target antigen, its anticipated frequency, and other variables that will be apparent to those of skill. Target antigens expressed on the surfaces of host cells will form an antigen-antibody complex. Methods of preparing antibodies or fragments thereof for use according to the present invention are known to those of skill and/or disclosed in the scientific literature listed below.

Receptors and Ligands. The present invention may also be used to directly select for the cognate receptor of a known ligand, hapten, or epitope, for example, by contacting host cells containing an expression library with a labeled ligand or a ligand conjugated to a toxin. The known ligand may be soluble or may be associated with membrane bilayers or a solid support such as beads, etc. The known ligand may be another receptor, or fragment thereof, which binds the receptor encoded by the target polynucleotide. In another embodiment, the ligand of a known receptor is identified. For example, insert polynucleotide (e.g. DNA) is cloned in-frame with a polynucleotide (e.g. DNA) sequence encoding a receptor transmembrane domain. The transmembrane domain may be naturally occurring, or nonnaturally occurring. The transmembrane domain directs the polypeptide (candidate ligand) encoded by the insert polynucleotide (e.g. DNA) to be expressed on the cell surface. See U.S. Pat. No. 5,866,341. The cells are contacted with receptor polypeptide or a fragment thereof. The receptor or receptor fragment may be labeled or may be conjugated to a toxin. The receptor or receptor fragment may be soluble, hydrophobic, associated with membranes, associated with membrane vesicles, associated with lipid bilayers, associated with lipid bilayer vesicles, associated with a solid support such as beads, etc. Labels for ligands, receptors, etc., include those in Example 14 for antibodies.

As another example, the host cells are contacted with an antibody which recognizes the receptor or ligand encoded by the target polynucleotide. Alternatively, the host cells are contacted with known ligand, and the antibody recognizes the ligand, the receptor, or the ligand-receptor complex.

As used herein, the term "receptors" means any protein capable of specifically binding a ligand, hapten, or epitope. Examples of receptors that may identified by binding known ligand, epitopes, or haptens, include adhesion molecules such as cadherins, selecting, fasciclins, integrins, leukocyte adhesion receptor, neuroglian, VLA family molecules and the like. Examples of receptors that may identified by binding to known growth factors include growth hormone receptors, insulin receptors, interleukin receptors and the like. Examples of receptors that may identified by binding to known ligands include chemokine receptors and G-protein coupled receptors. Examples of specific protein binding interactions useful in the instant invention are described in Creighton, T. E., in *Proteins, Structure and Molecular Principles*, W. H Freeman and Company, New York, N.Y. (1984); and, adhesion molecules are described in Pigott, R., et al., in *The Adhesion Molecule*, Academic Press, Harcourt Brace & Co., New York, N.Y. (1993).

Nondividing Cells. A major technical obstacle to identifying candidate pharmaceutical targets is the nondividing state of terminally differentiated such as musculoskeletal or other cells. Because vectors currently used for library production do not replicate in nondividing cells, it is not possible to recover a gene of interest in nondividing cells by conventional methods. Moreover, it is difficult to identify an expressed gene in a library based on its function using some current cloning vectors because of the low expression level of cloned genes. Although vaccinia-based vectors replicate in nondividing cells and express polypeptides encoded by insert polynucleotides (e.g. DNA) at a high level, the very low cloning efficiency of vaccinia using homologous recombination and the low titers obtained through direct ligation have precluded the use of vaccinia virus for library production.

The trimolecular recombination method of the present invention overcomes the obstacle of low cloning efficiency or low titer in vaccinia virus. As described herein, recombination efficiencies of 90% to 100% and relatively high titers have been achieved using trimolecular recombination. This contrasts with efficiencies of less than 1% using standard methods. For example, combining trimolecular recombination, in vitro stem cell differentiation of cells such as musculoskeletal cells, and direct or indirect selection, allows for the identification of genes that control growth and development. The genes identified are candidate pharmaceutical targets.

Additionally, it will be possible to identify insert polynucleotides (e.g. DNAs) which stimulate proliferation of nondividing cells, for example, using a cell cycle-specific promoter or a promoter induced during proliferation, coupled to a suicide gene. The nonadherent cells are those that express an insert polynucleotide (e.g. DNA) which induces proliferation, while the normally nondividing cells which do not contain such an insert remain adherent.

Functional Gene Discovery. One of the most powerful tools available to molecular biologists for gene discovery has been the ability to efficiently screen representative cDNA libraries constructed in lambda phage. Many microbial and some classes of mammalian genes were first detected and isolated by using functional or biochemical assays to screen lambda phage libraries. In spite of the enormously important advances enabled by this technology, lambda phage only grow in bacterial cells, thus, they are not useful for functional studies in eucaryotic cells. No bioassay that depends on cell differentiation or protein processing characteristic of mammalian cells can be employed to screen lambda phage libraries. The presently available solutions to this problem are to employ relatively inefficient methods for introducing DNA into mammalian cells by transfection or, if the efficiency of an infectious vector is crucial, to employ cDNA libraries constructed in a retroviral vector. This latter approach is indeed powerful but it too suffers from significant limitations. Retroviral expression depends on integration of the viral genome into nuclear DNA. This gives rise to numerous influences on expression levels that are a function of the locus of integration. More importantly, the retroviral genome cannot be recovered from cells that are no longer dividing. As a result this technology also cannot be applied to bioassays for which the readout is either terminal differentiation or cell death. This is not just an uninteresting special situation. It is fundamental to identifying critical genes involved in many important biological processes including the pathways whereby stem cells give rise to fully differentiated, non-proliferating tissue components, the mechanisms of apoptosis, as well as the targets of immune cytotoxicity described above.

The methods described here open this door to discovery. They teach how to construct a representative cDNA library in a vector infectious for mammalian cells and they describe how genes that function in cell differentiation or cell death can be selected from such a library. The viral vectors described can be employed as the "lambda phage" of mammalian cells.

Suicide Genes. In another embodiment, a target polynucleotide is selected based on its induction of a suicide gene construct. The target polynucleotide may encode a transcript and/or a polypeptide which stimulates expression of the suicide gene. By "suicide gene construct" or "suicide gene" is meant a nucleic acid which causes cell death when expressed. Polynucleotides useful as suicide genes include apoptosis-inducing genes such as p53 and other toxic sequences and cell death-inducing sequences which are known in the art, and include those disclosed herein. In this embodiment, the host cells are engineered to comprise a suicide gene construct, as described in Examples 7, 11, and 12, and in the section below. Preferred suicide genes include the toxins disclosed in Example 14 (antibody section) such as Pseudomonas exotoxin A chain, diphtheria A chain, ricin A chain, abrin A chain, modeccin A chain, alpha-sarcin, etc.

Sensitization to an Agent. In another modification, the method can be used to select target polynucleotides which sensitize host cells to killing by an agent. Such an agent may include an infective agent, a DNA-damaging agent, a therapeutic agent, an antisense construct, etc.

Thus, in this embodiment, the direct selection method comprises: providing a plurality of host cells which contain recombinant vector comprising insert polynucleotides; culturing the host cells under conditions such that the insert polynucleotides are expressed; exposing the host cells to a compound which induces death in a cell expressing the target polynucleotide; removing the nonviable cell or the target polynucleotide, thereby directly selecting the target polynucleotide.

Alternatively, an indirect selection method may be used, wherein the host cells are sensitive to an agent, and the target polynucleotide desensitizes cells to that agent. Thus, viable cells would be selected in an indirect selection method.

Antisense. Antisense molecules are usually single stranded DNA or RNA molecules, or their substituted analogues, which down-regulate expression of gene products, for example, by binding to the target RNA through Watson and Crick base pairing and prevent the translation of these RNAs or enhancing mRNA degradation (Stein C A, *Antisense Nucleic Acid Drug Dev* 8(2):129–32 (1998); Crooke S T, *Antisense Nucleic Acid Drug Dev* 8(2):115–22 (1998); Akhtar S, *J Drug Target*. 5(4):225–34 (1998); Mizuno, T., et al., *Proc. Natl. Acad. Sci. USA*, 81, (1983); Crooke S T, *Biotechnol Genet Eng Rev* 15:121–57 (1998); Zamecnik, in Prospects for Antisense Nucleic Acid Therapy of Cancer and Aids, ed., Wickstrom, Wiley-Liss, New York)). They are usually 15 to 30 nucleotides long, but can be as long as the full length RNA transcript and have been used widely to inhibit expression of various proteins (Zamecnik, P. C. and Stevenson, M. L. *Proc. Natl. Acad. Sci., USA*, 75, 280 (1978); Agrawal, S., *Proc. Natl. Acad. Sci., USA*, 85, 7089, (1988)).

Thus, in another embodiment, a target polynucleotide which encodes a product necessary or essential for cell adherence, viability, etc., is isolated based on antisense inhibition of the endogenous transcript. In this embodiment, the insert polynucleotides are cloned in the library vector in either orientation.

In an alternative embodiment, a target polynucleotide which encodes a negative regulator of a product necessary for cell adherence, viability, etc., is selected based on antisense inhibition of the endogenous transcript. Thus, the host cells are unable to adhere, or to remain viable, or to grow, etc., and a target polynucleotide is selected that allows host cells to adhere, remain viable, or grow, etc. In this embodiment, the insert polynucleotides are cloned in the library vector in either orientation.

By "antisense" is meant nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the insert polynucleotides in a reverse orientation to a viral promoter which permits the synthesis of a complementary strand. Once introduced into a cell, this transcribed strand combines with natural sequences produced by the cell to form duplexes. These duplexes then block either transcription or translation of the natural sequence. In this manner, nonviable phenotypes may be generated. The designation "negative" is sometimes used in reference to the antisense strand, and "positive" is sometimes used in reference to the sense strand.

Differentiation Genes. Many mammalian cells in culture require the presence of factors in the media which permit growth. In the absence of such factors, many cell types do not grow in tissue culture. In several cases the relevant factors have been defined. For example, in the absence of exogenous interleukin-2, certain T cells do not proliferate in culture.

Melanoma formation proceeds via a series of steps through which normal melanocytes evolve into fully metastatic melanomas. During this process the progressing tumor cells gradually lose their requirements for specific exogenous factors (Table 1). Normal melanocytes require factors such as phorbol ester, fibroblast growth factor (FGF), melanocyte stimulating hormone-alpha (MSH-α), insulin, or insulin-like growth factor-1 (IGF-1). In contrast, metastatic melanoma cells often require none of these factors. Cell lines with intermediate phenotypes require progressively fewer factors. Genes responsible for circumventing the requirement for various growth factor can be identified by introducing libraries produced from cell lines arrested at later stages of transformation into cell lines arrested at earlier stages of transformation. The recipient cell line contains a suicide gene which is activated if the cells go beyond their usual stage of transformation, thus allowing the direct or indirect selection of genes involved in tumorigenesis and metastasis.

TABLE 1

GRADUAL LOSS OF THE GROWTH FACTOR REQUIREMENT OF MELANOCYTES DURING MELANOMA FORMATION MELANOMA PROGRESSION

| Cell Type | Requirements | Phenotype |
|---|---|---|
| Melanocyte | TPA<br>FGF<br>α-MSH<br>IGF-1 | Normal |
| Nevus | TPA<br>FGF<br>α-MSH<br>IGF-1 | Similar to melanocyte |
| Early melanoma | FGF1<br>α-MSH<br>IGF-1 | Immortalized |
| Primary melanoma | IGF-1 | Tumorigenic |
| Metastatic melanoma | | Migratory |

The direct or indirect selection method may be used to isolate genes involved in differentiation using any tissue or cell specific promoter to drive a suicide gene. For example, to identify a gene involved in myeloid cell development, hematopoietic stem cells would be engineered to contain a suicide gene under the control of a myeloid cell/tissue specific promoter such as CD11b. The hematopoietic stem cells are then used as host cells in the tri-molecular recombination method and/or direct or indirect selection method. As another example, murine ES cells are engineered which express a suicide gene upon differentiation into myeloid cells. In this example, the ES cells may be electroporated with CD11b promoter driving a suicide gene and selected with hygromycin to obtain stable clones. After transfer into the ES cells, target polynucleotides would be selected by expression of the suicide gene, or alternatively, by lack of expression of the suicide gene.

Examples of other tissue restricted promoters are listed below but this invention may be carried out using any promoter with restricted expression. "Tissue restricted promoters" are also referred to herein and elsewhere as differentiation-specific promoters, and other grammatically equivalent or art-known terms.

Neural: Neuron specific RIβ subunit of cAMP-PK promoter, Tryptophan Hydroxylase promoter, Neural specific enolase promoter, Tyrosine hydroxylase promoter, Tα1 α-tubulin promoter;

Lung: α1 collagen gene promoter, rat clara cell 10 protein promoter, human surfactant protein SP-C promoter, preproendothelin promoter;

Liver: human apolipoprotein E promoter;

Heart: alpha B crystallin promoter, murine alpha myosin heavy chain promoter;

Thymus: lck proximal promoter;

T cells: CD2 promoter, CD4 promoter, CD3 promoter;

B cells: IGEμ, CD19 promoter;

Osteoclast and osteoblast specific promoter: Mouse pro-α1(I) promoter, Tartrate Resistant Acid Phosphatase (TRAP) promoter, CD11b promoter.

A wide variety of cells may be used as recipients, including stem cells, pluripotent cells such as zygotes, embryos, ES cells, other cells such as lymphoid and myeloid stem cells, neural stem cells, transformed cells such as tumour cells, infected cells, differentiated cells, etc. Suicide gene constructs may be introduced into the cells by any convenient means, for example, conventional techniques such as transfection (e.g. lipofection, calcium phospate precipitation, electroporation, etc.), microinjection, viral infection, or any other means known in the art and/or disclosed herein.

Examples of ES cell lines which may be used in this invention are: porcine (e.g. U.S. Pat. No. 5,523,226, "Transgenic Swine Compositions and Methods"); murine (e.g. D3, R1, CGR8, AB1 ES cell lines); primate (e.g. rhesus monkey); rodent; marmoset; avian (e.g. chicken); bovine; rabbit; sheep; and horse.

Genes Involved in Musculoskeletal Disease. Musculoskeletal diseases are highly prevalent in our society. With the continual aging of our population the physical, mental and financial burden of conditions like osteoarthritis (which affects 40 million Americans) and osteoporosis (which affects 25 million Americans) are predicted to increase significantly. Thus, there is a tremendous demand for the development of effective therapeutic interventions for these diseases. Unfortunately, our limited understanding of both the etiology of these diseases and the basic molecular and cellular biology of the musculoskeletal system has greatly hampered efforts to identify potential targets for therapeutic intervention. Tissue culture techniques have been developed that allow progenitor stem cells to develop in vitro into functionally mature, terminally differentiated cells such as chondrocytes, osteoblasts, osteoclasts, and myocytes. Using these techniques, it is possible to investigate the regulation of musculoskeletal cell differentiation.

A major technical obstacle to identifying candidate pharmaceutical targets is the nondividing state of terminally differentiated musculoskeletal cells. The vectors currently used for library production do not replicate in nondividing cells, thus it is not possible to recover a gene of interest by current methods. Moreover, it is difficult to identify an expressed gene based on its function using some current cloning vectors because of the low expression level of cloned genes. Although vaccinia-based vectors replicate in nondividing cells and express polypeptides encoded by insert polynucleotides (e.g. DNA) at a high level, the very low cloning efficiency of homologous recombination and the low titers obtained using direct ligation has limited vaccinia's utility as a vector for library production. Thus, vaccinia vectors have not been used to identify previously unknown polynucleotides (e.g. genes) of interest from a complex population of clones (i.e. insert polynucleotides).

The trimolecular recombination method of the present invention overcomes the obstacle of low cloning efficiency in vaccinia virus. As described herein, recombination efficiencies of 90% to 100% with relatively high titers have been achieved using trimolecular recombination. This contrasts with efficiencies of less than 1% using standard methods. Combining trimolecular recombination, in vitro musculoskeletal cell differentiation, and direct or indirect selection allows the identification of genes that control growth and development. The genes identified are candidate pharmaceutical targets.

Stem cells. The genes that regulate differentiation of mature tissues from precursors or stem cells have been especially difficult to study because terminally differentiated cells often cease to proliferate. As a result it is in effect impossible to recover specific functional genes that induce differentiation following DNA transfection or retroviral transduction in current methods. It is, however, possible to design a system using poxvirus or other vectors that takes advantage of differentiation-induced cell death. Under these conditions, genes that promote differentiation can be isolated from a vaccinia or other library that expresses polynucleotides (e.g. cDNA) of the differentiated cell type by "lethality based selection" or other selection methods of the invention.

Every differentiated cell is distinguished from its precursors by expression of some specific gene product. Transcriptional activation of the promoter for that gene often serves as a surrogate marker of differentiation. If a construct of that specific promoter driving expression of a toxin such as the diphtheria A chain is transfected into a proliferating precursor, then any gene that promotes differentiation will result in cell death. If a differentiation promoting insert is introduced as a recombinant in a vector (e.g. a vaccinia expression vector), then it can be readily recovered from dying differentiating cells. These methods are applicable to any stem cell population that can be induced to differentiate into a defined cell type or tissue. Stem cells have been described for a wide variety of tissues including but not limited to different types of blood cells, epidermal cells, neurons, glial cells, kidney cells, and liver cells. Also among these are the different stem cells of the musculoskeletal system including the precursors of chondrocytes, osteoblasts, osteoclasts, and myocytes.

Osteoclasts. Bone is the only organ that contains a cell type, the osteoclast, whose function is to destroy the organ in which it develops and resides. This destruction, or resorption, of bone occurs throughout life and in the healthy individual is counterbalanced by de novo bone formation in a processs called bone remodeling. The genetic control of osteoclast differentiation is a well understood example of stem cell differentiation. The methods and strategies of the present invention can be applied to identify genes that regulate stem cell differentiation in pathways leading to differentiated cells such as osteoclasts. This is illustrated specifically for the analysis of osteoclast differentiation.

Strategies are described to detect and isolate genes that positively or negatively regulate differentiation including genes that are expressed in the differentiating cell itself or that are a secreted product of another cell which influences differentiation in a paracrine fashion. In any case a cell type or cell line that can be induced to differentiate into mature osteoclasts in response to a specific signal, preferably RANK Ligand (RANKL), is employed to detect and isolate polynucleotides (e.g. genes expressed in a recombinant vaccinia virus library) that regulate osteoclast differentiation. In a preferred embodiment, RAW cells are employed. RAW cells are a continuously growing murine myelomonocytic cell line that can be induced to differentiate into osteoclasts by treatment with a range of concentrations of RANK ligand (RANKL), preferably 10 ng/ml (Hsu, H. et al., Proc Natl Acad Sci USA 96(7):3540–45 (1999); Owens, J. M. et al., J Cell Physiol 179:170 (1999)). These or similarly responsive cells can be transfected with a suicide gene construct comprising a promoter that normally drives expression of a gene product that is recognized as a marker of fully differentiated osteoclasts but which is linked in this construct to a suicide gene. In a preferred embodiment the promoter is that of the osteoclast differentiation marker TRAP and the suicide gene encodes the A chain of diphtheria toxin (TRAP/DT-A).

Detection and Isolation of Genes that Positively Regulate Differentiation

DNA sense strand based strategy. A vaccinia library, preferably a cDNA library, is constructed for functional gene selection, for example, using cDNA derived from cells that include but are not limited to mature bone marrow derived osteoclasts, or RAW cells or other precursors that have been induced to differentiate into osteoclasts. cDNA may be isolated from either fully mature cells or cells that have been induced to initiate the differentiation program but have not yet completed the process and may express higher levels of the downstream regulatory products. RAW cells or other osteoclast progenitor cells that have been transfected with a TRAP/DT-A or similar suicide gene construct are infected with the vaccinia cDNA library. Infection at a multiplicity of infection (MOI) of between 0.1 and 10 is preferred. Any vaccinia recombinant that encodes a gene product that promotes differentiation to the mature TRAP expressing phenotype will result in synthesis of the suicide gene, and death of the host cell. Such cells and their contents will be released from the cell monolayer. Vaccinia virus recombinants extracted from the cells and cell contents released into the culture supernatant (i.e. liquid medium or culture medium) are enriched for the desired vaccinia recombinants. This selection process can be repeated through multiple cycles until the desired level of enrichment is achieved. TRAF6 (Lomaga, M. A. et al., *Genes Dev* 13:1015 (1999)), c-Fos (Wang, Z. Q. et al., *Nature* 360:741 (1992)), and c-Src (Soriano, P. et al., *Cell* 64:693 (1991)), are examples of the type of positive regulators of osteoclast differentiation that can be isolated through this method.

The invention also provides for the use of this method to isolate insert polynucleotides (e.g. DNA) involved in differentiation of other cells and progenitors, such as those described herein and others well-known in the art.

DNA antisense strand based strategy. A limitation of the insert expression strategy is that certain regulatory products, for example those encoded by very long cDNA, may be difficult to clone as a functional full-length product. Antisense inhibition is an alternative strategy that does not depend on cloning of full-length cDNA. In this case, total cDNA derived from the same cells as in the sense strand based strategy is cloned into the vaccinia transfer plasmid in a manner preventing translation, such as in reverse orientation. The resulting insert cannot produce the normal product but can down-regulate expression of the endogenous mRNA and/or protein sequence, such as by hybridizing to and inhibiting translation or promoting degradation of complementary cellular mRNA sequences. RAW cells or other progenitor cells containing insert polynucleotides (e.g. DNA) in a vector and also containing TRAP/DT-A or similar suicide construct are treated with an agent that induces differentiation, for example, 10 ng/ml RANKL. Under these conditions almost all host cells differentiate and undergo suicide gene-mediated death. Only cells containing a recombinant vector with an insert that inhibits expression of an essential regulator of differentiation will survive and remain adherent. Virus extracted from the remaining adherent monolayer will, therefore, be enriched for sequences homologous to the desired positive regulators of differentiation.

This selection process can also be repeated through several cycles until the desired degree of enrichment of recombinants in the adherent monolayer is achieved. The antisense polynucleotide (e.g. gene) fragments obtained can be employed to select the actual full-length coding sequence. TRAF6 (Lomaga, M. A. et al., *Genes Dev* 13:1015 (1999)), c-Fos (Wang, Z. Q. et al., *Nature* 360:741 (1992)), and c-Src (Soriano, P. et al., *Cell* 64:693 (1991)), are examples of the types of positive regulators of osteoclast differentiation that can be isolated through this method.

The invention also provides for the use of this method to isolate insert polynucleotides (e.g. DNA) involved in differentiation of other cells and progenitors, such as those described herein and others well-known in the art.

Detection and Isolation of Genes that Negatively Regulate Differentiation.

DNA sense strand based strategy. A vaccinia library is constructed from insert polynucleotides (such as DNA, for example, cDNA) derived from cells that include but are not limited to bone marrow derived osteoclastic progenitors, an enriched fraction of progenitors, or RAW cells or other precursors that have been induced to differentiate into osteoclasts. Polynucleotides such as cDNA may be isolated from cells that include but are not limited to immature precursor cells or cells that have been induced to initiate the differentiation program but have not yet completed the process and may express higher levels of the downstream regulatory products.

It is of particular interest to determine whether other alternative cell types that have irreversibly differentiated from the same stem cell population express inhibitory factors for differentiation of the alternative lineages. For example, dendritic cells differentiate from the same precursors that under other conditions give rise to osteoclasts. cDNA is cloned in the sense orientation for infection of indicator (i.e. host) cells transfected with TRAP/DT-A or similar suicide construct as described above. The indicator (i.e. host) cells are treated with an agent that induces differentiation, preferably 10 ng/ml RANKL. Under these conditions almost all transfectants differentiate and undergo suicide gene mediated cell death. Only cells that are infected with, i.e., contain, a vaccinia recombinant that inhibits differentiation will survive and remain adherent. Virus extracted from the remaining adherent cells will, therefore, be enriched for sequences homologous to the desired negative regulators of differentiation. This selection process can be repeated through several cycles until the desired degree of enrichment of recombinants (i.e. target polynucleotides) in the adherent monolayer is achieved. A negative intracellular regulator of osteoclast differentiation has not yet been isolated. However, it has been suggested that the Est-1 transcription factor plays such a role in differentiation of B lymphocytes (Bories, J. C. et al. *Nature* 377(6550):635–8 (1995)).

The invention also provides for the use of this method to isolate insert polynucleotides (e.g. DNA) involved in differentiation of other cells and progenitors, such as those described herein and others well-known in the art.

DNA antisense based strategy. Polynucleotides such as total cDNA derived from the same cells as in the sense strand based strategy above is cloned into the vaccinia vector in reverse orientation so that the recombinant gene product synthesized in infected cells cannot encode the normal gene product but can hybridize to and inhibit translation or promote degradation of complementary cellular mRNA sequences. If the targeted sequence encodes an essential factor that inhibits cell differentiation, then in the absence of an effective inhibitory signal RAW cells or other progenitor cells transfected with TRAP/DT-A or similar suicide construct will either spontaneously differentiate or will differentiate in response to otherwise suboptimal signals. Differentiation to the mature TRAP expressing phenotype will result in synthesis of the toxin, i.e., suicide gene, and death of the infected cell. Such cells and their contents will be released from the cell monolayer. Vaccinia virus recombinants extracted from the cells and cell contents released into the culture supernatant (i.e. liquid medium or culture medium) are enriched for sequences homologous to the desired negative regulators of differentiation. This selection process can be repeated through multiple cycles until the desired level of enrichment is achieved. The antisense gene fragments obtained can be employed to select the actual full-length coding sequence. A negative intracellular regulator of osteoclast differentiation has not as yet been isolated. However, it has been suggested that the Est-1 transcription factor plays such a role in differentiation of B lymphocytes (Bories, J. C. et al. *Nature* 377(6550):635–8 (1995)).

The invention also provides for the use of this method to isolate insert polynucleotides (e.g. DNA) involved in differentiation of other cells and progenitors, such as those described herein and others well-known in the art.

Detection and Isolation of Secreted Products that Regulate Differentiation

Many of the methods described so far select for polynucleotides (e.g. genes) that promote cell lethality or loss of adherence. In a preferred embodiment of the methods described so far it is envisioned that the insert polynucleotide (e.g. cDNA, gene or other DNA) populations tested are or can be both expressed and function in the same type of cell. In another embodiment polynucleotides (e.g. cDNA, gene or other DNA) expressed in one type of cell may function in the activation or differentiation of another type of cell. If such gene products can also function in autocrine fashion when they are introduced into the target indicator cell, then the strategies that can be employed remain the same, only the source of polynucleotide (e.g. cDNA, gene, or other insert DNA) incorporated into a vaccinia library is different. However, if the polynucleotide (e.g. cDNA, gene, or other insert DNA) to be identified and isolated functions only in paracrine fashion, such that it is being produced in one cell and affects activation or differentiation of a second cell, then the strategy of "lethality based" (e.g. lysis/nonadherence based) selection described in the previous paragraphs is not applicable since the expressing cell does not itself become non-viable or non-adherent. Nevertheless, as described below, the efficiency with which vaccinia recombinants can be introduced in a wide variety of cells and the high level of expression from replicating viral genomes is a great advantage for screening functional gene expression even where direct selection is not possible.

A vaccinia library is constructed in the sense orientation from insert polynucleotides (e.g. DNA, preferably cDNA) derived from cells that include but are not limited to bone marrow derived stromal cells and/or lymphoid cells. Producer cells are selected that do not either induce or inhibit induction of differentiation of RAW cells or other osteoclast progenitors. These may include but are not limited to fibroblastoid or lymphoid cells and cell lines or RAW cells themselves. In a preferred embodiment, RAW cells are employed as an indicator target for differentiation. These or similarly responsive cells are transfected with an indicator gene (e.g. reporter gene) construct comprising a promoter that normally drives expression of a gene product that is recognized as a marker of fully differentiated osteoclasts but which is linked in this construct to expression of an easily detected indicator gene (e.g. reporter gene) product. In a preferred embodiment the promoter is that of the osteoclast differentiation marker TRAP and the indicator gene (e.g. reporter gene) encodes the enzyme luciferase (TRAP/luciferase).

Multiple cultures of producer cells are separately infected with recombinant vaccinia virus expanded from a small initial pool, preferably an initial pool of between 1 and 1000 viral pfu is expanded to 10 to 10,000 pfu prior to infection of between 100 and 10,000 producer cells. Each pool of infected producer cells is cocultured with indicator cells that have been transfected with TRAP/luciferase or a similar indicator construct.

The invention also provides for the use of this method to isolate insert polynucleotides (e.g. DNA) involved in differentiation of other cells and progenitors, such as those described herein and others well-known in the art.

Secreted molecules that induce differentiation. Membrane expression or secretion of any recombinant polynucleotide (e,g, gene or other insert DNA) that promotes differentiation of the indicator cells to the mature TRAP expressing phenotype will result in synthesis of luciferase in those cells and, upon addition of luciferase assay reagents as is well known in the art, will give rise to a readily detectable signal from wells that express that recombinant gene product. Vaccinia recombinants are extracted from positive wells and further diluted to isolate in a repetition of the same assay with producer and indicator cells the specific recombinant with differentiation promoting activity. RANKL (Lacey, D. L. et al., *Cell* 93:165–76 (1998)) is itself an example of a positive regulator of osteoclast differentiation that could have been isolated through this method.

The invention also provides for the use of this method to isolate insert polynucleotides (e.g. DNA) involved in differentiation of other cells and progenitors, such as those described herein and others well-known in the art.

Secreted molecules that inhibit differentiation. RAW cells or other progenitor cells transfected with TRAP/luciferase or similar indicator construct are treated with an agent that induces differentiation, in a preferred embodiment with RANKL at the lowest concentration that, in the absence of vaccinia recombinants, reproducibly induces differentiation and a positive indicator signal in every microculture of producer and indicator cells. Under these conditions, only microcultures that include a producer cell infected with a recombinant gene that leads to membrane expression or secretion of an inhibitor of osteoclast differentiation to the mature TRAP expressing phenotype will fail to induce luciferase synthesis and, upon addition of luciferase assay reagents, will not give rise to a readily detectable signal. Vaccinia recombinants are extracted from these negative wells and further diluted to isolate in a repetition of the same assay with producer and indicator cells the specific recombinant with differentiation inhibiting activity. Osteoprotegerin (OPG), Simonet, W. S. et al., *Cell* 89:309–19 (1997), which is identical to osteoclastogenesis inhibitory factor (OCIF), Yasuda, H. et al., *Endocrinology* 139:1329–37 (1998), is an example of a type of negative regulator of osteoclast differentiation that can be isolated through this method.

The invention also provides for the use of this method to isolate insert polynucleotides (e.g. DNA) involved in differentiation of other cells and progenitors, such as those described herein and others well-known in the art.

Cell Proliferation Genes. Genes whose aberrant expression or function may contribute to cell proliferation disorders fall into two general categories: (1) dominant transforming genes, including oncogenes, and (2) recessive cell proliferation genes, including tumor suppressor genes and genes encoding products involved in programmed cell death ("apoptosis").

Oncogenes generally encode proteins that are associated with the promotion of cell growth. Because cell division is a crucial part of normal tissue development and continues to play an important role in tissue regeneration, oncogene activity, properly regulated, is essential for the survival of the organism. However, inappropriate expression or improperly controlled activation of oncogenes may drive uncontrolled cell proliferation and result in the development of severe diseases, such as cancer. Weinberg, 1994, CA Cancer J. Clin. 44:160–170.

Tumor suppressor genes, on the other hand, normally act as "brakes" on cell proliferation, thus opposing the activity of oncogenes. Accordingly, inactivation of tumor suppressor genes, e.g., through mutations or the removal of their growth inhibitory effects may result in the loss of growth control, and cell proliferative diseases such as cancer may develop. Weinberg, 1994, CA Cancer J. Clin. 44:160–170.

Related to tumor suppressor genes are genes whose product is involved in the control of apoptosis; rather than regulating proliferation of cells, they influence the survival of cells in the body. In normal cells, surveillance systems are believed to ensure that the growth regulatory mechanisms are intact; if abnormalities are detected, the surveillance system switches on a suicide program that culminates in apoptosis.

Several genes that are involved in the process of apoptosis have been described. See, for example, Collins and Lopez Rivas, 1993, TIBS 18:307–308; Martin et al., 1994, TIBS 19:26–30. Gene products which have been implicated in the control of or participation in apoptosis include bcl-2 (Korsymeyer, 1992, Immunol. Today 13:285–288), c-myc (Shi et al., 1992, Science 257:212–214; Evan et al., 1992, Cell 69:119–128), p53 (Rotter et al., 1993, Trends Cell. Biol. 3:46–49), TRPM-2/SGP (Kryprianou et al., 1991, Cancer Res. 51:162–166), and Fas/APO-1 (Itoh et al., 1991, Cell 66:233–243). Cells that are resistant to apoptosis have an advantage over normal cells, and tend to outgrow their normal counterparts and dominate the tissue. As a consequence, inactivation of genes involved in apoptosis may result in the progression of tumors, and, in fact, is an important step in tumorigenesis.

Mutations in tumor suppressor genes and genes encoding products involved in the control of apoptosis are typically recessive; i.e., both copies of the gene, the maternally inherited copy and the paternally inherited one, must be inactivated by mutation to remove the effect of the gene product. Usually, a single functional copy of such genes is sufficient to maintain tumor suppression. Predisposition to certain hereditary cancers involves mutant tumor suppressor genes. For example, if an individual inherits a single defective tumor suppressor gene from her father, initially her health will be uncompromised, since each cell still contains a functional copy of the gene inherited from her mother. However, as cells divide, mutations accumulate. Thus, at one point, the remaining normal copy in a cell may be inactivated by mutation to remove the function of the tumor suppressor, thereby completing one of the steps toward tumor formation. Such a cell may give rise to descendant cells which represent the early stages of cancer.

Of course, individuals who inherit a full normal complement of tumor suppressor genes can develop cancer as well. However, because two inactivating mutations are required, the development of the disease is much less frequent in such "normal" individuals, i.e., not predisposed to cancer.

Tumor suppressor genes and oncogenes participate in growth control pathways in normal cells in such a way that the appropriate level of cell division is maintained. Disruption of these pathways by mutation of the component genes, oncogenes or tumor suppressor genes, is the underlying cause of cancer. Growth control in complex organisms like humans is a very important and complicated process. Thus, multiple genetic pathways for growth control are involved.

Some pathways operate in all cell types in the body. Other pathways are much more specific and function only in certain cells.

For example, signaling pathways in cell lines derived from a certain tumor type can be studied with the present invention. The invention can be used to study the role of the HER-2/neu oncogene in breast carcinoma by expressing dominant negative mutations of signaling proteins in breast cancer cell lines. HER-2/neu (c-erbB-2) is overexpressed in 30% of breast tumors and its presence is correlated with lower survival rates of patients with these tumors (Elledge, R. M., et al., Seminars in Oncology 19:244 (1992). The HER-2/neu protein demonstrates close sequence homology with, but is distinct from, the epidermal growth factor receptor (EGFR) (Scheuter, A. L., et al., Science 229:976 (1985)). The unregulated growth characteristics of HER-2/neu-positive tumors is hypothesized to arise, at least in part, from the effect of HER-2/neu on intracellular signaling pathways (Kumar, R., et al., Mol. Cell. Biol. 11: 979 (1991)). The invention described herein can be used to isolate cells expressing dominant negative mutations of cellular signaling proteins known to interact with the EGF receptor such as PI3K, PLCγ1, Grb2, Syp, Nck, Shc, and p9i in several cell lines derived from breast tumors (see Table 2).

TABLE 2

Properties of cell lines derived from carcinoma of the breast

| Cell Type | EGFR | HER2/neu | Tumorigenic in Nude Mice | Derived From |
|---|---|---|---|---|
| MDA-MB-468 | + | — | + | Human adenocarcinoma of breast, from pleural effusion |
| MDA-MB-453 | — | + | — | Human carcinoma of breast from effusion |
| MCF-7 | — | — | + | Human adenocarcinoma of breast, from pleural effusion |
| SKBR-3 | + | + | + | Human adenocarcinoma of breast, from malignant pleural effusion |

For another example, efficient study of regulatory proteins, such as early events in the Ras-regulated serine/threonine kinase pathways, requires a transfection system that allows rapid selection of transfected cells. The present invention will allow an analysis of when this pathway diverges into the Ras-MEK-MAPK axis and the RasMEKK-SEK-SAPK (JNK) axis (Sanchez, I., et al., Nature 372:794 (1994); Yan, M., et al., Nature 372:798 (1994); Derijard, B., et al., Science 267:682 (199S)).

Apart from understanding the genetic basis for one of the major causes of cell death, discovery of new cell proliferation genes has significant medical and commercial benefits. The potential value of such genes derives from opportunities to diagnose and treat cell proliferation disorders, such as cancer, more successfully and efficiently.

Cell proliferation genes can be of medical value in the identification of individuals predisposed to cancer. Because early detection and surgical resection play a vital role in survival rates, methods that facilitate early diagnosis are extremely important. One way to decrease the length of time between the appearance of tumor tissue and its detection is to survey candidate patients more frequently and more thoroughly. However, such methods of surveillance are expensive; thus it is necessary to limit scrutiny to high risk individuals. Consequently, information about genetic predisposition to cancer is extremely desirable. Because most genes that influence hereditary cancer are also involved in tumor progression, isolation of genes by somatic cell genetics has the potential to uncover such predisposing genes. Germline testing for such genes offers the chance to rate an individual's probability of contracting cancer, and expensive cancer screening efforts may be limited to those most likely to benefit from them.

Cell proliferation genes can be of medical value in the classification of already existing tumors based on genotype. Lowe et al., 1994, Science 266:807–810. In the past, oncologists have relied on histological examination of biopsy specimens. Though useful, histological analyses are generally hampered by their subjectivity and imprecision. Methods that classify tumors based on their genetic composition have the potential to improve the reliability of classification. Detailed knowledge about tumor genotype may serve as a prognostic indicator for the tumor and may assist in guiding the therapeutic choice.

Identification and isolation of cell proliferation genes affords important therapeutic opportunities. Numerous approaches use information about cell proliferation genes including, but not limited to the following: 1) transfer of wildtype tumor suppressor genes into tumor cells that have lost tumor suppressor activity; 2) inhibition of the activity of oncogenes in tumors, an approach that is being followed by several pharmaceutical companies in the development of ras farnesylation inhibitors; and 3) selective induction of tumor suppressor genes in normal cells to induce a state of temporary cell cycle arrest. These methods have the potential to be much more selective and efficacious than conventional chemo- or radiotherapy.

Tumor Suppressor Genes. Many tumor suppressor genes cause growth arrest when overexpressed in normal cells, as well as in certain tumor cell lines. Examples for tumor suppressor genes include p53 (Lin et al., 1992, Proc. Natl. Acad. Sci. U.S.A. 89:9210–4), Rb (Francke et al., 1976, Cytogenet. Cell Genet. 16:131–134; Cavanee et al., 1983, Nature 305:779–784; Friend et al., 1987, Proc. Natl. Acad. Sci. U.S.A. 84:9059; Lee et al., 1987, Nature 329:642–645; Huang et al., 1988, Science 242:1563–1566; Harbour et al., 1988, Science 241:353–357; Yokota et al., 1988, Oncogene 3:471–475) and p16 (Kamb et al., 1994, Science 264: 436–440; Nobori et al., 1994, Nature 368:753–756). Generally, tumor suppressor genes trigger growth arrest in cells at one of several positions in the cell cycle. Most frequently, however, tumor suppressors are found to cause growth arrest at the $G_1/S$ stage.

Though the details of growth control pathways are known in only a few cases, it is generally believed that overexpression of tumor suppressor genes in cell lines that contain inactivating mutations downstream in the respective growth control pathways will not have a growth inhibitory effect. In order to result in a growth arresting effect in the target cell, any particular tumor suppressor must be expressed in an appropriate cell line which contains intact downstream components of its respective growth control pathway. For example, overexpression of p16 in cells that are retinoblastoma-negative ($Rb^-$) has little or no effect on growth, while overexpression of p16 in a wide variety of $Rb^+$ lines, for example the $Rb^+$ melanoma cell line HS294T (Horuk et al., 1993, J. Biol. Chem. 268:541–546), causes $G_1$ arrest. Stone et al., 1996, Cancer Res., in press. The reason is that Rb participates in a growth control pathway along with p16, acting downstream of p16; consequently, overexpression of p16 in the absence of Rb protein has no growth arresting effect.

In one embodiment of the invention, a selection system has been designed based on the tumor suppressor p16, which is described in more detail, infra. In another embodiment of the invention, selection systems are designed based on the gene encoding Rb. Overexpression of Rb is known to cause arrest in many cell lines.

In still another embodiment, selection systems are generated based on the breast cancer susceptibility tumor suppressor gene BRCA1. BRCA1 has been shown to arrest growth of breast epithelial cell lines (Holt et al., 1996, Nat. Genet. 12:298–302).

In another embodiment of the invention, selection systems are designed based on the p53 pathway. Regulated expression of p53 and its downstream targets, such as the CDK inhibitor p21 induces either apoptosis or G1 arrest in a variety of cell lines.

In still other embodiments of the invention, other tumor suppressor genes are used in order to design selection systems for the identification of novel cell proliferation genes. In principal, any gene whose expression can be manipulated to cause cell growth arrest, can be used. Examples include, but are not limited to, WT1, VHL, BRCA2, NF1, NF2, P15, P21, P18, P19, P27, P57.

CDK Inhibitors. In one embodiment of the invention, selection systems are generated based on expression of CDK inhibitors in suitable host cells.

All CDK inhibitors defined to date, including p15, p16, p18, p19, p21, p27, p57 cause cell cycle arrest when they are overexpressed in certain cell lines. In some cases, such as p16, some details are already known with respect to downstream pathway components. In other cases, most details of the pathway of growth control within which the genes function are still to be elucidated. Apart from their preferred in vitro targets, i.e., CDK4 and CDK6 in the cases of p15, p16, and p18, and CDK4, CDK6, and CDK2 (and CDK4, CDK6) in the case of p21, p27, and p57, the identification of components of the pathways that act downstream by direct or indirect selection systems will greatly facilitate the ability to manipulate these growth control pathways to achieve a therapeutic advantage.

Many cell lines respond to ectopic expression of CDK inhibitors by entering a state of arrest, and may be used for CDK inhibitor based selection systems accordingly. Exceptions are lines that have lost the activity of downstream mediators of the CDK inhibitor pathways. For example, $Rb^-$ cell lines cannot be forced into arrest by overexpression of p16. In addition, certain cell lines may have incurred mutations in downstream genes other than Rb. For instance, specific mutations in CDK4 render the mutant protein resistant to inhibition by p16. This defect has been shown to result from single amino acid substitutions in CDK4 protein that prevent binding of p16 to the enzyme without impairing catalytic activity. Wolfel et al., 1995, Science 269:1281–1284. Similar mutations could interfere with the ability of other CDK inhibitors to carry out their tumor suppressor activity. Recipient cell lines should have intact growth control pathways downstream of the particular CDK inhibitor such that they respond to ectopic CDK inhibitor expression by entering cell cycle arrest.

Oncogene Pathways. In another embodiment, selection systems are generated based on dissection of oncogene pathways. For example, a dominant-negative oncogene or a dominant-negative fragment of an oncogene may be ectopically expressed such that growth is inhibited or apoptosis is induced.

Many forms of dominant-negative oncogene mutants have been engineered. For example, in the case of receptor tyrosine kinases, receptor mutants lacking an intact enzymatic domain have been shown to dominant-negatively inhibit the function, and thus signal transduction, of the wild-type receptor. Redemann et al., 1992, Mol. Cell. Biol. 12:491–498; Kashles et al., 1991, Mol. Cell. Biol. 11:1454–1463; Millauer et al., 1994, Nature 367: 576–579. Further, naturally occurring dominant negative oncogenes have been identified, which have variable effects that depend heavily on the specific cell line in which they are expressed. Below (Table 3) are listed several examples from the literature of the effects of dominant negative proto-oncogenes on the growth and/or transformation properties of specific cells.

TABLE 3

| GENE | RECIPIENT CELL | EFFECT | REFERENCE |
|---|---|---|---|
| c-JUN | MCF7 | inhibition of colony formation | Chen et al., 1996, Mol. Carcinog. 15:215–226 |
| EGF-R | Rat-1 | inhibition of DNA synthesis | Daub et al., 1996, Nature 379:557–560 |
| GRB2 | NIH3T3 | inhibition of transformation | Xie et al., 1995, J. Biol. Chem. 270:30717–30724 |
| RAF | NIH3T3 | inhibition of growth in soft agar | Denko et al., 1995, Somat. Cell. Mol. Genet. 21: 241–253 |
| RAF | GH4 | ras-induced promoter activation | Pickett et al., 1995, Mol. Cell. Biol. 15: 6777–6784 |
| MAX | NIH3T3 | natural growth regulation | Arsura et al., 1995, Mol. Cell. Biol. 15: 6702–6709 |
| RAS | SK-N-MC | inhibition of ERK2 activation | van Weering et al., 1995, Oncogene 11:2207–2214 |
| SRC | endothelial | inhibition of c-FOS activation | Simonson et al., 1996, J. Biol. Chem. 271: 77–82 |

In principle, dominant negative proto-oncogenes can serve in the same way as tumor suppressor genes to arrest cells or prevent cell growth under certain conditions, thus providing a basis for selection of target polynucleotides.

Genes Involved in Degenerative Disease. Interleukin 1 ("IL-1") is a major pro-inflammatory and immunoregulatory protein that stimulates fibroblast differentiation and proliferation, the production of prostaglandins, collagenase and phospholipase by synovial cells and chondrocytes, basophil and eosinophil degranulation and neutrophil activation. Oppenheim, J. H. et al, Immunology Today, 7, pp. 45–56 (1986). As such, it is involved in the pathogenesis of chronic and acute inflammatory and autoimmune diseases. For example, in rheumatoid arthritis, IL-1 is both a mediator of inflammatory symptoms and of the destruction of the cartilage proteoglycan in afflicted joints. Wood, D. D. et al., Arthritis Rheum 26, 975, (1983); Pettipher, E. J. et al., Proc. Natl. Acad. Sci. USA 71, 295 (1986); Arend, W. P. and Dayer, J. M., Arthritis Rheum 38, 151 (1995). IL-1 is also a highly potent bone resorption agent. Jandiski, J. J., J. Oral Path 17, 145 (1988); Dewhirst, F. E. et al., J. Immunol. 8, 2562 1985). It is alternately referred to as "osteoclast activating factor" in destructive bone diseases such as osteoarthritis and multiple myeloma. Bataille, R. et al., Int. J. Clin. Lab. Res. 21(4), 283 (1992). In certain proliferative disorders, such as acute myelogenous leukemia and multiple myeloma, IL-1 can promote tumor cell growth and adhesion. Bani, M. R., J. Natl. Cancer Inst. 83, 123 (1991); Vidal-Vanaclocha, F., Cancer Res. 54, 2667 (1994). In these disorders, IL-1 also stimulates production of other cytokines such as IL-6, which can modulate tumor development (Tartour et al., Cancer Res. 54, 6243 (1994). IL-1 is predominantly produced by peripheral blood monocytes as part of the inflammatory response and exists in two distinct agonist forms, IL-1α and IL-1β. Mosely, B. S. et al., Proc. Nat. Acad. Sci., 84, pp. 4572–4576 (1987); Lonnemann, G. et al., Eur. J. Immunol., 19, pp. 1531–1536 (1989).

IL-1β is synthesized as a biologically inactive precursor, pIL-1β. pIL-1β lacks a conventional leader sequence and is not processed by a signal peptidase. March, C. J., Nature, 315, pp. 641–647 (1985). Instead, pIL-1β is cleaved by interleukin-1.beta. converting enzyme ("ICE") between Asp-116 and Ala-117 to produce the biologically active C-terminal fragment found in human serum and synovial fluid. Sleath, P. R., et al., J. Biol. Chem., 265, pp. 14526–14528 (1992); A. D. Howard et al., J. Immunol., 147, pp. 2964–2969 (1991). ICE is a cysteine protease localized primarily in monocytes. It converts precursor IL-1β to the mature form. Black, R. A. et al., FEBS Lett., 247, pp. 386–390 (1989); Kostura, M. J. et al., Proc. Natl. Acad. Sci. USA, 86, pp. 5227–5231 (1989). Processing by ICE is also necessary for the transport of mature IL-1β through the cell membrane.

ICE, or its homologs, also appears to be involved in the regulation of programmed cell death or apoptosis. Yuan, J. et al., Cell, 75, pp. 641–652 (1993); Miura, M. et al., Cell, 75, pp. 653–660 (1993);Nett-Fiordalisi, M. A. et al., J. Cell Biochem., 17B, p. 117 (1993). In particular, ICE or ICE homologs are thought to be associated with the regulation of apoptosis in neurodegenerative diseases, such as Alzheimer's and Parkinson's disease. Marx, J. and M. Baringa, Science, 259, pp. 760–762 (1993); Gagliardini, V. et al., Science, 263, pp. 826–828 (1994). Therapeutic applications for inhibition of apoptosis may include treatment of Alzheimer's disease, Parkinson's disease, stroke, myocardial infarction, spinal atrophy, and aging.

ICE has been demonstrated to mediate apoptosis (programmed cell death) in certain tissue types. Steller, H., Science, 267, p. 1445 (1995); Whyte, M. and Evan, G., Nature, 376, p. 17 (1995); Martin, S. J. and Green, D. R., Cell, 82, p. 349 (1995); Alnemri, E. S., et al., J. Biol. Chem., 270, p. 4312 (1995); Yuan, J. Curr. Opin. Cell Biol., 7, p. 211 (1995). A transgenic mouse with a disruption of the ICE gene is deficient in Fas-mediated apoptosis (Kuida, K. et al., Science 267, 2000 (1995). This activity of ICE is distinct from its role as the processing enzyme for pro-IL-1β. It is conceivable that in certain tissue types, inhibition of ICE may not affect secretion of mature IL-1β, but may inhibit apoptosis.

Enzymatically active ICE has been previously described as a heterodimer composed of two subunits, p20 and p10 (20 kDa and 10 kDa molecular weight, respectively). These subunits are derived from a 45 kDa proenzyme (p45) by way of a p30 form, through an activation mechanism that is autocatalytic. Thornberry, N. A. et al., Nature, 356, pp. 768–774 (1992). The ICE proenzyme has been divided into several functional domains: a prodomain (p14), a p22/20 subunit, a polypeptide linker and a p10 subunit. Thornberry et al., supra; Casano et al., Genomics, 20, pp. 474–481 (1994).

Full length p45 has been characterized by its cDNA and amino acid sequences. PCT patent applications WO 91/15577 and WO 94/00154. The p20 and p10 cDNA and amino acid sequences are also known. Thornberry et al., supra. Murine and rat ICE have also been sequenced and cloned. They have high amino acid and nucleic acid sequence homology to human ICE. Miller, D. K. et al., Ann. N.Y. Acad. Sci., 696, pp. 133–148 (1993); Molineaux, S. M. et al., Proc. Nat. Acad. Sci., 90, pp. 1809–1813 (1993). The three-dimensional structure of ICE has been determined at atomic resolution by X-ray crystallography. Wilson, K. P., et al., Nature, 370, pp. 270–275 (1994). The active enzyme exists as a tetramer of two p20 and two p10 subunits.

Additionally, there exist human homologs of ICE with sequence similarities in the active site regions of the enzymes. Such homologs include TX (or ICE.sub.rel-II or ICH-2) (Faucheu, et al., EMBO J., 14, p. 1914 (1995); Kamens J., et al., J. Biol. Chem., 270, p. 15250 (1995); Nicholson et al., J. Biol. Chem., 270 15870 (1995)), TY (or ICE.sub.rel-III) (Nicholson et al., J. Biol. Chem., 270, p. 15870 (1995); ICH-1 (or Nedd-2) (Wang, L. et al., Cell, 78, p. 739 (1994)), MCH-2, (Fernandes-Alnemri, T. et al., Cancer Res., 55, p. 2737 (1995), CPP32 (or YAMA or apopain) (Fernandes-Alnemri, T. et al., J. Biol. Chem., 269, p. 30761 (1994); Nicholson, D. W. et al., Nature, 376, p. 37 (1995)), and CMH-1 (or MCH-3) (Lippke, et al., J. Biol. Chem., (1996); Fernandes-Alnemri, T. et al., Cancer Res., (1995)). Each of these ICE homologs, as well as ICE itself, is capable of inducing apoptosis when overexpressed in transfected cell lines. Inhibition of one or more of these homologs with the peptidyl ICE inhibitor Tyr-Val-Ala-Asp-chloromethylketone results in inhibition of apoptosis in primary cells or cell lines. Lazebnik et al., Nature, 371, p. 346 (1994).

Accordingly, the direct or indirect selection method may identify molecules similar to ICE that are involved in diseases such as chronic and acute forms of IL-1-mediated diseases, apoptosis-mediated diseases, as well as inflammatory, autoimmune, proliferative, infectious, or degenerative diseases. Degenerative diseases include Parkinson's Disease, Pick's Disease, Alzheimer's Disease, as well as Rosenthal fibres in Cerebellar Astrocytomas, Cytoplasmic bodies in muscle and Mallory bodies in Alcoholic Liver Disease. Additional IL-1- and apoptosis-mediated diseases include inflammatory diseases, autoimmune diseases, proliferative disorders, infectious diseases, degenerative diseases, necrotic diseases, osteoarthritis, acute pancreatitis, chronic pancreatitis, asthma, adult respiratory distress syndrome, glomerulonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, inflammatory bowel disease, Crohn's disease, psoriasis, graft vs. host disease, osteoporosis, multiple myeloma-related bone disorder, acute myelogenous leukemia, chronic myelogenous leukemia, metastatic melanoma, Kaposi's sarcoma, multiple myeloma sepsis, septic shock, Shigellosis, Alzheimer's disease, Parkinson's disease, cerebral ischemia, myocardial ischemia, spinal muscular atrophy, multiple sclerosis, AIDS-related encephalitis, HIV-related encephalitis, aging, alopecia, and neurological damage due to stroke.

Apoptosis. In another embodiment, direct or indirect selection is based on the phenomenon of apoptosis, i.e., programmed cell death.

Cells in culture can be induced to undergo apoptotic death by a variety of stimuli, depending on the particular cells. For example, certain cells enter apoptosis after exposure to glucocorticoids, tumor necrosis factors, or other natural agents. In addition, many cell types undergo apoptosis when exposed to radiation or chemotherapeutics. Further, cells may be engineered to contain genes which have been implicated in the control of or participation in apoptosis under the control of an inducible promoter. Such genes include, but are not limited to bcl-2 (Korsymeyer, 1992, Immunol. Today 13:285–288), c-myc (Shi et al., 1992, Science 257:212–214; Evan et al., 1992, Cell 69:119–128), p53 (Rotter et al., 1993, Trends Cell. Biol. 3:46–49), TRPM-2/SGP (Kryprianou et al., 1991, Cancer Res. 51:162–166), and Fas/APO-1 (Itoh et al., 1991, Cell 66:233–243).

Cell types which can be induced to undergo apoptosis include, for example, lymphocytes, tumor cells derived from lymphocytes, and tumors of epithelial cell origin. Activation of the FAS antigen receptor in maturing lymphocytes activates an apoptosis program. FAS antigen can be activated either by exogenous application of a FAS antibody (Velcich et al., 1995, Cell Growth Differ. 6:749–757) or by ectopic expression of an activated form of the receptor. Treatment with certain steroid hormones or cross-linking of the T cell receptors on the cell surface using, for example, an antibody, can also induce apoptosis in lymphocytes, related cell or tumor lines, and tumors of epithelial origin The 3DO line, for instance, responds to receptor cross-linking by undergoing apoptosis (Vito et al., 1996, Science 271:521–525), while murine thymoma W7 cells undergo apoptosis in response to dexamethasone (Bourgeois et al., 1993, Mol. Endocrinol. 7:840–851). Other cell lines undergo apoptosis when cultured at low density or in the absence of specific serum factors (Ishizaki et al., 1995, Mol. Endocrinol. 7:840–851). In Friend erythroleukemia cells, overexpression of p53 results in apoptosis (Abrahamson et al., 1995, Mol. Cell. Biol. 15:6953–6960). Overexpression of certain oncogenes in some tumor lines may, paradoxically, also induce apoptosis (Harrington et al., 1994, Curr. Opin. Genet. Dev. 4:120–129). The morphogen retinoic acid induces programmed cell death in the P19 embryonic stem cell (Okazawa et al., 1996, J. Cell Biol. 132:955–968). It is also possible to use various forms of trauma to induce apoptosis in a variety of cell types. For instances, treatment of many cell types by DNA-damaging agents (e.g., certain chemotherapeutics, radiation) causes an apoptotic response. Such mechanisms may be used in the direct or indirect selection system of the invention. For example, genes which induce cell death may be used as a suicide gene.

Cell Cycle Regulators and FACS. The method of the invention is useful to identify target polynucleotides causing cells to arrest in a growth phase or to move out of one growth phase and into another. In some embodiments, it may be desirable to identify polynucleotides causing cell arrest, for example at G1. Alternatively, a polynucleotide may cause host cells arrested in a particular growth phase to move past that phase or to move into another phase. Similarly, it may be desirable in some circumstances to isolate polynucleotides that accelerate movement of a non-arrested but slowly moving cell type into either the next phase or just through the cell cycle, or to delay the onset of the next phase. For example, it may be possible to alter the activities of certain enzymes, for example kinases, phosphatases, proteases or ubiquitination enzymes, that contribute to initiating cell phase changes.

In a preferred embodiment, a light scattering assay is used as the viability assay, as is well known in the art. When viewed in the fluorescence activated cell sorter (FACS), cells have particular characteristics as measured by their forward and 90 degree (side) light scatter properties. These scatter properties represent the size, shape and granule content of the cells. These properties account for two parameters to be measured as a readout for the viability. Briefly, the DNA of dying or dead cells generally condenses, which alters the 90 degree scatter; similarly, membrane blebbing can alter the forward scatter. Alterations in the intensity of light scattering, or the cell-refractive index indicate alterations in viability.

Thus, in general, for light scattering assays, a standard is determined for a particular cell type by the forward and side scattering properties of a live cell population. This standard for scattering is subsequently used for comparison to the host cells.

In a preferred embodiment, the viability assay utilizes aviability dye. There are a number of known viability dyes that stain dead or dying cells, but do not stain growing cells. For example, annexin V is a member of a protein family which displays specific binding to phospholipid (phosphotidylserine) in a divalent ion dependent manner. This protein has been widely used for the measurement of apoptosis (programmed cell death) as cell surface exposure of phosphatidylserine is a hallmark early signal of this process. Suitable viability dyes include, but are not limited to, annexin, ethidium homodimer-1, DEAD Red, propidium iodide, SYTOX Green, etc., and others known in the art; see the Molecular Probes Handbook of Fluorescent Probes and Research Chemicals, Haugland, Sixth Edition,; see Apoptosis Assay on page 285 in particular, and Chapter 16.

Protocols for viability dye staining for cell viability are known, see Molecular Probes catalog, supra. In this embodiment, the viability dye such as annexin is labeled, either directly or indirectly, and combined with a cell population.

Annexin is commercially available, i.e., from PharMingen, San Diego, Calif., or Caltag Laboratories, Millbrae, Calif. Preferably, the viability dye is provided in a solution wherein the dye is in a concentration of about 100 ng/ml to about 500 ng/ml, more preferably, about 500 ng/ml to about 1 μg/ml, and most preferably, from about 1 μg/ml to about 5 μg/ml. In a preferred embodiment, the viability dye is directly labeled; for example, annexin may be labeled with a fluorochrome such as fluorescein isothiocyanate (FITC), Alexa dyes, TRITC, AMCA, APC, tri-color, Cy5, and others known in the art or commercially available. In an alternate preferred embodiment, the viability dye is labeled with a first label, such as a hapten such as biotin, and a secondary fluorescent label is used, such as fluorescent streptavidin. Other first and second labeling pairs can be used as will be appreciated by those in the art.

Once added, the viability dye is allowed to incubate with the cells for a period of time, and washed, if necessary. The cells are then sorted as outlined below to remove the viable cells and retain the nonviable cells.

In a preferred embodiment, exclusion dye staining is used as the viability assay. Exclusion dyes are those which are excluded from living cells, i.e. they are not taken up passively (they do not permeate the cell membrane of a live cell). However, due to the permeability of dead or dying cells, they are taken up by dead cells. Generally, but not always, the exclusion dyes bind to DNA, for example via intercalation, and does not fluoresce, or fluoresces poorly, in the absence of intercalation. Preferably, the exclusion dye does bind DNA; this eliminates the need for a wash step. Alternatively, exclusion dyes that require the use of a secondary label may also be used. Preferred exclusion dyes include, but are not limited to, ethidium bromide; ethidium homodimer-1; propidium iodine; SYTOX green nucleic acid stain; Calcein AM, BCECF AM; fluorescein diacetate; TOTO® and TO-PRO™ (from Molecular Probes; supra, see chapter 16) and others known in the art.

Protocols for exclusion dye staining for cell viability are known, see the Molecular Probes catalog, supra. In general, the exclusion dye is added to the cells at a concentration of from about 100 ng/ml to about 500 ng/ml, more preferably, about 500 ng/ml to about 1 μg/ml, and most preferably, from about 0.1 μg/ml to about 5 μg/ml, with about 0.5 μg/ml being particularly preferred. The cells and the exclusion dye are incubated for some period of time, washed, if necessary, and then the cells sorted as outlined below, to remove non-viable cells from the population.

In addition, there are other cell viability assays which may be run, including for example enzymatic assays, which can measure extracellular enzymatic activity of either live cells (i.e. secreted proteases, etc.), or dead cells (i.e. the presence of intracellular enzymes in the media; for example, intracellular proteases, mitochondrial enzymes, etc.). See the Molecular Probes Handbook of Fluorescent Probes and Research Chemicals, Haugland, Sixth Edition, chapter 16 in particular.

In a preferred embodiment, at least one cell viability assay is run, with at least two different cell viability assays being preferred, when the fluors, are compatible. When only 1 viability assay is run, a preferred embodiment utilizes light scattering assays (both forward and side scattering). When two viability assays are run, preferred embodiments utilize light scattering and dye exclusion, with light scattering and viability dye staining also possible, and all three being done in some cases as well. Viability assays thus allow the separation of nonviable or dying cells from viable ones.

In addition to a cell viability assay, a preferred embodiment utilizes a cell proliferation assay. By "proliferation assay" herein is meant an assay that allows the determination that a cell is either proliferating, i.e. replicating, or not replicating.

In a preferred embodiment, the proliferation assay is a dye inclusion assay. A dye inclusion assay relies on dilution effects to distinguish between cell phases. Briefly, a dye (generally a fluorescent dye as outlined below) is introduced to cells and taken up by the cells. Once taken up, the dye is trapped in the cell, and does not diffuse out. As the cell population divides, the dye is proportionally diluted. That is, after the introduction of the inclusion dye, the cells are allowed to incubate for some period of time; cells that lose fluorescence over time are dividing, and the cells that remain fluorescent are arrested in a non-growth phase.

Generally, the introduction of the inclusion dye may be done in one of two ways. Either the dye cannot passively enter the cells (e.g. it is charged), and the cells must be treated to take up the dye; for example through the use of a electric pulse. Alternatively, the dye can passively enter the cells, but once taken up, it is modified such that it cannot diffuse out of the cells. For example, enzymatic modification of the inclusion dye may render it charged, and thus unable to diffuse out of the cells. For example, the Molecular Probes CellTracker™ dyes are fluorescent chloromethyl derivatives that freely diffuse into cells, and then glutathione S-transferase-mediated reaction produces membrane impermeant dyes.

Suitable inclusion dyes include, but are not limited to, the Molecular Probes line of CellTracker™ dyes, including, but not limited to CellTracker™ Blue, CellTracker™ Yellow-Green, CellTracker™ Green, CellTracker™ Orange, PKH26 (Sigma), and others known in the art; see the Molecular Probes Handbook, supra; chapter 15 in particular.

In general, inclusion dyes are provided to the cells at a concentration ranging from about 100 ng/ml to about 5 µg/ml, with from about 500 ng/ml to about 1 µg/ml being preferred. A wash step may or may not be used. The cells and the inclusion dye are incubated for some period of time, to allow cell division and thus dye dilution. The length of time will depend on the cell cycle time for the particular cells; in general, at least about 2 cell divisions are preferred, with at least about 3 being particularly preferred and at least about 4 being especially preferred. Because of the length of time required, vaccinia virus MVA or another vector less cytopathic than vaccinia is preferred.

The cells are then sorted as outlined below, to create populations of cells that are replicating and those that are not. As will be appreciated by those in the art, in some cases, for example when screening for anti-proliferation agents, the bright (i.e. fluorescent) cells are collected; in other embodiments, for example for screening for proliferation agents, the low fluorescence cells are collected. Alterations are determined by measuring the fluorescence at either different time points or in different cell populations, and comparing the determinations to one another or to standards.

In one embodiment, at least one proliferation assay is run, with more than one being preferred. Thus, a proliferation assay results in a population of proliferating cells and a population of arrested cells.

In another embodiment, either after or simultaneously with one or more of the proliferation assays outlined above, at least one cell phase assay is done. A "cell phase" assay determines at which cell phase the cells are arrested, M, G1, S, or G2.

In a preferred embodiment, the cell phase assay is a DNA binding dye assay. Briefly, a DNA binding dye is introduced to the cells, and taken up passively. Once inside the cell, the DNA binding dye binds to DNA, generally by intercalation, although in some cases, the dyes can be either major or minor groove binding compounds. The amount of dye is thus directly correlated to the amount of DNA in the cell, which varies by cell phase; G2 and M phase cells have twice the DNA content of G1 phase cells, and S phase cells have an intermediate amount, depending on at what point in S phase the cells are. Suitable DNA binding dyes are permeant, and include, but are not limited to, Hoechst 33342 and 33258, acridine orange, 7-AAD, LDS 751, DAPI, and SYTO 16, Molecular Probes Handbook, supra; chapters 8 and 16 in particular.

In general, the DNA binding dyes are added in concentrations ranging from about 1 µg/ml to about 5 µg/ml. The dyes are added to the cells and allowed to incubate for some period of time; the length of time will depend in part on the dye chosen. In one embodiment, measurements are taken immediately after addition of the dye. The cells are then sorted as outlined below, to create populations of cells that contain different amounts of dye, and thus different amounts of DNA; in this way, cells that are replicating are separated from those that are not. As will be appreciated by those in the art, in some cases, for example when screening for anti-proliferation agents, cells with the least fluorescence (and thus a single copy of the genome) can be separated from those that are replicating and thus contain more than a single genome of DNA. Alterations are determined by measuring the fluorescence, for example, at different time points or in different cell populations, and comparing the determinations to one another or to standards.

In a preferred embodiment, the cell phase assay is a cyclin destruction assay. In this embodiment, the host cells contain a fusion nucleic acid which comprises nucleic acid encoding a cyclin destruction box and a nucleic acid encoding a detectable molecule. "Cyclin destruction boxes" are known in the art and are sequences that cause destruction via the ubiquitination pathway of proteins containing the boxes during particular cell phases. That is, for example, G1 cyclins may be stable during G1 phase but degraded during S phase due to the presence of a G1 cyclin destruction box. Thus, by linking a cyclin destruction box to a detectable molecule, for example green fluorescent protein, the presence or absence of the detectable molecule can serve to identify the cell phase of the cell population. In a preferred embodiment, multiple boxes are used, preferably each with a different fluor, such that detection of the cell phase can occur.

A number of cyclin destruction boxes are known in the art, for example, cyclin A has a destruction box comprising the sequence RTVLGVIGD (SEQ ID NO:12); the destruction box of cyclin B1 comprises the sequence RTALGDIGN (SEQ ID NO:13). See Glotzer et al., Nature 349:132–138 (1991). Other destruction boxes are known as well: YMTVSIIDRFMQDSCVPKKMLQLVGVT (rat cyclin B) (SEQ ID NO:14); KFRLLQETMYMTVSIIDRFMQN-SCVPKK (mouse cyclin B) (SEQ ID NO:15); RAILID-WLIQVQMKFRLLQETMYMTVS (mouse cyclin 131) (SEQ ID NO:16); DRFLQAQLVCRKKLQWGI-TALLLASK (mouse cyclin 132) (SEQ ID NO:17); and MSVLRGKLQLVGTAAMLL (mouse cyclin A2) (SEQ ID NO:18).

The nucleic acid encoding the cyclin destruction box is operably linked to nucleic acid encoding a detectable molecule. The fusion proteins are constructed by methods known in the art. For example, the nucleic acids encoding the destruction box is ligated to a nucleic acid encoding a detectable molecule. By "detectable molecule" herein is meant a molecule that allows a cell or compound comprising the detectable molecule to be distinguished from one that does not contain it, i.e., an epitope, sometimes called an antigen TAG, a specific enzyme, or a fluorescent molecule. Preferred fluorescent molecules include but are not limited to green fluorescent protein (GFP), blue fluorescent protein (BFP), yellow fluorescent protein (YFP), red fluorescent protein (RFP), and enzymes including luciferase and β-galactosidase. When antigen TAGs are used, preferred embodiments utilize cell surface antigens. The epitope is preferably any detectable peptide which is not generally found on the cytoplasmic membrane, although in some instances, if the epitope is one normally found on the cells, increases may be detected, although this is generally not preferred. Similarly, enzymatic detectable molecules may also be used; for example, an enzyme that generates a novel or chromogenic product.

Accordingly, the results of sorting after cell phase assays generally result in at least two populations of cells that are in different cell phases. In addition, positive controls can be used. For example, in the cell cycling assays, agents known to alter cell cycling may be used. For example, p21 is a molecule known to arrest cells in the G1 cell phase, by binding G1 cyclin-CDK complexes.

The practice of the present invention will employ, unless otherwise indicated, conventional techniques of cell biology, cell culture, molecular biology, transgenic biology, microbiology, virology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); *Molecular Cloning: A Laboratory Manual*, Sambrook et al., ed., Cold Springs Harbor Laboratory, New York (1992), DNA Cloning, Volumes I and II (D. N. Glover ed., 1985); Oligonucleotide Synthesis (M. J. Gaited., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986); and in Ausubel et al., *Current Protocols in Molecular Biology*, John Wiley and Sons, Baltimore, Md. (1989).

General principles of antibody engineering are set forth in *Antibody Engineering*, 2nd edition, C. A. K. Borrebaeck, Ed., Oxford Univ. Press (1995). General principles of protein engineering are set forth in *Protein Engineering, A Practical Approach*, Rickwood, D., et al., Eds., IRL Press at Oxford Univ. Press, Oxford, Eng. (1995). General principles of antibodies and antibody-hapten binding are set forth in: Nisonoff, A., *Molecular Immunology*, 2nd ed., Sinauer Associates, Sunderland, Mass. (1984); and Steward, M. W., *Antibodies, Their Structure and Function*, Chapman and Hall, New York, N.Y. (1984). Additionally, standard methods in immunology known in the art and not specifically described are generally followed as in *Current Protocols in Immunology*, John Wiley & Sons, New York; Stites et al. (eds), *Basic and Clinical-Immunology* (8th ed.), Appleton & Lange, Norwalk, Conn. (1994) and Mishell and Shiigi (eds), *Selected Methods in Cellular Immunology*, W.H. Freeman and Co., New York (1980).

EXAMPLES

Example 1

Construction and Characterization of Vaccinia Expression Vectors

This example describes the construction and characterization of a new set of direct ligation vectors designed to be universally applicable for the generation of chimeric vaccinia genomes. The aim was to modify the genome of vNotI/tk so as to acquire direct ligation vectors which are more universally useful. First, the insertion site was changed by placing the sites for two unique restriction enzymes at the beginning of the thymidine kinase gene. This allows one to fix the orientation of the insert polynucleotide (e.g. DNA) and eliminates the production of contaminating wildtype genomes after religation of viral arms. Second, in order to generate a direct ligation vector which would express high levels of protein, the thymidine kinase gene was preceded by a strong constitutive vaccinia virus promoter.

These new ligation vectors contain a pair of unique restriction sites, NotI and ApaI, to eliminate religation of poxvirus arms and fix the orientation of the insert polynucleotide (e.g. DNA) behind strongly expressing constitutive vaccinia promoters. The insertion cassette has been placed at the beginning of the thymidine kinase gene in vaccinia to utilize drug selection in the isolation of recombinants.

Materials and Methods

Plasmid Construction. Pairs of oligonucleotides were constructed which, when annealed, contained the 7.5 k gene promoter (MM436: GGCCAAAAATTGAAAAACTA-GATCTATTTATTGCACGCGGCCGCCATGGGCCC (SEQ ID NO:19) and MM437: GGCCGGGCCCATGGCG-GCCGCGTGCAATAAATA-GATCTAGTTTTTCAATTTTT (SEQ ID NO:20)), or the synthetic EL promoter (MM438: GGCCAAAAAT-TGAAATTTATTTTTTTTTTTG-GAATATAAAGCGGCCGCCAT GGGCCC (SEQ ID NO:21) and MM439: GGCCGGGCCCATGGCGGC-CGCTTTATATTCC AAAAAAAAAAAATAAAATTTCAATTTTT (SEQ ID NO:22))

and restriction sites for NotI and ApaI. The double-stranded oligonucleotides were annealed by ramping from 94° C. to 20° C. over two hours and ligated into the NotI site present in pJNotI/tk, a plasmid containing the HindIII J fragment from vNotI/tk, resulting in plasmids p7.5/tk and pEL/tk.

A Polymerase Chain Reaction (PCR) was performed on pBI221 a plasmid containing the *E.coli* gusA gene encoding for β-glucuronidase (β-glu), using primers MM440 (GG-GAAAGGGGCGGCCGCC ATGTTACGTCCTGTA-GAAACC) (SEQ ID NO:23) and MM441 (GG-GAAAGGGGGGCCCTCATTGTTTGCCTCCCTGCTG) (SEQ ID NO:24), or MM440 and MM442 (GG-GAAAGGGGCGGCCGCCTC ATTGTTTGCCTCCCT-GCTG) (SEQ ID NO:25), and the resulting fragment was cloned into pCRII (TA®) cloning kit, Invitrogen). The plasmids were excised with NotI (MM440/MM442 product) and cloned into pJNot/tk digested with NotI yielding pJNot/tk-GUS, or excised with NotI and ApaI (MM440/MM441 product), and inserted into pEL/tk and p7.5/tk previously digested with ApaI and NotI yielding p7.5/tk-GUS and pEL/tk-GUS.

Pairs of oligonucleotides were constructed which, when annealed, contained the 7.5 k gene promoter and the nucleotide sequence encoding for a cytotoxic T-cell epitope for ovalbumin (11) (SIINFEKL; SEQ ID NO:26) (75ova: GGC-CAAAAAT TGAAAAACTA GATCTATTTA TTGCAC-CATG AGTATAATCA ACTTTGAAAA ACTGTAGTGA (SEQ ID NO:27) and 75ovarv: GGCCTCACTA CAGTTTTTCA AAGTTGATTA ATACTCATGG TGCAATAAAT AGATCTAGTT TTTCAATTTTT (SEQ ID NO:28)) or the EL promoter and the peptide SIINFEKL (SEQ ID NO:29) ELova: GGCCAAAAATTGAAATTT-TATTTTTTTTTTTGGAATATAAACCATGAGTAT AAT-CAACTTTGAAAAACTGTAGTGA (SEQ ID NO:30) and Elovarv: GGCCTCACTACAGTTTTTCAAAGTTGAT-TATACTCATGGTTTATATTCCAAA AAAAAAAAATAAAATTTCAATTTTT (SEQ ID NO:31)).

The double-stranded oligonucleotides were annealed by ramping from 94° C. to 20° C. over two hours and ligated into the NotI site present in pJNotI/tk, a plasmid containing the HindIII J fragment from vNotI/tk resulting in plasmids p7.5/tk-ova and pEL/tk-ova.

Generation of Recombinant Viruses. Cells and viruses were maintained and manipulated as described by Earl, et al. (1991, In Ausubel, et al., (eds.), Current Protocols in Molecular Biology. Greene Publishing Associates/Wiley Interscience, New York). Recombinant viruses were made using homologous recombination by infecting CV-1 cells at a multiplicity of infection (moi) of 0.05 and two hours later transfecting DNA into the infected cells using lipofectamine (Life Technologies Incorporated) as suggested by the manufacturer. After 72 hours the cells were harvested and isolated plaques were selected by passage in Hutk⁻ cells in the presence of bromodeoxyuridine (Earl, et al., 1991, In Ausubel, et al. (eds.), Current Protocols in Molecular Biology. Greene Publishing Associates/Wiley Interscience, New York) or HAT supplemented media (Weir, et al., 1982, Proc. Nat. Acad. Sci. USA, 79:1210–1214).

Vaccinia virus was generated from viral DNA by rescue with fowlpox virus (Scheiflinger, et al., 1992, Proc. Natl. Acad. Sci. USA 89:9977–9981). Vaccinia virus was isolated from infected HeLa cells by banding and sedimentation in sucrose (Earl, et al., 1991, In Ausubel, et al. (eds.), Current Protocols in Molecular Biology. Greene Publishing Associates/Wiley Interscience, New York). The purified virions were treated with Proteinase K (Boehringer Mannheim) and gently extracted with buffer saturated phenol, phenol:chloroform (50:50), and chloroform before precipitation with 2.5 volumes of ethanol in 0.3M sodium acetate and resuspended in TE (10 mM TrisHCl, pH8.0. 1 mM EDTA (Earl, et al., 1991, In Ausubel, et al. (eds.), Current Protocols in Molecular Biology. Greene Publishing Associates/Wiley Interscience, New York). Confluent wells of BSC-1 cells from a 12 well dish were infected with fowlpox virus and after a two hour incubation at 37° C. were transfected with 0.6 µg full length vaccinia DNA using Lipofectamine (Life Technologies Incorporated) as suggested by the manufacturer. After 24, 48, and 72 hours the cells were harvested, lysed by three freeze-thaw cycles and screened by plaque assay on BSC-1 cells (Earl, et al., 1991, In Ausubel, et al., (eds.), Current Protocols in Molecular Biology. Greene Publishing Associates/Wiley Interscience, New York).

Generation of Recombinant Viruses by Direct Ligation. The 1.1 kB Eco RI/Eco RV restriction endonuclease fragment containing ovalbumin from pHbeta-Ova-neo (Pulaski, et al., 1996, Proc. Natl. Acad. Sci. USA, 93:3669–3674) was inserted into the EcoRI and EcoRV sites of pBluescript KS+ (Stratagene), generating pBS.ova. The DNA product from a Polymerase Chain Reaction (PCR) on pBS.ova using primers VV0LZ5 (GCAGGTGCGGCCGCCGTGGATC-CCCCGGGCTGCAGG) (SEQ ID NO:31) and VVTLZ3 (GTACCGGGCCCACAAAAA CAAAATTAGTTAGT-TAGGCCCCCCCTCGA) (SEQ ID NO:32) was digested with ApaI and NotI (Life Technologies, Inc.), gel purified from low melting point agarose (Bio-Rad) using beta Agarase (Life Technologies, Inc.) following the recommendations of the manufacturer, and cloned into pBluescript KS+ that had been digested with NotI and ApaI, generating pBS.VVova. A DNA. fragment encoding ovalbumin was excised from pBS.VVova by digestion of this plasmid with ApaI and NotI and purified after electrophoresis through a low melting point agarose gel using beta Agarase. One microgram of purified vEL/tk DNA was digested with ApaI and NotI and centrifuged through a Centricon 100 concentrator (Amicon) to remove the small intervening fragment. The vEL/tk DNA arms and the DNA fragment encoding ovalbumin were ligated overnight at room temperature, at a 4:1 (insert: virus) molar ratio, in 30 microliters with 5 units T4 DNA Ligase. The ligation product was transfected using lipofectamine (Life Technologies, Inc.) into a well of confluent BSC-1 cells from a 12 well plate two hours after infection with fowlpox virus at 1 pfu/cell. Three days later the cells were harvested and isolated plaques were selected by passage in Hutk– cells in the presence of bromodeoxyuridine (Earl, et al., 1991 In Ausubel, et al (eds.), Current Protocols in Molecular Biology. Greene Publishing Associates/Wiley Interscience, New York).

Analysis of Viral DNA Genomes. BSC-1 cells were infected at high multiplicity of infection (moi) by vaccinia WR, vEL/tk, v7.5/tk, or vNotI/tk. After 24 hours the cells were harvested and resuspended in Cell Suspension Buffer (Bio-Rad Genomic DNA Plug Kit) at $1 \times 10^7$ cells/ml. An equal volume of 2% CleanCut agarose (Bio-Rad) preincubated at 50° C. was added and the cell suspension was formed into 100 µl plugs. After hardening at 4° C. the plugs were treated as previously described to digest protein (Merchlinsky, et al., 1989. J. Virol. 63:1595–1603). The plugs were equilibrated in the appropriate restriction enzyme buffer and 1 mM PMSF for 16 hours at room temperature, incubated with restriction enzyme buffer, 100 ng/ml Bovine Serum Albumin and 50 units NotI or ApaI for two hours at 37° C. (NotI) or room temperature (ApaI)-prior to electrophoresis.

Figure 2B:
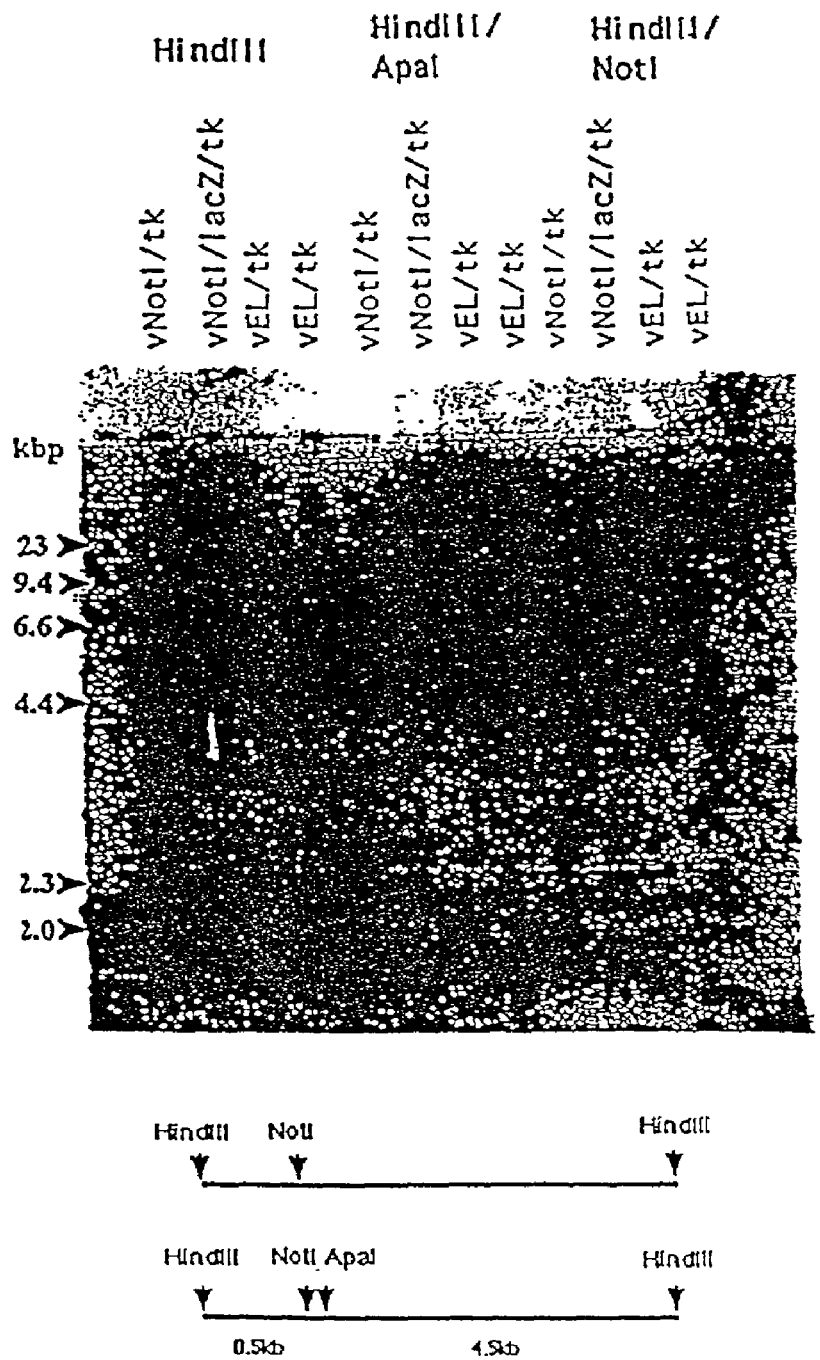

One well of a 6 well dish of BSC-1 was infected with v7.5/tk or vEL/tk at high multiplicity of infection (moi) and after 48 hours the cells were harvested, pelleted by low speed centrifugation, rinsed with Phosphate-Buffered Saline (PBS), and the DNA was isolated using DNAzol (Gibco). The final DNA product was resuspended in 50 microliters of TE (10 mM TrisHCl, pH8.0. 1 mM EDTA) and 2.5 microliters were digested with HindIII, HindIII and ApaI, or HindIII and NotI, electrophoresed through a 1.0% agarose gel, and transferred to Nytran (Schleicher and Schuell) using a Turboblotter (Schleicher and Schuell). The samples were probed with p7.5/tk (FIG. 2A) or pEL/tk (FIG. 2B) labeled with $^{32}$P using Random Primer DNA Labeling Kit (Bio-Rad) in QuickHyb (Stratagene) and visualized on Kodak XAR film.

One well of a 6 well dish of BSC-1 cells was infected with v7.5/tk, vEL/tk, vNotI/tk, vpNotI, vNotI/lacZ/tk, or wild type vaccinia WR at high multiplicity of infection (moi) and after 48 hours the cells were harvested, pelleted by low speed centrifugation, rinsed with Phosphate-Buffered Saline (PBS), and the DNA was isolated using DNAzol (Gibco). The final DNA product was resuspended in 50 microliters of TE (10 mM TrisHCl, pH8.0. 1 mM EDTA) and used in a PCR (30 cycles, 1 minute 94° C., 2 minutes 55° C., 3 minutes 72° C., MJ Research PTC-100) with primers MM407 (GGTCCCTATTGTTACAGATGGAAGGGT) (SEQ ID NO:33) and MM408 (CCTTCGTTTGCCAT-ACGCTCACAG) (SEQ ID NO:34). The nucleotide sequence was determined by $^{35}$S sequencing using Sequenase Version 2.0 DNA Sequencing Kit (Amersham), and visualized after electrophoresis through 8% denaturing polyacrylamide gels by exposure to Bio-Max film (Kodak).

Determination of β-Glucuronidase Activity. A well of BSC-1 cells from a 12 well plate was infected at an moi of 1 with vNotI/tk-GUS, v7.5/tk-GUS and vEL/tk-GUS, the cells were harvested 20 hours post infection, resuspended in 0.5 ml PBS, and disrupted by three cycles of freeze-thawing. The extract was clarified by a short microfuge spin (one minute, 14,000 rpm) and the supernatant was analyzed for β-glu units as described by Miller, 1972, Experiments in Molecular Genetics, Cold Spring Harbor Laboratory, Cold Spring Harbor, N.Y. as adapted for 96-well plates. The $A_{405}$ values were determined on a microplate reader (Dynatech MR3000) and the β-glu activity was determined by comparison to β-glu (Clontech) standards analyzed in the same assay.

Analysis of Cytotoxic T Cell Response. Confluent monolayers of MC57G cells in wells of a 6 well plate were infected at an moi of 1 with vEL/tk, v7.5/tk-ova, vEL/tk-ova, vEL/tk-ovaFL clone 1, and vEL/tk-ovaFL clone 2 (vEL,/tk-ovaFL are virus clones of full length ovalbumin generated by direct ligation). At 16 hours post infection cells were harvested, labeled with 100 microcuries $^{51}$Chromium (Dupont) for 1 hour at 37° C., and $10^4$ cells were added to wells of a 96 well round bottom plate in quadruplicate. A sample of uninfected MC57G cells incubated with 1 micromolar purified ova 257–264 peptide was also incubated with $^{51}$Cr as a positive control and untreated MC57G cells were used as a negative control. T cells specific for ova 257–264 were added to target cells at ratios of 2:1 and 10:1. Cells were incubated at 37° C. for 4 hours, supernatants were harvested, and $^{51}$Cr release determined. Spontaneous release was derived by incubating target cells with media alone and maximal release was determined by incubating target cells with 5% Tritonx 100. Percentage of specific lysis was calculated using the formula: % specific lysis=((experimental release-spontaneous release)/(maximal release-spontaneous release))×100. In each case the mean of quadruplicate wells was used in the above formula.

Results

Construction of Direct Ligation Vectors. The vaccinia WR genome is approximately 190 kilobases in length and rich in A and T residues. The complete sequence of the vaccinia WR genome was provided by P. Earl of the Bernard Moss laboratory (Laboratory of Viral Diseases, NIAID, NIH, Bethesda, Md.). A restriction enzyme search of the complete sequence of the vaccinia WR genome using Mac Vector (IBI) revealed a lack of restriction sites for ApaI, AscI, Bsp120I, FseI, RsrII, SfiI, SrfI and SgfI. The ready availability of highly active and pure preparations of the enzyme as well as the generation of a staggered end upon digestion led us to choose to use ApaI as the second site in conjunction with the NotI site already present in vNot/tk.

Vaccinia virus based expression vectors are most useful when the foreign protein is expressed constitutively. The expression of foreign proteins during the early stage of viral replication is essential for cytotoxic T cell response (Bennick, et al. 1990, Topics Microbiol. Immunol. 163:153–184) and high levels of total protein expression have been observed using promoters active during the late stage of viral replication. We decided to incorporate the promoters corresponding to the constitutively expressed 7.5 k gene (Mackett, et al., 1984, J. Virology, 49:857–864) and a constitutively expressed synthetic promoter EL noted for high level expression.

A useful feature of vNotI/tk that must be retained in any new vector is the ability to discriminate for recombinant viral genomes using selection against an active thymidine kinase gene. The introduction of the ApaI site within the coding sequence for the tk gene necessitates an increase in the total number of amino acids in order to accommodate the restriction enzyme site. A comparison of the amino acid sequence for thymidine kinase genes from a variety of animal and viral species showed the region of greatest heterogeneity was at the N terminus of the protein, suggesting that this region of the protein could tolerate a modest increase in the number of amino acids.

The recombination-independent cloning vectors were constructed by making plasmid intermediates containing the modified thymidine kinase (tk) gene and replacing the tk sequence in the vNotI/tk genome by homologous recombination. Two sets of oligonucleotide pairs were constructed which, when annealed, contained the promoter for the 7.5 k gene or the synthetic EL sequence and restriction sites for NotI and ApaI. The modified thymidine kinase genes were constructed by annealing the double-stranded oligonucleotides and ligating the product into the NotI site present at the beginning of the thymidine kinase gene in pJNotI/tk, a plasmid containing the HindIII J fragment from vNotI/tk. The oligonucleotide pairs annealed to and eliminated the NotI site in pJNotI/tk generating a new NotI site closely followed by an ApaI site after the promoter and flanking the nucleotides coding for the initial methionine in the thymictine kinase gene resulting in plasmids p7.5/tk and pEL/tk (FIG. 1). The acquisition of the ApaI site was verified by restriction enzyme analysis of plasmid DNA and the nucleotide sequence of the thymidine kinase gene promoter was determined and found to be as depicted in FIG. 1.

The recombinant viruses derived from p7.5/tk and pEL/tk were isolated using a strategy relying on positive drug selection in the presence of HAT (hypoxanthine, aminopterin, thymidine) (Weir, et al., 1982, Proc. Nat. Acad. Sci. USA 79:1210–1214). The viruses vpNotI, a virus that contains a copy of pBR322 inserted at the NotI site of vNotI/tk (Merchlinsky, et al., 1992, Virology 190:522–526), and vNotI/lacZ/tk, a virus with a copy of the lacZ gene interrupting the thymidine kinase in vNotI⁻ (Merchlinsky, et al., 1992, Virology. 190:522–526) are thymidine kinase negative (tk⁻) viruses that are identical to vNotI/tk except for the inserted DNA at the beginning of the tk gene. The plasmids p7.5/tk and pEL/tk were recombined with vpNotI and vNotI/lacZ/tk helper viruses in CV-1 cells and the infected monolayers were harvested and passaged in the presence of HAT media on Hutk⁻ cells. Individual plaques were passaged and isolated an additional three rounds on Hutk⁻ cells before expansion and analysis.

Analysis of the Structure of the Viral Genomes. The growth of v7.5/tk and vEL/tk virus in HAT supplemented media implies these viruses, in contrast to vpNot and vNot/lacZ/tk, contain an active thymidine kinase (tk) gene. However, an active tk gene could arise from multiple crossovers which delete the 7.5 k or EL promoter sequences, generating a virus with the normal tk promoter. The v7.5/tk and vEL/tk genomes should contain a unique site for both NotI and ApaI within the HindIII J fragment. The genomic structure of the isolated virus stocks was analyzed by restriction enzyme digestion of DNA in agarose plugs derived from virus infected cells using NotI or ApaI and electrophoresis of the products through 1% agarose (FIG. 3). Uncut vaccinia WR (lane 2) migrates at a size of 190 kilobase pairs as compared to multimers of bacteriophage lambda (lane 1). After digestion with NotI vaccinia WR is cleaved into two fragments approximately 150 and 40 kilobase pairs in length (7th lane from left) whereas the vNot/tk, vEL/tk, and v7.5/tk were cleaved into fragments of about 110 and 80 kilobase pairs. When the same samples were digested with ApaI, only one fragment the size of the uncut genome was observed for both vaccinia WR and vNot/tk while vEL/tk and v7.5/tk gave the same sized fragments observed after digestion with NotI. Therefore, both v7.5/tk and vEL/tk contain a unique site for both ApaI and NotI, the sites are at the same locus as the NotI site in vNot/tk, and the sites are in a more central location in the genome than the HindIII F fragment which contains the NotI site in vaccinia WR. The background of cellular DNA fragments was more pronounced in the ApaI digestion, which has a six base pair recognition site, than for the NotI digest.

The genomes for vEL/tk and v7.5/tk were analyzed by Southern blotting to confirm the location of the ApaI and NotI sites in the HindIII J fragment as shown in FIG. 2. The filters were hybridized to $^{32}$P labeled HindIII J fragment derived from the p7.5/tk or pEL/tk. The genomes for v7.5/tk and vEL/tk have an ApaI site that does not appear in vNotI/tk (compare lanes 7 and 8 to lane 5 in each blot) whereas digestion with NotI and HindIII yield a set of fragments of equivalent size. The 0.5 kilobase HindIII/NotI or HindIII/ApaI fragment from the left hand side of HindIII J produced from NotI or ApaI digestion has electrophoresed off the bottom of the agarose gel.

The definitive characterization of the promoter sequence utilized products of Polymerase Chain Reaction (PCR). A pair of primers flanking the beginning of the tk gene were used to generate a DNA fragment from the viruses vNotI/tk, v7.5/tk, or vEL/tk and their cognate plasmids as shown in FIG. 4. The PCR products for v7.5/tk and vEL/tk are the same size as those observed for the plasmids used to generate the viruses (p7.5/tk and pEL/tk) and larger than those seen for vaccinia WR and vNotI/tk. The PCR fragments were cloned into the plasmid pCRII, the nucleotide sequence was determined and shown to match the sequence displayed in FIG. 1.

Quantitation of Promoter Activity. The v7.5/tk and vEL/tk vectors have been designed to constitutively express elevated levels of insert protein in comparison to vNotI/tk. The level of RNA synthesis was measured by infecting confluent BSC-1 cells in the presence and absence of cytosine arabinoside (AraC) at an moi of 5, harvesting the cells, isolating the RNA using Trizol (Life Technologies) and analyzing the level of thymidine kinase RNA synthesis by primer extension (Weir, et al., 1990, Nucleic Acids Research 16:10267–10282). Incubation with AraC blocks viral DNA replication, allowing one to identify the class of viral promoter.

The early class of viral promoters are active prior to DNA replication and will be unaffected by AraC in the infection. Late promoters are only expressed after the onset of DNA replication and their activity is abrogated in the presence of AraC. Perusal of the products on a denaturing polyacrylamide gel demonstrated that significantly more (estimated to be at least ten fold) tk RNA primer extension products were synthesized in vEL/tk infections as compared to vNot/tk. In cells infected with vNot/tk a single RNA start site insensitive to AraC incubation was observed whereas in vEL/tk infections two distinct start sites, one resistant to AraC and corresponding to the appropriate early start site (Davison, et al., 1989, J. Mol. Biol. 210:749–769), and one species sensitive to AraC and corresponding to the appropriate late start of RNA (Davison, et al. 1989, J. Mol. Biol. 210: 771–784) were observed (data not shown). The pattern of RNA species derived from infection with v7.5/tk was similar to that observed for vEL/tk with the absolute levels of RNA expression intermediate to that observed for vEL/tk and vNot/tk.

In order to verify the levels of expression for genes inserted into the viral vectors the *E.coli* gusA gene encoding for β-glucuronidase (β-glu) was cloned into vNotI/tk, v7.5/tk and vEL/tk viral vectors and the relative promoter strength was measured. The DNA fragment encoding for the β-glu gene was inserted into plasmids containing each promoter generating pJNot/tk-GUS, p7.5/tk-GUS and pEL/tk-GUS. The correct orientation of the insert β-glu gene in pJNot/tk was verified by restriction enzyme analysis. The plasmids were recombined with vNotI/tk and the recombinant viruses identified by staining with X-glu (Carroll, et al., 1995, BioTechniques 19:352–355), passaged for three rounds through Hutk⁻ cells, and expanded to generate the viral stocks vNotI/tk-GUS, v7.5/tk-GUS and vEL/tk-GUS. The structures of the recombinant viruses were verified by Southern blot analysis.

The level of expression of β-glu by vNotI/tk-GUS, v7.5/v7.5/tk-GUS and vEL/tk-GUS was measured from infected confluent monolayers of BSC-1 cells in the presence or absence of AraC (FIG. 5). The level of β-glu expression for the v7.5/tk-GUS and vEL/tk was much higher than that observed for vNotI/tk-GUS and highest (approximately twenty fold higher) in the vEL/tk-GUS. Expression of β-glu was observed for all three viruses in the presence of cytosine arabinoside, indicating that each promoter is a member of the early class of viral promoters. The level of β-glu in vNotI/tk-GUS was unchanged in the presence or absence of AraC indicating that this promoter is only active early during infection, whereas the β-glu levels in v7.5/tk-GUS and vEL/tk-GUS were lower in the presence of AraC, indicating these promoters are active both early and late times during infection.

Biochemical Characterization of Virus Vectors. The v7.5/tk and vEL/tk vectors were initially isolated by growth in the presence of HAT supplemented media and are designed to contain an active tk gene to allow selection for viruses with inserts via passage in Hutk⁻ cells in the presence of bromodeoxyuridine (Earl, et al., 1991, In Ausubel, et al. (eds.), Current Protocols in Molecular Biology. Greene Publishing Associates/Wiley Interscience, New York). Both vectors were tested by plaque assay in Hutk⁻ cells using drug selection and the results for vEL/tk are shown in FIG. 6. Incubation without drug or with HAT supplement at a concentration sufficient to interfere with plaque formation for vpNot or vNot/lacZ/tk, (data not shown), gave an equivalent number of like-sized plaques. Surprisingly, an equal number of plaques, albeit much smaller in size, were observed for vEL/tk with incubation in 25 mM bromodeoxyuridine, a concentration sufficient to interfere with the ability of vaccinia WR to plaque on Hutk⁻ cells (data not shown). Addition of 125 mM bromodeoxyuridine was sufficient to inhibit plaque formation for vEL/tk (FIG. 6) and v7.5/tk (data not shown). The higher concentration of bromodeoxyuridine did not interfere with the growth of tk⁻ viruses such as vNotI/lacZ/tk (data not shown) or affect the viability of the Hutk⁻ cell line.

Construction of Recombinant Virus by Direct Ligation. Direct ligation vectors will only be useful for the generation of complex expression libraries if the production of infectious virus from the naked DNA is facile and efficient. Previously, helper virus activity was supplied in cells transfected with DNA ligation products by coinfection with conditionally lethal temperature sensitive virus (Merchlinsky, et al., 1992, Virology. 190:522–526) or fowlpox (Scheiflinger, et al., 1992, Proc. Natl. Acad. Sci. USA, 89:9977–9981). Since high levels of replicating wild type virus interfere with the ability to package viral DNA and vaccinia virus can recombine with the input DNA, only conditionally defective vaccinia virus can be used as helper (Merchlinsky, et al., 1992, Virology, 190:522–526). Fowlpox should be a superior helper virus as it is used at 37° C., will not revert to a highly replicating strain, and, since it does not recombine with vaccinia DNA or productively infect primate cell lines, can be used at higher moi than vaccinia. In order to determine if fowlpox can serve as an efficient helper virus a series of wells from a 12 well plate containing BSC-1 cells were infected with varying Mois of fowlpox and transfected with full length vaccinia WR DNA, the cells were harvested after 24, 48, or 72 hours and the virus titer was determined as shown in Table 4. Transfection of DNA without fowlpox or fowlpox infection alone resulted in no plaques. The level of rescued vaccinia increased with later harvest and was proportional to the moi of the fowlpox infection.

TABLE 4

| FPV moi | Day harvested | Titer (pfu × $10^{-3}$) |
|---|---|---|
| 0.2 | 1 | 0 |
|  | 2 | 0.12 |
|  | 3 | 300 |
| 0.5 | 1 | 0 |
|  | 2 | 0.23 |
|  | 3 | 500 |
| 1.0 | 1 | 0 |
|  | 2 | 1.1 |
|  | 3 | 700 |

Table 4. Packaging of vaccinia DNA by fowlpox virus. Vaccinia DNA was transfected into BSC-1 cells infected with fowlpox virus using lipofectamine as described in Materials and Methods. The cells were harvested at 1, 2, or 3 days post transfection, lysed by freeze-thaw cycles and assayed for infectious virus by plaque assay on BSC-1 cells.

A 1.1 kilobase pair fragment of the ovalbumin cDNA (Pulaski, et al., 1996, Proc. Natl. Acad. Sci. USA 93:3669–3674) was used as a model insert to study the generation of functional recombinant virus by direct ligation. The ovalbumin insert was modified to include a NotI site at its 5' end, translation stop codons, a vaccinia transcriptional stop signal and an ApaI site at its 3' end. This insert was digested with NotI and ApaI and ligated with purified vEL/tk DNA arms that had been digested with NotI and ApaI. The ligation mix was transfected into fowlpox infested BSC-1 cells, cells were harvested, and after three days the cell extract was passaged on Hutk⁻ cells, cells in the presence or absence of 125 mM bromodeoxyuridine. The titer obtained without drug selection was $2.7\times10^3$ pfu and with drug selection $2.8\times10^3$ pfu. Individual plaques were picked from Hutk⁻ cells in the presence and absence of bromodeoxyuridine and tested for the presence of the ovalbumin insert by dot blot hybridization with an ovalbumin cDNA probe. All 15 plaques picked in the presence of bromodeoxyuridine, and all 10 plaques picked in its absence contained the ovalbumin insert. These viruses were named vEL/tk-ovaFL. Two individual clones were expanded further and tested for the ability to sensitize host cells to lysis by ova 257–264 specific cytotoxic T lymphocytes (CTL). The results of this experiment are shown in Table 5. As controls, vaccinia recombinant for an ova 257–264 minigene, v7.5/tk-ova and vEL/tk-ova, were generated by homologous recombination. These ova peptide recombinant viruses were tested in concert with the vEL/tk-ovaFL clones for the ability to sensitize host cells to lysis by ova specific CTL. As shown in Table 5, infection with either full length or minigene ovalbumin vaccinia recombinants was as efficient as pulsing with 1 μM purified OVA 257–264 peptide for sensitization of target cells to lysis by OVA-specific CTL.

TABLE 5

|  | Effector:Target Ratio | |
|---|---|---|
| MC57G Cells | 2:1 | 10:1 |
|  | (Percent Specific Lysis) | |
| Untreated | −1.3 | −1.3 |
| ova257–264 peptide, 1 μM | 54 | 83 |

TABLE 5-continued

|  | Effector:Target Ratio | |
|---|---|---|
| MC57G Cells | 2:1 | 10:1 |
| vEL/tk | −0.5 | 0 |
| v7.5/tk-ova Homologous Recombination | 50 | 78 |
| vEL/tk-ova Homologous Recombination | 47 | 71 |
| vEL/tk-ovaFL Direct Ligation Clone 1 | 48 | 70 |
| vEL/tk-ovaFL Direct Ligation Clone 2 | 46 | 74 |

Table 5. Cell mediated lymphocytotoxicity (CML) assay on recombinant vaccinia virus infected cells. Virally infected MC57G cells were generated as described in (Materials and Methods). One sample of MC57G cells was treated with ova 257–264 peptide (1 μM), another sample of cells was left untreated. Cells were incubated with two different ratios of ova specific cytotoxic T lymphocytes for 4 hours at 37° C. and percent specific lysis was determined as described in Materials and Methods.

Discussion

Large DNA viruses are particularly useful expression vectors for the study of cellular processes as they can express many different proteins in their native form in a variety of cell lines. In addition, gene products expressed in recombinant vaccinia virus have been shown to be efficiently processed and presented in association with MHC class I for stimulation of cytotoxic T cells. The gene of interest is normally cloned in a plasmid under the control of a promoter flanked by sequences homologous to a non-essential region in the virus and the cassette is introduced into the genome via homologous recombination. A panoply of vectors for expression, selection and detection have been devised to accommodate a variety of cloning and expression strategies. However, homologous recombination is an ineffective means of making a recombinant virus in situations requiring the generation of complex libraries or when the insert polynucleotide (e.g. DNA) is large. An alternative strategy for the construction of recombinant genomes relying on direct ligation of viral DNA "arms" to an insert and the subsequent rescue of infectious virus has been explored for the genomes of poxvirus (Merchlinsky, et al., 1992, Virology 190:522–526; Pfleiderer, et al., 1995, J. General Virology 76:2957–2962; Scheiflinger, et al., 1992, Proc. Natl. Acad. Sci. USA 89:9977–9981), herpesvirus (Rixon, et al., 1990, J. General Virology 71:2931–2939) and baculovirus (Ernst, et al., 1994, Nucleic Acids Research 22:2855–2856).

Poxviruses are ubiquitous vectors for studies in eukaryotic cells as they are easily constructed and engineered to express foreign proteins at high levels. The wide host range of the virus allows one to faithfully express proteins in a variety of cell types. Direct cloning strategies have been devised to extend the scope of applications for poxvirus viral chimeras in which the recombinant genomes are constructed in vitro by direct ligation of DNA fragments to vaccinia "arms" and transfection of the DNA mixture into cells infected with a helper virus (Merchlinsky, et al., 1992, Virology 190:522–526; Scheiflinger, et al., 1992, Proc. Natl. Acad. Sci. USA 89:9977–9981). This approach has been used for high level expression of foreign proteins (Pfleiderer, et al., 1995, J. Gen. Virology 76:2957–2962) and to efficiently clone fragments as large as 26 kilobases in length (Merchlinsky, et al., 1992, Virology 190:522–526).

Naked vaccinia virus DNA is not infectious because the virus cannot utilize cellular transcriptional machinery and relies on its own proteins for the synthesis of viral RNA. Previously, temperature sensitive conditional lethal (Merchlinsky, et al., 1992, Virology 190:522–526) or non-homologous poxvirus fowlpox (Scheiflinger, et al., 1992, Proc. Natl. Acad. Sci. USA 89:9977–9981) have been utilized as helper virus for packaging. An ideal helper virus will efficiently generate infectious virus but not replicate in the host cell or recombine with the vaccinia DNA products. Fowlpox virus has the properties of an ideal helper virus as it is used at 37° C., will not revert to a highly replicating strain, and, since it does not recombine with vaccinia DNA or productively infect primate cell lines, can be used at relatively high moi.

The utility of the vaccinia based direct ligation vector vNotI/tk, has been described by Merchlinsky, et al. (1992, Virology 190:522–526). This genome lacks the NotI site normally present in the HindIII F fragment and contains a unique NotI site at the beginning of the thymidine kinase gene in frame with the coding sequence. This allows the insertion of DNA fragments into the NotI site and the identification of recombinant genomes by drug selection. The vNotI/tk vector will only express foreign proteins at the level of the thymidine kinase gene, a weakly expressed gene only made early during viral infection. Thus, the vNotI/tk vector can be used to efficiently clone large DNA fragments but does not fix the orientation of the DNA insert or lead to high expression of the foreign protein.

This example describes the construction and characterization of a pair of vaccinia DNA vector genomes v7.5/tk and vEL/tk suitable for direct ligation. The v7.5/tk and vEL/tk vectors were designed to contain unique restriction sites for NotI and ApaI at the beginning of the thymidine kinase gene allowing the oriented cloning of DNA and eliminating the intact genomes arising from relegation of vaccinia vector arms.

To induce high levels of protein expression the sequences encoding for the viral 7.5 k promoter and a synthetic EL promoter devised by Chakrabarti and Moss were used to replace the endogenous thymidine kinase promoter. The levels of expression induced by either promoter was much higher than that observed in vNotI/tk and the promoters were active at all times post infection. These continuous expression vectors are applicable in cases dependent on early expression, such as T-cell epitope presentation, as well as for bulk expression of proteins.

Use of the thymidine kinase gene as the insertion site for foreign DNA allows selection for recombinants and against helper or wild type genomes. The level of tk expression in v7.5/tk and vEL/tk should be much higher than in vaccinia WR or vNot/tk. However, the ApaI site at the beginning of the tk gene in v7.5/tk and vEL/tk was formed from vNot/tk by adding extra nucleotides at the NotI site. The additional nucleotides increase the amino acid sequence at the N terminus of the wild type tk gene from Met-Asn-Gly to Met-Gly-Pro-Ala-Ala-Asn-Gly (SEQ ID NO:35) in v7.5/tk and vEL/tk. Modifications in the expression level and N terminal amino acid sequence of the thymidine kinase gene may increase (more protein) or decrease (different sequence) the sensitivity of the virus to bromodeoxyuridine. Plaques, albeit smaller, were observed with v7.5/tk and vEL/tk infection at a concentration of bromodeoxyuridine sufficient to completely suppress plaque formation for wild type vaccinia WR. Plaque formation was suppressed at five-fold higher concentrations of bromodeoxyuridine, a level of drug that does not interfere with the viability of the cells or impede the ability of tk⁻ virus to form plaques. The explanation for the altered sensitivity to bromodeoxyuridine awaits further characterization of the protein as the altered thymidine kinase gene may have a different reaction rate for formation of the triphosphate form of the bromodeoxyuridine or a reduced ability to bind bromodeoxyuridine.

The development of direct ligation vectors has increased the possible applications for poxvirus expression vectors. The v7.5/tk and vEL/tk vectors were designed to incorporate the advantages of oriented cloning, high levels of expression of foreign protein, and the selection for recombinant viruses, into direct ligation vectors. They were shown to express high levels of proteins at all times during infection. The utility of these vectors was demonstrated by constructing recombinants containing a CTL epitope for ovalbumin (constructed by homologous recombination with a plasmid) or the ovalbumin coding sequence (constructed by direct ligation protocol) and showing how both recombinants were able to elicit a strong CTL response.

The application of these vectors to protocols for construction of complex expression libraries requires efficient production of recombinants and strong selection to eliminate or minimize wild type and contaminants. The use of two restriction sites allows one to design cloning strategies for the oriented cloning of DNA fragments such as products of PCR (Pfleiderer, et al., 1995, J. General Virology 76:2957–2962) and increases the frequency of the desired recombinant as wild type genomes can no longer be generated by ligation of vaccinia arms. When v7.5/tk or vEL/tk DNA previously digested with NotI and ApaI was transfected into cells infected with fowlpox the virus titer was one hundred fold lower than for intact uncut DNA. Also, all plaques isolated in the presence and absence of bromodeoxyuridine (15 with bromodeoxyuridine and 10 without) during the isolation of the vEL/tk-ovaFL contained the ovalbumin insert. The efficiency of infectious virus formation is also increased with the use of fowlpox, helper virus at relatively high moi. Also, transfection of large DNA fragments varies with the type and preparation of lipid (Miles Carroll, personal communication) and we are presently assaying different lipid mixtures and cell types as well as investigating other parameters to find optimum conditions for the direct ligation protocol. The v7.5/tk and vEL/tk vectors provide a set of universally applicable direct ligation cloning vectors for poxviruses.

Example 2

Trimolecular Recombination

Production of an Expression Library. This example describes a tri-molecular recombination method employing modified vaccinia virus vectors and related transfer plasmids that generates close to 100% recombinant vaccinia virus and, for the first time, allows efficient construction of a representative DNA library in vaccinia virus.

Construction of the Vectors.

The previously described vaccinia virus transfer plasmid pJ/K, a pUC 13 derived plasmid with a vaccinia virus thymidine kinase gene containing an in-frame Not I site (Merchlinsky, M. et al., Virology 190:522–526), was further modified to incorporate a strong vaccinia virus promoter followed by Not I and Apa I restriction sites. Two different vectors, p7.5/tk and pEL/tk, included, respectively, either the 7.5K vaccinia virus promoter or a strong synthetic early/late (E/L) promoter (FIG. 1). The Apa I site was preceded by a strong translational initiation sequence including the ATG codon. This modification was introduced within the vaccinia virus thymidine kinase (tk) gene so that it was flanked by regulatory and coding sequences of the viral tk gene. The modifications within the tk gene of these two new plasmid vectors were transferred by homologous recombination in the flanking tk sequences into the genome of the Vaccinia Virus WR strain derived vNotI⁻ vector to generate new viral vectors v7.5/tk and vEL/tk. Importantly, following Not I and Apa I restriction endonuclease digestion of these viral vectors, two large viral DNA fragments were isolated each including a separate non-homologous segment of the vaccinia tk gene and together comprising all the genes required for assembly of infectious viral particles. Further details regarding the construction and characterization of these vectors and their alternative use for direct ligation of DNA fragments in vaccinia virus are described in Example 1.

Generation of an Increased Frequency of Vaccinia Virus Recombinants.

Standard methods for generation of recombinants in vaccinia virus exploit homologous recombination between a recombinant vaccinia transfer plasmid and the viral genome. Table 6 shows the results of a model experiment in which the frequency of homologous recombination following transfection of a recombinant transfer plasmid into vaccinia virus infected cells was assayed under standard conditions. To facilitate functional assays, a minigene encoding the immunodominant 257–264 peptide epitope of ovalbumin in association with H-2K$^b$ was inserted at the Not 1 site in the transfer plasmid tk gene. As a result of homologous recombination, the disrupted tk gene is substituted for the wild type viral tk+ gene in any recombinant virus. This serves as a marker for recombination since tk– human 143B cells infected with tk– virus are, in contrast to cells infected with wild type tk+ virus, resistant to the toxic effect of BrdU. Recombinant virus can be scored by the viral pfu on 143B cells cultured in the presence of 125 mM BrdU.

The frequency of recombinants derived in this fashion is of the order of 0.1% (Table 6).

TABLE 6

Generation of Recombinant Vaccinia Virus by Standard Homologous Recombination

| Virus* | DNA | Titer w/o BrdU | Titer w/ BrdU | % Recombinant** |
|---|---|---|---|---|
| vaccinia | — | $4.6 \times 10^7$ | $3.0 \times 10^3$ | 0.006 |
| vaccinia | 30 ng pE/Lova | $3.7 \times 10^7$ | $3.2 \times 10^4$ | 0.086 |
| vaccinia | 300 ng pE/Lova | $2.7 \times 10^7$ | $1.5 \times 10^4$ | 0.056 |

*vaccinia virus strain vNotI
**% Recombinant = (Titer with BrdU/Titer without BrdU) × 100

This recombination frequency is too low to permit efficient construction of a cDNA library in a vaccinia vector. The following two procedures were used to generate an increased frequency of vaccinia virus recombinants.

(1) One factor limiting the frequency of viral recombinants generated by homologous recombination following transfection of a plasmid transfer vector into vaccinia virus infected cells is that viral infection is highly efficient whereas plasmid DNA transfection is relatively inefficient. As a result many infected cells do not take up recombinant plasmids and are, therefore, capable of producing only wild type virus. In order to reduce this dilution of recombinant efficiency, a mixture of naked viral DNA and recombinant plasmid DNA was transfected into Fowl Pox Virus (FPV) infected mammalian cells. As previously described by others (Scheiflinger, F., et al., 1992, Proc. Natl. Acad. Sci. USA 89:9977–9981), FPV does not replicate in mammalian cells but provides necessary helper functions required for packaging mature vaccinia virus particles in cells transfected with non-infectious naked vaccinia DNA. This modification of the homologous recombination technique alone increased the frequency of viral recombinants approximately 35 fold to 3.5% (Table 7).

TABLE 7

Generation of Recombinant Vaccinia Virus by Modified Homologous Recombination

| Virus | DNA | Titer w/o BrdU | Titer w/ BrdU | % Recombinant* |
|---|---|---|---|---|
| FPV | None | 0 | 0 | 0 |
| None | vaccinia WR | 0 | 0 | 0 |
| FPV | vaccinia WR | $8.9 \times 10^6$ | $2.0 \times 10^2$ | 0.002 |
| FPV | vaccinia WR + pE/Lova (1:1) | $5.3 \times 10^6$ | $1.2 \times 10^5$ | 2.264 |
| FPV | vaccinia WR + pE/Lova (1:10) | $8.4 \times 10^5$ | $3.0 \times 10^4$ | 3.571 |

*% Recombinant = (Titer with BrdU/Titer without BrdU) × 100

Table 7. Confluent monolayers of BSC1 cells ($5 \times 10^5$ cells/well) were infected with moi=1.0 of fowlpox virus strain HP1. Two hours later supernatant was removed, cells were washed 2× with Opti-Mem I media, and transfected using lipofectamine with 600 ng vaccinia strain WR genomic DNA either alone, or with 1:1 or 1:10 (vaccinia:plasmid) molar ratios of plasmid pE/Lova. This plasmid contains a fragment of the ovalbumin cDNA, which encodes the SIINFEKL epitope (SEQ ID NO:26), known to bind with high affinity to the mouse class I MHC molecule K$^b$. Expression of this minigene is controlled by a strong, synthetic Early/Late vaccinia promoter. This insert is flanked by vaccinia tk DNA. Three days later cells were harvested, and virus extracted by three cycles of freeze/thaw in dry ice isopropanol/37° C. water bath. Crude virus stocks were titered by plaque assay on human TK-143B cells with and without BrdU.

(2) A further significant increase in the frequency of viral recombinants was obtained by transfection of FPV infected cells with a mixture of recombinant plasmids and the two large (approximately 80 kilobases and 100 kilobases) fragments of vaccinia virus v7.5/tk DNA produced by digestion with NotI and Apa I restriction endonucleases. Because the Not I and Apa I sites have been introduced into the tk gene, each of these large vaccinia DNA arms includes a fragment of the tk gene. Since there is no homology between the two tk gene fragments, the only way the two vaccinia arms can be linked is by bridging through the homologous tk sequences that flank the inserts in the recombinant transfer plasmid. The results in Table 8 show that >99% of infectious vaccinia virus produced in triply transfected cells is recombinant for a DNA insert as determined by BrdU resistance of infected tk– cells.

TABLE 8

Generation of 100% Recombinant Vaccinia Virus Using Tri-Molecular Recombination

| Virus | DNA | Titer w/o BrdU | Titer w/ BrdU | % Recombinant* |
|---|---|---|---|---|
| FPV | Uncut v7.5/tk | $2.5 \times 10^6$ | $6.0 \times 10^3$ | 0.24 |
| FPV | NotI/ApaI v7.5/tk arms | $2.0 \times 10^2$ | 0 | 0 |
| FPV | NotI/ApaI v7.5/tk arms + pE/Lova (1:1) | $6.8 \times 10^4$ | $7.4 \times 10^4$ | 100 |

*% Recombinant = (Titer with BrdU/Titer without BrdU) × 100

Table 8. Genomic DNA from vaccinia strain V7.5/tk (1.2 micrograms) was digested with ApaI and NotI restriction endonucleases. The digested DNA was divided in half. One of the pools was mixed with a 1:1 (vaccinia:plasmid) molar ratio of pE/Lova. This plasmid contains a fragment of the ovalbumin cDNA, which encodes the SIINFEKL epitope, known to bind with high affinity to the mouse class I MHC molecule $K^b$. Expression of this minigene is controlled by a strong, synthetic Early/Late vaccinia promoter. This insert is flanked by vaccinia tk DNA. DNA was transfected using lipofectamine into confluent monolayers ($5\times10^5$ cells/well) of BSC1 cells, which had been infected 2 hours previously with moi=1.0 FPV. One sample was transfected with 600 ng untreated genomic V7.5/tk DNA. Three days later cells were harvested, and the virus was extracted by three cycles of freeze/thaw in dry ice isopropanol/37° C. water bath. Crude viral stocks were plaqued on TK-143 B cells with and without BrdU selection.

Construction of a Representative cDNA Library in Vaccinia Virus. A cDNA library is constructed in the vaccinia vector to demonstrate representative expression of known cellular mRNA sequences.

Additional modifications have been introduced into the p7.5/tk transfer plasmid and v7.5/tk viral vector to enhance the efficiency of recombinant expression in infected cells. These include introduction of translation initiation sites in three different reading frames and of both translational and transcriptional stop signals as well as additional restriction sites for DNA insertion.

First, the HindIII J fragment (vaccinia tk gene) of p7.5/tk was subcloned from this plasmid into the HindIII site of pBS phagemid (Stratagene) creating pBS.Vtk.

Second, a portion of the original multiple cloning site of pBS.Vtk was removed by digesting the plasmid with SmaI and PstI, treating with Mung Bean Nuclease, and ligating back to itself, generating pBS.Vtk.MCS–. This treatment removed the unique SmaI, BamHI, SalI, and PstI sites from pBS.Vtk.

Third, the object at this point was to introduce a new multiple cloning site downstream of the 7.5 k promoter in pBS.Vtk.MCS–. The new multiple cloning site was generated by PCR using 4 different upstream primers, and a common downstream primer. Together, these 4 PCR products would contain either no ATG start codon, or an ATG start codon in each of the three possible reading frames. In addition, each PCR product contains at its 3 prime end, translation stop codons in all three reading frames, and a vaccinia virus transcription double stop signal. These 4 PCR products were ligated separately into the NotI/ApaI sites of pBS.Vtk.MCS–, generating the 4 vectors, p7.5/ATG0/tk, p7.5/ATG1/tk, p7.5/ATG3/tk, and p7.5/ATG4/tk whose sequence modifications relative to the p7.5/tk vector are shown in FIG. 8. Each vector includes unique BamHI, SmaI, PstI, and SalI sites for cloning DNA inserts that employ either their own endogenous translation initiation site (in vector p7.5/ATG0/tk) or make use of a vector translation initiation site in any one of the three possible reading frames (p7.5/ATG1/tk, p7.5/ATG3/tk, and p7.5/ATG4/tk).

In a model experiment cDNA was synthesized from poly-A+ mRNA of a murine tumor cell line (BCA39) and ligated into each of the four modified p7.5/tk transfer plasmids. The transfer plasmid is amplified by passage through procaryotic host cells such as *E. coli* as described herein or as otherwise known in the art. Twenty micrograms of Not I and Apa I digested v/tk vaccinia virus DNA arms and an equimolar mixture of the four recombinant plasmid cDNA libraries was transfected into FPV helper virus infected BSC-1 cells for tri-molecular recombination. The virus harvested had a total titer of $6\times10^6$ pfu of which greater than 90% were BrdU resistant.

In order to characterize the size distribution of cDNA inserts in the recombinant vaccinia library, individual isolated plaques were picked using a sterile pasteur pipette and transferred to 1.5 ml tubes containing 100 µl Phosphate Buffered Saline (PBS). Virus was released from the cells by three cycles of freeze/thaw in dry ice/isopropanol and in a 37° C. water bath. Approximately one third of each virus plaque was used to infect one well of a 12 well plate containing tk– human 143B cells in 250 µi final volume. At the end of the two hour infection period each well was overlayed with 1 ml DMEM with 2.5% fetal bovine serum (DMEM-2.5) and with BrdU sufficient to bring the final concentration to 125 µg/ml. Cells were incubated in a $CO_2$ incubator at 37° C. for three days. On the third day the cells were harvested, pelleted by centrifugation, and resuspended in 500 µl PBS. Virus was released from the cells by three cycles of freeze/thaw as described above. Twenty percent of each virus stock was used to infect a confluent monolayer of BSC-1 cells in a 50 mm tissue culture dish in a final volume of 3 ml DMEM-2.5. At the end of the two hour infection period the cells were overlayed with 3 ml of DMEM-2.5. Cells were incubated in a $CO_2$ incubator at 37° C. for three days. On the third day the cells were harvested, pelleted by centrifugation, and resuspended in 300 µl PBS. Virus was released from the cells by three cycles of freeze/thaw as described above. One hundred microliters of crude virus stock was transferred to a 1.5 ml tube, an equal volume of melted 2% low melting point agarose was added, and the virus/agarose mixture was transferred into a pulsed field gel sample block. When the agar worms were solidified they were removed from the sample block and cut into three equal sections. All three sections were transferred to the same 1.5 ml tube, and 250 µl of 0.5M EDTA, 1% Sarkosyl, 0.5 mg/ml Proteinase K was added. The worms were incubated in this solution at 37° C. for 24 hours. The worms were washed several times in 500 µl 0.5×TBE buffer, and one section of each worm was transferred to a well of a 1% low melting point agarose gel. After the worms were added the wells were sealed by adding additional melted 1% low melting point agarose. This gel was then electorphoresed in a Bio-Rad pulsed field gel electrophoresis apparatus at 200 volts, 8 second pulse times, in 0.5×TBE for 16 hours. The gel was stained in ethidium bromide, and portions of agarose containing vaccinia genomic DNA were excised from the gel and transferred to a 1.5 ml tube. Vaccinia DNA was purified from the agarose using β-Agarase (Gibco) following the recomendations of the manufacturer. Purified vaccinia DNA was resuspended in 50 µl dd$H_2O$. One microliter of each DNA stock was used as the template for a Polymerase Chain Reaction (PCR) using vaccinia TK specific primers MM428 and MM430 (which flank the site of insertion) and Klentaq Polymerase (Clontech) following the recommendations of the manufacturer in a 20 µl final volume. Reaction conditions included an initial denaturation step at 95° C. for 5 minutes, followed by 30 cycles of: 94° C. 30 seconds, 55° C. 30 seconds, 68° C. 3 minutes. Two and a half microliters of each PCR reaction was resolved on a 1% agarose gel, and stained with ethidium bromide. Amplified fragments of diverse sizes were observed. When corrected for flanking vector sequences amplified in PCR the inserts range in size between 300 and 2500 bp.

Representative expression of gene products in this library was established by demonstrating that the frequency of specific cDNA recombinants in the vaccinia library was indistinguishable from the frequency with which recombinants of the same cDNA occur in a standard plasmid library. This is illustrated in Table 9 for an IAP sequence that was previously shown to be upregulated in murine tumors.

Twenty separate pools with an average of either 800 or 200 viral pfu from the vaccinia library were amplified by infecting microcultures of 143B tk– cells in the presence of BrdU. DNA was extracted from each infected culture after three days and assayed by PCR with sequence specific primers for the presence of a previously characterized endogenous retrovirus (IAP, intracisternal A particle) sequence. Poisson analysis of the frequency of positive pools indicates a frequency of one IAP recombinant for approximately every 500 viral pfu (Table 9). Similarly, twenty separate pools with an average of either 1,400 or 275 bacterial cfu from the plasmid library were amplified by transformation of DH5α bacteria. Plasmid DNA from each pool was assayed for the presence of the same IAP sequence. Poisson analysis of the frequency of positive pools indicates a frequency of one IAP recombinant for every 450 plasmids (Table 9).

TABLE 9

Limiting dilution analysis of IAP sequences in a recombinant Vaccinia library and a conventional plasmid cDNA library

| | #Wells Positive by PCR | $F_0$ | $\mu$ | Frequency |
|---|---|---|---|---|
| #PFU/well | Vaccinia Library | | | |
| 800 | 18/20 | 0.05 | 2.3 | 1/350 |
| 200 | 6/20 | 0.7 | 0.36 | 1/560 |
| #CFU/well | Plasmid Library | | | |
| 1400 | 20/20 | 0 | — | — |
| 275 | 9/20 | 0.55 | 0.6 | 1/450 |

$F_0$ = fraction negative wells; $\mu$ = DNA precursors/well = $-\ln F_0$

Similar analysis was carried out with similar results for representation of an alpha tubulin sequence in the vaccinia library. The comparable frequency of arbitrarily chosen sequences in the two libraries constructed from the same tumor cDNA suggests that although construction of the Vaccinia library is somewhat more complex and is certainly less conventional than construction of a plasmid library, it is equally representative of tumor cDNA sequences.

Discussion

The above-described tri-molecular recombination strategy yields close to 100% viral recombinants. This is a highly significant improvement over current methods for generating viral recombinants by transfection of a plasmid transfer vector into vaccinia virus infected cells. This latter procedure yields viral recombinants at a frequency of the order of only 0.1%. The high yield of viral recombinants in tri-molecular recombination makes it possible, for the first time, to efficiently construct genomic or cDNA libraries in a vaccinia virus derived vector. In the first series of experiments a titer of 6×10⁶ recombinant virus was obtained following transfection with a mix of 20 micrograms of Not I and Apa I digested vaccinia vector arms together with an equimolar concentration of tumor cell cDNA. This technological advance creates the possibility of new and efficient screening and selection strategies for isolation of specific genomic and cDNA clones.

The tri-molecular recombination method as herein disclosed may be used with other viruses such as mammalian viruses including vaccinia and herpes viruses. Typically, two viral arms which have no homology are produced. The only way that the viral arms can be linked is by bridging through homologous sequences that flank the insert in a transfer vector such as a plasmid. When the two viral arms and the transfer vector are present in the same cell the only infectious virus produced is recombinant for a DNA insert in the transfer vector.

Libraries constructed in vaccinia and other mammalian viruses by the tri-molecular recombination method of the present invention may have similar advantages to those described here for vaccinia virus and its use in identifying target antigens in the CTL screening system of the invention. Similar advantages are expected for DNA libraries constructed in vaccinia or other mammalian viruses when carrying out more complex assays in eukaryotic cells. Such assays include but are not limited to screening for DNA encoding receptors and ligands of eukaryotic cells.

Example 3

Direct Selection Using Target Epitope-Specific Cytotoxic T Cells

In this example, a model system was assayed to determine the level of enrichment that can be obtained through a procedure that selects for DNA recombinants that encode the target epitopes of tumor specific cytotoxic T cells.

Methods and Results

A specific vaccinia recombinant that encodes a well characterized ovalbumin peptide (SIINFEKL) (SEQ ID NO:26) was diluted with non-recombinant virus so that it constituted either 0.2%, 0.01%, or 0.001% of viral pfu. This ovalbumin peptide is known to be processed and presented to specific CTL in association with the murine class I MHC molecule H-2K$^b$. An adherent monolayer of MC57G cells that express H-2K$^b$ were infected with this viral mix at m.o.i.=1 (approximately 5×10⁵ cell/well). MC57G cells do not themselves express ovalbumin peptide, but do express H-2K$^b$, which allows them to associate with and present ovalbumin peptide to the T cells.

Following 12 hours of infection with the recombinant vaccinia virus expressing ovalbumin peptide, ovalbumin peptide-specific CTL, derived by repeated in vitro stimulation of ovalbumin primed splenic T cells with the immunodominant ovalbumin SIINFEKL peptide, were added for 30 min.

During this time, some of the adherent cells infected with a recombinant particle that leads to expression of the ovalbumin peptide interacted with a specific cytotoxic T cell and underwent a lytic event. Cells that underwent a lytic event were released from the monolayer. After 30 min, the monolayer was gently washed, and the floating cells and the remaining adherent cells were separately harvested Virus extracted from each cell population was titred for the frequency of ovalbumin recombinant viral pfu. Virus extracted from floating cells was then used as input to another enrichment cycle with fresh adherent MC57G cells and ovalbumin peptide-specific CTL. It was observed that, following enrichment of VVova to greater than 10% of total virus, further enrichment of the recombinant virus was accelerated if the m.o.i. in succeeding cycles was reduced from 1 to 0.1. The results, presented in Table 10, demonstrate marked enrichment of VVova recombinant virus from an initial concentration of 0.2% to 49% or from 0.01% to 39% in 5 enrichment cycles and from 0.001% to 18% in 6 enrichment cycles. Note that with 5×10⁵ adherent MC57G cells per well and m.o.i=1, an initial concentration of 0.001% VVova recombinant virus is equivalent, on average, to seeding only 5 recombinant pfu among 5×10⁵ wild type vaccinia virus in a single culture well. A very substantial enrichment is achieved even under these conditions.

TABLE 10

Multiple Cycles of Enrichment for Vvova

| | | % Vvova in floating cells* | | |
|---|---|---|---|---|
| Enrichment Cycle # | | Exp. 1 | Exp. 3 | Exp. 3 |
| moi = 1 | 0 | 0.2 | 0.01 | 0.001 |
| | 1 | 2.1 | 0.3 | nd |
| | 2 | 4.7 | 1.1 | nd |
| | 3 | 9.1 | 4.9 | nd |
| | 4 | 14.3 | 17.9 | 1.4 |
| | 5 | 24.6 | | 3.3 |
| | 6 | | | 18.6 |
| moi = 0.1 | 5 | 48.8 | 39.3 | |

*Vvova = (Titer with BrdU/Titer without BrdU) × 100
nd = not determined

Discussion

The above described selection method for isolating DNA clones that encode target epitopes of specific cytotoxic T cells from a viral library is far more efficient than existing methods for accomplishing this same goal. Prior to the present invention, the most widely employed method requires transfection of numerous small pools of recombinant plasmids into separate target populations in order to assay T cell simulation by a minor component of some pool. Because this requires screening out many negative plasmid pools, it is a far more labor intensive procedure than the positive selection method described herein. For a given investment of resource, the method described here can detect positive DNA clones that occur at a much lower frequency than would otherwise be possible. The design principle of this strategy can be directly extended to screening and selection of DNA clones with specific antibodies as well as with CTL.

Example 4

A Deregulated Ribosomal Protein L3 Gene Encodes a Shared Murine Tumor Rejection Antigen We have developed novel antigen discovery technology that allows for the selection of genes encoding CTL epitopes from a cDNA library constructed in a poxvirus. Using this technology we have determined that a shared murine tumor antigen is encoded by an alternate allele of the ribosomal protein L3 gene. The immunogenic L3 gene is expressed at significant albeit reduced levels in normal tissues including thymus. Immunization with a vaccinia recombinant of the immunogenic L3 cDNA induces protective immunity against tumor challenge. It is of particular interest that a deregulated allele of a housekeeping gene can serve as an immunoprotective antigen and that thymic expression does not preclude immunogenicity of an upregulated tumor product. These observations emphasize that tolerance to a self-protein is not absolute but must be defined in relation to quantitative levels of expression. The ribosomal protein described may be representative of a class of shared tumor antigens that arise as a result of deregulated expression of a self-protein without compromising immune tolerance to normal tissues. Such antigens would be suitable for immunotherapy of cancer in vital organs.

Methods

Total RNA was isolated from BCA 39 tumor cells using the Perfect RNA Total RNA Isolation Kit™ (5 Prime 3 Prime, Inc., Boulder, Colo.). Poly A+ mRNA was isolated from the total RNA using Dynabeads™ (Dynal, Lake Success, N.Y.). Two micrograms of poly A+ mRNA was converted to double stranded cDNA using the Great Lengths cDNA Synthesis Kit™ (Clontech, Palo Alto, Calif.). The double stranded cDNA was then inserted in vaccinia virus vector v7.5/tk (5).

Balb/cByJ (Jackson Labs) mice were immunized intraperitoneally with 2×10⁶ irradiated (6,500 cGy) BCA 34 cells. Two weeks later the mice were boosted by subcutaneous injection of 2×10⁶ irradiated BCA 34 cells. One week following the second immunization splenocytes were harvested, divided into 12 parts and cultured in 12 well plates with 6×10⁵ irradiated (10,000 cGy), mitomycin C treated BCA 34 cells per well. At weekly intervals viable T cells were purified using Lympholyte-M (Accurate Chemical, Westbury, N.Y.) and cultured in 12 well plates at 1.5×10⁶ T cells per well. To each well was also added 4×10⁶ irradiated (5000 cGy) Balb/c spleen, along with 6×10⁵ irradiated, mitomycin C treated BCA 34 cells.

A specific vaccinia recombinant that encodes the well characterized ovalbumin 257–264 peptide (SIINFEKL) that is immunodominant in association with H-2K$^b$ was diluted with non-recombinant virus so that it initially constituted either 0.2%, 0.01%, or 0.001% of total viral pfu. An adherent monolayer of MC57G cells (H-2$^b$) were infected with this viral mix at m.o.i.=1 (approximately 5×10⁵ cells/well). Following 12 hours infection, ovalbumin peptide-specific CTL, derived by repeated in vitro stimulation of ovalbumin primed splenic T cells with the immunodominant SIINFEKL peptide, were added. During this incubation those adherent cells which were infected with a recombinant particle that expresses the ovalbumin peptide are targeted by specific cytotoxic T cell and undergo a lytic event which causes them to be released from the monolayer. Following incubation with CTL, the monolayer is gently washed, and both floating cells and the remaining adherent cells are separately harvested. Virus extracted from each cell population was titred for the frequency of recombinant (BRdU resistant) viral pfu. Virus extracted from floating cells was then used as input to another enrichment cycle with fresh adherent MC57G cells and ovalbumin peptide-specific CTL. It was observed that following enrichment of VVova to greater than 10% of total virus, further enrichment of the recombinant virus was accelerated if the m.o.i. in succeeding cycles was reduced from 1 to 0.1.

Confluent monolayers of BCN in wells of a 12 well plate were infected with moi=1.0 vaccinia BCA39 cDNA library. At 12 hours post-infection the monolayers were washed 3× with media, and 2.5×10⁶ CTL were added the wells in a 250 μl volume. The T cells and targets were incubated at 37° C. for 4 hours. Following the incubation the supernatant was harvested, and the monolayer gently washed 3× with 250 μl media. Virus was released from the cells by freeze/thaw, and titers determined by plaque assay on BSC1 cells. The selected virus population (floating cells in cultures that received specific T cells) was amplified on BSC1 cells in one well of a 12 well plate for 2 days. The virus was then harvested and titered. This viral stock was subjected to three additional enrichment cycles. The selected virus population was not amplified prior to the next cycle.

Virus from the fourth enrichment cycle was divided into 40 pools of 5 pfu each. Each pool was amplified on BSC1 cells in a 96 well plate, with 1 pool/well. After 4 days the virus was harvested (P1), and used to infect monolayers of BCN in a 96 well plate at moi=5, with 1 pool per well. As a control, a monolayer of BCN was infected with moi=5 vNotI/tk (Merschlinsky et al., *Virology* 190:522 (1992)). At 5 hours post-infection, 2×10$^4$ washed CTL were added to each well. The final volume in each well was 225 µl. The cells were incubated at 37° C. for 18 hours. The cells were then pelleted by centrifugation, 150 µl supernatant was harvested and tested for IFNγ by ELISA. Twenty seven of the forty pools of 5 pfu were positive for the ability to stimulate CTL. Suggesting, by Poisson analysis, that specific recombinants were enriched to greater than 20%. Individual clones were picked from 5 positive pools and assayed as above.

Monolayers of B/C.N in a 6 well plate were infected with moi=1.0 of v7.5/tk, vF5.8, or vH2.16. At 14 hours post-infection cells were harvested along with the control targets: B/C.N, BCA 34, and BCA 39. The target cells were labeled with 100 microcuries $^{51}$Chromium (Dupont, Boston, Mass.) for 1 hour at 37° C., and 10$^4$ cells were added to wells of a 96 well round bottom plate in quadruplicate. Tumor specific CTL were added to target cells at the indicated ratios. Cells were incubated at 37° C. for 4 hours. Supernatants were harvested and $^{51}$Cr release determined. Spontaneous release was derived by incubating target cells with media alone. Maximal release was determined by incubating target cells with 5% Triton×100. Percentage of specific lysis was calculated using the formula: % specific lysis=((experimental release-spontaneous release)/(maximal release-spontaneous release))×100. In each case the mean of quadruplicate wells was used in the above formula.

Two micrograms of total RNA was converted to cDNA using a dT primer and Superscript II™ Reverse Transcriptase (BRL, Gaithersburg, Md.). cDNA was used as the template for a PCR using L3 specific primers; L3.Fl.S (CGGCGAGATGTCTCACAGGA) (SEQ ID NO:36) and L3.Fl.AS (ACCCCACCATCTGCACAAAG) (SEQ ID NO:37); and Klentaq DNA Polymerase Mix (Clontech) in a 20 microliter final volume. Reaction conditions included an initial denaturation step of 94° C. for 3 minutes, followed by 30 cycles of: 94° C. 30 seconds, 60° C. for 30 seconds, 68° C. for 2 minutes. These PCR products contained the region of L3 between position 3 and 1252. The PCR products were purified using Centricon 100™ columns (Amicon, Beverly, Mass.), digested with Sau3AI, and resolved on a 3% Agarose/ethidium bromide gel.

Adult female Balb/cByJ mice (2 mice per group) were immunized by subcutaneous injection of 5×10$^6$ pfu of vH2.16, or v7.5/tk. Seven days following the immunization splenocytes were harvested and cultured in 12 well plates along with 1 micromolar peptide L3$_{48-56}$(I54). After seven days the viable T cells were purified using Lympholyte-M, and 1×10$^6$ T cells were added to wells of a 12 well plate along with 1 micromolar peptide and 4×10$^6$ irradiated (5000 cGy) Balb/c spleen cells per well.

Adult female Balb/cByJ mice were immunized by subcutaneous injection of 10×10$^6$ pfu of vH2.16, vPKIa, v7.5/tk or Phosphate Buffered Saline. Secondary immunizations were given 21 days later. Mice were challenged with tumor by subcutaneous injection of 2×10$^5$ BCA 34 cells twenty one (primary immunization only) or fourteen days following immunization.

Results and Discussion

Prospects for development of broadly effective tumor vaccines have been advanced by evidence that several self-proteins can be recognized as tumor antigens by immune T cells (Van den Eynde et al., *J. Exp. Med.* 173:1373 (1991); M. B. Bloom et al., *J. Exp. Med.* 185:453 (1997); Van Der Bruggen et al., *Science* 254:1643 (1991); Gaugler et al., *J. Exp. Med.* 179:921 (1994); Boel et al., *Immunity* 2:167 (1995); Van Den Eynde et al., *J. Exp. Med.* 182:689 (1995); Kawakami et al., *Proc. Natl. Acad. Sci. U.S.A.* 91:3515 (1994); Kawakami et al., *Proc. Natl. Acad. Sci. U.S.A.* 91:6458 (1994); Brichard et al., *J. Exp. Med.* 178:489 (1993)). Such normal, nonmutated gene products may serve as common target antigens in tumors of certain types arising in different individuals. Clinical evidence for induction of protective immunity following vaccination with such shared tumor antigens is, currently, very limited (Marchand et al., *Int. J. Cancer* 80:219 (1999); Rosenberg et al., *Nat. Med.* 4:321 (1998); Overwijk et al., *Proc. Natl. Acad. Sci.* 96:2982 (1999); Brandle et al., *Eur. J. Immunol.* 28:4010 (1998)). It is, moreover, not at all clear whether the T cell responses to these self-proteins represent a surprising breakdown in immunological tolerance or are a consequence of qualitative or quantitative changes in the expression of the self-proteins in tumor cells. In the latter case, normal tissue tolerance could be maintained and vaccine induced immunity to self-proteins whose expression is systematically altered in tumors might be applicable even to cancer of vital organs. We report here that a ribosomal protein allele that is systematically deregulated in multiple murine tumors during the transformation process is a tumor rejection antigen and that the principal correlate of immunogenicity is a dramatic change in quantitative expression in tumors relative to normal tissues and thymus.

Previously, we have reported that cross-protective immunity is induced among three independently derived murine tumor cell lines (Sahasrabudhe et al., *J. Immunology* 151:6302 (1993)). These tumors, BCA 22, BCA 34, and BCA 39 were derived by in vitro mutagenesis of independent subcultures of the B/C.N line, a cloned, immortalized, anchorage-dependent, contact inhibited, nontumorigenic fibroblast cell line derived from a Balb/c embryo (Collins et al., *Nature* 299:169 (1982); Lin et al., *JNCI* 74:1025 (1985)). Strikingly, immunization with any of these tumor cell lines, but not with B/C.N provided protection against challenge with not only homologous tumor cells, but also against challenge with the heterologous tumor cell lines. Following immunization with any of these three tumor cell lines, CD8+ cytolytic T lymphocyte (CTL) lines and clones could be generated which in vitro displayed crossreactive specificity for the same three tumors, but not for the non-tumorigenic B/C.N cells from which they derived.

In order to move from an immunological definition to a molecular definition of this shared tumor antigen(s), we developed a novel and efficient method for the identification of genes that encode CTL target epitopes. In this approach a cDNA library from the BCA 39 tumor cell line was constructed in a modified vaccinia virus expression vector (Merchlinsky et al., Virology 238:444 (1997); E. Smith et al., Manuscript in preparation). Five hundred thousand plaque forming units (pfu) of this library were used to infect a monolayer of antigen-negative B/C.N cells at a multiplicity of infection (moi) of 1. Following 12 hours infection, BCA 34 tumor specific CTL were added to the target cell monolayer at an effector to target ratio that gives approximately 50% lysis in a standard $^{51}$Cr release assay. CTL specific for the heterologous BCA 34 tumor cell line were used in order to facilitate the identification of antigen(s) which are shared between these two tumor cell lines. Since adherence is an energy dependent process, it was expected that cells that undergo a CTL mediated lytic event would come off of the monolayer and could be recovered in the supernatant. By harvesting virus from floating cells following cell mediated lymphocytotoxicity (CML), it was possible to enrich for viral recombinants that had sensitized the host cell to lysis. An essential feature of this procedure is that it lends itself to repetition. The virus harvested following one cycle of enrichment can be used as input for additional cycles of selection using fresh monolayers and fresh CTL until the desired level of enrichment has been achieved. In a model experiment with CTL specific for a known recombinant, it was possible to demonstrate that specific recombinants could be enriched from an initial dilution of 0.001% to approximately 20% in 6 cycles of selection (Table 10). At this level it is a simple matter to pick individual plaques for further characterization.

Figure 11A:
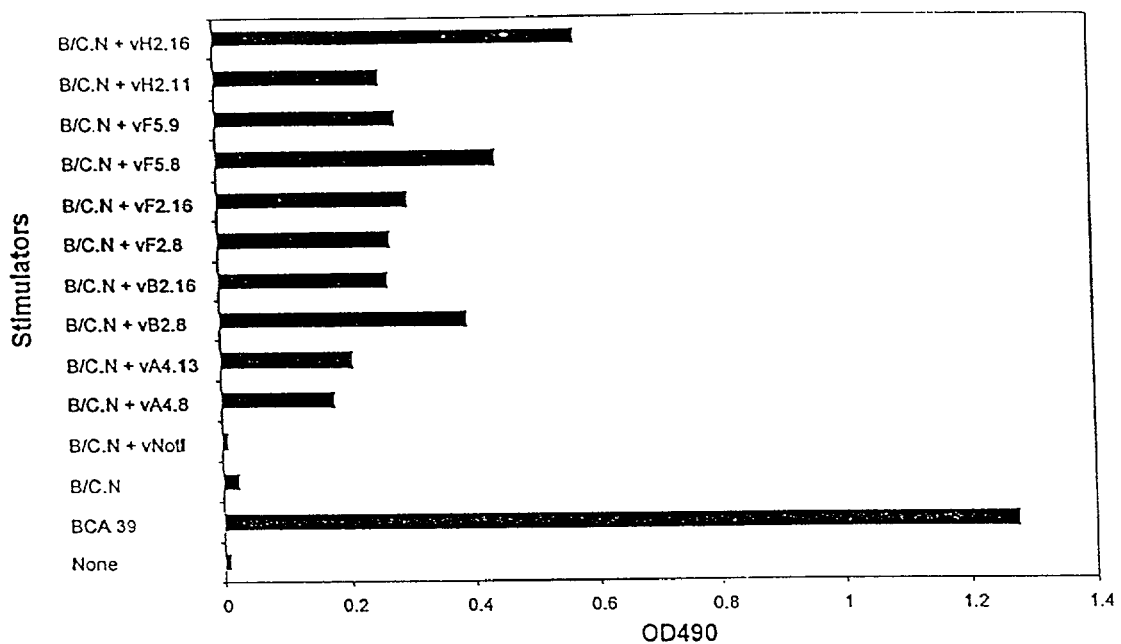

The poxvirus expression library was subjected to 4 cycles of selection with tumor-specific CTL. Individual plaques of the selected viral recombinants were expanded and used to infect separate cultures of B/C.N cells. These cells were assayed for the ability to stimulate specific CTL to secrete interferon gamma (IFNγ) (FIG. 11A), or for sensitization to lysis by the tumor-specific CTL (FIG. 11B). Ten viral clones were isolated all of which conferred upon B/C.N the ability to stimulate a line of tumor-specific CTL to secrete IFNγ. All 10 clones contained the same sized (1,300 bp) insert (Smith et al., unpublished data). Sequence analysis confirmed that clones F5.8 and H2.16 contained the same full-length cDNA. It appeared, therefore, that all ten clones were recombinant for the same cDNA. In all, 6 of 6 CTL lines that were generated by immunization with BCA 34 demonstrated specificity for this antigen.

A search of GenBank revealed that this cDNA is highly homologous to the murine ribosomal protein L3 gene (Peckham et al., *Genes and Development* 3:2062 (1989)). Sequencing the entire H2.16 clone revealed only a single nucleotide substitution that coded for an amino acid change when compared to the published L3 gene sequence. This C170T substitution generates a Threonine to Isoleucine substitution at amino acid position 54. The F5.8 clone also contained this nucleotide substitution.

Figure 13B:
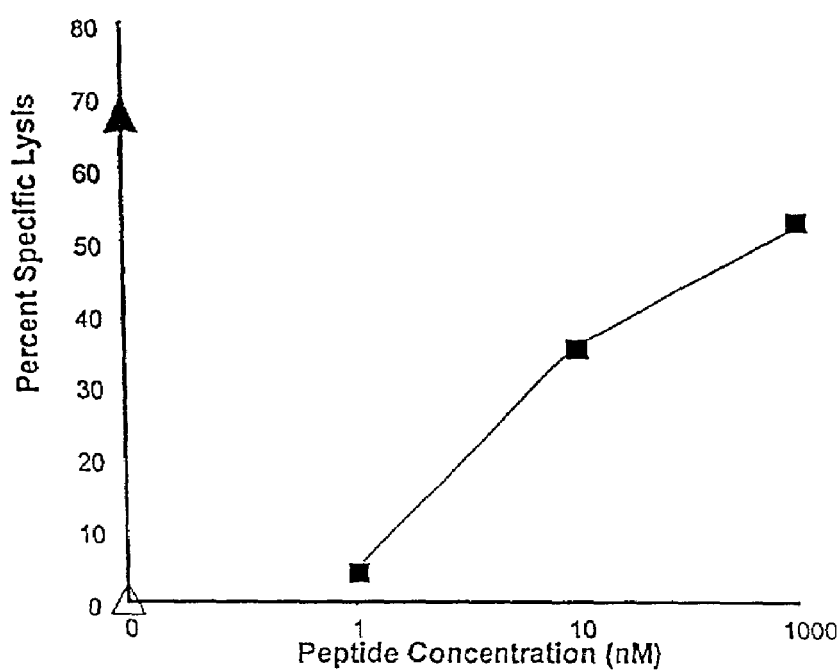

Since CTL recognize antigen as peptide presented by a Major Histocompatibility Complex (MHC) molecule, it was of interest to identify the peptide epitope recognized by these class I MHC-restricted tumor-specific CD8+ T cells. It was considered likely that the altered amino acid (Ile 54) would be included in the peptide recognized by the CTL. This hypothesis was supported by the demonstration that a vaccinia virus clone recombinant for only the first 199 bp (63 amino acids) of H2.16 (vH2$_{199}$) was able to sensitize B/C.N to lysis by tumor-specific CTL (Smith et al., unpublished data). A Computer screen of peptide-binding motifs suggested that there are two epitopes encoded within this region that could associate with high affinity to the class I MHC molecule K$^d$ (FIG. 12) (Parker et al., *J. Immunology* 152:163 (1994)). These two peptides, L3$_{45-54}$ (I54) and L3$_{48-56}$ (I54) were synthesized and tested for the ability to sensitize B/C.N cells to lysis by tumor-specific CTL. As shown in FIG. 13A, peptide L3$_{48-56}$ (I54) sensitized B/C.N to lysis, while L3$_{45-54}$ (I54), and the wild type L3$_{48-56}$ (T54) did not. It was determined that 10 nM L3$_{48-56}$ (I54) was sufficient to sensitize targets to lysis by CTL, whereas 100 mM L3$_{48-56}$ (T54) did not (FIG. 13B). These results demonstrate that peptide L3$_{48-56}$ (I54) is a target epitope recognized by the tumor-specific CTL.

To analyze expression of the different L3 gene products, oligo-dT primed cDNA was synthesized from RNA of tumors and the B/C.N cell line from which they derived. The first strand cDNA was subjected to PCR amplification using a pair of primers which amplify nearly the entire mouse L3 mRNA. Sequence analysis of these PCR products showed that B/C.N and BCB13 L3 cDNA contained a C at position 170 (same as published sequence). BCB 13 is a tumor cell line that was derived from the B/C.N cell line, but that is not immunologically cross-protective with the BCA tumor cell lines (Sahasrabudhe et al., *J. Immunology* 151:6302 (1993)). Sequence analysis of the PCR products from the crossreactive BCA 39, BCA 34, and BCA 22 tumors suggested that these cell lines express two different species of L3 mRNA. One species contains a C at 170, and the other contains a T at 170, as in the H2.16 clone. The sequence of all L3 cDNAs were identical except for this one base substitution.

There are two possible ways to account for the origin of the new L3 RNA in tumor cells. Either the L3 (C170T)gene expressed in these tumors is a somatic mutant of the wild type gene or there are multiple germ line alleles of L3, at least one of which gives rise to an immunogenic product when deregulated during the process of tumor transformation. We considered the first hypothesis unlikely because the crossreactive BCA 39, BCA 34, and BCA 22 tumors were independently derived. It would be remarkable if the same mutant epitope was generated in all three tumors. On the other hand, Southern blots of different restriction digests of genomic DNA from BCA 39 and B/C.N suggested that there are multiple copies of the L3 gene in the mouse genome (Smith et al., unpublished data). The L3 gene has also been reported to be multi-allelic in both the rat and the cow (Kuwano et al., *Biochemical and Biophysical Research Communications* 187:58 (1992); Simonic et al., *Biochemica et Biophysica Acta* 1219:706 (1994)). Further analysis was required to test the hypothesis that different L3 alleles in the germ line are subject to differential regulation in tumors and normal cells.

Figure 14A:
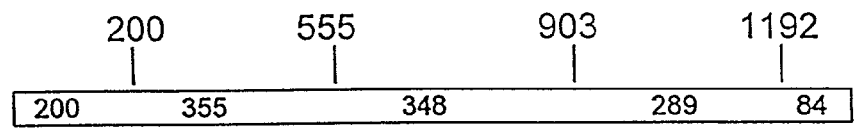
Figure 14A:
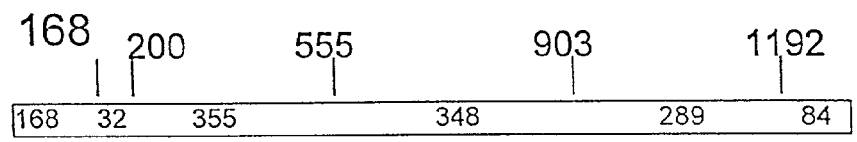
Figure 14B:
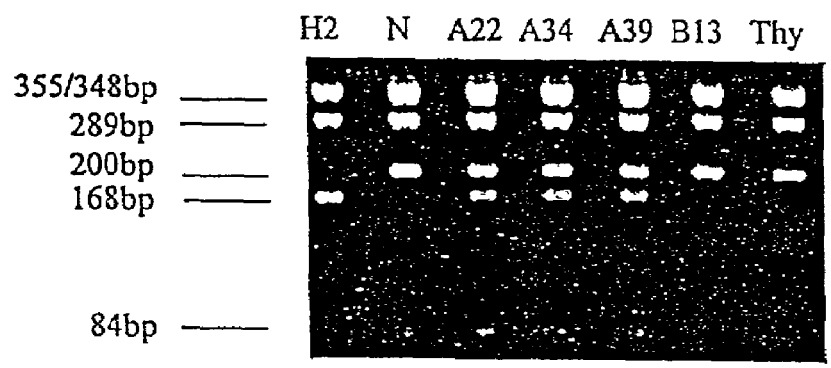
Figure 14C:
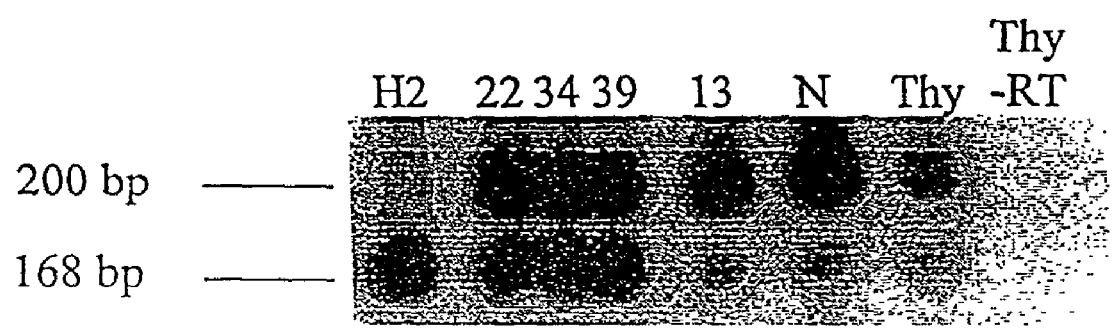

The nucleotide sequence of the published L3 from position 168 to 171 is GACC. The sequence of H2.16 in this same region is GATC (FIG. 12). This new palindrome is the recognition sequence for a number of restriction endonucleases, including Sau3AI. As shown in the restriction map of FIG. 14A, a Sau3A I digest of L3 is expected to generate fragments of 200, 355, 348, 289, and 84 base pairs, while a Sau 3A I digest of H2.16 would generate a 168 bp fragment in place of the 200 bp fragment. This difference in the Sau 3AI digestion products was used to confirm that the three BCA cell lines express at least two different L3 alleles. The L3 RT-PCR products from all 5 cell lines and thymus RNA was digested with Sau 3AI and analyzed on an agarose gel. As shown in FIG. 14B all 3 BCA lines express both versions of L3. Remarkably, when this assay was repeated using greater amounts of starting material, the 168 bp fragment was also detectable in the digests of B/C.N, BCB13 and normal thymus cDNA (Smith et al., unpublished data). To enhance the sensitivity of this assay, the PCR was repeated using a P$^{32}$ end-labeled 5' L3 specific primer. The radiolabeled PCR products were digested with Sau3AI and resolved on an agarose gel. As shown in FIG. 14C, B/C.N, BCB13 and thymus contain the 168 bp fragment. Quantitative analysis indicates that the ratio of 200 bp:168 bp fragments in the BCA tumors is 2:1 while the ratio of the same fragments detected in B/C.N, BCB13, and thymus is approximately 20:1. Low levels of expression of this immunogenic L3 allele was also observed when RNA from kidney, heart, and skeletal muscle was analyzed (Smith et al., unpublished data). These results suggest that gene deregulation associated with the transformation process in the crossreactive tumors leads to the expression of higher levels of this germ line L3 (C170T) allele, and that this altered L3 gene was not generated by somatic mutation of the L3 gene that is predominantly expressed in normal tissues. We have termed this new L3 allele (C170T), the immunogenic L3 allele (iL3).

It is particularly intriguing that the immunogenic L3 allele is also expressed, albeit at a 10 fold reduced level, in normal thymus. This level of expression is evidently not sufficient to tolerize all T cells with functional avidity for the level of deregulated iL3 expressed in some tumors. The observation that although B/C.N and BCB13 express low levels of iL3, they are not susceptible to lysis by the tumor specific CTL suggests, however, that higher affinity T cells have been tolerized. To our knowledge this is the first instance in which a tumor antigen has been reported to be expressed in the thymus. These observations emphasize that tolerance to a self-protein is not absolute but must be defined in relation to quantitative levels of expression (Targoni et al., *J. Exp. Med.* 187:2055 (1998); C. J. Harrington et al., *Immunity* 8:571 (1998)).

Figure 15B:
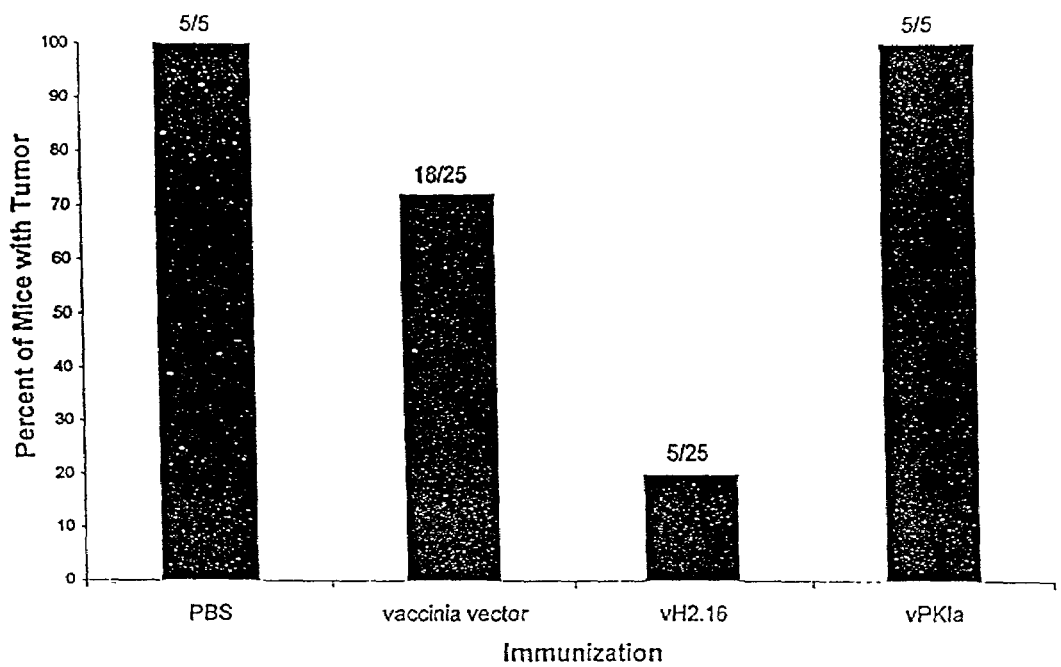
Figure 15C:
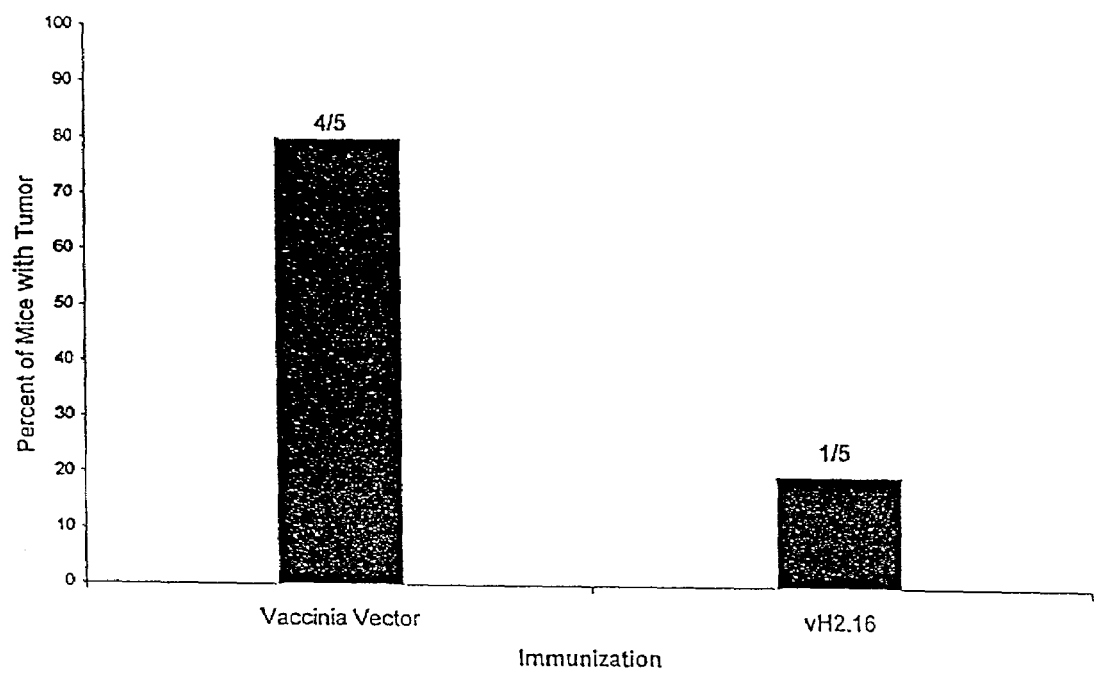

If broadly effective vaccines are to be developed based on expression of shared tumor antigens, then it is critical to demonstrate that such antigens can be immunoprotective. The largest number of shared antigens have been identified for human tumors, but clinical Immunotherapy trials employing these antigens have so far been inconclusive, in part because of uncertainty regarding optimal vaccination strategies (Pardoll, D. M., *Nat. Med.* 4:525 (1998)). In mice, where immunotherapeutic strategies could be more thoroughly investigated, very few shared tumor antigens have been identified. It was, therefore, of considerable interest to determine whether immunization with iL3 recombinant vaccinia virus would induce tumor specific CTL and protect mice from tumor challenge (Overwijk et al., *Proc. Natl. Acad. Sci.* 96:2982 (1999); Moss, B., *Science* 252:1662 (1991); Irvine et al., *J. Immunology* 154:4651 (1995); McCabe et al., *Cancer Research* 55:1741 (1995); Estin et al., *Proc. Natl. Acad. Sci.* 85:1052 (1988); J. Kantor et al., *JNCI* 84:1084 (1992); V. Bronte et al., *Proc. Natl. Acad. Sci.* 94:3183 (1997)). Immunization of Balb/c mice with vaccinia virus recombinant for the iL3 gene (H2.16) generated CTL that were able to lyse both BCA 34 and BCA 39 tumor cells, but not B/C.N in vitro (FIG. 15A). Mice immunized twice or even once with vaccinia virus recombinant for iL3 were able to reject challenge with BCA 34 tumor cells (FIGS. 15B and 15C). Mice immunized with empty viral vector, or control vaccinia recombinant for the Inhibitor Protein of cAMP-dependent Protein Kinase (PKIa) were unable to reject this tumor challenge (Olsen, S. R. and Uhler, M. D., *J. Biol. Chem.* 266:11158 (1991); Mueller et al., Manuscript in Preparation). These results demonstrate that the iL3 self-protein is an immunoprotective tumor antigen.

We have developed a new strategy to identify genes that encode CTL epitopes based on CTL mediated selection from a tumor cDNA library in a modified vaccinia virus vector (Merchlinsky et al., *Virology* 238:444 (1997); E. Smith et al., manuscript in preparation). We have applied this strategy to identify a deregulated housekeeping gene that encodes a tumor rejection antigen shared by three independently derived murine tumors. This ribosomal protein may be representative of a larger class of immunoprotective shared tumor antigens that become immunogenic as a result of deregulated expression of self-proteins without compromising immune tolerance to normal tissues. Such antigens would be well suited for immunotherapy of cancer in vital organs.

Example 5

Cytotoxic CD4+ T Lymphocytes

The method described for direct selection of vaccinia cDNA recombinants that encode T cell target epitopes exploits T cell lytic activity to release from an adherent monolayer those target cells that are sensitized to lysis by infection with specific vaccinia recombinants which encode antigens recognized by the T cell. This is a simple basis for fractionating cells that have undergone a CD8 T cell mediated lytic event from other cells that have not been sensitized to CTL lysis.

Similarly, as would be appreciated by one of ordinary skill in the art, this method can be performed using cytotoxic CD4+ T cells. To be applicable to CD4+ T cells, it would be necessary to either induce cytotoxic CD4+ cells or to employ an independent method of fractionating cells that express the target antigen. It has been reported that selection of human cytotoxic CD4+ T cells in vitro is strongly promoted by the synergistic activity of IL-12 and IL-18 (Hashimoto, W. et al., *J. Immunol.* 163:583–9 (1999)). We initially confirmed that this cytokine combination promotes selection of human cytotoxic CD4+ T cells and extended the observation to a murine primary CD4+ T cell response.

Naïve CD4+ CD45RA+ T cells were isolated from PBL of an HLA-A2+ normal donor and stimulated in vitro with autologous dendritic cells pulsed with heat-inactivated influenza virus. The dendritic cells were derived from PBMC by culture with GM-CSF+IL-4 for 7 days. DC were pulsed with heat-inactivated influenza virus (1000 HAU) and transferred to monocyte conditioned medium for 3 more days to induce maturation prior to T cell stimulation. Cultures of naïve T cells and antigen-pulsed dendritic cells received rhIL-2 (20 U/ml), rhIL-12 (20 U/ml, R&D Systems), rhIL-18 (10 ng/ml, R&D Systems), rhIFN-g (1 ng/ml), and mouse anti-human IL-4 (50 mg/ml, Pharmingen). Cells were restimulated after 7 days using identical conditions with fresh autologous DC pulsed with virus. Cytotoxic activity was assayed at day 14 in a 4 hr $^{51}$Cr release assay using autologous monocytes+/–heat-inactivated virus or K562 control targets. The results shown in FIG. 16 demonstrate the induction of a striking flu-specific CD4+ cytotoxic T cell response.

We wished to determine whether a similar cytotoxic CD4+ response could be induced with murine CD4+ T cells specific for a non-viral antigen. Naïve CD4+ mouse T lymphocytes from heterozygous DO11.10 transgenic females were cultured for 9 days in the presence of BALB/c bone marrow-derived mature dendritic cells pulsed with OVA 323–339(10 mM). Recombinant murine cytokines were purchased from R&D Systems and used at the same concentrations as indicated above for the human cytokines. Rat anti-mouse IL-4 (11B11, Pharmingen) was used at 50 mg/ml. B/c.N (H-$_2^d$) targets were incubated 72 hours with rmIFN-g (1000 U/ml) to induce expression of class II MHC molecules prior to a 4 hr $^{51}$Cr release assay. The four panels of FIG. 17 demonstrate that OVA (323–339) specific cytotoxic cells are efficiently induced only in the presence of all 4 cytokines and anti-IL-4 antibody. As expected for this OVA (323–339) class II MHC restricted response, all the T cells recovered were CD4 positive.

Construction of recombinant libraries that target endosomal expression. In order to be applicable to selection of CD4+ epitopes, the vector must be modified so that endogenously synthesized recombinant proteins can be processed in association with class II MHC. A strategy to accomplish this was described by Sanderson, S. et al., *Proc Natl Acad Sci USA* 92:7217–21 (1995) who demonstrated that proteins fused to class II invariant chain (Ii), when synthesized endogenously, are targeted to the endosomal pathway and can be efficiently processed and presented as peptide-MHC class II complexes. It was determined that an amino terminal fusion of the Ii-80 fragment encompassing the first 80 amino acid residues of the invariant chain fused to either ovalbumin or hen egg lysozyme allowed efficient processing and presentation of OVA and HEL peptide epitopes in association with class II MHC. Thus, the Ii-80 sequence is incorporated into the vaccinia expression system for selection of target epitopes of class II MHC restricted CD4+ T cells.

An alternative strategy to confer lytic activity on CD4+ T cells is to transduce or transfect such cells with a Fas Ligand recombinant in a retroviral or other vector. A similar strategy has been demonstrated to confer lytic activity on cells that are not otherwise programmed for this function (Zhang, H-G. et al., *Nature Biotech.* 16:1045–9 (1998)). Importantly, the lytic activity remains antigen specific. T cells modified in this fashion are be employed to select vaccinia cDNA recombinants that encode their target epitopes without bias to their specificity that might be imposed by IL-12/IL-18 driven selection for cytolytic activity.

Example 6

Additional Screening Strategies

Products of trimolecular recombination such as libraries, may also be subject to indirect selection methods such as screening methods as an alternative to the direct selection methods of the invention. In some cases, such as when a target epitope is recognized by non-cytolytic CD4+ T lymphocytes, the strategy of "lethality based" selection described in the embodiments and examples of this invention may not be applicable because the expressed function (i.e., the target epitope or target polynucleotide) does not render the expressing cell non-viable or non-adherent (e.g., via recognition and lysis by a cytotoxic T cell, or by direct toxicity of the gene product). Nevertheless, the efficiency with which vaccinia recombinants can be introduced in a wide variety of cells and the high level of expression obtained from a replicating viral genome is a great advantage for screening functional gene expression even where direct selection is not possible. An example of such screening is described in an earlier embodiment of the invention to detect and isolate genes that encode secreted molecules that regulate stem cell differentiation.

Similar screening strategies are possible using many biological assays, as would be appreciated by the person of ordinary skill in the art. For example, cells expressing recombinants can be screened for the ability to induce antigen-specific immune cells such as non-cytotoxic T cells to secrete lymphokines or cytokines. In one version of this strategy, antigen-specific, non-cytolytic CD4+ T cells are stimulated in microcultures with a defined number of antigen presenting cells (APC) (preferably at an effector:target ratio of between 5:1 and 100:1) that have been infected with recombinant vaccinia virus. Preferably, the APC are infected with recombinant vaccinia virus that is expanded from a small initial pool. Preferably an initial pool of between 1 and 1000 viral pfu is expanded to 10 to 10,000 pfu. Any microculture that includes APC infected with a recombinant viral pool that includes a recombinant that encodes the specific target antigen will have activated T cells induced to secrete a characteristic lymphokine, preferably IFN-g, or TNFa, or GM-CSF. Sensitive bioassays for these cytokines are known in the art. Viral recombinants extracted from those microcultures that score positive in the bioassay are enriched for recombinants that encode the target antigen. Further similar rounds of screening can be performed with dilutions of these recombinants to isolate a viral cDNA recombinant that encodes the specific target antigen.

Example 7

Identification of Genes Involved in Muskuloskeletal Stem Cell Differentiation and Disease Using Suicide and Other Reporter Gene Constructs Functionally mature and terminally differentiated cells of the musculoskeletal system, as defined by the expression of a specific gene product (a marker) that is only produced in those cells, are derived from stem cells. These stem cells are instructed to initiate the appropriate differentiation program by soluble factors, which initiate a signaling cascade that results in new gene expression. The products of new gene expression are directly involved in the cellular differentiation process. It has been demonstrated in other cell systems that the signal that normally initiates this differentiation process can be circumvented by introducing a downstream gene into the stem cell. Culture systems have been developed that reproduce the normal differentiation of chondrocytes, osteoblasts, and osteoclasts from progenitor cells. Appropriate markers are used to evaluate the authenticity and purity at various stages of differentitation.

Recombinant libraries will be prepared in vaccina virus from developing and mature cells of each cell type. The libraries will be used to infect a stem cell line which has been modified to contain a suicide gene construct such that if the differentiation program is initiated, the cell will die and release its recombinant virus. This virus, containing the gene that regulates the differentiation program, can be readily recovered by washing, aspiration, etc., as described herein. To verify the function of the recovered target polynucleotides in humans, the full-length human cDNA may be isolated and introduced into human primary stem cells, which can then be assessed for development into the appropriate lineage.

Combining trimolecular recombination, in vitro musculoskeletal cell differentiation, and direct selection allows for the identification of genes that control growth and development. The genes identified are candidate pharmaceuticals or pharmaceutical targets.

Stem cells. The genes that regulate differentiation of mature tissues from precursors or stem cells have been especially difficult to study because terminally differentiated cells often cease to proliferate. As a result it is in effect impossible to recover specific functional genes that induce differentiation following DNA transfection or retroviral transduction. It is, however, possible to design a system in which differentiation results in cell death. Under these conditions, genes that promote differentiation can be isolated from a vaccinia library that expresses cDNA of the differentiated cell type by "lethality based selection." Every differentiated cell is distinguished from its precursors by expression of some specific gene product. Transcriptional activation of the promoter for that gene often serves as a surrogate marker of differentiation. If a construct of that specific promoter driving expression of a toxin such as the diphtheria A chain is transfected into a proliferating precursor, then any gene that promotes differentiation will result in cell death. If that gene is introduced as a recombinant in a vaccinia expression vector, then it can be as readily recovered from dying differentiated cells as from the targets of CTL lysis. These methods are applicable to any stem cell population that can be induced to differentiate into a well-defined cell type or tissue. Stem cells have been described for a wide variety of tissues including but not limited to different types of blood cells, epidermal cells, neurons, glial cells, kidney cells, and liver cells. Among these also are the different stem cells of the musculoskeletal system including the precursors of chondrocytes, osteoblasts, osteoclasts, and myocytes.

Osteoclasts. Bone is the only organ that contains a cell type, the osteoclast, whose function is to destroy the organ in which it develops and resides. This destruction, or resorption, of bone occurs throughout life and in the healthy individual is counterbalanced by de novo bone formation in a processs called bone remodeling. The genetic control of osteoclast differentiation is one of the best understood examples of stem cell differentiation. The methods and strategies of this invention can be applied to identify genes that regulate stem cell differentiation just as they have been applied to identify the targets of immune cytotoxicity. This is illustrated specifically for the analysis of osteoclast differentiation.

Strategies are described to detect and isolate both genes that positively or negatively regulate differentiation including genes that are expressed in the differentiating cell itself or that are a secreted product of another producing cell that influences differentiation in a paracrine fashion. In all cases a cell type or cell line that can be induced to differentiate into mature osteoclasts in response to a specific signal, preferably RANK Ligand (RANKL), is employed to detect and isolate recombinant vaccinia virus expressing genes that regulate osteoclast differentiation. In a preferred embodiment, RAW cells are employed. RAW cells are a continuously growing murine myelomonocytic cell line that can be induced to differentiate into osteoclasts by treatment with a range of concentrations of RANK ligand (RANKL), preferably 10 ng/ml (Hsu, H. et al., Proc Natl Acad Sci USA 96(7):3540–45 (1999); Owens, J. M. et al., *J Cell Physiol* 179:170 (1999)). These or similarly responsive cells can be transfected with a suicide gene construct comprising a promoter that normally drives expression of a gene product that is recognized as a marker of fully differentiated osteoclasts but which is linked in this construct to expression of a suicide gene. In a preferred embodiment the promoter is that of the osteoclast differentiation marker TRAP and the suicide gene encodes the A chain of diphtheria toxin (TRAP/DT-A).

Detection and Isolation of Genes that Positively Regulate Differentiation sNA sense strand based strategy. A vaccinia cDNA library is constructed for functional gene selection from cDNA derived from cells that include but are not limited to mature bone marrow derived osteoclasts, or RAW cells or other precursors that have been induced to differentiate into osteoclasts. cDNA may be isolated from either fully mature cells or cells that have been induced to initiate the differentiation program but have not yet completed the process and may express higher levels of the downstream regulatory products. RAW cells or other osteoclast progenitor cells that have been transfected with a TRAP/DT-A or similar suicide gene construct are infected with the vaccinia cDNA library, infection at a multiplicity of infection (MOI) of between o.1 and 10 is preferred. Any vaccinia recombinant that encodes a gene product that promotes differentiation to the mature TRAP expressing phenotype will result in synthesis of the toxin, and death of the infected cell. Such cells and their contents will be released from the cell monolayer. Vaccinia virus recombinants extracted from the cells and cell contents released into the culture supernatant are enriched for the desired vaccinia recombinants. As described for selection of recombinants that encode cytotoxic target antigens, this selection process can be repeated through multiple cycles until the desired level of enrichment is achieved. TRAF6 (Lomaga, M. A. et al., *Genes Dev* 13:1015 (1999)), c-Fos (Wang, Z. Q. et al., *Nature* 360:741 (1992)), and c-Src (Soriano, P. et al., *Cell* 64:693 (1991)), are examples of positive regulators of osteoclast differentiation that could have been isolated through this method.

DNA antisense strand based strategy. A limitation of the cDNA expression strategy is that certain regulatory products encoded by very long cDNA may be difficult to clone as a functional intact product. Antisense inhibition is an alternative strategy that does not depend on cloning of full-length cDNA. In this case, total cDNA derived from the same cells as in the sense strand based strategy is cloned into the vaccinia transfer plasmid in reverse orientation so that the recombinant gene product synthesized in infected cells cannot encode the normal gene product but can hybridize to and inhibit translation or promote degradation of complementary cellular mRNA sequences. To detect sequences required for differentiation, RAW cells or other progenitor cells transfected with TRAP/DT-A or similar suicide construct are treated with an agent that induces differentiation, in a preferred embodiment with 10 ng/ml RANKL. Under these conditions almost all transfectants differentiate and undergo suicide gene mediated cell death. Only cells that have been infected with a vaccinia recombinant that inhibits expression of an essential regulator of differentiation will survive and remain adherent. Virus extracted from the remaining adherent monolayer will, therefore, be enriched for sequences homologous to the desired positive regulators of differentiation. This selection process can also be repeated through several cycles until the desired degree of enrichment of recombinants in the adherent monolayer is achieved. The antisense gene fragments obtained can be employed to select the actual full-length coding sequence. TRAF6 (Lomaga, M. A. et al., *Genes Dev* 13.1015 (1999)), c-Fos (Wang, Z. Q. et al., *Nature* 360:741 (1992)), and c-Src (Soriano, P. et al., *Cell* 64:693 (1991)), are examples of positive regulators of osteoclast differentiation that could have been isolated through this method.

Detection and Isolation of Genes that Negatively Regulate Differentiation.

DNA sense strand based strategy. A vaccinia cDNA library is constructed from cDNA derived from cells that include but are not limited to bone marrow derived osteoclastic progenitors, an enriched fraction of progenitors, or RAW cells or other precursors that have been induced to differentiate into osteoclasis. cDNA may be isolated from cells that include but are not limited to immature precursor cells or cells that have been induced to initiate the differentiation program but have not yet completed the process and may express higher levels of the downstream regulatory products. It is of particular interest to determine whether other alternative cell types that have irreversibly differentiated from the same stem cell population express inhibitory factors for differentiation of the alternative lineages. For example, dendritic cells differentiate from the same precursors that under other conditions give rise to osteoclasts. cDNA is cloned in the sense orientation for infection of indicator cells transfected with TRAP/DT-A or similar suicide construct as described above. The indicator cells are treated with an agent that induces differentiation, preferably 10 ng/ml RANKL. Under these conditions almost all transfectants differentiate and undergo suicide gene mediated cell death. Only cells that are infected with a vaccinia recombinant that inhibits differentiation will survive and remain adherent. Virus extracted from the remaining adherent monolayer will, therefore, be enriched for sequences homologous to the desired negative regulators of differentiation. This selection process can be repeated through several cycles until the desired degree of enrichment of recombinants in the adherent monolayer is achieved. A negative intracellular regulator of osteoclast differentiation has not as yet been isolated. However, it has been suggested that the Est-1 transcription factor plays such a role in differentiation of B lymphocytes (Bories, J. C. et al. *Nature* 377(6550):635–8 (1995)).

DNA antisense based strategy. Total cDNA derived from the same cells as in the sense strand based strategy is cloned into the vaccinia vector in reverse orientation so that the recombinant gene product synthesized in infected cells cannot encode the normal gene product but can hybridize to and inhibit branslation or promote degradation of complementary cellular mRNA sequences. If the targeted sequence encodes an essential factor that inhibits cell differentiation, then in the absence of an effective inhibitory signal RAW cells or other progenitor cells transfected with TRAP/DT-A or similar suicide construct will either spontaneously differentiate or will differentiate in response to otherwise suboptimal signals. Differentiation to the mature TRAP expressing phenotype will result in synthesis of the toxin, and death of the infected cell. Such cells and their contents will be released from the cell monolayer. Vaccinia virus recombinants extracted from the cells and cell contents released into the culture supernatant are enriched for sequences homologous to the desired negative regulators of differentiation. As described for selection of recombinants that encode cytotoxic target antigens, this selection process can be repeated through multiple cycles until the desired level of enrichment is achieved. The antisense gene fragments obtained can be employed to isolate the actual full-length coding sequence. A negative intracellular regulator of osteoclast differentiation has not as yet been isolated. However, it has been suggested that the Est-1 transcription factor plays such a role in differentiation of B lymphocytes (Bories, J. C. et al. *Nature* 377(6550):635–8 (1995)).

Detection and Isolation of Secreted Products that Regulate Differentiation

In another embodiment of the epresent invention, inserts are selected based on autocrine or paracrine activity. Thus, gene products such as proteins or peptides expressed in a host cells may function on that host cell after being secreted, or may function on a second cell after being secreted. Such second cell may be the same type of cell as the host cell or may be a different type of cell from the host cell. The secreted gene product may modulate differentiation, such as activating or inhibiting differentiation. If the gene to be identified and isolated functions only in paracrine fashion, that is being produced in one cell that affects activation or differentiation of a second cell, then the strategy of "lethality based" selection described in the previous paragraphs is not applicable since the expressing cell does not itself become non-viable or non-adherent. Nevertheless, as described below, the efficiency with which vaccinia recombinants can be introduced in a wide variety of cells and the high level of expression from replicating viral genomes is a great advantage for screening functional gene expression even where direct selection is not possible.

A vaccinia library is constructed in the sense orientation from cDNA derived from cells that include but are not limited to bone marrow derived stromal cells and/or lymphoid cells. Producer cells are selected that do not either induce or inhibit induction of differentiation of RAW cells or other osteoclast progenitors. These may include but are not limited to fibroblastoid or lymphoid cells and cell lines or RAW cells themselves. In a preferred embodiment, RAW cells are employed as an indicator target for differentiation. These or similarly responsive cells are transfected with an indicator gene (e.g. reporter gene) construct comprising a promoter that normally drives expression of a gene product that is recognized as a marker of fully differentiated osteoclasts but which is linked in this construct to expression of an easily detected indicator gene (e.g. reporter gene) product. In a preferred embodiment the promoter is that of the osteoclast differentiation marker TRAP and the indicator gene (e.g. reporter gene) encodes the enzyme luciferase (TRAP/luciferase).

Multiple cultures of producer cells are separately infected with recombinant vaccinia virus expanded from a small initial pool, preferably an initial pool of between 1 and 1000 viral pfu is expanded to 10 to 10,000 pfu prior to infection of between 100 and 10,000 producer cells. Each pool of infected producer cells is cocultured with indicator cells that have been transfected with TRAP/luciferase or a similar indicator construct.

Secreted molecules that induce differentiation. Membrane expression or secretion of any recombinant gene product that promotes differentiation of the indicator cells to the mature TRAP expressing phenotype will result in synthesis of luciferase in those cells and, upon addition of luciferase assay reagents as is well known in the art, will give rise to a readily detectable signal from wells that express that recombinant gene product. Vaccinia recombinants are extracted from positive wells and further diluted to isolate in a repetition of the same assay with producer and indicator cells the specific recombinant with differentiation promoting activity. RANKL (Lacey, D. L. et al., *Cell* 93:165–76 (1998)) is itself an example of a positive regulator of osteoclast differentiation that could have been isolated through this method.

Secreted molecules that inhibit differentiation. RAW cells or other progenitor cells transfected with TRAP/luciferase or similar indicator construct are treated with an agent that induces differentiation, in a preferred embodiment with RANKL at the lowest concentration that, in the absence of vaccinia recombinants, reproducibly induces differentiation and a positive indicator signal in every microculture of producer and indicator cells. Under these conditions, only microcultures that include a producer cell infected with a recombinant gene that leads to membrane expression or secretion of an inhibitor of osteoclast differentiation to the mature TRAP expressing phenotype will fail to induce luciferase synthesis and, upon addition of luciferase assay reagents, will not give rise to a readily detectable signal. Vaccinia recombinants are extracted from these negative wells and further diluted to isolate in a repetition of the same assay with producer and indicator cells the specific recombinant with differentiation inhibiting activity. Osteoprotegerin (OPG), Simonet, W. S. et al., *Cell* 89:309–19 (1997), which is identical to osteoclastogenesis inhibitory factor (OCIF), Yasuda, H. et al., *Endocrinology* 139:1329–37

(1998), is an example of a type of negative regulator of osteoclast differentiation that can be isolated through this method.

Vector Construction

TRAP/DT-A. The pTH-1 vector has been described (I. H. Maxwell, F. Maxwell, and L. M. Glode. 1986 Cancer Research 46: 4660–4664). This vector contains the diptheria toxin A chain gene, with expression controlled by the human metallothionein IIA promoter. The metallothionein IIA promoter can be excised from this vector by digestion with XmaIII and NcoI, and replaced with another promoter. The pTH-1 vector is digested with XmaIII, blunt ended with T4 DNA Polymerase, and then digested with NcoI. These manipulations remove the metallothionein IIA promoter, and leave the vector with a 5' blunt end, and a 3' NcoI overhang. The $TRAP_{(-1846-+2)}$ promoter can be excised from pBSmTRAP5' (S. V. Reddy, T. Scarcez, J. J. Windle, R. J. Leach, J. E. Hundley, J. M. Chirgwin, J. Y. Chou, and G. D. Roodman. 1993 J. Bone and Mineral Research 8: 1263–1270) with SmaI and BglII. The TRAP promoter is prepared for insertion into pTH-1 by ligation of an oligodeoxynucleotide adapter that converts the BglII overhang into a NcoI overhang. This adapter is constructed from 2 single stranded oligodeoxynucleotides. BglII-NcoI Sense: 5' GATCTCGGTAACCGC 3' (SEQ ID NO:38); BglII-NcoI Antisense: 5' CATGGCGGTTACCGA 3' (SEQ ID NO:39). These two oligos are annealed together, and then ligated onto the TRAP molecule using T4 DNA Ligase. The modified TRAP is then inserted into the blunt/NcoI sites of pTH-1.

Other DT-A constructs, pIBI30-DT-A, and a plasmid with an attenuated DT-A sequence, pIBI30–176 have been reported (Palmiter et al., Cell 50:435–43 (1987)). One possible advantage of the attenuated sequence is that a transfectant with leaky expression is less likely to undergo spontaneous lysis.

TRAP/Luciferase. The pKB5 vector was constructed by insertion of the mouse TRAP promoter (−1846 bp to +2 bp (positions are relative to the ATG start codon of TRAP)) into the KpnI and BglII sites of the pGL2 Basic vector (Promega). In this vector the TRAP promoter controls expression of the luciferase gene. Construction of this vector has been described (S. V. Reddy, T. Scarcez, J. J. Windle, R. J. Leach, J. E. Hundley, J. M. Chirgwin, J. Y. Chou, and G. D. Roodman. 1993 J. Bone and Mineral Research 8: 1263–1270).

GST-OPGL. For synthesis of murine and human RANKL in bacteria, the murine and human OPGL cDNA was cloned into the SmaI and Hind3 sites of pGEX-2TK (Amersham Pharmacia) to generate a GST fusion protein. Following purification of the fusion protein on glutathione sepharose, the glutathione S-tyransferase (GST) affinity tag is separated from the recombiannt protein by digestion with thrombin. Approximately 30 mg of purified RANKL can be recovered from a 1 liter bacterial culture.

Preparation of total bone marrow cell suspension. Long bones (tibias and femurs) are removed from 4–6 day old euthanized pups. Bones will be dissected free of adherent soft tissue and curretted with a scalpel blade into 2 or 3 ml of prewarmed Medium 199 with Hank's Salts (Sigma, St. Louis, Mo.), pH 7.0, buffered with 10 mM HEPES containing 100 µg/ml penicillin\streptomycin. The resulting suspension of cells and bone fragments will be gently triturated ten times with a transfer pipette whose tip has been cut back to a diameter of approximately 5 mm.

Mesenchymal Stem Cells and their Role in the Musculoskeletal System

Mesenchymal stem cells are pluripotent and have the capacity to differentiate into mature cells with the phenotypic expression of fat, muscle, bone, cartilage, ligament, and tendon (Gerson, S. et al., Nature Med. 5, 262–64 (1999); Majumdar, M. et al., J. Cell. Physiol. 176, 57–66 (1998)). Mesenchymal stem cells are critical during limb development and populate the limb bud, giving rise to the various mature mesenchymal tissues in the limb (Johnson, R., and Tabin, C. Cell 90,979–990 (1997)). The signals necessary for this process are poorly defined but are recapitulated in adult tissues during skeletal repair processes.

Mesenchymal stem cells remain in post-embryonic tissues and are present in periosteum, perichondrium, muscle, bone marrow and at other sites (Bruder, S. et al., J. Cell. Biochem. 64, 278–94 (1997)). These cells retain the capacity to undergo differentiation and develop the characteristics of differentiated cells necessary for skeletal repair processes. Successful skeletal repair involves the capacity of these cells to respond to appropriate stimuli. Fracture healing is an example of this process, whereby mesenchymal cells proliferate, undergo chondrogenesis, with subsequent bone formation occurring by endochondral ossification. Ultimately this results in fracture union and healing with subsequent remodeling of the new bone. More complete knowledge of the genes involved in this process will provide targets to improve repair processes and provide the possibility of therapeutic intervention.

In other diseases of the musculoskeletal system, adequate repair rarely, if ever, occurs. An example of inadequate repair involves repair of articular cartilage defects. Joint formation is completed during embryologic development and the joint surface is composed of articular chondrocytes embedded in a highly specialized matrix. Articular cartilage is a low friction surface that is highly resistant to compressive and shear forces. Mature articular chondrocytes are terminally differentiated and have little capacity to initiate repair. Loss of the articular surface, with exposure of the underlying subchondral bone, occurs with increasing frequency with aging and is the pathological process that occurs in osteoarthritis.

Currently there are several therapies that have been used to repair articular cartilage defects, but none of these treatments have had a high degree of efficacy. In a procedure call mosaic-plasty, cores of articular cartilage and underlying bone are taken from one location and transplanted to a new location, filling in an articular cartilage defect. Frequently, several separate cores are required to fill a defect. While there is an attempt to harvest the tissue from sites with minimal need for the cartilage, this procedure has significant donor morbidity. Similarly, while there is an attempt to match the donor cartilage to the normal contour of the cartilage defect, incongruency of the repaired cartilage inevitably remains and the wear resistance of the transplanted tissue is limited.

Other procedures currently in use depend upon the development of normal tissue from transplanted cells. In the first case, terminally differentiated articular chondrocytes are harvested from a joint surface, the cell population expanded in culture, and transplanted into the defective surface (Brittberg, M. et al., N. Eng. J. Med. 331, 889–895 (1994)). The cells are placed under a covering of periosteum. Although early results suggested excellent reconstitution of the tissue, later results are less promising (Buckwalter, J. Bull. Am. Acad. Orthop. Surg. 44, 24–26 (1996)). In the second case, periosteum is harvested from the bone surface and placed over the cartilage defect with the cambium layer, which contains the highest proportion of mesenchymal cells, facing the defect. In both of these cases, the cellular transplants are performed in association with preparation of the underlying subchondral bone surface. However, instead of forming ahyaline cartilage surface with a high content of aggregating proteoglycans, a fibrocartilaginous reparative tissue, characterized by the expression of type I collagen and an absence of aggregating proteoglycans, forms. This tissue has inferior mechanical properties compared to normal articular cartilage. Similar results have been reported in combination with cell and perichondrial tissue transplantation. Since one of the important differences between fibrocartilage and hyaline cartilage is the production of type II collagen and aggrecan by hyaline cartilage, identification of genes and signals important in the maintenance of these genes could have tremendous clinical relevance for the development of effective reparative tissue.

Chondrogenesis. Chondrogenesis is the formation of cartilage cells and tissues from mesenchymal stem cells. At an early stage of limb development mesenchymal cells condense and shift from the production of type I to type II collagen (Erlebacher, A. et al., Cell 80, 371–378 (1995)). The cells also begin to produce and secrete aggregating proteoglycans. A highly cellular and distinct lining tissue surrounds this early cartilage anlagen, which is the earliest precursor to the skeleton. This lining tissue persists and becomes the periosteurni, in areas where it surrounds bone, and the perichondrium, in areas where it surrounds cartilage. The periosteal and perichondrial tissue contains mesenchymal stem cells and during development, additional cartilage cells differentiate form this tissue as the skeleton increases in width during development (Erlebacher, A. et al., Cell 80, 371–378 (1995)). In the adult, this tissue provides a reservoir of cells for skeletal repair processes.

As development proceeds, the chondrocytes undergo a process of maturation that results in endochondral bone formation. In the center of the cartilaginous anlagen, chondrocytes hypertrophy, and increase approximately 5 to 10-fold in size. Associated with cell hypertrophy is an increase in alkaline phosphatase activity and the expression of type X collagen. Type X collagen is a globular collagen which is expressed only in chondrocytes undergoing terminal differentiation and committed to completion of endochondral ossification (Castagnola, P. et al., J Cell Biol 102, 2310–2317 (1986)). Although the mechanisms involved in the process are not understood, the phenotypic changes are essential for normal bone development and defects in type X collagen expression are associated with chondrodysplasias (Warman, M. L. et al., Nature Genet. 5, 79–82 (1993)). Terminally differentiated chondrocytes undergo apoptosis and the calcified cartilage serves as a template for the primary bone formation. Vascular ingrowth into the region of calcified cartilage precedes bone formation. As the central region of the bone becomes ossified, the cartilaginous regions move toward opposite ends of the long bone and constitute the growth plate which is necessary for skeletal growth throughout development. The process of chondrocyte hypertrophy and terminal differentiation continues through adolescence. The entire process is recapitulated during fracture healing.

C3H10T½ Cells: A Model for Chondrogenesis and Osteoblastogenesis.

Several cell lines have been used to study chondrogenesis and the factors associated with this process. C3H10T½ cells are a multipotential murine embryonic mesenchymal cell line with the potential to undergo chondrogenesis, osteogenesis, myogenesis, and adipogenesis (Denker, A. et al., Differentiation 64, 67–76 (1999)). These cells can undergo muscle differentiation and myotubule formation following treatment with 5-azacytidine. Chondrogenesis and adipocitogenesis also occur following this treatment (Taylor, S. and Jones, P., Cell 17, 771–79 (1979)). C3H10T½ cells are particularly responsive to differentiation following treatment with BMPs. In the presence of BMPs the cells can undergo differentiation along three lineages (Atkinson, B. et al. J. Cell Biochem. 65, 325–39 (1997); Katagiri, T. et al., Biochem. Biophys. Res. Commun. 172,295–299 (1990); Wang, E. et al., Growth Factors 9, 57–71 (1993)), although myogenic differentiation is inhibited. However, in high density cultures, BMP treatment preferentially favors chondrogenesis. TGF-β also stimulates chondrogenesis in these cells, as does azacytadine. Similar to primary mesenchymal cells, N-cadherin is induced during chondrogenesis and appears to play an important role in this process (Haas, A., and Tuan, R. Differentiation 64, 77–89 (1999)).

Sox 9 is a member of the Sox family, a group of transcription factors important in developmental processes (Pevny, L., and Lovell-Badge, R. Curr. Opin. Genet. Dev. 7, 338–44 (1997)). Sox9 expression is high in chondroprogenitor cells and in chondrocytes during endochondral bone formation (Wright, E. et al., Nat. Genet. 9, 15–20 (1995)). Sox9 appears to be an important regulator of type II collagen, a chondrocyte specific gene (Lefebvre, V. et al., Mol. Cell Biol. 17, 2336–2346 (1997)). Zehentner, B., Dony, C., and Burtscher, H. J. Bone Min. Res. 14, 1734–41 (1999) have recently shown that BMP-2 causes a 4-fold induction in Sox9 expression in C3H10T½ cells and a marked upregulation of type II collagen gene expression. While the plating density of the C3H10T½ cells was not defined in this study, low levels of type II collagen were expressed under basal conditions. Surprisingly, type X collagen, a marker of a differentiated chondrocyte committed to endochondral bone formation, was induced. In control cultures, no type X collagen could be observed, while high levels were observed following BMP-2 treatment (200 ng/ml). Anti-sense oligonucleotides to Sox9 partially inhibited the induction of type II and type X collagen expression (Zehentner, B., Dony, C., and Burtscher, H. J. Bone Min. Res. 14, 1734–41 (1999)). Thus, marked induction of chondrocyte specific genes occurs in C3H10T½ cells following BMP-2 treatment. The hedgehog proteins can synergistically enhance differentiation of C3H10T½ cells (Nakamura, T. et al., Biochem. Biophys. Res. Commun. 247, 465–69 (1997)).

Osteoblast differentiation has been characterized in C3H10T½ cells (Katagiri, T. et al., Biochem. Biophys. Res. Commun. 172, 295–299 (1990); Wang, E. et al., Growth Factors 9, 57–71 (1993); Harada, H. et al., J. Biol. Chem. 274, 6972–6978 (1999)). BMP-2 stimulates the differentiation of osteoblasts, and differential display has been used with C3H10T½ cells to clone osteoblast-specific genes following differentiation (Kobayashi, T. et al., Gene 198, 341–49 (1997)). The osteoblast phenotype is characterized by the expression of several genes, including alkaline phosphatase, osteocalcin, and osteopontin. CBFA1 (core-binding factor) has been identified as a transcription factor essential for osteoblast differentiation. Targeted disruption of this gene in mice results in the absence of osteoblast formation (Komori, T. et al., Cell 89, 755–64 (1997)) and this gene is involved in the human disorder cleidocranial dysplasia (Lee, B. et al., Nat. Genet. 16, 307–10 (1997)). Recently, it has been shown that co-transfection of BMP-4 and CBFA1 synergistically enhanced the expression of the osteocalcin, osteopontin, alkaline phosphatase, and type I collagen genes. The expression of osteocalcin, alkaline phosphatase, and osteopontin were undetectable in mock-transfected cells, but were highly expressed in the CBFA1 and BMP-4 transfected cells (Harada, H. et al., *J. Biol. Chem.* 274, 6972–6978 (1999)).

Osteoarthritis and Type X Collagen Expression. Chondrocytes express type II collagen, and are distinguished from other mesenchymal cells by the expression of this structural collagen. Chondrocytes can further differentiate into cells that calcify cartilage, ultimately leading to bone formation. This process is called endochondral ossification. Chondrocytes which undergo endochondral ossification, such as growth plate chondrocytes or chondrocytes in skeletal repair processes (fracture healing) express type X collagen. Articular chondrocytes (which line the joint) do not express type X collagen, but in arthritis, these cells begin to express this gene. Thus, type X collagen is a marker of both reparative and disease processes involving chondrocytes.

C3H10T½ cells are a multipotential murine embryonic mesenchymal cell line that normally express type I collagen and are induced to express type II collagen when they undergo chondrogenesis. Chondrogenesis is enhanced by high density plating of the cultures and by growth factors. Zehentner, et al., *J. Bone Min. Res.* 14:1734–41, (1999) show that BMP-2 markedly enhances the expression of type II collagen. Even more importantly, type X collagen, which cannot be detected in control cultures, is strongly expressed in the treated cultures. Other markers of chondrogenic differentiation, including aggrecan, are markedly induced.

Detection and isolation of genes that positively or negatively regulate differentiation of chondrocytes and osteoblasts. As described earlier, the invention comprises methods to detect and isolate genes that either positively or negatively regulate stem cell differentiation including genes that are expressed in the differentiating cell itself and that are a secreted or membrane product of another producing cell that influences differentiation in a paracrine fashion. In a preferred embodiment, the method is applied to detect and isolate recombinant vaccinia virus expressing genes that regulate differentiation of chondrocytes and osteoblasts. One or more cell types or cell lines are required that can be induced to differentiate into chondrocytes or osteoblasts in response to a specific signal. In a preferred embodiment, high density cultures of C3H10T½ cells are induced by BMP-2 to differentiate into chondrocytes. In another preferred embodiment continued differentiation of the same pluripotent C3H10T½ cells into osteoblasts is induced by TGFβ (Joyce, M. et al., *J. Cell Biol.* 110:2195–207 (1990)). Further discrimination in the readout of cell differentiation is possible by employing C3H10T½ cells transfected with promoter/suicide or promoter/indicator constructs (as previously described for isolation of genes that regulate osteoclast differentiation) where, in this case, the promoter is specific for expression of either a marker of chondrocyte differentiation or a marker of osteoblast differentiation. As markers of chondrocyte differentiation, type II collagen or aggrecan are preferred, and type X collagen is especially preferred. As a marker of osteoblast differentiation, osteocalcin is especially preferred.

The most important and meaningful information regarding the collagen promoter construct is whether or not it is expressed in a manner consistent with the in vivo expression pattern. If it is not, then it is uncertain that it would be a good marker or endpoint for the differentiated phenotype. Tissue specific expression patterns have been examined in mice transgenic for either the mouse type X collagen promoter (Ann. NY Acad Sci. 785:248–50, 1996) or the chicken type X promoter (Nature 365: 56–61, 1993). Interestingly, the chicken type X collagen promoter (in the mouse), provides an expression pattern identical to the in vivo expression of the mouse type X collagen gene. The mouse type X collagen promoters tested were expressed in a number of different tissues, including brain, skin, and in some cases hypertrophic chondrocytes. More importantly, a mutation that should cause a chondrodysplasia (and does in the chicken constructs) did not cause this using the mouse sequences. Thus, the chicken promoter, at least, appears to offer expression with the specificity of the normal gene. The mouse promoter appears to be less specific. The chicken type X collagen promoter is preferred for this embodiment of the invention.

Vector Construction

Osteocalcin-DT-A. The OC2 promoter will be excised from pOC2CAT with XhoI and HindIII. Adapters will be ligated onto this molecule in order to convert the XhoI overhang into a XmaIII overhang. This will be done using oligos XhoI-XmaIII sense: 5' GGCCGAAATAACCGC 3' (SEQ ID NO:40), and XhoI-XmaIII antisense: 5' TCGAGCGGTTATTTC 3' (SEQ ID NO:41). The HindIII overhang will be converted into a NcoI overhang using oligos H3-NcoI sense 5' AGCTTCGGTAACCGC 3' (SEQ ID NO:42), and H3-NcoI antisense 5' CATGGCGGTTAC-CGA 3' (SEQ ID NO:43). These adapters will be annealed together, and then ligated onto the OC2 molecule. The adapter modified OC2 promoter will then be inserted into the XmaIII and NcoI sites of pTH-1.

Osteocalcin-Luciferase. The pGL3-Basic Vector (Promega) contains a promoterless luciferase gene. The 1.1 Kb Osteocalcin promoter has been described (B. Frenkel, C. Capparelli, M. van Auken, J. Bryan, J. L. Stein, G. S. Stein, J. B. Lian. 1997. *Endocrinology* 138: 2109–2116). The OC2 promoter is available in vector pOC2-CAT. The OC2 promoter can be excised from this vector with XhoI and HindIII, and inserted into the matching XhoI and HindIII sites of pGL3-Basic Vector. This new vector, pOC2-Luc, will have the luciferase gene controlled by the OC2 promoter.

Chicken Collagen X-DT-A. The B640-CAT construct has been described (S. W. Volk, P. Luvalle, T. Leask, P. S. Leboy. 1998 *J. Bone Min. Res.* 13: 1521–1529). This vector contains the Chick Collagen X "B" Fragment/promoter controlling expression of the CAT gene. The "B" Fragment/promoter can be excised from this construct using PstI and SalI. Adapters will be ligated onto this molecule in order to convert the PstI overhang into a XmaIII overhang. This will be done using oligos PstI-XmaIII sense: 5' GGCCG-GAAATAACCGCTGCA 3' (SEQ ID NO:44), and PstI-XmaIII antisense: 5' GCGGTTATTTCC 3' (SEQ ID NO:45). The SalI overhang will be converted into a NcoI overhang using oligos SalI-NcoI sense 5' CTGAGGAAATAACCGC 3' (SEQ ID NO:46), and SalI-NcoI antisense 5' CATGGCG-GTTATTTCC 3' (SEQ ID NO:47). These adapters will be annealed together, and then ligated onto the Chick Collagen X promoter molecule. The adapter modified Chick Collagen X promoter will then be inserted into the XmaIII and NcoI sites of pTH-1.

Chicken Collagen-X-Luciferase. The B640-Luciferase was constructed by insertion of the 1610 bp upstream "B" fragment and promoter of Chick Collagen X into the SpeI and SalI sites of pRLnull (Promega). In this vector the Chick Collagen X "B" Fragment/promoter controls expression of the luciferase gene. Construction of this vector has been described (S. W. Volk, P. Luvalle, T. Leask, P. S. Leboy. 1998 *J. Bone Min. Res*. 13: 1521–1529).

All of the elements required to apply the methods of this invention to detect and isolate genes that regulate differentiation of chondrocytes and osteoblasts are available: (i) Precursor cells, C3H10T½, can be induced to differentiate into either chondrocytes or osteoblasts by addition of well-defined soluble factors, BMP-2 under high density culture conditions for chondrocytes and TGFb for osteoblasts; (ii) tissue-specific markers of differentiation are known, type X collagen for chondrocytes and osteocalcin for osteoblasts, whose promoters have been isolated and can be employed for construction of differentiation sensitive suicide or other reporter gene (e.g. indicator gene) constructs; (iii) representative vaccinia cDNA libraries in either the sense or anti-sense orientation can be constructed from precursors of chondrocytes and osteoblasts such as C3H10T½ that are either undifferentiated or have been induced to differentiate by specific factors. To screen for genes that encode positive or negative regulators that act in paracrine fashion, cDNA vaccinia libraries can be constructed from total bone marrow or enriched stromal or lymphoid cells. Employing these reagents, all of the same strategies previously described to detect and isolate genes that regulate osteoclast differentiation can be applied to chondrocyte and osteoblast differentiation. Some issues of special interest in this situation include whether differentiated osteoblasts express factors that inhibit differentiation to chondrocytes and vice versa. Examples of positive regulators of differentiation that could have been isolated through this method include CBFA1 (Mundlos, S. et al., *Cell* 89:773 (1997); Otto, F. et al., *Cell* 89:765 (1997); Inada, M. et al., *Dev Dyn* 214:279 (1999)); Ihh, indian hedgehog signaling (Vortkamp, A. et al., *Science* 273:613 (1996); St-Jacques, B. et al., *Genes Dev* 13:2072 (1999)); and PTHrP, parathyroid hormone-related peptide (Lanske, B. et al., *J Clin Invest* 104:399 (1999); Karaplis, A. C. et al., *Genes Dev* 8:277 (1994)).

Human differentiation factors and stem cells. The C3H10T½ precursor to osteoblasts and chondrocytes and the previously described RAW precursor to osteoclasts are of murine origin. Although the gene products identified through use of these cell lines will also be of murine origin, there are strong and numerous precedents for homology between factors that regulate differentiation of homologous tisues in mice and humans. In general, the murine genes isolated can be used to isolate human homologs which can then be tested for the ability to regulate differentiation of the corresponding human stem cells. In an increasing number of instances human stem cells are becoming available. In particular several human stem cell lines have been recently isolated by SV40 transformation from both embryonic cartilage and adult cartilage, Moulton P J. et al., *British Journal of Rheumatology*. 36(5):522–9 (1997); Goldring M B. and Berenbaum F. *Osteoarthritis & Cartilage*. 7(4):386–8, (1999). These cell lines will have to be induced to express type X collagen. It is expected that they will provide suitable human material to directly detect and isolate human genes that regulate chondrocyte and osteoblast differentiation.

Example 8

Preparation of cDNA and Transfer Plasmid

Isolation of Total RNA. Several commercial vendors, including Qiagen and Eppendorf, provide the reagents and materials necessary for the isolation of total RNA from tissue and cells grown in culture. Cells grown in monolayer cultures are harvested directly from culture flasks using a lysis solution that contains guanidine isothiocyanate (GITC) and beta-mercaptoethanol (B-ME). Following lysis, ethanol is added and the RNA is isolated by binding of the lysed sample to a silica gel based membrane (Qiagen), or to an RNA Binding Matrix (Eppindorf). The bound RNA is washed, and high quality RNA is eluted in water.

Isolation of mRNA. Oligo $(dT)_{25}$ chains covalently coupled to magnetic beads (Dynal) are used to select Poly A+ mRNA from total RNA. Briefly, total RNA is hybridized with the dT beads in 10 mM Tris-HCL, pH 7.5, 0.5M LiCl, 1 mM EDTA. Following binding the beads and bound mRNA are isolated using a magnet, washed with 10 mM Tris-HCl pH 8, 0.15M LiCl, 1 mM EDTA, and the mRNA is eluted with water.

cDNA Synthesis. Double stranded cDNA is synthesized from the mRNA isolated above using a variant of the protocol originally described by Gubler and Hoffman (*Gene*, 25: 263 (1983)).

First Strand. Up to 5 micrograms of mRNA can be converted to cDNA using either a $dT_{15}$ primer or random heptamer primers. In either case the primer is modified at its 5' end to include the recognition sequence for a restriction endonuclease such as SalI. The mRNA is incubated with the primer at 70° C. for 10 minutes, chilled on ice, 4 μl 5× First Strand Buffer (250 mM Tris-HCl pH 8.3, 375 mM KCl, 15 mM $MgCl_2$), 1μl 0.1M DTT, 1 μl 10 mM dNTP mix and a RNaseH deficient Moloney Murine Leukemia Virus (M-MLV) Reverse Transcriptase (RT) (Superscript II, Life Technologies) is added to a final volume of 20 microliters. The first strand reaction is allowed to proceed for 1 hour at 37° C. The reaction is terminated by placement on ice.

Second Strand. 91 μl water, 30 μl second strand buffer (100 mM Tris-HCl pH 6.9, 450 mM KCl, 23 mM $MgCl_2$, 0.75 mM beta-NAD+, 50 mM $(NH4)_2SO_4$), 3 μl 10 mM dNTP mix, 10 units *E. coli* DNA Ligase, 40 units *E. coli* DNA Polymerase I, and 2 units *E. coli* RNase H are added to the first strand reaction to give a final volume of 150 μl. The second stand reaction is incubated at 16° C. for 2 hours, after which 10 units of T4 DNA Polymerase is added, and incubated at 16° C. for another 10 minutes. The reaction is halted by the addition of 10 μl 0.5M EDTA. The cDNA is purified by extraction with phenol:chloroform:isoamyl alcohol (25:24:1), followed by precipitation with ethanol and salt (NaCl, NaOAc, or $NH_4OAc$).

Modification of cDNA for Ligation. The cDNA may be modified for ligation into the transfer vectors by either of 2 methods.

Method 1. The cDNA is phosphorlyated using T4 Polynucleotide Kinase (PNK) and ATP. The cDNA is then digested with the restriction endonuclease whose recognition sequence was built into the cDNA synthesis primer. For example, SalI can be used. cDNA modified with this procedure will be blunt ended at it's 5' end, and will have a SalI overhang at it's 3' end.

Method 2. A phosphorylated adapter containing for example, a BamHI overhang, is ligated onto the cDNA using T4 DNA Ligase and an overnight incubation at 14° C. Following ligation the cDNA is digested with SalI. This cDNA will contain a BamHI overhang at it's 5' end, and a SalI overhang at it's 3' end.

Size Selection. Small molecular weight cDNAs (<600 bp) may be removed prior to cloning by size selection. Methods of size selection include size exclusion column chromatography, or separation through an agarose gel. In the latter method, the cDNA is resolved by electrophoresis through a 0.8% agarose/Tris Boric Acid EDTA (TBE) gel. cDNA smaller than 600 bp is removed by excising the portion of the gel that contains this small cDNA, the gel is then run in reverse to concentrate the cDNA, which is then excised and purified from the agarose using methods that are well known in the art.

Preparation of Transfer Vector. The transfer vectors may be prepared for cloning by known means. A preferred method involves cutting 1–5 micrograms of vector with the appropriate restriction endonucleases (for example SmaI and SalI or BamHI and SalI) in the appropriate buffers, at the appropriate temperatures for at least 2 hours. Linear digested vector is isolated by electorphoresis of the digested vector through a 0.8% agarose gel. The linear plasmid is excised from the gel and purified from agarose using methods that are well known.

Ligation. The cDNA and digested transfer vector are ligated together using well known methods. In a preferred method 50–100 ng of transfer vector is ligated with varying concentrations of cDNA using T4 DNA Ligase, using the appropriate buffer, at 14° C. for 18 to 24 hours.

Transformation. Aliquots of the ligation reactions are transformed by electroporation into E. coli bacteria such as DH10B or DH5 alpha using methods that are well known. The transformation reactions are plated onto LB agar plates containing a selective antibiotic (ampicillin) and grown for 14–18 hours at 37° C. All of the transformed bacteria are pooled together, and plasmid DNA is isolated using well known methods.

Preparation of buffers mentioned in the above description of preferred methods according to the present invention will be evident to those of skill.

Example 9

Introduction of Vaccinia Virus DNA Fragments and Transfer DNA into Tissue Culture Cells for Trimolecular Recombination A cDNA or other library is constructed in the 4 transfer plasmids as described in Example 2, or by other art-known techniques. Trimolecular recombination is employed to transfer this cDNA library into vaccinia virus. Confluent monolayers of BSC1 cells are infected with fowlpox virus HP1 at a moi of 1–1.5. Infection is done in serum free media supplemented with 0.1% Bovine Serum Albumin. The BSC1 cells may be in 12 well or 6 well plates, 60 mm or 100 mm tissue culture plates, or 25 cm², 75 cm², or 150 cm² flasks. Purified DNA from v7.5/tk or vEL/tk is digested with restriction endonucleases ApaI and NotI. Following these digestions the enzymes are heat inactivated, and the digested vaccinia arms are purified using a centricon 100 column. Transfection complexes are then formed between the digested vaccinia DNA and the transfer plasmid cDNA library. A preferred method uses Lipofectamine or Lipofectamine Plus (Life Technologies, Inc.) to form these transfection complexes. Transfections in 12 well plates usually require 0.5 micrograms of digested vaccinia DNA and 10 ng to 200 ng of plasmid DNA from the library. Transfection into cells in larger culture vessels requires a proportional increase in the amounts of vaccinia DNA and transfer plasmid. Following a two hour infection at 37° C. the fowlpox is removed, and the vaccinia DNA, transfer plasmid transfection complexes are added. The cells are incubated with the transfection complexes for 3 to 5 hours, after which the transfection complexes are removed and replaced with 1 ml DMEM supplemented with 2.5% Fetal Bovine Serum. Cells are incubated in a $CO_2$ incubated at 37° C. for 3 days. After 3 days the cells are harvested, and virus is released by three cycles of freeze/thaw in dry ice/isopropanol/37° C. water bath.

Example 10

Transfection of Mammalian Cells

This example describes alternative methods to transfect cells with vaccinia DNA and transfer plasmid. Trimolecular recombination can be performed by transfection of digested vaccinia DNA and transfer plasmid into host cells using for example, calcium-phosphate precipitation (F. L. Graham, A. J. Van der Eb (1973) *Virology* 52: 456–467, C. Chen, H. Okayama (1987) *Mol. Cell. Biol.* 7: 2745–2752), DEAE-Dextran (D. J. Sussman, G. Milman (1984) *Mol. Cell. Biol.* 4: 1641–1643), or electroporation (T. K. Wong, E. Neumann (1982) *Biochem. Biophys. Res. Commun.* 107: 584–587, E. Neumann, M. Schafer-Ridder, Y. Wang, P. H. Hofschneider (1982) *EMBO J.* 1: 841–845).

Example 11

Direct Selection for Binding Partners Using Two Hybrid System and Suicide Gene Constuct The two hybrid system is based on the fact that many eucaryotic transcriptional activators are comprised of two physically and functionally separable domains, a DNA-binding domain (DNA-BP) and an activation domain (AD). The two domains are normally part of the same protein. However, the two domains can be separated and expressed as distinct proteins. Two additional proteins (X and Y) are expressed as fusions to the DNA-BP and AD peptides. If X and Y interact, the AD is co-localized to the DNA-BP bound to the promoter, resulting in the transcription of the suicide gene.

The following is an example of the two hybrid transcriptional activation direct selection system. This system is composed of two fusion polynucleotides, one of which may be expressed by a tissue- or cell- or differentiation-specific promoter or a constitutive promoter and the second is found in a poxvirus vector:

1) a fusion of known protein X with the GAL4 DNA-BP;
2) a fusion of a test protein Y with the VP16 activation domain;

where protein X and Y interact (for example, the SV40 large T antigen which associates with the p53 protein). A third construct provides the GAL4 DNA binding site, the minimal promoter of the adenovirus E1b, and the suicide gene.

ES, or any readily transected cells such as Cos 7 or 293 cells, are "seeded" with the first and third constructs either before or after infection with a library cloned in a poxvirus or other vector. The constructs preferably also contain a selectable marker such as PGK neo. The poxvirus vector contains insert polynucleotides fused to the VP16 activation domain preceded by a strong constitutive poxvirus promoter. The inserts may be in each reading frame. The ES cells are cultured and nonviable cells are removed from viable/adherent cells.

Examples of protein binding partners that would be identified using this method are as follows:

1) the GAL4 DNA binding domain fused to the Fos leucine zipper domain (DFosLZ), and
2) the VP16 activation domain fused to the Jun leucine zipper (AJunLZ); or 1) the GAL4 DNA binding domain fused to the Jun leucine zipper domain (DJunLZ), and
2) the VP16 activation domain fused to the Fos leucine zipper (AFosLZ).

The construction of these fusions have been previously described in Dang et al., (1991) Molecular and Cellular Biology 11:954–962, and components to create the vectors of this system (except leucine zipper components) may be obtained from Clontech-Mammalian Matchmaker two hybrid assay kit.

An example of a gene system whose expression is dependent on the presence of two interacting fusion proteins is the G5E1b promoter, which contains 5 copies of the 17 mer GAL4 DNA binding site 5' of the minimal promoter of the Adenovirus E1b, driving the expression of a CAT reporter gene (e.g. indicator gene). For a direct selection method, the CAT gene is replaced by a suicide gene. Alternatively, the CAT gene or other maker is used in an indirect selection method such as a screening method.

Example 12

Genetic Recombination-Dependent Suicide Gene

This system makes use of a recipient cell containing a stuffer DNA fragment flanked by lox sites preceding a suicide gene. See Lasko, et al., (1992), *Proc. Natl. Acad. Sci. USA* 89:6232–6236 for description of a vector containing a stuffer DNA fragment flanked by lox sites preceding a reporter gene (e.g. indicator gene). The expression of the suicide gene is dependent on the removal of the stuffer DNA sequence mediated by the Cre recombinase enzyme through site directed recombination of lox sites found flanking the stuffer DNA. The Cre gene is under transcriptional control of a differentially expressed gene. Cells that are induced by a target polynucleotide to undergo differentiation express Cre, which removes the stuffer DNA fragment from the suicide gene contruct, allowing, the suicide gene to be expressed and the target polynucleotide to be selected.

Example 13

Analysis of Isolated Target Polynucleotides and Isolation of Full-Length cDNA

DNA sequencing, DNA or RNA blotting, immunoprecipitation, immuno-blotting, and other methods of analyzing insert DNA isolated according to the methods of the present invention, and encoded products thereof, may be carried out by any convenient methods known to those of skill. For example, the immunoprecipitation protocol of Clark et al., *Leukocyte Typing II, Vol. II*, pp. 155–167 (1986), is one preferred method. Southern, Northern, or other blot analysis methods known to those of skill may be employed, using hybridization probes prepared by known methods, such as that of Hu et al. (*Gene* 18:271–277 (1982)). DNA sequencing also may be accomplished by known methods, including the dideoxynucleotide method of Sanger et al., *Proc. Natl. Acad. Sci.* (*USA*) 74:5463–5467 (1977).

Selection of Full Length cDNA. This section presents methods for facilitating selection of corresponding full length cDNAs from fragments of differentially expressed genes or other target polynucleotides identified by methods of the invention. A single stranded biotinylated probe is synthesized from isolated cDNA fragments and is used to select the longer cDNA that contain a complementary sequence by solution hybridization to single stranded circles rescued from a phagemid tumor cDNA library. This method is especially well-suited to the use of DNA fragments isolated by the modified differential display method employing two arbitrary primers. The same arbitrary primers employed for PCR amplification of a given fragment in differential display can be modified to generate a single stranded hybridization probe from that fragment. This avoids the need to sequence, select and synthesize a new pair of fragment specific primers for each new fragment of interest.

(i) The two oligonucleotides of a pair of PCR primers employed in differential display are modified: (biotin-dT)-dT-(biotin-dT) is incorporated at the 5' end of one primer and a phosphate is incorporated at the 5' end of the second primer. These modified primers are incorporated by PCR into the two strands of a differential display fragment that was selected following the original PCR amplification with the same unmodified arbitrary primers. From this double stranded PCR product, the strand labelled with a 5' phosphate is digested with λ exonuclease to generate a single stranded biotin-labeled probe.

(ii) Single stranded (ss) DNA circles are rescued from a phagemid cDNA library using the M13K07 packaging defective phage as helper virus. This library is constructed in the pcDNA3.1/Zeo(+) phagemid (Invitrogen, Carlsbad, Calif.) with insertion of (ApaI)oligo-dT primed cDNA between the ApaI and Eco RV restriction sites. A key manipulation to achieve the efficient ligation necessary for construction of a high titer cDNA library is to insure that cDNA inserts are 5' phosphorylated by treating with T4 polynucleotide kinase prior to ligation. The biotin-labeled single stranded probe generated from the differential display fragment is hybridized in solution to the ssDNA circles of the phagemid library. The biotin-labeled hybridization complexes can then be separated from unrelated ssDNA on streptavidin magnetic beads and the ss circles eluted for further analysis (FIG. 18).

As a test of this enrichment method, a model plasmid mix was prepared that included 1% of a specific arbitrarily selected recombinant clone, 3f IAP. A biotinylated ss-probe was prepared from the 3f RDA fragment and used to select single stranded phagemid circles from the 1% plasmid mix. Following elution from streptavidin beads, the single stranded circles were hybridized to a sequence specific oligonucleotide in order to prime synthesis of the second plasmid strand prior to bacterial transformation. Plasmid DNA was prepared from 63 transformed colonies. 63 of 63 of these plasmid preparations expressed the target 3F IAP insert. This method therefore appears to be very efficient.

The same method appears to work with similar efficiency in the more stringent case of a differential display fragment (B4) representing a previously unidentified sequence that is expressed in all four murine tumors at a concentration approximately 10 fole greater than in the non-tumorigenic parental cells. 5 out of 5 transformants randomly picked following selection of single strand circles with the 200 bp B4 DNA fragment had longer inserts that were positive by PCR with sequence specific primers. This method therefore appears to be very efficient.

Example 14

Antibodies

Standard reference works setting forth general principles of immunology include Current Protocols in Immunology, John Wiley & Sons, New York; Klein, J., Immunology: The Science of Self-Nonself Discrimination, John Wiley & Sons, New York (1982); Kennett, R., et al., eds., Monoclonal Antibodies, Hybridoma: A New Dimension in Biological Analyses, Plenum Press, New York (1980); Campbell, A., "Monoclonal Antibody Technology" in Burden, R., et al., eds., Laboratory Techniques in Biochemistry and Molecular Biology, Vol. 13, Elsevere, Amsterdam (1984).

Host cells comprising recombinant vaccinia virus or other recombinant vector are contacted with antibody specific for an epitope of interest. Target epitopes expressed on the cell surface form complexes with the antibodies. The antibody may be conjugated to or bound to or associated with a toxic agent, and thereby cause the target cells to become nonviable. or nonadherent. Alternatively, the antibody is labeled and FACS is used to separate cells or complement-dependent cytotoxicity (CDC) or antibody-dependent cellular cytotocity (ADCC) is used to select target polynucleotides. See U.S. Pat. No. 5,500,362 for ADCC and CDC assays. Such assays may be modified for use in the present selection method by, for example, omitting the $^{51}Cr$ labeling of cells, as will be apparent to one of ordinary skill in the art. See, e.g. Hellstrom et al., *Proc. Natl. Acad. Sci. USA* 82:1499–1502 (1985).

Cells which bind target antigen-specific antibody are lysed or otherwise become nonviable or nonadherent or are sorted via one of the techniques described above, otherwise disclosed herein or known in the art. Nonadherent cells or recombinant vector DNA are separated from the adherent cells which do not express the target antigen.

The initial rounds of selection may employ a panel of antibodies directed against an epitope or group of epitopes common to the family of antigens to which the target antigen belongs. This will be sufficient to narrow the number of clones for future rounds. Two such rounds may be adequate, but the number of rounds may vary as mentioned above. Alternatively, a single round of selection may be performed employing a single first antibody or a group of first antibodies recognizing only the target antigen.

Antibodies generated against a target epitope can be obtained by direct injection of the epitope or polypeptide into an animal or by administering the polypeptides to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polynucleotide encoding the polypeptide from an expression library using the method of the present invention.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of interest.

Antibodies useful in the present invention may also be obtained from a patient, preferably a mammalian patient such as a small or large animal, including dogs, cats, horses, birds, monkeys, ferrets, gerbils, hamsters, rats, mice, goats, cows, donkeys, etc., preferably a human patient Antibodies may be obtained from a patient sample such as a tissue sample or fluid sample, preferably a serum sample.

Antibodies may be obtained from a patient having a disease, recovering from a disease, or recovered from a disease. For example, such diseases include an infectious disease, an infection, a cancer, an autoimmune disease and a degenerative disease, or any disease as disclosed herein or otherwise known in the art.

Infectious agents causing infectious diseases and infections include those described herein or otherwise known in the art. Alternatively, antibody may be obtained from pooled patient samples.

The antibodies useful in the present invention may be prepared by any of a variety of methods. For example, cells expressing the target protein or an antigenic fragment thereof can be administered to an animal in order to induce the production of sera containing polyclonal antibodies. In another method, a preparation of target protein is prepared and purified to render it substantially free of natural contaminants. Such a preparation is then introduced into an animal in order to produce polyclonal antisera of greater specific activity.

In a highly preferred method, antibodies useful in the present invention are monoclonal antibodies (or target protein-binding fragments thereof). Such monoclonal antibodies can be prepared using hybridoma technology (Kohler et al., Nature 256:495 (1975); Kohler et al., Eur. J. Immunol. 6:511 (1976); Kohler et al., Eur. J. Immunol. 6:292 (1976); Hammerling et al., In: Monoclonal Antibodies and T-Cell Hybridomas, Elsevier, N.Y., (1981) pp. 563–681). In general, such procedures involve immunizing an animal (preferably a mouse) with an target protein antigen or, more preferably, with a target protein-expressing cell. Suitable cells can be recognized by their capacity to bind an anti-target protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 g/ml of streptomycin. The splenocytes of immunized mice are extracted and fused with a suitable myeloma cell line. Any suitable myeloma cell line may be employed in accordance with the present invention; however, it is preferable to employ the parent myeloma cell line (SP2O), available from the American Type Culture Collection, Mannassas, Va. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the target protein antigen.

Alternatively, additional antibodies capable of binding to the target protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, target-protein specific antibodies are used to immunize an animal, preferably a mouse. The splenocytes of such an animal are then used to produce hybridoma cells, and the hybridoma cells are screened to identify clones which produce an antibody whose ability to bind to the target protein-specific antibody can be blocked by the target protein antigen. Such antibodies comprise anti-idiotypic antibodies to the target protein-specific antibody and can be used to immunize an animal to induce formation of further target protein-specific antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, target protein-binding fragments can be produced through the application of recombinant DNA technology or through synthetic chemistry.

In a preferred embodiment, the antibody or antibody fragment is conjugated with a toxic agent which kills cells that express a target protein. Toxic agents useful in the invention include toxins (e.g. an enzymatically active toxin of bacterial, fungal, plant or animal origin, or fragments thereof). Examples of suitable toxins include diphtheria toxin, ricin, and cholera toxin.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII and PAP-S), momordica charantia inhibitor, curin, crotin, sapaonaria officinalis inhibitor, gelonin, mitogellin, restrictocin, phenomycin, enomycin and the tricothecenes.

Further suitable labels for the target protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, 131I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc.

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy et al., Clin. Chim. Acta 70:1–31 (1976), and Schurs et al., Clin. Chim. Acta 81:1–40 (1977). Coupling techniques mentioned in the latter are the glutaraldehyde method, the periodate method, the dimaleimide method, the m-maleimidobenzyl-N-hydroxysuccinimide ester method, all of which methods are incorporated by reference herein.

Conjugates of the antibody and cytotoxic agent are made using a variety of bifunctional protein coupling agents such as N-succinimidyl-3-(2-pyridyldithiol)proprionate (SPDP), iminothiolane (IT), bifunctional derivatives of imidoesters (such as dimethyl adipimidate HCL), active esters (such as disuccinimidyl suberate), aldehydes (such as dimethyl adipimidate HCL), active esters (such as disuccinimidyl suberate), aldehydes (such as glutaraldehyde), bis-azido compounds (such as bis-p-(azidobenzoyl)hexanediamine), bis-diazonium derivatives (such as bis-p(diazoniumbenzoyl)-ethylenediamine), diisocyantes (such as toluene 2,6-diisocyanate), and bis-active fluorine compounds (such as 1,5-difluoro-2,4-dinitrobenzene). For example, aricin immunotoxin can be prepared as described in Vitetta et al., Science 238: 1098 (1987). Carbon-14 labeled 1-isothiocyanatobenzyl-3-methyldiethylene triaminepentaacetic acid (MX-DTPA) is an exemplary chelating agent for conjugation of radionucleotide to the antibody. See WO94/11026.

Example 15

Induction of Cytotoxic T Cells Specific for Human Tumors in HLA and Human CD8 Transgenic Mice In this example, HLA and human CD8 transgenic mice were tolerized with a non-tumorigenic, immortalized normal human cell line, i.e., parent cell line, that does not express costimulator activity for murine T cell. After tolerization, the mice were subsequently immunized with B7 (costimulator) transfected tumor cells derived from the parent cell line by in vitro mutagenesis or oncogene transformation. The HLA transgene permits selection of a high affinity, HLA-restricted T cell repertoire in the mouse thymus. In addition, a human CD8 transgene is required because murine CD8 does not interact efficiently with human class I MHC. Subsequent to immunization with B7 transfected tumor cells, splenic CD8+ T cells are isolated and stimulated again in vitro in the absence of costimulation with non-tumorigenic, immortalized human cells. Two pathways of tolerance induction for antigens shared by the tumorigenic and non-tumorigenic cell lines may be activated through these manipulations. As known to those skilled in the art, antigen exposure in very young mice favors tolerance induction by mechanisms that may include both clonal deletion and induction of T cell anergy. Further, restimulation of activated T cells through their antigen-specific receptors in the absence of costimulator activity induces apoptotic elimination of those T cells. This immunization regimen enriched for tumor-specific CTL that did not crossreact with the homologous normal cells.

A series of tumor cell lines were used that were all derived from a single immortalized, non-tumorigenic cell line. The non-tumorigenic cells were used to induce tolerance to the large number of normal human proteins that are also expressed in tumor cells. Availability of a panel of tumors independently derived from the same normal cells by diverse carcinogens or oncogene transformation makes it possible to filter out antigenic changes that are carcinogen specific or that may arise by random genetic drift during in vitro propagation of a tumor cell line.

Cytotoxic T cells specific for human bladder tumor cell lines were induced and isolated from (HLA-A2/K$^b$×human CD8)F$_1$ hybrid double transgenic mice that had been tolerized to the normal cell line from which the tumors derive. Neonatal mice were injected intraperitoneally with 5×10$^6$ non-tumorigenic SV-HUC. Seven weeks later they were immunized with 5×10$^6$ B7.1 transfected ppT11.B7 tumor cells. ppT11 is one of several independent tumor cell lines derived from SV-HUC by in vitro carcinogenesis (Christian, et al., 1987, Cancer Res. 47: 6066–6073; Pratt, et al., 1992, Cancer Res. 52: 688–695; Bookland, et al., 1992, Cancer Res. 52: 1606–1614). One week after immunization, spleen was removed and a single cell suspension prepared. CD8 positive T cell precursors were enriched on anti-Lyt-2 coated MACS (Magnetic cell sorting beads) as recommended by the manufacturer (Miltenyi Biotech, Sunnyvale, Calif.). $1.5 \times 10^6$ CD8 enriched T cells were then restimulated in vitro with $4 \times 10^5$ SV-HUC in 3 ml of RPMI 1640+10% fetal bovine serum. The rationale is that any SV-HUC specific T cells that escape neonatal tolerance induction and are activated in vivo by stimulation with crossreactive determinants of ppT11.B7, might now be induced to undergo apoptosis by restimulation in vitro with costimulator activity negative SV-HUC cells. After 24 hours, T cells are again stimulated with ppT11.B7 in the presence of 2000 Units/ml of recombinant murine IL-6. On day 7 the cycle of SV-HUC stimulation followed 24 hours later by restimulation with ppT11.B7 is repeated. This second round of stimulation with ppT11.B7 is carried out in the presence of 10 nanogram/ml recombinant murine IL-7 and 50 Units/ml recombinant murine IL-2. CTL activity is determined 5 days later by standard chromium release assay from labeled targets SV-HUC, ppT11.B7 and YAC-1, a cell line sensitive to non-specific killing by murine NK cells. The results in Table 11 show that CTL from ppT11.B7 immunized mice that were not previously tolerized to SV-HUC are equally reactive with SV-HUC and ppT11 target cells. In contrast, following neonatal tolerization with SV-HUC, cytolytic T cells at an effector:target ratio of 5:1 are significantly more reactive with ppT11.B7 tumor cells than with SV-HUC. Note that B7 costimulator activity is not required at the effector stage as similar results are obtained with B7 transfected or non-transfected target cells.

Table 11: Tumor-specific response in (HLA-A2/$K^b \times$ human CD8)$F_1$ hybrid transgenic mice neonatally tolerized with SV-HUC parental cells and then immunized with B7 costimulator transfected ppT11.B7 human bladder tumor cells.

TABLE 11

| Tolerogen: | None | | SV-HUC | |
|---|---|---|---|---|
| Immunogen: | ppT11.B7 | | ppT11.B7 | |
| | Effector:Target Ratio | | | |
| Target | 5:1 | 10:1 | 2:1 | 5:1 |
| SV-HUC | 29 | 68 | 14 | 19 |
| ppT11.B7 | 14 | 70 | 17 | 51 |
| YAC-1 | 6 | 6 | nd | 3 | nd = not done

The significance of this experimental protocol is that it offers a means of selecting murine, HLA-restricted cytolytic T cells specific for human epithelial tumor cells. As noted previously, it has proved exceedingly difficult to isolate such T cells directly from either patient PBL or tumor infiltrating lymphocytes of tumors other than melanoma and perhaps renal cell carcinoma. In addition, this same strategy can be implemented in two stages. Differentially immunogenic molecules of the human tumor can first be identified employing tumor-specific CTL restricted to a variety of different animal MHC. These antigens can subsequently be characterized in human subjects or transgenic mice for the ability to be processed and presented in association with different human HLA types. An advantage of this two stage approach is that numerous different MHC molecules are available in a variety of inbred strains and these can be employed to capture an equally broad range of tumor-specific immunogenic peptides in the initial screening. See also Example 25.

Example 16

Induction of Cytotoxic T Cells Specific for Target Antigens of Tumors or Infected Cells Human tumor-specific T cells have been induced in vitro by stimulation of PBL with autologous tumors or autologous antigen presenting cells pulsed with tumor lysates (van Der Bruggen, P. et al., Science 254: 1643–1647 (1991); Yasumura, S. et al., Cancer Res. 53: 1461–68 (1993); Yasumura, S. et al., Int. J. Cancer 57: 297–305 (1994); Simons, J. W. et al., Cancer Res. 57: 1537–46 (1997); Jacob, L. et al., Int. J. Cancer 71:325–332 (1997); Chaux, P. et al., J. Immunol. 163:2928–2936 (1999)). PBL have been derived from either patients deliberately immunized with tumor, with tumor modified to enhance its immunogenicity, or with tumor extracts, or patients whose only prior stimulation was in the natural course of disease. T cells with reactivity for infectious agents could be similarly derived by in vitro stimulation of T cells with autologous cells that have been either infected in vitro or were infected in vivo during the natural course of exposure to the infectious agent. The conditions described in Example 5 to promote stimulation of primary cytotoxic CD4+ T cell responses in the presence of IL-2, IFNg, anti-IL-4, IL-12 and IL-18 have also been determined to promote primary cytotoxic CD8+ T cell responses. CD4+ and CD8+ T cells or antibody selected under these or other conditions to be specific for either tumor cells or cells infected with either a virus, fungus or mycobacteria or T cells or antibodies specific for the target antigens of an autoimmune disease could be employed in the selection and screening methods of this invention to detect and isolate cDNA that encode these target antigens and that have been incorporated into a representative cDNA library using the methods of this invention.

In spite of demonstrated success in the induction of human T cell responses in vitro against a number of antigens of tumors and infected cells, it is not certain that these represent the full repertoire of responses that might be induced in vivo. Because safety considerations limit the possibilities of experimental immunization in people, there is a need for an alternative animal model to explore immune responses to human disease antigens. The major obstacle to developing such a model is that numerous molecules expressed in normal human cells are strongly immunogenic in other species. It is, therefore, be necessary to devise a means of inducing tolerance to normal human antigens in another species in order to reveal immune responses to any human disease-specific antigens. It is now recognized that activation of antigen-specific T lymphocytes requires two signals of which one involves presentation of a specific antigenic complex to the T cell antigen receptor and the second is an independent costimulator signal commonly mediated by interaction of the B7 family of molecules on the surface of the antigen presenting cell with the CD28 molecule on the T cell membrane. Delivery of an antigen-specific signal in the absence of a costimulator signal not only fails to induce T cell immunity but results in T cell unresponsiveness to subsequent stimulation (Lenschow, D. J. et al., Ann. Rev. Immunol. 14:233–258 (1996)). Additional studies have revealed a key role for another pair of interactions between the CD40 molecule on the antigen presenting cell and CD40 ligand on the T cell. This interaction results in upregulation of the B7 costimulator molecules (Roy, M. et al., Eur. J. Immunol. 25:596–603 (1995)). In the presence of anti-CD40 ligand antibody either in vivo or in vitro, the interaction with CD40 is blocked, B7 costimulator is not up regulated, and stimulation with a specific antigenic complex results in T cell tolerance rather than T cell immunity (Bluestone, J. A. et al., Immunol. Rev. 165:5–12 (1998)). Various protocols to block either or both CD40/CD40 ligand interactions and B7/CD28 interactions have been shown to effectively induce transplantation tolerance (Larsen, C. et al., Nature 381:434–438 (1996); Kirk et al., Nature Medicine 5:686–693 (1999)). An example of the effect of anti-CD40 ligand antibody (anti-CD 154) in blocking the reactivity of murine T cells to specific transplantation antigens is shown in FIG. 20. DBA/2 (H-$2^d$) mice were immunized with $10^7$ C57B1/6 (H-$2^b$) spleen cells intraperitoneally and, in addition, were injected with either saline or 0.5 mg monoclonal anti-CD40 ligand antibody (MR1, anti-CD154, Pharmingen 09021D) administered both at the time of immunization and two days later. On day 10 following immunization, spleen cells from these mice were removed and stimulated in vitro with either C57B1/6 or control allogeneic C3H (H-$2^k$) spleen cells that had been irradiated (20 Gy). After 5 days in vitro stimulation, C57B1/6 and C3H specific cytolytic responses were assayed at various effector:target ratios by $^{51}$Cr release assay from specific labeled targets, in this case, either C3H or C57B1/6 dendritic cells pulsed with syngeneic spleen cell lysates. The results in FIG. 20 show that significant cytotoxicity was induced against the control C3H alloantigens in both saline and anti-CD154 treated mice whereas a cytotoxic response to C57B1/6 was induced in the saline treated mice but not the anti-CD 154 treated mice. This demonstrates specific tolerance induction to the antigen employed for immune stimulation at the time CD40/CD40 ligand interactions were blocked by anti-CD154.

A tolerization protocol similar to the above employing either anti-CD154 alone or a combination of anti-CD154 and anti-B7 or anti-CD28 could be employed to induce tolerance to normal human xenoantigens in mice prior to immunization with a human tumor. In one embodiment, the normal antigens would be expressed on immortalized normal cells derived from the same individual and tissue from which a tumor cell line is derived. In another embodiment, the normal and tumor antigens would derive from cell lysates of normal and tumor tissue of the same individual each lysate pulsed onto antigen presenting cells for presentation to syngeneic murine T cells both in vivo and in vitro. In a preferred embodiment, the tumors would derive by in vitro mutagenesis or oncogene transformation from an immortalized, contact-inhibited, anchorage-dependent, non-tumorigenic cell line so that very well-matched non-tumorigenic cells would be available for tolerance induction.

An alternative to the tolerization protocols is depletion of T cells that are activated by normal antigens prior to immunization with tumor. Activated T cells transiently express CD69 and CD25 with peak expression between 24 and 48 hours post-stimulation. T cells expressing these markers following activation with normal cells or normal cell lysates can be depleted with anti-CD69 and anti-CD25 antibody coupled directly or indirectly to a matrix (e.g. solid surface) such as magnetic beads. Subsequent immunization of the remaining T cells with tumor cells or tumor cell lysates either in vitro or in vivo following adoptive transfer will preferentially give rise to a tumor-specific response.

In one embodiment, the mice to be tolerized to normal human cells or lysates and subsequently immunized with tumor cells or lysates are any of a variety of commercially available inbred and outbred strains. Because murine T cells are restricted to recognize peptide antigens in association with murine MHC molecules which are not expressed by human cells, effective tolerization or stimulation requires either transfection of human cells with murine MHC molecules or re-presentation of human normal and tumor antigens by mouse antigen presenting cells. Dendritic cells are especially preferred as antigen presenting cells because of their ability to re-present antigenic peptides in both the class I and class II MHC pathways (Huang, et al., Science 264:961–965 (1994); Inaba, et al., J. Exp. Med. 176:1702 (1992); Inaba, et al., J. Exp. Med. 178:479–488 (1993)). In another embodiment, mice double transgenic for human HLA and human CD8 or CD4 are employed. The HLA transgene permits selection of a high affinity, HLA-restricted T cell repertoire in the mouse thymus. In addition, a human CD8 or CD4 transgene is required because murine CD8 and CD4 do not interact efficiently with the cognate human class I or class II MHC molecules. The use of non-transgenic mice to generate human tumor-specific T cells would lead to identification of any human tumor antigens that can be processed in association with murine MHC molecules. Since multiple murine strains with diverse MHC molecules are available, this could encompass a wide range of antigens. However, it would have to be separately determined by stimulation of human T cells with autologous antigen presenting cells whether these tumor-specific antigens also express peptides that can be processed and presented in association with human HLA. Such peptides may or may not overlap with those initially detected in association with murine MHC molecules but would derive from the same set of proteins. By employing HLA transgenic mice it is possible to more directly address the relevance of antigenic peptides to human MHC. There can, however, be no assurance that peptide processing will be identical in murine and human antigen presenting cells. It is essential, therefore, to confirm that HLA-restricted, human tumor antigen-specific T cells are indeed also crossreactive on human tumor cells. Finally, no matter how the issue of processing and presentation in association with human HLA is addressed, it must in all cases be determined whether human T cells are reactive to the identified antigens or whether they have been rendered tolerant, perhaps due to expression of the same or a related antigen in some other non-homologous normal tissue. Relevant information on this point can be obtained through in vitro stimulation of human T cell responses with the identified antigens or antigenic peptides presented by autologous antigen presenting cells. Ideally, it would be shown that patients with antigen positive tumors have an increased frequency of T cells reactive with the purported tumor-specific antigen. To demonstrate that the antigen-specific human T cells induced can be effective in eradicating tumors, the selected human T cells could be adoptively transferred into SCID mice bearing a human tumor xenograft as described by Renner, C. et al., Science 264: 833–835 (1994). However, definitive evidence for clinical relevance would await the results of a human clinical trial.

Conditions for in vitro stimulation of primary human T cell responses are described in Example 5 and are applicable to both CD4+ and CD8+ responses. The strategies described for induction of either human or murine T cell or antibody responses specific for human tumors are equally applicable to induction of T cell or antibody responses to target antigens of human cells infected with either a virus, fungus or mycobacteria. Indeed, in this case the same uninfected cell population affords an immediately available normal control population for tolerance induction and to confirm infectious specificity.

The construction of transgenic mice is well known in the art and is described, for example, in Manipulating the Mouse Embroy: A laboratory Manual, Hogan, et al., Cold Spring Harbor Press, second edition, 1994. Human CD8 transgenic mice may be constructed by the method of LaFace, et al., J. Exp. Med. 182: 1315–25 (1995). Construction of new lines of transgenic mice expressing the human CD8alpha and CD8beta subunits may be made by insertion of the corresponding human cDNA into a human CD2 minigene based vector for T cell-specific expression in transgenic mice (Zhumabekov, et al., J. Immunol. Methods 185:133–140 (1995)). HLA class I transgenic mice may be constructed by the methods of Chamberlain, et al., Proc. Natl. Acad. Sci. USA 85:7690–7694 (1988) or Bernhard, et al., J. Exp. Med. 168: 1157–62 (1988) or Vitiello, et al., J. Exp. Med. 173: 1007–1015 (1991) or Barra, et al., J. Immunol. 150: 3681–9 (1993).

Construction of additional HLA class I transgenic mice may be achieved by construction of an H-2Kb cassette that includes 2 kb of upstream regulatory region together with the first two introns previously implicated in gene regulation (Kralova, et al., 1992, EMBO J. 11: 4591–4600). Endogenous translational start sites are eliminated from this region and restriction sites for insertion of HLA cDNA are introduced into the third exon followed by a polyA addition site. By including an additional 3 kb of genomic H-2Kb sequence at the 3' end of this construct, the class I gene can be targeted for homologous recombination at the H-2Kb locus in embryonic stem cells. This has the advantage that the transgene is likely to be expressed at a defined locus known to be compatible with murine class I expression and that these mice are likely to be deficient for possible competition by H-2Kb expression at the cell membrane. It is believed that this will give relatively reproducible expression of diverse human HLA class I cDNA introduced in the same construct.

Example 17

Independent Human Tumor Cell Lines Derived from a Non-Tumorigenic, Immortalized Cell Line This example describes a set of human tumors independently derived by different carcinogens or oncogene transformation from the same cloned, non-tumorigenic parental cell line. The parental cell line is useful for tolerizing mice and the independently-derived tumors useful for immunizing mice in the generation of tumor antigen-specific CTLs. A similar approach is used to generate infection-induced or infectious agent-encoded antigens. Likewise, this approach is easily modified to generate any differentially-expressed antigen, such as those that are development-specific or induced under certain conditions.

Additionally, the availability of related normal and tumor cell lines has considerable advantages for the molecular and immunological analysis of potential cancer vaccines. It provides a readily available source of normal control cells and RNA, and also makes it possible to focus on molecular features that are carcinogen independent. Molecular features that are shared by several independent tumors are unlikely to be the products of random genetic drift during in vitro propagation.

A set of human uroepithelial tumors derived from an SV40 immortalized human uroepithelial cell line, SV-HUC, were developed in the laboratory of Dr. Catherine Reznikoff (University of Wisconsin, Madison). The parent cell line is contact inhibited, anchorage dependent and non-tumorigenic in nude mice (Christian, et al., 1987, Cancer Res. 47: 6066–6073). A series of independent tumor cell lines were derived by either ras transformation (Pratt, et al., 1992, Cancer Res. 52: 688–695) or in vitro mutagenesis of SV-HUC with different carcinogens including some that are bladder-specific (Bookland, et al., 1992, Cancer Res. 52: 1606–1614). Transformed cells were initially selected on the basis of altered in vitro growth requirements and each was shown to be tumorigenic in nude mice. A subset of these tumors is selected that retain the phenotype of transitional cell carcinoma. Table 12 lists the parental cells and the carcinogens employed to derive these 5 tumor lines in vitro.

TABLE 12

Human Uroepithelial Cell Lines

| Parental Line | Immortalization |
|---|---|
| SV-HUC | SV40 immortalized normal bladder epithelial cells |
| Tumor Line | Carcinogen or Oncogene transformation |
| MC pT7 | 3-methylcholanthrene |
| MC ppT11-A3 | 3-methylcholanthrene followed by 4-aminobiphenyl |
| MC ppT11-HA2 | 3-methylcholanthrene followed by N-hydroxy-4-acetylaminobiphenyl |
| HA-T2 | N-hydroxy-4-aminobiphenyl |
| SV-HUC/ras-T | EJ/ras |

Experiments apply both representational difference analysis and modified differential display to identify gene fragments differentially expressed in the MC ppT11-A3 tumor (ppT11A3) relative to the parental SV-HUC. All differentially expressed fragments are tested by Northern analysis and RNase protection assay for parallel expression in mRNA of the other tumor cell lines. Only those DNA clones expressed in at least 3 of the 5 SV-HUC derived tumor cell lines are selected for further characterization.

Similar analysis of tumor-specific antigens can be carried out as described in the other Examples with tumors derived from SV40 large T or HPV E6 or E7 immortalized cell lines representative of other human tissues. Published examples include: prostatic epithelium (Parda et al., 1993, The Prostate 23: 91–98), mammary epithelium (Band et al., 1990, Cancer Res. 50: 7351–73–57), and bronchial epithelium (Gerwin et al., 1992, Proc. Natl. Acad. Sci. USA 89: 2759–2763; Klein-Szanto et al., 1992, Proc. Natl. Acad. Sci. USA 89: 6693–6697).

It will be important to confirm for each tumor encoded target antigen identified by T cells or antibodies reactive with in vitro derived tumor cell lines, that the same antigen is also expressed in a significant proportion of tumors that arise spontaneously in vivo. Antigen expression should be characterized in a panel of at least 20 patient tumors. This sample size is sufficient to estimate the proportion of patients expressing the antigen with a standard error no greater than 0.11% (SE=sqrt[p*(1−p)/n] where p=true proportion and n=sample size. SE is maximal for p=0.5, so that for 10/20 patients, SE=±0.11; for any other value of p, SE is smaller.) In some cases, as a surrogate for antigen expression, it will be possible to screen for expression of a tumor-specific cDNA. However, in other instances, it may be necessary to assay antign expression more directly. For T cell defined antigens this introduces a requirement for expression of the appropriate MHC restriction element. If this MHC molecule is not naturally expressed in some tumors, it needs to be introduced by transfection or infection with a viral recombinant.

Example 18

Identifying Target Antigens for Use in Vaccines

The subsections below describe two strategies that can be used to identify target antigens or epitopes that are candidates for use in immunogenic formulations or vaccines or other therapeutic methods. The two strategies described herein may be applied to identify target epitopes which include, but are not limited to, tumor specific epitopes, epitopes specific to a cell infected with a virus, fungus or mycobacteria, epitopes specific to an autoimmune disease, or any epitope capable of inducing a specific CTL response, either naturally or upon immunization. See also Example 25.

Induction of Cytotoxic T Lymphocytes Specific for Human Tumors and their Use to Select DNA Recombinants that Encode Target Epitopes Cytotoxic T cells specific for human tumors are induced in animals which have been tolerized with a non-tumorigenic, immortalized normal human cell line that does not express costimulator activity. These animals are subsequently immunized with costimulator transfected (e.g., B7 transfected) tumor cells derived by in vitro mutagenesis or oncogene transformation from that same normal immortalized human cell line. An alternative source of matched normal and tumor cell pairs that could be employed in this same fashion is to derive normal and tumor cell lines from different tissue samples of the same patient. For purposes of immunization, costimulator activity could also be introduced in these tumor cells by transfection with murine B7. This immunization regimen gives rise to tumor-specific CTL that are not crossreactive on the homologous normal cells. The primary purpose of inducing tumor-specific CTL is that they can be employed, as described below, to select for clones of recombinant tumor DNA that encode the target antigen. Such antigens, because they are differentially immunogenic in tumor as compared to normal cells, are candidates for immunogenic formulations or vaccines. Mammals of different species, most commonly diverse strains of inbred mice, can be employed for this purpose. Whether a particular formulation or vaccine is immunogenic in any particular individual will depend on whether specific peptides derived from that antigen can be processed and presented in association with the particular MHC molecules expressed by that individual. To narrow the focus of this selection process to antigens from which peptides can be derived that associate with a particular human HLA molecule, it is possible, as described in other Examples, to derive directly HLA restricted CTL from HLA and human CD8 transgenic mice. Alternatively, differentially immunogenic molecules of the human tumor can be initially identified employing tumor-specific CTL restricted to any animal MHC. Antigens so identified can subsequently be characterized for the ability to be processed and presented in association with different human HLA types by primary in vitro stimulation of human peripheral blood lymphocytes (PBL), or, as described in other Examples, by immunization of HLA and human CD8 transgenic mice. The HLA transgene permits selection of a high affinity, HLA-restricted T cell repertoire in the mouse thymus. In addition, a human CD8 transgene is most preferable because murine CD8 does not interact efficiently with human class I MHC.

The method to determine differential immunogenicity can be carried out in normal mice if genes encoding mouse MHC molecules are introduced into the human cell lines by transfection (Kriegler, M., 1991, Gene transfer and expression: A laboratory manual, W.H. Freeman and Co., New York). Alternatively, antigens of the human cell lines may be re-presented by murine professional antigen presenting cells in vivo (Huang, et al., 1994, Science, 264:961–965) and in vitro (Inaba, et al., 1992, J. Exp. Med. 176:1702; Inaba, et al., 1993, J. Exp. Med. 178:479–488). To induce T cell tolerance during re-presentation of human antigens by murine dendritic cells it may be necessary to block costimulator activity with anti-B7.1 and anti-B7.2 antibodies. Specificity of the CTL generated in this way may be determined by comparing lysis of human tumor and normal target cells that have been transfected with HLA class I or that have been infected with HLA class I or that have been infected with HLA class I recombinant vaccinia virus.

Since immunogenicity of antigen in any individual depends on whether peptides derived from the antigen can be presented to T cells in association with MHC molecules of that particular individual, it may be separately determined by immunization of human volunteers or of human CD8 and HLA transgenic mice, which human HLA molecules are able to present peptides of any identified antigen. The two issues of immunogenicity and HLA associated presentation can be addressed simultaneously if HLA transgenic mice rather than normal mice are employed in the initial immunization.

The construction of transgenic mice is well known in the art and is described, for example, in Manipulating the Mouse Embryo: A laboratory Manual, Hogan, et al., Cold Spring Harbor Press, second edition, 1994. Human CD8 transgenic mice may be constructed by the method of LaFace, et al., J. Exp. Med. 182: 1315–25 (1995). Construction of new lines of transgenic mice expressing the human CD8alpha and CD8beta subunits may be made by insertion of the corresponding human cDNA into a human CD2 minigene based vector for T cell-specific expression in transgenic mice (Zhumabekov, et al., J. Immunol. Methods 185:133–140 (1995)). HLA class I transgenic mice may be constructed by the methods of Chamberlain, et al., Proc. Natl. Acad. Sci. USA 85:7690–7694 (1988) or Bernhard, et al., J. Exp. Med. 168: 1157–62 (1988) or Vitiello, et al., J. Exp. Med. 173: 1007–1015 (1991) or Barra, et al., J. Immunol. 150: 3681–9 (1993).

Construction of additional HLA class I transgenic mice may be achieved by construction of an H-2Kb cassette that includes 2 kb of upstream regulatory region together with the first two introns previously implicated in gene regulation (Kralova, et al., 1992, EMBO J. 11: 4591–4600). Endogenous translational start sites are eliminated from this region and restriction sites for insertion of HLA cDNA are introduced into the third exon followed by a polyA addition site. By including an additional 3 kb of genomic H-2Kb sequence at the 3' end of this construct, the class I gene can be targeted for homologous recombination at the H-2Kb locus in embryonic stem cells. This has the advantage that the transgene is likely to be expressed at a defined locus known to be compatible with murine class I expression and that these mice are likely to be deficient for possible competition by H-2Kb expression at the cell membrane. It is believed that this will give relatively reproducible expression of diverse human HLA class I cDNA introduced in the same construct.

Most preferably, the tumor cell lines are a panel of tumor cell lines that are all derived from a single immortalized, non-tumorigenic cell line. Non-tumorigenic cells are most preferable for inducing tolerance to the large number of normal human proteins that are also expressed in tumor cells.

Preferably, screening is performed on such a panel of tumor cell lines, independently derived from the same normal cells by diverse carcinogens or oncogene transformation. Screening of such a panel of tumor cell lines makes it possible to filter out antigenic changes that are carcinogen specific or that may arise by random genetic drift during in vitro propagation of a tumor cell line.

The tumor-specific CTLs generated as described above can be used to screen expression libraries prepared from the target tumor cells in order to identify clones encoding the target epitope. DNA libraries constructed in a viral vector infectious for mammalian cells as described herein can be employed for the efficient selection of specific recombinants by CTLs. Major advantages of these infectious viral vectors are 1) the ease and efficiency with which recombinants can be introduced and expressed in mammalian cells, and 2) efficient processing and presentation of recombinant gene products in association with MHC molecules of the infected cell. At a low multiplicity of infection (m.o.i.), many target cells will express a single recombinant which is amplified within a few hours during the natural course of infection.

A representative DNA library is constructed in vaccinia virus. Preferably, a tri-molecular recombination method employing modified vaccinia virus vectors and related transfer plasmids is used to construct the representative DNA library invacciniavirus. This method generates close to 100% recombinant vaccinia virus (see Example 2).

In a preferred embodiment (see also Example 1), a vaccinia virus transfer plasmid pJ/K, a pUC 13 derived plasmid with a vaccinia virus thymidine kinase gene containing an in-frame Not I site, is further modified to incorporate one of two strong vaccinia virus promoters, e.g., either a 7.5K vaccinia virus promoter or a strong synthetic early/late (E/L) promoter, followed by Not I and Apa I restriction sites. The Apa I site is preferably preceded by a strong translational initiation sequence including the ATG codon. This modification is preferably introduced within the vaccinia virus thymidine kinase (tk) gene so that it is flanked by regulatory and coding sequences of the viral tk gene. Each of the two modifications within the tk gene of a plasmid vector may be transferred by homologous recombination in the flanking tk sequences into the genome of the Vaccinia Virus WR strain derived vNotI⁻vector to generate two new viral vectors.

Importantly, following Not I and Apa I restriction endonuclease digestion of these two viral vectors, two large viral DNA fragments can be isolated each including a separate non-homologous segment of the vaccinia tk gene and together comprising all the genes required for assembly of infectious viral particles.

In one embodiment, such modifications are introduced in the Modified Virus Ankara (MVA) strain of vaccinia, which is replication deficient in mammalian cells (Meyer, et al., 1991. J. Gen. Virol. 72:1031–1038).

In a preferred embodiment, the following method is used to enrich for, and select for those cells infected with the recombinant viruses that express the target epitopes of specific cytotoxic T cells. An adherent monolayer of cells is infected with a recombinant viral library, e.g. a vaccinia recombinant viral library, at m.o.i. less than or equal to 1. It is important that these cells do not themselves express the target epitopes recognized by specific CTLs but that these epitopes are represented in the viral library. In addition, for selection by CTLs, the infected cells must express an appropriate MHC molecule that can associate with and present the target peptide to T cells.

After 12 hours infection with recombinant virus, the monolayer is washed to remove any non-adherent cells. CTLs of defined specificity are added for 30 min. During this time, some of the adherent cells infected with a recombinant particle that leads to expression of the target epitope will interact with a specific CTL and undergo a lytic event. Cells that undergo a lytic event are released from the monolayer and can be harvested in the floating cell population. The above-described protocol is repeated for preferably five or more cycles, to increase the level of enrichment obtained by this procedure.

Screening Cytotoxic Lymphocytes Generated Against Products of Genes Differentially Expressed in Tumor Cells for Activity Against Authentic Tumor Cells The products of genes that are differentially expressed in a tumor are used to generate HLA-restricted CTLs (e.g., by immunization of transgenic animals or in vitro stimulation of human PBL with antigen presenting cells that express the appropriate MHC). The CTLs so generated are assayed for activity against authentic tumor cells in order to identify the differentially expressed gene which encodes the effective target epitope.

In essence, this approach to identify tumor-specific antigens is the reverse of the strategy described in the preceding section. Rather than isolating CTLs generated against authentic tumor cells to screen expression libraries of tumor-specific cDNA, the tumor-specific cDNA or gene products (i.e., the product of genes differentially expressed in tumors) are used to generate CTLs which are then screened using authentic tumor. This strategy is quite advantageously used to identify target epitopes for many human tumor types where it has not been possible to generate tumor-specific CTL directly from patients. This strategy provides an additional advantage in that cryptic tumor antigens can be identified. Rather than only assaying for what is immunogenic on a tumor cell, this embodiment of the invention allows for the evaluation and assessment of tumor cell products that can become immunogenic if the representation of tumor-specific T cells is first augmented by vaccination.

Differentially expressed genes derived from the tumor can be identified using standard techniques well known to those skilled in the art (e.g., see Liang & Pardee, 1992, Science 257:967–971, which is incorporated by reference herein in its entirety). Preferably, the improved differential display methods described in Sections 9.2 and 9.3, infra, may be used to reduce false positives and enhance the efficiency for isolating full length cDNAs corresponding to the identified DNA fragments. Each differentially expressed gene product is potentially immunogenic, and may be represented as a low-abundance or high abundance transcript.

In order to identify the differentially expressed gene products that might be candidates for tumor immunotherapy, it is necessary to have a means of delivering the product for immunization in an environment in which T cell responses to peptides associated with human HLA can be induced. To this end, the differentially expressed cDNA is incorporated into an expression vector, preferably a viral vector (such as the vaccinia vectors described herein) so that quantities of the gene product adequate for immunization are produced. Immunization can be accomplished using the recombinantly expressed gene product formulated in a subunit vaccine (e.g., mixed with a suitable adjuvant that can promote a cell mediated immune response). Preferably a recombinant viral expression vector, such as vaccinia, can be used to immunize (Bennock & Yewdell, 1990, Current Topics In Microbiol. and Immunol. 163:153–178). Most preferably, transgenic mice are employed which express a human class I MHC molecule, so that HLA-restricted murine cytotoxic T cells specific for the gene product can be induced and isolated (Shirai, M., et al., 1995, J. Immunol. 154:2733–42; Wentworth et al., 1996, Eur. J. of Immunol. 26:97–101). Alternatively, human PBL are stimulated in vitro with antigen presenting cells that express homologous HLA.

The significance of HLA compatibility is that T cells recognize peptides that bind to, and are transported to the surface of antigen presenting cells in association with major histocompatibility molecules. T cells of HLA transgenic mice are, therefore, primed to recognize a specific peptide in association with the expressed human HLA and crossreactivity with human tumor cells depends on expression of that same tumor peptide in association with the same HLA molecule.

The CTLs induced by the immunization can be tested for cross reactivity on HLA compatible tumors that express the corresponding mRNA. The CTLs can be assayed for their ability to kill authentic tumor cells in vitro or in vivo. To this end, assays described in other Examples can be used, or other similar assays for determining tumor cell specificity and killing which are well known to those skilled in the art.

Using this approach, target epitopes which are particularly good candidates for tumor immunotherapy in human patients are identified as those which meet the following criteria: (a) the gene is differentially expressed in multiple human tumors; (b) the gene products are immunogenic in association with HLA; and (c) the specific CTLs induced are cross reactive on human tumor cells.

Example 19

Construction of MVA Trimolecular Recombination Vectors

In order to construct a Modified Vaccinia Ankara (MVA) vector suitable for trimolecular recombination, two unique restriction endonuclease sites must be inserted into the MVA tk gene. The complete MVA genome sequence is known (GenBank U94848). A search of this sequence revealed that restriction endonucleases AscI, RsrII, SfiI, and XmaI do not cut the MVA genome. Restriction endonucleases AscI and XmaI have been selected due to the commercial availability of the enzymes, and the size of the recognition sequences, 8 bp and 6 bp for AscI and XmaI respectively. In order to introduce these sites into the MVA tk gene a construct will be made that contains a reporter gene (e.g. indicator gene) (*E. coli* gusA) flanked by XmaI and AscI sites. The Gus gene is available in pCRII.Gus (M. Merchlinsky, D. Eckert, E. Smith, M. Zauderer. 1997 Virology 238: 444–451). This reporter gene (e.g. indicator gene) construct will be cloned into a transfer plasmid containing vaccinia tk DNA flanks and the early/late 7.5 k promoter to control expression of the reporter gene (e.g. indicator gene). The Gus gene will be PCR amplified from this construct using Gus specific primers. Gus sense 5' ATGTTACGTCCTGTAGAAACC 3' (SEQ ID NO:48), and Gus Antisense 5' TCATTGTTTGCCTCCCTGCTG 3' (SEQ ID NO:49). The Gus PCR product will then be PCR amplified with Gus specific primers that have been modified to include NotI and XmaI sites on the sense primer, and AscI and ApaI sites on the antisense primer. The sequence of these primers is: NX-Gus Sense 5' AAAGCGGCCGCCCCGGGATGTTACGTCC 3' (SEQ ID NO:50) AA-Gus antisense 5' AAAGGGCCCGGCGCGCCTCATTGTTTGCC 3' (SEQ ID NO:51).

This PCR product will be digested with NotI and ApaI and cloned into the NotI and ApaI sites of p7.5/tk (M. Merchlinsky, D. Eckert, E. Smith, M. Zauderer. 1997 Virology 238: 444–451). The 7.5 k-XmaI-gusA-AscI construct will be introduced into MVA by conventional homologous recombination in permissive QT35 or BHK cells. Recombinant plaques will be selected by staining with the Gus substrate X-Glu (5-bromo-3 indoyl-b-D-glucuronic acid; Clontech) (M. W. Carroll, B. Moss. 1995 Biotechniques 19: 352–355). MVA-Gus clones, which will also contain the unique XmaI and AscI sites, will be plaque purified to homogeneity. Large scale cultures of MVA-Gus will be amplified on BHK cells, and naked DNA will be isolated from purified virus. After digestion with XmaI and AscI the MVA-Gus DNA can be used for trimolecular recombination in order to construct cDNA expression libraries in MVA.

MVA is unable to complete its life cycle in most mammalian cells. This attenuation can result in a prolonged period of high levels of expression of recombinant cDNAs, but viable MVA cannot be recovered from infected cells. The inability to recover viable MVA from selected cells would prevent the repeated cycles of selection required to isolate functional cDNA recombinants of interest. A solution to this problem is to infect MVA infected cells with a helper virus that can complement the host range defects of MVA. This helper virus can provide the gene product(s) which MVA lacks that are essential for completion of its life cycle. It is unlikely that another host range restricted helper virus, such as fowlpox, would be able to complement the MVA defect(s), as these viruses are also restricted in mammalian cells. Wild type strains of vaccinia virus would be able to complement MVA. In this case however, production of replication competent vaccinia virus would complicate additional cycles of selection and isolation of recombinant MVA clones. A conditionally defective vaccinia virus could be used which could provide the helper function needed to recover viable MVA from mammalian cells under nonpermissive conditions, without the generation of replication competent virus.

The vaccinia D4R open reading frame (orf) encodes a uracil DNA Glycosylase enzyme. This enzyme is essential for vaccinia virus replication, is expressed early after infection (before DNA replication), and disruption of this gene is lethal to vaccinia. It has been demonstrated that a stably transfected mammalian cell line expressing the vaccinia D4R gene was able to complement a D4R deficient vaccinia virus (G. W. Holzer, F. G. Falkner. 1997 J. Virology 71: 4997–5002). A D4R deficient vaccinia virus would be an excellent candidate as a helper virus to complement MVA in mammalian cells.

In order to construct a D4R complementing cell line the D4R orf will be cloned from vaccinia strain v7.5/tk by PCR amplification using primers D4R-Sense 5' AAAGGATCCATAATGAATTCAGTGACTGTATCACACG 3' (SEQ ID NO:52) and D4R Antisense 5' CTTGCGGCCGCTTAATAAATAAACCCTTGAGCCC 3' (SEQ ID NO:53). The sense primer has been modified to include a BamHI site, and the anti-sense primer has been modified to include a NotI site. Following PCR amplification and digestion with BamHI and NotI the D4R orf will be cloned into the BamHI and NotI sites of pIRESHyg (Clontech). This mammalian expression vector contains the strong CMV Immediate Early promoter/Enhancer and the ECMV internal ribosome entry site (IRES). The D4RIRESHyg construct will be transfected into BSC1 cells and transfected clones will be selected with hygromycin. The IRES allows for efficient translation of a polycistronic mRNA that contains the D4Rorf at the 5' end, and the Hygromycin phosphotransferase gene at the 3' end. This results in a high frequency of Hygromycin resistant clones being functional (the clones express D4R). BSC1 cells that express D4R (BSC1.D4R) will be able to complement D4R deficient vaccinia, allowing for generation and propagation of this defective strain.

To construct D4R deficient vaccinia, the D4R orf (position 100732 to 101388 in vaccina genome) and 983 bp (5' end) and 610 bp (3' end) of flanking sequence will be PCR amplified from the vaccinia genome. Primers D4R Flank sense 5' ATTGAGCTCTTAATACTTTTGTCGGG-TAACAGAG 3' (SEQ ID NO:54) and D4R Flank anti sense 5' TTACTC GAGAGTGTCGCAATTTGGATTTT 3' (SEQ ID NO:55) contain a Sac (Sense) and XhoI (Antisense) site for cloning and will amplify position 99749 to 101998 of the vaccinia genome. This PCR product will be cloned into the SacI and XhoI sites of pBluescript II KS (Stratagene), generating pBS.D4R.Flank. The D4R gene contains a unique EcoRI site beginning at nucleotide position 3 of the 657 bp orf, and a unique PstI site beginning at nucleotide position 433 of the orf. Insertion of a Gus expression cassette into the EcoRI and PstI sites of D4R will remove most of the D4R coding sequence. A 7.5 k promoter—Gus expression vector has been constructed (M. Merchlinsky, D. Eckert, E. Smith, M. Zauderer. 1997 Virology 238: 444–451). The 7.5-Gus expression cassette will be isolated from this vector by PCR using primers 7.5 Gus Sense 5' AAAGAATTCCTTTATTGTCATCGGCCAAA (SEQ ID NO:56) and 7.5Gus antisense 5' AATCTGCAGTCAT-TGTTTGCCTCCCTGCTG 3' (SEQ ID NO:57). The 7.5 Gus sense primer contains an EcoRI site and the 7.5 Gus antisense primer contains a PstI site. Following PCR amplification the 7.5Gus molecule will be digested with EcoRI and PstI and inserted into the EcoRI and PstI sites in pBS.D4R.Flank, generating pBS.D4R$^-$/7.5Gus$^+$. D4R$^-$/Gus$^+$ vaccinia can be generated by conventional homologous recombination by transfecting the pBS.D4R$^-$/7.5Gus$^+$ construct into v7.5/tk infected BSC1.D4R cells. D4R$^-$/Gus$^+$ virus can be isolated by plaque purification on BSC1.D4R cells and staining with X-Glu. The D4R– virus can be used to complement and rescue the MVA genome in mammalian cells.

Example 20

Construction and Use of D4R Trimolecular Recombination Vectors

Poxvirus infection can have a dramatic inhibitory effect on host cell protein and RNA synthesis. These effects on host gene expression could, under some conditions, interfere with the selection of specific poxvirus recombinants that have a defined physiological effect on the host cell. Some strains of vaccinia virus that are deficient in an essential early gene have been shown to have greatly reduced inhibitory effects on host cell protein synthesis. Therefore, production of recombinant cDNA libraries in a poxvirus vector that is deficient in an early gene function may be advantageous for selection of certain recombinants that depend on continued active expression of some host genes. Disruption of essential viral genes prevents viral replication. Replication defective strains of vaccinia are rescued by providing the missing function through transcomplementation, such as by an host cell-encoded or helper virus-encoded gene under the control of an inducible promoter.

Infection of a cell population with a poxvirus library constructed in a replication deficient strain should greatly attenuate the effects of infection on host cell signal transduction mechanisms, differentiation pathways, and transcriptional regulation. An additional and important benefit of this strategy is that expression of the essential gene under the control of a inducible promoter can itself be the means of selecting recombinant virus that directly or indirectly lead to activation of that transcriptional regulatory region. Examples include the promoter of a gene activated as a result of crosslinking surface immunoglobulin receptors on early B cell precursors or the promoter of a gene that encodes a marker induced following stem cell differentiation. Additional examples of inducible promoters include cell type-restricted promoters, tissue-restricted promoters, temporally-regulated promoters, spatially-regulated promoters, proliferation-induced promoters, cell-cycle specific promoters, etc., such as those described herein or well-known in the art. If such a promoter drives expression of an essential viral gene, then only those viral recombinants that directly or indirectly activate expression of that transcriptional regulator will replicate and be packaged as infectious particles. This method has the potential to give rise to much lower background then selection methods based on expression of dipA or a CTL target epitope because uninduced cells will contain no replication competent vaccinia virus that might be released through non-specific bystander effects. The selected recombinants can be further expanded in a complementing cell line or in the presence of a complementing helper virus or transfected plasmid.

A number of essential early vaccinia genes have been described. Preferably, a vaccinia strain deficient for the D4R gene could be employed. The vaccinia D4R open reading frame (orf) encodes a uracil DNA glycosylase enzyme. This enzyme is required for viral DNA replication and disruption of this gene is lethal to vaccinia (A. K. Millns, M. S. Carpenter, and A. M. Delange. 1994 Virology 198:504–513). It has been demonstrated that a stably transfected mammalian cell line expressing the vaccinia D4R gene is able to complement a D4R deficient vaccinia virus (G. W. Holzer, F. G. Falkner. 1997 J. Virology 71: 4997–5002). In the absence of D4R complementation, infection with the D4R deficient vaccinia results in greatly reduced inhibition of host cell protein synthesis (Holzer and Falkner). It has also been shown that a foreign gene inserted into the tk gene of D4R deficient vaccinia continues to be expressed at high levels, even in the absence of D4R complementation (M. Himly, M. Pfleiderer, G. Holzer, U. Fischer, E. Hannak, F. G. Falkner, and F. Dorner. 1998 Protein Expression and Purification 14: 317–326). The replication deficient D4R strain is, therefore, well-suited for selection of viral recombinants that depend on continued active expression of some host genes for their physiological effect.

To implement this strategy for selection of specific recombinants from representative cDNA libraries constructed in a D4R deficient vaccinia strain the following cell lines and vectors are required:

1. D4R expressing complementing cell line is required for expansion of D4R deficient viral stocks.
2. The D4R gene must be deleted or inactivated in a viral strain suitable for trimolecular recombination.
3. Plasmid or viral constructs must be generated that express D4R under the control of different inducible promoters, e.g., cell-specific promoters, tissue-specific promoters, proliferation-specific promoters, etc., such as the promoter for expression of type X collagen following induction of chondrocyte differentiation from C3H10T½ progenitor cells. Stable transfectants of these constructs in the relevant cell line are required to rescue specific recombinants. Alternatively, a helper virus expressing the relevant construct can be employed for induction in either cell lines or primary cultures.

Construction of a D4R Complementing Cell Line

A D4R complementing cell line is constructed as follows. First, the D4R orf (position 100732 to 101388 in vaccinia genome) is cloned from vaccinia strain v7.5/tk by PCR amplification using the following primers:

D4R-sense, 5' AAA<u>GAATTCA</u> TAATGAATTC AGT-GACTGTA TCACACG 3' (SEQ ID NO:58);

and D4R-antisense: 5' CTT<u>GGATCCT</u> TAATAAATAA ACCCTTGAGC CC 3' (SEQ ID NO:59).

The sense primer is modified to include an EcoRI site, and the anti-sense primer is modified to include a BamHI site (both underlined). Following standard PCR amplification and digestion with EcoRI and BamHI, the resulting D4R orf is cloned into the EcoRI and BamHI sites of pIRESneo (available from Clontech, Palo Alto, Calif.). This mammalian expression vector contains the strong CMV immediate early promoter/enhancer and the ECMV internal ribosome entry site (IRES). The D4R/IRESneo construct is transfected into BSC1 cells and transfected clones are selected with G418. The IRES allows for efficient translation of a polycistronic mRNA that contains the D4Rorf at the 5' end, and the neomycin phosphotransferase gene at the 3' end. This results in a high frequency of G418 resistant clones being functional (the clones express D4R). Transfected clones are tested by northern blot analysis using the D4R gene as probe in order to identify clones that express high levels of D4R mRNA. BSC1 cells that express D4R (BSC1.D4R) are able to complement D4R deficient vaccinia, allowing for generation and propagation of D4R defective viruses.

Construction of D4R Deficient Vaccinia Vector

A D4R-deficient vaccinia virus, suitable for trimolecular recombination as described in Example 19, supra, is constructed by disruption of the D4R orf (position 100732 to 101388 in vaccinia genome) through the insertion of an *E. coli* GusA expression cassette into a 300-bp deletion, by the following method.

In order to insert the GusA gene, regions flanking the insertion site are amplified from vaccinia virus as follows. The left flanking region is amplified with the following primers:

D4R left flank sense: 5'AAT<u>AAGCTTT</u> GACTCCAGAT ACATATGGA 3' (SEQ ID NO:60); and D4R left flank antisense: 5' AAT<u>CTGCAGC</u> ACCAGT-TCCA TCTTT 3' (SEQ ID NO:61).

These primers amplify a region extending from position 100167 to position 100960 of the vaccinia genome, and have been modified to include a HindIII (Sense) and PstI (Antisense) site for cloning (both underlined). The resulting PCR product is digested with HindIII and PstI, and cloned into the HindIII and PstI sites of pBS (available from Stratagene), generating pBS.D4R.LF. The right flanking region is amplified with the following primers:

D4R right flank sense: 5' AAT<u>GGATCCT</u> CATC-CAGCGG CTA 3' (SEQ ID NO:62); and D4R right flank antisense: 5' AAT<u>GAGCTCT</u> AGTAC-CTACA ACCCGAA 3' (SEQ ID NO:63).

These primers amplify a region extending from position 101271 to position 101975 of the vaccinia genome, and have been modified to include a BamHI (Sense) and SacI (Antisense) site for cloning (both underlined). The resulting PCR product is digested with BamHI and SacI, and cloned into the BamHI and SacI sites of pBS.D4R.LF, creating pBS.D4R.LF/RF.

An expression cassette comprising the GusA coding region operably associated with a poxvirus synthetic early/late (E/L) promoter, is inserted into pBS.D4R.LF/RF by the following method. The E/L promoter-Gus cassette is derived from the pEL/tk-Gus construct described in Merchlinsky, M., et al., Virology 238: 444–451 (1997). The NotI site immediately upstream of the Gus ATG start codon is removed by digestion of pEL/tk-Gus with NotI, followed by a fill in reaction with Klenow fragment and religation to itself, creating pEL/tk-Gus(NotI−). The E/L-Gus expression cassette is isolated from pEL/tk-Gus(NotI−) by standard PCR using the following primers:

EL-Gus sense: 5' AAA<u>GTCGACG</u> GCCAAAAATT GAAATTTT 3' (SEQ ID NO:64); and

EL-Gus antisense: 5' AAT<u>GGATCCT</u> CATTGTTTGC CTCCC 3' (SEQ ID NO:65).

The EL-Gus sense primer contains a SalI site and the EL-Gus antisense primer contains a BamHI site (both underlined). Following PCR amplification the EL-Gus cassette is digested with SalI and BamHI and inserted into the SalI and BamHI sites in pBS.D4R.LF/RF generating pBS.D4R−/ELGus. This transfer plasmid contains an EL-Gus expression cassette flanked on both sides by D4R sequence. There is also a 300 bp deletion engineered into the D4R orf.

D4R−/Gus+ vaccinia viruses suitable for trimolecular recombination are generated by conventional homologous recombination following transfection of the pBS.D4R−/ELGus construct into v7.5/tk-infected BSC1.D4R cells. D4R−/Gus+ virus are isolated by plaque purification on BSC1.D4R cells and staining with X-Glu (M. W. Carroll, B. Moss. 1995. Biotechniques 19: 352–355). This new strain is designated v7.5/tk/Gus/D4R.

DNA purified from v7.5/tk/Gus/D4R is used to construct representative vaccinia cDNA libraries by trimolecular recombination carried out in the BSC1.D4R complementing cell line.

Preparation of Host Cells Expressing D4r Under the Control of Inducible Promoters Host cells which express the D4R gene upon induction of an inducible promoter are prepared as follows. Plasmid constructs are generated that express the vaccinia D4R gene under the control of an inducible promoter. Examples of inducible promoters include, but are not limited to cell-specific promoters, tissue-specific promoters, proliferation-specific promoters, and the promoter for a marker of differentiation, such as type X collagen. The vaccinia D4R orf is amplified by PCR using primers D4R sense and D4R antisense described above. These PCR primers are modified as needed to include desirable restriction endonuclease sites. The D4R orf is then cloned in a suitable eukaryotic expression vector (which allows for the selection of stably transformed cells) in operable association of any appropriate promoter such as the type X collagen promoter employing methods known to those skilled in the art.

The construct is then stably transfected into a cell line suitable for selection or screening, for example, C3H110T½ progenitor cells. The resulting host cells are used in the selection and screening methods described throughout the application, using libraries prepared in v7.5/tk/Gus/D4R. Differentiation results in the induction of expression of the D4R gene product. Expression of D4R complements the defect in the v7.5/tk/Gus/D4R genomes in which the libraries are produced, allowing the production of infectious virus particles.

Example 21

Method to Identify Upstream Genes

Once a polynucleotide of interest is identified, the methods of the present invention may be used to identify other polynucleotides (e.g., genes) that regulate expression of that polynucleotide.

The method is similar to those previously described herein. This example uses a marker of breast cancer transformation, e.g., C35, as the polynucleotide being regulated. However, any polynucleotide for which an upstream regulator is desired may be used in this method.

The transcriptional regulatory region of, for example, C35 is cloned into a DNA construct in which it can drive expression of a selective gene product such as an epitope, suicide gene, or a gene that complements an otherwise replication defective viral vector. This construct is transferred into and expressed in host cells that do not normally express C35, e.g. normal non-tumorigenic breast epithelial cells. The host cells are then infected with a viral library recombinant for cDNA derived from a cell population that is undergoing or has undergone tumor transformation. Specific recombinants of any cDNA that induces expression of C35 are selected through activation of the selective construct. Expression of the selected cDNAs can then be characterized in a diverse panel of normal and tumor tissues to identify those genes that may serve as unique target molecules for cancer therapy (e.g., not expressed in adult normal tissues). Such therapy could include induction of immune responses or administration of therapeutic antibodies specific for products of the newly identified cDNAs.

For example, genes could be identified that regulate a polynucleotide of interest involved in tumor transformation such as a marker of tumor transformation. Upstream regulators may be, in some cases, even more useful as a therapeutic targets than the polynucleotides/genes they regulate. For example, genes that regulate expression of a polynucleotide encoding a marker of tumor transformation may be especially useful because they have particular properties such as surface membrane expression or are involved in particular pathways such as signal transduction that are therapeutic modes different from the initial polynucleotide of interest. In addition, such upstream regulators may be relevant to tumor transformation in a wider range of tissues than the initial polynucleotide of interest. For example, the same upstream genes that regulate overexpression of C35 in human breast and bladder cancer may also regulate overexpression of different tumor markers in lung and/or prostate cancer. Modes of therapy that target this upstream regulator (in contrast to targeting C35) would be useful in not only breast and bladder cancer but also in lung or prostate cancer.

Using this method, upstream regulators of any polynucleotide—including those isolated by methods other than methods of the invention—for which the promoter region has been identified can be isolated or identified.

Example 22

Attenuation of Poxvirus Mediated Host Shut-off by Reversible Inhibitor of DNA Synthesis As discussed infra, attenuated or defective virus is sometimes desired to reduce cytopathic effects. Cytopathic effects during virus infection might interfere with selection and identification of target polynucleotides that regulate specific gene expression in the host cell. Such effects can be attenuated with a reversible inhibitor of DNA synthesis such as hydroxyurea (HU) (Pogo, B. G. and S. Dales, Biogenesis of vaccinia: separation of early stages from maturation by means of hydroxyurea. Virology, 1971.43 (1):144–51). HU inhibits both cell and viral DNA synthesis by depriving replication complexes of deoxyribonucleotide precursors (Hendricks, S. P. and C. K. Mathews, Differential effects of hydroxyurea upon deoxyribonucleoside triphosphate pools, analyzed with vaccinia virus ribonucleotide reductase. J Biol Chem, 1998. 273(45):29519–23). Inhibition of viral DNA replication blocks late viral RNA transcription while allowing transcription and translation of genes under the control of early vaccinia promoters (Nagaya, A., B. G. Pogo, and S. Dales, Biogenesis of vaccinia: separation of early stages from maturation by means of rifampicin. Virology, 1970. 40(4):1039–51). Thus, treatment with reversible inhibitor of DNA synthesis such as HU allows the detection of effects of target polynucleotides (under the control, for example, of an early viral promoter) on host gene expression. Following appropriate incubation, HU inhibition can be reversed by washing the host cells so that the viral replication cycle continues and infectious recombinants can be recovered (Pogo, B. G. and S. Dales, Biogenesis of vaccinia: separation of early stages from maturation by means of hydroxyurea. Virology, 1971. 43(1):144–51).

The results in FIG. 21 demonstrate that induction of type X collagen synthesis, a marker of chondrocyte differentiation, in C3H10T½ progenitor cells treated with BMP-2 (Bone Morphogenetic Protein-2) is blocked by vaccinia infection but that its synthesis can be rescued by HU mediated inhibition of viral DNA synthesis. When HU is removed from cultures by washing with fresh medium, viral DNA synthesis and assembly of infectious particles proceeds rapidly so that infectious viral particles can be isolated as soon as 2 hrs post-wash. C3H10T½ cells were infected with WR vaccinia virus at MOI=1 and 1 hour later either medium or 400 ng/ml of BMP-2 in the presence or absence of 2 mM HU was added. After a further 21 hour incubation at 37° C., HU was removed by washing with fresh medium. The infectious cycle was allowed to continue for another 2 hours to allow for initiation of viral DNA replication and assembly of infectious particles. At 24 hours RNA was extracted from cells maintained under the 4 different culture conditions. Northern analysis was carried out using a type X collagen specific probe. The uninduced C3H10T½ cells have a mesenchymal progenitor cell phenotype and as such do not express type X collagen (first lane from left). Addition of BMP-2 to normal, uninfected C3H10T½ cells induces differentiation into mature chondrocytes and expression of type X collagen (compare first and second lanes from left), whereas addition of BMP-2 to vaccinia infected C3H10T½ cells fails to induce synthesis of type X collagen (third lane from left). In the presence of 2 mM HU, BMP-2 induces type X collagen synthesis even in vaccinia virus infected C3H10T½ cells (fourth lane from left).

This strategy for attenuating viral cytopathic effects is applicable to other cell types and to selection of target polynucleotides that regulate expression of other host genes.

Example 23

Expression Profiling

Many of the screening and/or selection methods described herein depend on expression of host cell genes or host cell transcriptional regulatory regions, which are directly or indirectly modified by target polynucleotides. It is important to note that many preferred embodiments of the present invention host cells are infected with a eukaryotic virus vector, preferably a poxvirus vector, and even more preferably a vaccinia virus vector. It is well understood by those of ordinary skill in the art that some host cell protein synthesis is rapidly shut down upon poxvirus infection in some cell lines, even in the absence of viral gene expression. This problem is not intractable, however, because in certain cell lines, inhibition of host protein synthesis remains incomplete until after viral DNA replication. See Moss, B., "Poxviridae and their Replication" IN Virology, 2d Edition, B. N. Fields, D. M. Knipe et al., Eds., Raven Press, p. 2096 (1990). It may be desirable to rapidly screen a variety of host cells for their ability to express gene products which are upregulated by a target polynucleotides upon infection by a virus vector, preferably a poxvirus vector, and even more preferably a vaccinia virus vector; and to screen desired host cells for differential expression of cellular genes upon virus infection. Expression profiling methods may be used to perform such screening. For example, expression profiling using microarrays is described in Duggan, D. J., et al., Nature Genet. 21(1 Suppl):10–14 (1999), which is incorporated herein by reference in its entirety.

According to this method, expression profiling is used to compare host cell gene expression patterns in uninfected host cells and host cells infected with a eukaryotic virus expression vector, preferably a poxvirus vector, even more preferably a vaccinia virus vector, where the particular eukaryotic virus vector is the vector used to construct the library of the present invention. In this way, suitable host cells which continue to undergo expression of the necessary inducible proteins upon infection with a given virus, can be identified.

Expression profiling is also used to compare host cell gene expression patterns in a given host cell, for example, comparing expression patterns when the host cell is infected with a fully infectious virus vector, and when the host cell is infected with a corresponding attenuated virus vector. Expression profiling in microarrays allows large-scale screening of host cells infected with a variety of attenuated viruses, where the attenuation is achieved in a variety of different ways, as described above.

Using this method, expression profiling in microarrays may be used to identify suitable host cells, suitable transcription regulatory regions, and/or suitable attenuated viruses in any of the selection/screening methods described herein.

Example 24

Additional Target Polynucleotides

As discussed above, in some embodiments, a first plurality of cells is screened. That is, the cells into which the library is introduced are screened for an altered phenotype. Thus, in this embodiment, the effect of the insert polynucleotides is seen in the same cells in which it is made; i.e. an autocrine effect. Also discussed above, in some embodiments, the library is introduced into a first plurality of cells, and the effect of the insert polynucleotides is screened in a second or third plurality of cells, different from the first plurality of cells, i.e. generally a different cell type. That is, the effect of the insert polynucleotides is due to an extracellular effect on a second cell; i.e. an endocrine or paracrine effect. This is done using standard techniques. The first plurality of cells may be grown in or on one media, and the media is allowed to touch a second plurality of cells, and the effect measured. Alternatively, there may be direct contact between the cells. Thus, "contacting" is functional contact, and includes both direct and indirect. In this embodiment, the first plurality of cells may or may not be screened.

If necessary, the cells are treated to conditions suitable for the expression of the insert polynucleotides (for example, when inducible promoters are used), to produce the insert polynucleotides.

Thus, the methods of the present invention comprise introducing a library of insert polynucleotides into a plurality of cells, a cellular library. Each of the insert polynucleotides may comprise a different, generally randomized, nucleotide sequence, or may be a portion of a cDNA, etc, as described above. The plurality of cells is then screened, as has been described above, for a cell exhibiting an altered phenotype. The altered phenotype is due to the presence of a target polynucleotide.

By "altered phenotype" or "changed physiology" or other grammatical equivalents herein is meant that the phenotype of the cell is altered in some way, preferably in some detectable and/or measurable way. As will be appreciated in the art, a strength of the present invention is the wide variety of cell types and potential phenotypic changes which may be tested using the present methods. Accordingly, as described above, any phenotypic change which may be observed, detected, or measured may be the basis of the screening methods herein. Suitable phenotypic changes include, but are not limited to: gross physical changes such as changes in cell morphology, cell growth, cell viability, adhesion to substrates or other cells, and cellular density; changes in the expression of one or more RNAs, proteins, lipids, hormones, cytokines, or other molecules; changes in the equilibrium state (i.e. half-life) or one or more RNAs, proteins, lipids, hormones, cytokines, or other molecules; changes in the localization of one or more RNAs, proteins, lipids, hormones, cytokines, or other molecules; changes in the bioactivity or specific activity of one or more RNAs, proteins, lipids, hormones, cytokines, receptors, or other molecules; changes in the secretion of ions, cytokines, hormones, growth factors, or other molecules; alterations in cellular membrane potentials, polarization, integrity or transport; changes in infectivity, susceptibility, latency, adhesion, and uptake of viruses and bacterial pathogens; etc. By "capable of altering the phenotype" herein is meant that the target polynucleotide can change the phenotype of the cell in some detectable and/or measurable way.

The altered phenotype may be detected in a wide variety of ways, as is described above and below, and will generally depend and correspond to the phenotype that is being changed. Generally, the changed phenotype is detected using, for example: microscopic analysis of cell morphology; standard cell viability assays, including both increased cell death and increased cell viability, for example, cells that are now resistant to cell death via virus, bacteria, or bacterial or synthetic toxins; standard labeling assays such as fluorometric indicator assays for the presence or level of a particular cell or molecule, including FACS or other dye staining techniques; biochemical detection of the expression of target compounds after killing the cells; etc. In some cases, as is more fully described herein, the altered phenotype is detected in the cell in which the randomized nucleic acid was introduced; in other embodiments, the altered phenotype is detected in a second cell which is responding to some molecular signal from the first cell.

An altered phenotype of a cell indicates the presence of a target polynucleotide. By "transdominant" herein is meant that the target polynucleotide indirectly causes the altered phenotype by acting on a second molecule, which leads to an altered phenotype. That is, a transdominant expression product has an effect that is not in cis, i.e., a trans event as defined in genetic terms or biochemical terms. A transdominant effect is a distinguishable effect by a molecular entity (i.e., the encoded peptide or RNA) upon some separate and distinguishable molecule; that is, not an effect upon the encoded entity itself. As such, transdominant effects include many well-known effects by pharmacologic agents upon molecules or pathways in cells or physiologic systems; for instance, the β-lactam antibiotics have a transdominant effect upon peptidoglycan synthesis in bacterial cells by binding to penicillin binding proteins and disrupting their functions. An exemplary transdominant effect by a peptide encoded by a target polynucleotide is the ability to inhibit NF-KB signaling by binding to IKB-a at a region critical for its function, such that in the presence of sufficient amounts of the encoded peptide (or encoded RNA), the signaling pathways that normally lead to the activation of NF-KB through phosphorylation and/or degradation of IKB-α are inhibited from acting at IKB-a because of the binding of the encoded peptide or encoded RNA. In another instance, signaling pathways that are normally activated to secrete IgE are inhibited in the presence of encoded peptide. Or, signaling pathways in adipose tissue cells, normally quiescent, are activated to metabolize fat. Or, in the presence of a peptide, intracellular mechanisms for the replication of certain viruses, such as HIV-I, or Herpes viridae family members, or Respiratory Syncytial Virus, for example, are inhibited.

A transdominant effect upon a protein or molecular pathway is clearly distinguishable from randomization, change, or mutation of a sequence within a protein or molecule of known or unknown function to enhance or diminish a biochemical ability that protein or molecule already manifests. For instance, a protein that enzymatically cleaves β-lactam antibiotics, a β-lactamase, could be enhanced or diminished in its activity by mutating sequences internal to its structure that enhance or diminish the ability of this enzyme to act upon and cleave β-lactam antibiotics. This would be called a cis mutation to the protein. The effect of this protein upon β-lactam antibiotics is an activity the protein already manifests, to a distinguishable degree. Similarly, a mutation in the leader sequence that enhanced the export of this protein to the extracellular spaces wherein it might encounter β-lactam molecules more readily, or a mutation within the sequence that enhance the stability of the protein, would be termed cis mutations in the protein. For comparison, a transdominant effector of this protein would include an agent encoded by a target polynucleotide, independent of the β-lactamase, that bound to the β-lactamase in such a way that it enhanced or diminished the function of the β-lactamase by virtue of its binding to β-lactamase.

In general, cis-effects are effects within molecules wherein elements that are interacting are covalently joined to each other although these elements might individually manifest themselves as separable domains. Trans-effects (transdominant in that under some cellular conditions the desired effect is manifested) are those effects between distinct molecular entities, such that molecular entity A, not covalently linked to molecular entity B, binds to or otherwise has an effect upon the activities of entity B. As such, most known pharmacological agents are transdominant effectors.

In a preferred embodiment, once a cell with an altered phenotype is detected, the cell is isolated from the plurality which do not have altered phenotype. This may be done in any number of ways, as is known in the art, and will in some instances depend on the assay or screen. Suitable isolation techniques include, but are not limited to, FACS, lysis selection using complement or CTLs cell cloning, scanning by Fluorimager, expression of a "survival" protein, expression of a suicide gene, induced expression of a cell surface protein or other molecule that can be rendered fluorescent or taggable for physical isolation; expression of an enzyme that changes a non-fluorescent molecule to a fluorescent one; overgrowth against a background of no or slow growth; death of cells and isolation of DNA or other cell vitality indicator dyes, etc., including those described above.

In a preferred embodiment, the target polynucleotide is isolated from the positive cell, as described above.

In a preferred embodiment, either the target polynucleotide or the molecule it encodes is used to identify interacting molecules, i.e. the molecules with which the encoded target molecule interacts. As will be appreciated by those in the art, there may be primary interacting molecules, to which the encoded target molecule binds or acts upon directly, and there may be secondary interacting molecules, which are part of the signalling pathway affected by the encoded target molecule; these might be termed "validated targets".

In a preferred embodiment, the target polynucleotide is used to pull out interacting molecules. For example, as outlined herein, if the target molecules are proteins, the use of epitope tags or purification sequences can allow the purification of primary interacting molecules via biochemical means (co-immunoprecipitation, affinity columns, etc.). Alternatively, the encoded peptide, when expressed in bacteria and purified, can be used as a probe against a cDNA expression library made from mRNA of the relevant cell type. Or, encoded peptides can be used as "bait" in either yeast or mammalian two or three hybrid systems. Such interaction cloning approaches have been very useful to isolate DNA-binding proteins and other interacting protein components. The peptide(s) can be combined with other pharmacologic activators to study the epistatic relationships of signal transduction pathways in question. It is also possible to synthetically prepare labeled peptide regulator polypeptide and use it to screen a cDNA library expressed in bacteriophage for those cDNAs which bind the peptide. Furthermore, it is also possible that one could use cDNA cloning via viral libraries to "complement" the effect induced by the peptide. In such a strategy, the peptide would be required to be stochiometrically titrating away some important factor for a specific signaling pathway. If this molecule or activity is replenished by over-expression of a cDNA from within a cDNA library, then one can clone the target. Similarly, cDNAs cloned by any of the above library systems can be reintroduced to mammalian cells in this manner to confirm that they act to complement function in the system the peptide acts upon. Other methods described above may be used to isolate molecules which regulate or interact with peptides and RNA encoded by target polynucleotides Once primary interacting molecules have been identified, secondary interacting molecules may be identified in the same manner, using the primary interacting as the "bait". In this manner, signalling pathways may be elucidated. Similarly, regulator molecules specific for secondary interacting molecules may also be discovered, to allow a number of regulator molecules to act on a single pathway, for example for combination therapies.

The screening methods of the present invention may be useful to screen a large number of cell types under a wide variety of conditions. Generally, the host cells are cells that are involved in disease states, and they are tested or screened under conditions that normally result in undesirable consequences on the cells. When a suitable target polynucleotide is found, the undesirable effect may be reduced or eliminated. Alternatively, normally desirable consequences may be reduced or eliminated, with an eye towards elucidating the cellular mechanisms associated with the disease state or signalling pathway.

In a preferred embodiment, the present methods are useful in cancer applications. The ability to rapidly and specifically kill tumor cells is a cornerstone of cancer chemotherapy. In general, using the methods of the present invention, libraries can be introduced into any tumor cell (primary or cultured), and target polynucleotides identified which by themselves induce apoptosis, cell death, loss of cell division or decreased cell growth. This may be done de novo, or by biased randomization toward known peptide agents, such as angiostatin, which inhibits blood vessel wall growth. Alternatively, the methods of the present invention can be combined with other cancer therapeutics (e.g. drugs or radiation) to sensitize the cells and thus induce rapid and specific apoptosis, cell death, loss of cell division or decreased cell growth after exposure to a secondary agent. Similarly, the present methods may be used in conjunction with known cancer therapeutics to screen for agonists to make the therapeutic more effective or less toxic. This is particularly preferred when the chemotherapeutic is very expensive to produce such as taxol.

Known oncogenes such as v-Abl, v-Src, v-Ras, and others, induce a transformed phenotype leading to abnormal cell growth when transfected into certain cells. This is also a major problem with micro-metastases. Thus, in a preferred embodiment, non-transformed cells can be transfected with these oncogenes, and then libraries introduced into these cells, to select for target polynucleotides which reverse or correct the transformed state. One of the signal features of oncogene transformation of cells is the loss of contact inhibition and the ability to grow in soft-agar. When transforming viruses are constructed containing v-Abl, v-Src, or v-Ras in viral vectors, infected into target 3T3 cells, and subjected to puromycin selection, all of the 3T3 cells hypertransform and detach from the plate. The cells may be removed by washing with fresh medium. This can serve as the basis of a screen, since cells which express a target polynucleotides will remain attached to the plate and form colonies.

Similarly, the growth and/or spread of certain tumor types is enhanced by stimulatory responses from growth factors and cytokines (PDGF, EGF, Heregulin, and others) which bind to receptors on the surfaces of specific tumors. In a preferred embodiment, the methods of the invention are used to inhibit or stop tumor growth and/or spread, by finding target polynucleotides capable of blocking the ability of the growth factor or cytokine to stimulate the tumor cell. The introduction of libraries into specific tumor cells with the addition of the growth factor or cytokine, followed by selection of target polynucleotides which block the binding, signaling, phenotypic and/or functional responses of these tumor cells to the growth factor or cytokine in question.

Similarly, the spread of cancer cells (invasion and metastasis) is a significant problem limiting the success of cancer therapies. The ability to inhibit the invasion and/or migration of specific tumor cells would be a significant advance in the therapy of cancer. Tumor cells known to have a high metastatic potential (for example, melanoma, lung cell carcinoma, breast and ovarian carcinoma) can have libraries introduced into them, and target polynucleotides selected which in a migration or invasion assay, inhibit the migration and/or invasion of specific tumor cells. Particular applications for inhibition of the metastatic phenotype, which could allow a more specific inhibition of metastasis, include the metastasis suppressor gene NM23, which codes for adinucleoside diphosphate kinase. Thus intracellular peptide activators of this gene could block metastasis, and a screen for its upregulation (by fusing it to a reporter gene (e.g. indicator gene)) would be of interest. Many oncogenes also enhance metastasis. Peptides which inactivate or counteract mutated RAS oncogenes, v-MOS, v-RAF, A-RAF, v-SRC, v-FES, and v-FMS would also act as anti-metastatics. Target polynucleotides which block the release of combinations of proteases required for invasion, such as the matrix metalloproteases and urokinase, could also be effective antimetastatics.

In a preferred embodiment, the libraries of the present invention are introduced into tumor cells known to have inactivated tumor suppressor genes, and successful reversal by either reactivation or compensation of the knockout would be screened by restoration of the normal phenotype. A major example is the reversal of p53-inactivating mutations, which are present in 50% or more of all cancers. Since p53's actions are complex and involve its action as a transcription factor, there are probably numerous potential ways a target polynucleotides could reverse the mutation. One example would be upregulation of the immediately downstream cyclin-dependent kinase p21CIP1/WAF1. To be useful such reversal would have to work for many of the different known p53 mutations. This is currently being approached by gene therapy; one or more small molecules which do this might be preferable.

Another example involves screening of target polynucleotides which restore the constitutive function of the brca-1 or brca-2 genes, and other tumor suppressor genes important in breast cancer such as the adenomatous polyposis *coli* gene (APC) and the *Drosophila* discs-large gene (Dlg), which are components of cell—cell junctions. Mutations of brca-1 are important in hereditary ovarian and breast cancers, and constitute an additional application of the present invention.

In a preferred embodiment, the methods of the present invention are used to create novel cell lines from cancers from patients. A target polynucleotide which inhibits the final common pathway of programmed cell death should allow for short- and possibly long-term cell lines to be established. Conditions of in vitro culture and infection of human leukemia cells will be established. There is a real need for methods which allow the maintenance of certain tumor cells in culture long enough to allow for physiological and pharmacological studies. Currently, some human cell lines have been established by the use of transforming agents such as Epstein-Barr virus that considerably alters the existing physiology of the cell. On occasion, cells will grow on their own in culture but this is a random event. Programmed cell death (apoptosis) occurs via complex signaling pathways within cells that ultimately activate a final common pathway producing characteristic changes in the cell leading to a non-inflammatory destruction of the cell. It is well known that tumor cells have a high apoptotic index, or propensity to enter apoptosis in vivo. When cells are placed in culture, the in vivo stimuli for malignant cell growth are removed and cells readily undergo apoptosis. The objective would be to develop the technology to establish cell lines from any number of primary tumor cells, for example primary human leukemia cells, in a reproducible manner without altering the native configuration of the signaling pathways in these cells. By introducing target polynucleotides which inhibit apoptosis, increased cell survival in vitro, and hence the opportunity to study signalling transduction pathways in primary human tumor cells, is accomplished. In addition, these methods may be used for culturing primary cells, i.e. non-tumor cells.

In a preferred embodiment, the present methods are useful in cardiovascular applications. In a preferred embodiment, cardiomyocytes may be screened for the prevention of cell damage or death in the presence of normally injurious conditions, including, but not limited to, the presence of toxic drugs (particularly chemotherapeutic drugs), for example, to prevent heart failure following treatment with adriamycin; anoxia, for example in the setting of coronary artery occlusion; and autoimmune cellular damage by attack from activated lymphoid cells (for example as seen in post viral myocarditis and lupus). Insert polynucleotides are introduced into cardiomyocytes, the cells are subjected to the insult, and target polynucleotides are selected that prevent any or all of: apoptosis; membrane depolarization (i.e. decrease arrythmogenic potential of insult); cell swelling; or leakage of specific intracellular ions, second messengers and activating molecules (for example, arachidonic acid and/or lysophosphatidic acid).

In a preferred embodiment, the present methods are used to screen for diminished arrhythmia potential in cardiomyocytes. The screens comprise the introduction of the insert polynucleotides encoding candidate target polynucleotides, followed by the application of arrythmogenic insults, with screening for target polynucleotides that block specific depolarization of cell membrane. This may be detected using patch clamps, or via fluorescence techniques). Similarly, channel activity (for example, potassium and chloride channels) in cardiomyocytes could be regulated using the present methods in order to enhance contractility and prevent or diminish arrhythmias.

In a preferred embodiment, the present methods are used to screen for enhanced contractile properties of cardiomyocytes and diminish heart failure potential. The introduction of the libraries of the invention followed by measuring the rate of change of myosin polymerization/depolymerization using fluorescent techniques can be done. Target polynucleotides which increase the rate of change of this phenomenon can result in a greater contractile response of the entire myocardium, similar to the effect seen with digitalis.

In a preferred embodiment, the present methods are useful to identify target polynucleotides that will regulate the intracellular and sarcolemmal calcium cycling in cardiomyocytes in order to prevent arrhythmias. Target polynucleotides are selected that regulate sodium-calcium exchange, sodium proton pump function, and regulation of calcium-ATPase activity.

In a preferred embodiment, the present methods are useful to identify molecules that diminish embolic phenomena in arteries and arterioles leading to strokes (and other occlusive events leading to kidney failure and limb ischemia) and angina precipitating a myocardial infarct are selected. For example, target polynucleotides which will diminish the adhesion of platelets and leukocytes, and thus diminish the occlusion events. Adhesion in this setting can be inhibited by the libraries of the invention being inserted into endothelial cells (quiescent cells, or activated by cytokines, i.e. IL-1, and growth factors, i.e. PDGF/EGF) and then screening for target polynucleotides that either: 1) downregulate adhesion molecule expression on the surface of the endothelial cells (binding assay); 2) block adhesion molecule activation on the surface of these cells (signaling assay); or 3) release in an autocrine manner peptides that block receptor binding to the cognate receptor on the adhering cell.

Embolic phenomena can also be addressed by activating proteolytic enzymes on the cell surfaces of endothelial cells, and thus releasing active enzyme which can digest blood clots. Thus, delivery of the libraries of the invention to endothelial cells is done, followed by standard fluorogenic assays, which will allow monitoring of proteolytic activity on the cell surface towards a known substrate. Target polynucleotides can then be selected which activate specific enzymes towards specific substrates.

In a preferred embodiment, arterial inflammation in the setting of vasculitis and post-infarction can be regulated by decreasing the chemotactic responses of leukocytes and mononuclear leukocytes. This can be accomplished by blocking chemotactic receptors and their responding pathways on these cells. Libraries can be inserted into these cells, and the chemotactic response to diverse chemokines (for example, to the IL-8 family of chemokines, RANTES) is inhibited in cell migration assays.

In a preferred embodiment, arterial restenosis following coronary angioplasty can be controlled by regulating the proliferation of vascular intimal cells and capillary and/or arterial endothelial cells. Libraries can be inserted into these cell types and proliferation in response to specific stimuli is monitored. One application may be target polynucleotides which block the expression or function of c-myc and other oncogenes in smooth muscle cells to stop their proliferation. A second application may involve the expression of libraries in vascular smooth muscle cells to selectively induce their apoptosis. Application of therapeutics derived from these target polynucleotides require targeted drug delivery; this is available with stents, hydrogel coatings, and infusion-based catheter systems. Target polynucleotides which downregulate endothelin-1A receptors or which block the release of the potent vasoconstrictor and vascular smooth muscle cell mitogen endothelin-1 may also be candidates for therapeutics. Target polynucleotides can be isolated from these libraries which inhibit growth of these cells, or which prevent the adhesion of other cells in the circulation known to release autocrine growth factors, such as platelets (PDGF) and mononuclear leukocytes.

The control of capillary and blood vessel growth is an important goal in order to promote increased blood flow to ischemic areas (growth), or to cut-off the blood supply (angiogenesis inhibition) of tumors. Libraries can be inserted into capillary endothelial cells and their growth monitored. Stimuli such as low oxygen tension and varying degrees of angiogenic factors can regulate the responses, and target polynucleotides isolated that produce the appropriate phenotype. Screening for antagonism of vascular endothelial cell growth factor, important in angiogenesis, would also be useful.

In a preferred embodiment, the present methods are useful in screening for decreases in atherosclerosis producing mechanisms to find target polynucleotides that regulate LDL and HDL metabolism. Libraries can be inserted into the appropriate cells (including hepatocytes, mononuclear leukocytes, endothelial cells) and target polynucleotides selected which lead to a decreased release of LDL or diminished synthesis of LDL, or conversely to an increased release of HDL or enhanced synthesis of HDL. Target polynucleotides can also be isolated from libraries which decrease the production of oxidized LDL, which has been implicated in atherosclerosis and isolated from atherosclerotic lesions. This could occur by decreasing its expression, activating reducing systems or enzymes, or blocking the activity or production of enzymes implicated in production of oxidized LDL, such as 15-lipoxygenase in macrophages.

In a preferred embodiment, the present methods are used in screens to regulate obesity via the control of food intake mechanisms or diminishing the responses of receptor signaling pathways that regulate metabolism. Target polynucleotides that regulate or inhibit the responses of neuropeptide Y (NPY), cholecystokinin and galanin receptors, are particularly desirable. Libraries can be inserted into cells that have these receptors cloned into them, and inhibitory target polynucleotides selected that are secreted in an autocrine manner that block the signaling responses to galanin and NPY. In a similar manner, target polynucleotides can be found that regulate the leptin receptor.

In a preferred embodiment, the present methods are useful in neurobiology applications. Libraries may be used for screening for anti-apoptotics for preservation of neuronal function and prevention of neuronal death. Initial screens would be done in cell culture. One application would include prevention of neuronal death, by apoptosis, in cerebral ischemia resulting from stroke. Apoptosis is known to be blocked by neuronal apoptosis inhibitory protein (NAIP); screens for its upregulation, or effecting any coupled step could yield peptides which selectively block neuronal apoptosis. Other applications include neurodegenerative diseases such as Alzheimer's disease and Huntington's disease.

In a preferred embodiment, the present methods are useful in bone biology applications. Osteoclasts are known to play a key role in bone remodeling by breaking down "old" bone, so that osteoblasts can lay down "new" bone. In osteoporosis one has an imbalance of this process. Osteoclast overactivity can be regulated by inserting libraries into these cells, and then looking for target polynucleotides that produce: 1) a diminished processing of collagen by these cells; 2) decreased pit formation on bone chips; and 3) decreased release of calcium from bone fragments.

The present methods may also be used to screen for agonists of bone morphogenic proteins, hormone mimetics to stimulate, regulate, or enhance new bone formation (in a manner similar to parathyroid hormone and calcitonin, for example). These have use in osteoporosis, for poorly healing fractures, and to accelerate the rate of healing of new fractures. Furthermore, cell lines of connective tissue origin can be treated with candidate libraries and screened for their growth, proliferation, collagen stimulating activity, and/or proline incorporating ability on the target osteoblasts. Alternatively, libraries can be expressed directly in osteoblasts or chondrocytes and screened for increased production of collagen or bone.

In a preferred embodiment, the present methods are useful in skin biology applications. Keratinocyte responses to a variety of stimuli may result in psoriasis, a proliferative change in these cells. Libraries can be inserted into cells removed from active psoriatic plaques, and target polynucleotides isolated which decrease the rate of growth of these cells.

In a preferred embodiment, the present methods are useful in the regulation or inhibition of keloid formation (i.e. excessive scarring). Libraries are inserted into skin connective tissue cells isolated from individuals with this condition, and target polynucleotides are isolated that decrease proliferation, collagen formation, or proline incorporation.

Results from this work can be extended to treat the excessive scarring that also occurs in burn patients. If a common peptide motif is found in the context of the keloid work, then it can be used widely in a topical manner to diminish scarring post burn.

Similarly, wound healing for diabetic ulcers and other chronic "failure to heal" conditions in the skin and extremities can be regulated by providing additional growth signals to cells which populate the skin and dermal layers. Growth factor mimetics may in fact be very useful for this condition. Libraries can be inserted into skin connective tissue cells, and target polynucleotides isolated which promote the growth of these cells under "harsh" conditions, such as low oxygen tension, low pH, and the presence of inflammatory mediators.

Cosmeceutical applications of the present invention include the control of melanin production in skin melanocytes. A naturally occurring peptide, arbutin, is a tyrosine hydroxylase inhibitor, a key enzyme in the synthesis of melanin. Libraries can be inserted into melanocytes and known stimuli that increase the synthesis of melanin is applied to the cells. Target polynucleotides can be isolated that inhibit the synthesis of melanin under these conditions.

In a preferred embodiment, the present methods are useful in endocrinology applications. The library technology can be applied broadly to any endocrine, growth factor, cytokine or chemokine network which involves a signaling peptide or protein that acts in either an endocrine, paracrine or autocrine manner that binds or dimerizes a receptor and activates a signaling cascade that results in a known phenotypic or functional outcome. The methods are applied so as to isolate a peptide which either mimics the desired hormone (i.e., insulin, leptin, calcitonin, PDGF, EGF, EPO, GMCSF, IL1–17, mimetics) or inhibits its action by either blocking the release of the hormone, blocking its binding to a specific receptor or carrier protein (for example, CRF binding protein), or inhibiting the intracellular responses of the specific cells to that hormone. Selection of target polynucleotides which increase the expression or release of hormones from the cells which normally produce them could have broad applications to conditions of hormonal deficiency.

In a preferred embodiment, the present methods are useful in infectious disease applications. Viral latency (herpes viruses such as CMV, EBV, HBV, and other viruses such as HIV) and their reactivation are a significant problem, particularly in immunosuppressed patients (patients with AIDS and transplant patients). The ability to block the reactivation and spread of these viruses is an important goal. Cell lines known to harbor or be susceptible to latent viral infection can be infected with the specific virus, and then stimuli applied to these cells which have been shown to lead to reactivation and viral replication. This can be followed by measuring viral titers in the medium and scoring cells for phenotypic changes. Libraries can then be inserted into these cells under the above conditions, and target polynucleotides are isolated which block or diminish the growth and/or release of the virus. As with chemotherapeutics, these experiments can also be done with drugs which are only partially effective towards this outcome, and target polynucleotides isolated which enhance the virucidal effect of these drugs.

One example of many is the ability to block HIV-1 infection. HIV-1 requires CD4 and a co-receptor which can be one of several seven transmembrane G-protein coupled receptors. In the case of the infection of macrophages, CCR-5 is the required co-receptor, and there is strong evidence that a block on CCR-5 will result in resistance to HIV-1 infection. There are two lines of evidence for this statement. First, it is known that the natural ligands for CCR-5, the CC chemokines RANTES, MIP1a and MIP1b are responsible for CD8+ mediated resistance to HIV. Second, individuals homozygous for a mutant allele of CCR-5 are completely resistant to HIV infection. Thus, an inhibitor of the CCR-5/HIV interaction would be of enormous interest to both biologists and clinicians. One infects a cell line that expresses CCR-5 with viral vectors containing library. Using an antibody to CCR-5 one can use FACS to sort desired cells based on the binding of this antibody to the receptor. All cells which do not bind the antibody will be assumed contain target polynucleotides which inhibit expression of this antibody binding site. These target polynucleotides can be further assayed for their ability to inhibit HIV-1 entry.

Viruses are known to enter cells using specific receptors to bind to cells (for example, HIV uses CD4, coronavirus uses CD13, murine leukemia virus uses transport protein, and measles virus usesCD44) and to fuse with cells (HIV uses chemokine receptor). Libraries can be inserted into target cells known to be permissive to these viruses, and target polynucleotides are isolated which block the ability of these viruses to bind and fuse with specific target cells.

In a preferred embodiment, the present invention finds use with infectious organisms. Intracellular organisms such as mycobacteria, listeria, *salmonella*, pneumocystis, *yersinia*, leishmania, *T. cruzi*, can persist and replicate within cells, and become active in immunosuppressed patients. There are currently drugs on the market and in development which are either only partially effective or ineffective against these organisms. Libraries can be inserted into specific cells infected with these organisms (pre- or post-infection), and target polynucleotides selected which promote the intracellular destruction of these organisms in a manner analogous to intracellular "antibiotic peptides" similar to magainins. In addition target polynucleotides can be selected which enhance the cidal properties of drugs already under investigation which have insufficient potency by themselves, but when combined with a specific peptide from a candidate library, are dramatically more potent through a synergistic mechanism. Finally, target polynucleotides can be isolated which alter the metabolism of these intracellular organisms, in such a way as to terminate their intracellular life cycle by inhibiting a key organismal event.

Antibiotic drugs that are widely used have certain dose dependent, tissue specific toxicities. For example renal toxicity is seen with the use of gentamicin, tobramycin, and amphotericin; hepatotoxicity is seen with the use of INH and rifampin; bone marrow toxicity is seen with chloramphenicol; and platelet toxicity is seen with ticarcillin, etc. These toxicities limit their use. Libraries can be introduced into the specific cell types where specific changes leading to cellular damage or apoptosis by the antibiotics are produced, and target polynucleotides can be isolated that confer protection, when these cells are treated with these specific antibiotics.

Furthermore, the present invention finds use in screening for target polynucleotides that block antibiotic transport mechanisms. The rapid secretion from the blood stream of certain antibiotics limits their usefulness. For example penicillins are rapidly secreted by certain transport mechanisms in the kidney and choroid plexus in the brain. Probenecid is known to block this transport and increase serum and tissue levels. Insert polynucleotides can be introduced into specific cells derived from kidney cells and cells of the choroid plexus known to have active transport mechanisms for antibiotics. Target polynucleotides can then be isolated which block the active transport of specific antibiotics and thus extend the serum half life of these drugs.

In a preferred embodiment, the present methods are useful in drug toxicities and drug resistance applications. Drug toxicity is a significant clinical problem. This may manifest itself as specific tissue or cell damage with the result that the drug's effectiveness is limited. Examples include myeloablation in high dose cancer chemotherapy, damage to epithelial cells lining the airway and gut, and hair loss. Specific examples include adriamycin induced cardiomyocyte death, cisplatinin-induced kidney toxicity, vincristine-induced gut motility disorders, and cyclosporin-induced kidney damage. Libraries can be introduced into specific cell types with characteristic drug-induced phenotypic or functional responses, in the presence of the drugs, and target polynucleotides isolated which reverse or protect the specific cell type against the toxic changes when exposed to the drug. These effects may manifest as blocking the drug induced apoptosis of the cell of interest, thus initial screens will be for survival of the cells in the presence of high levels of drugs or combinations of drugs used in combination chemotherapy.

Drug toxicity may be due to a specific metabolite produced in the liver or kidney which is highly toxic to specific cells, or due to drug interactions in the liver which block or enhance the metabolism of an administered drug. Libraries can be introduced into liver or kidney cells following the exposure of these cells to the drug known to produce the toxic metabolite. Target polynucleotides can be isolated which alter how the liver or kidney cells metabolize the drug, and specific molecules identified which prevent the generation of a specific toxic metabolite. The generation of the metabolite can be followed by mass spectrometry, and phenotypic changes can be assessed by microscopy. Such a screen can also be done in cultured hepatocytes, cocultured with readout cells which are specifically sensitive to the toxic metabolite. Applications include reversible (to limit toxicity) inhibitors of enzymes involved in drug metabolism.

Multiple drug resistance, and hence tumor cell selection, outgrowth, and relapse, leads to morbidity and mortality in cancer patients. Libraries can be introduced into tumor cell lines (primary and cultured) that have demonstrated specific or multiple drug resistance. Target polynucleotides can then be identified which confer drug sensitivity when the cells are exposed to the drug of interest, or to drugs used in combination chemotherapy. The readout can be the onset of apoptosis in these cells, membrane permeability changes, the release of intracellular ions and fluorescent markers. The cells in which multidrug resistance involves membrane transporters can be preloaded with fluorescent transporter substrates, and selection carried out for peptides which block the normal efflux of fluorescent drug from these cells. Libraries are particularly suited to screening for encoded peptides which reverse poorly characterized or recently discovered intracellular mechanisms of resistance or mechanisms for which few or no chemosensitizers currently exist, such as mechanisms involving LRP (lung resistance protein). This protein has been implicated in multidrug resistance in ovarian carcinoma, metastatic malignant melanoma, and acute myeloid leukemia. Particularly interesting examples include screening for target polynucleotides which reverse more than one important resistance mechanism in a single cell, which occurs in a subset of the most drug resistant cells, which are also important applications. Applications would include screening for inhibitors of both MRP (multidrug resistance related protein) and LRP for treatment of resistant cells in metastatic melanoma, for inhibitors of both p-glycoprotein and LRP in acute myeloid leukemia, and for inhibition (by any mechanism) of all three proteins for treating pan-resistant cells.

In a preferred embodiment, the present methods are useful in improving the performance of existing or developmental drugs. First pass metabolism of orally administered drugs limits their oral bioavailability, and can result in diminished efficacy as well as the need to administer more drug for a desired effect. Reversible inhibitors of enzymes involved in first pass metabolism may thus be a useful adjunct enhancing the efficacy of these drugs. First pass metabolism occurs in the liver, thus inhibitors of the corresponding catabolic enzymes may enhance the effect of the cognate drugs. Reversible inhibitors would be delivered at the same time as, or slightly before, the drug of interest. Screening of libraries in hepatocytes for inhibitors (by any mechanism, such as protein downregulation as well as a direct inhibition of activity) of particularly problematical isozymes would be of interest. These include the CYP3A4 isozymes of cytochrome P450, which are involved in the first pass metabolism of the anti-HIV drugs saquinavir and indinavir. Other applications could include reversible inhibitors of UDP-glucuronyltransferases, sulfotransferases, N-acetyltransferases, epoxide hydrolases, and glutathione S-transferases, depending on the drug. Screens would be done in cultured hepatocytes or liver microsomes, and could involve antibodies recognizing the specific modification performed in the liver, or cocultured readout cells, if the metabolite had a different bioactivity than the untransformed drug. The enzymes modifying the drug would not necessarily have to be known, if screening was for lack of alteration of the drug.

In a preferred embodiment, the present methods are useful in immunobiology, inflammation, and allergic response applications. Selective regulation of T lymphocyte responses is a desired goal in order to modulate immune-mediated diseases in a specific manner. Libraries can be introduced into specific T cell subsets (TH1, TH2, CD4+, CD8+, and others) and the responses which characterize those subsets (cytokine generation, cytotoxicity, proliferation in response to antigen being presented by a mononuclear leukocyte, and others) modified by members of the library. Target polynucleotides can be selected which increase or diminish the known T cell subset physiologic response. This approach will be useful in any number of conditions, including: 1) autoimmune diseases where one wants to induce a tolerant state (select a peptide that inhibits T cell subset from recognizing a self-antigen bearing cell); 2) allergic diseases where one wants to decrease the stimulation of IgE producing cells (select peptide which blocks release from T cell subsets of specific B-cell stimulating cytokines which induce switch to IgE production); 3) in transplant patients where one wants to induce selective immunosuppression (select peptide that diminishes proliferative responses of host T cells to foreign antigens); 4) in lymphoproliferative states where one wants to inhibit the growth or sensitize a specific T cell tumor to chemotherapy and/or radiation; 5) in tumor surveillance where one wants to inhibit the killing of cytotoxic T cells by Fas ligand bearing tumor cells; and 5) in T cell mediated inflammatory diseases such as Rheumatoid arthritis, Connective tissue diseases (SLE), Multiple sclerosis, and inflammatory bowel disease, where one wants to inhibit the proliferation of disease-causing T cells (promote their selective apoptosis) and the resulting selective destruction of target tissues (cartilage, connective tissue, oligodendrocytes, gut endothelial cells, respectively).

Regulation of B cell responses will permit a more selective modulation of the type and amount of immunoglobulin made and secreted by specific B cell subsets. Libraries can be inserted into B cells and target polynucleotides selected which inhibit the release and synthesis of a specific immunoglobulin. This may be useful in autoimmune diseases characterized by the overproduction of auto antibodies and the production of allergy causing antibodies, such as IgE. Target polynucleotides can also be identified which inhibit or enhance the binding of a specific immunoglobulin subclass to a specific antigen either foreign of self. Finally, target polynucleotides can be selected which inhibit the binding of a specific immunoglobulin subclass to its receptor on specific cell types.

Similarly, target polynucleotides which affect cytokine production may be selected, generally using two cell systems. For example, cytokine production from macrophages, monocytes, etc. may be evaluated. Similarly, molecules which mimic cytokines, for example erythropoetin and IL1–17, may be selected, or molecules that bind cytokines such as TNF-.alpha., before they bind their receptor.

Antigen processing by mononuclear leukocytes (ML) is an important early step in the immune system's ability to recognize and eliminate foreign proteins. Insert polynucleotides can be introduced into ML cell lines and target polynucleotides selected which alter the intracellular processing of foreign peptides and sequence of the foreign peptide that is presented to T cells by MLs on their cell surface in the context of Class II MHC. One can look for members of the library that enhance immune responses of a particular T cell subset (for example, the peptide would in fact work as a vaccine), or look for a library member that binds more tightly to MHC, thus displacing naturally occurring peptides, but nonetheless the agent would be less immunogenic (less stimulatory to a specific T cell clone). This target polynucleotide would in fact induce immune tolerance and/or diminish immune responses to foreign proteins. This approach could be used in transplantation, autoimmune diseases, and allergic diseases.

The release of inflammatory mediators (cytokines, leukotrienes, prostaglandins, platelet activating factor, histamine, neuropeptides, and other peptide and lipid mediators) is a key element in maintaining and amplifying aberrant immune responses. Libraries can be inserted into MLs, mast cells, eosinophils, and other cells participating in a specific inflammatory response, and target polynucleotides selected which inhibit the synthesis, release and binding to the cognate receptor of each of these types of mediators.

In a preferred embodiment, the present methods are useful in biotechnology applications. Library expression in mammalian cells can also be considered for other pharmaceutical-related applications, such as modification of protein expression, protein folding, or protein secretion. One such example would be in commercial production of protein pharmaceuticals in CHO or other cells. Libraries resulting in target polynucleotides which select for an increased cell growth rate (perhaps peptides mimicking growth factors or acting as agonists of growth factor signal transduction pathways), for pathogen resistance (see previous section), for lack of sialylation or glycosylation (by blocking glycotransferases or rerouting trafficking of the protein in the cell), for allowing growth on autoclaved media, or for growth in serum free media, would all increase productivity and decrease costs in the production of protein pharmaceuticals Target polynucleotides encoding polypeptides or peptides displayed on the surface of circulating cells can be used as tools to identify organ, tissue, and cell specific peptide targeting sequences. Any cell introduced into the bloodstream of an animal expressing a library targeted to the cell surface can be selected for specific organ and tissue targeting. The target polynucleotide sequence identified can then be coupled to an antibody, enzyme, drug, imaging agent or substance for which organ targeting is desired.

Other target polynucleotides which may be selected using the present invention include: 1) target polynucleotides which block the activity of transcription factors, using cell lines with reporter genes; 2) target polynucleotides which block the interaction of two known proteins in cells, using the absence of normal cellular functions, the mammalian two hybrid system or fluorescence resonance energy transfer mechanisms for detection; and 3) target polynucleotides may be identified by tethering a random peptide to a protein binding region to allow interactions with molecules sterically close, i.e. within a signalling pathway, to localize the effects to a functional area of interest.

Example 25

In Vitro Depletion of T Cells Specific for Alloantigens

Human peripheral blood T lymphocytes were stimulated in vitro with autologous dendritic cells (DC) that were pulsed with lysate from allogeneic prostate tumor cell lines. After several cycles of restimulation with dendritic cells pulsed with tumor lysate, the CTL were tested for reactivity against tumor and the normal prostate epithelial cells from which they were derived by oncogene transformation. The NK-sensitive target, K5 62, was included as a control for non-specific lysis. The results in Table 13 demonstrate that these T cells were not only capable of lysing the tumor, but were equally reactive against the normal prostate cells. These data indicate that a strong T cell response is induced to tissue-specific antigens and/or alloantigens that are common to tumor and normal cells from the same donor and that are presented to allogeneic T cells by the dendritic cells. In order to isolate a minority population of tumor-specific T cells, it is therefore preferred to induce tolerance or otherwise deplete T cells reactive to normal cellular antigens of the tumor donor.

Bisindolylmaleimide VIII (Bis VIII) is one of a class of protein kinase C (PKC) inhibitors that has been shown to mediate apoptotic events. This compound dramatically enhances T cell sensitivity to activation induced cell death (AICD) (Zhou, T., et al. 1999. *Nature Medicine* 5:42–48). Mouse splenic T cells activated by plate bound anti-CD3 antibody underwent dose dependent apoptosis in the presence of Bis VIII. A dose of 10 mM induced almost 100% T cell death. This property provides a method for the in vitro elimination of alloactivated T cells.

The protocol for T cell stimulation was modified as follows. 3×10$^4$ immature DCs were incubated with 1×10$^5$ irradiated, apoptotic non-tumorigenic cells in 1 ml volumes of a 24-well plate for four hours in a 37° C., 5% $CO_2$, humidified incubator. 5×10$^5$ naïve T cells (from the DC donor) were added to the wells for 24 hours. 10 mM Bis VIII was then added and incubation continued for another 24-hours. This resulted in killing of 95% of the total number of T cells, presumably those activated by normal prostate antigens and allogeneic MHC molecules. All cells were removed from the wells and washed at least 3 times to remove residual Bis VIII. The remaining tumor-specific T cells were "rescued" by restimulation for 12 days in vitro with fresh DCs pulsed with irradiated, apoptotic tumor cells. The selected cells continued to be restimulated every 12 days with tumor-pulsed DCs or irradiated tumor and autologous filler cells until their numbers were sufficient for cytokine ELISA and $^{51}$Cr release assays. These CD8$^+$ CTL were specific for a shared antigen expressed by 2 prostate tumor cell lines, but did not recognize the normal prostate epithelial cells nor K562 (Table 14). The difference in recognition at an effector:target cell ratio of 5:1 is significant enough for use in antigen discovery. These CTL may be cloned and expanded to identify the shared antigen(s) being recognized.

TABLE 13

| Target | 10:1 | 5:1 | 2.5:1 |
| --- | --- | --- | --- |
| KiGT (tumor) | 37 | 27 | 18 |
| FNC267B1 (normal) | 32 | 28 | 15 |
| K562 | 13 | 6 | 3 |

Table 13. Non-tumor specific CTL induced by repeated stimulation with tumor-pulsed dendritic cells. Human peripheral blood T lymphocytes were serially stimulated by autologous dendritic cells pulsed with allogeneic tumor cell lysate (KiGT). After 3 stimulations, CTL were tested for the ability to lyse tumor cells or the normal prostate epithelial cells from which the tumor was derived by oncogene transformation. Numbers represent percent specific lysis at the indicated effector:target cell ratios in a standard 4 hour $^{51}$chromium release assay.

TABLE 14

| Target | 30:1 | 10:1 | 5:1 |
| --- | --- | --- | --- |
| KiGT (tumor) | 62 | 60 | 48 |
| 30Gy (tumor) | 69 | 58 | 44 |
| FNC267B1 (normal) | 16 | 9 | 6 |
| K562 | 2 | 0 | 0 |

Table 14. Prostate tumor specific CTL induced by the bis VIII tolerance method. As described in the text, a protein kinase C inhibitor, bis VIII, was employed to deplete human T cells reactive to antigens of normal prostate epithelial cells (FNC267B 1). The remaining tumor-specific T cells were rescued by stimulation with autologous dendritic cells pulsed with the KiGT tumor. Specificity of the selected T cells was tested in a chromium release assay. Shared antigens expressed by a closely related tumor cell line (30 Gy) are also recognized.

The present invention is not to be limited in scope by the specific embodiments described which are intended as single illustrations of individual aspects of the invention, and any constructs, viruses or enzymes which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference. The disclosure and claims of U.S.

application Ser. No. 08/935,377, filed Sep. 22, 1997; U.S. application Ser. No. 60/192,586, filed Mar. 28, 2000; U.S. application Ser. No. 60/265,880; filed Feb. 5, 2001; U.S. application Ser. No. 60/271,422, filed Feb. 27, 2001; and U.S. application Ser. No. 60/271,424, filed Feb. 27, 2001, are herein incorporated by reference.

What is claimed is:

1. A method of selecting a target polynucleotide, comprising:
   (a) introducing into a population of mammalian host cells a library of insert polynucleotides; wherein at least one of said insert polynucleotides comprises the target polynucleotide; wherein said library is constructed in a vaccinia virus vector using trimolecular recombination and wherein expression of said target polynucleotide directly or indirectly promotes host cell death;
   (b) culturing said host cells under conditions such that said insert polynucleotides are expressed; and
   (c) collecting insert polynucleotides from those host cells which undergo cell death; wherein said cell death is not the result of a cytotoxic T lymphocyte-induced lytic event.

2. The method of claim 1, further comprising:
   (d) introducing said collected polynucleotides into a population of host cells, wherein expression of said target polynucleotide directly or indirectly promotes host cell death;
   (e) culturing said host cells under conditions such that said insert polynucleotides are expressed; and
   (f) collecting insert polynucleotides from those host cells which undergo cell death.

3. The method of claim 2, further comprising repeating steps (d)–(f) one or more times, thereby enriching for said target polynucleotide.

4. The method claim 3, further comprising purifying said collected polynucleotides.

5. The method of claim 1, wherein said cell death is the result of a cellular effect selected from the group consisting of cell lysis, expression of a suicide gene product, apoptosis, loss of viability, loss of membrane integrity, loss of structural stability, cell disruption, disruption of cytoskeletal elements, inability to maintain membrane potential, arrest of cell cycle, inability to generate energy, growth arrest, cytotoxic effects, cytostatic effects, genotoxic effects, and growth suppressive effects.

6. The method of claim 1, wherein said population of host cells is selected from the group consisting of: tumor cells, metastatic tumor cells, primary cells, transformed primary cells, immortalized primary cells, dividing cells, non dividing cells, terminally differentiated cells, pluripotent stem cells, committed progenitor cells, uncommitted stem cells, progenitor cells, muscle cells, epithelial cells, nervous system cells, circulatory system cells, respiratory system cells, endocrine cells, endocrine-associated cells, skeletal system cells, connective tissue cells, musculoskeletal cells, chondrocytes, osteoblasts, osteoclasts, myocytes, fully differentiated blood cells, fully differentiated epidennal cells, neurons, glial cells, kidney cells, liver cells, muscle cell progenitors, epithelial cell progenitors, nervous system cell progenitors, circulatory system cell progenitors, respiratory system cell progenitors, endocrine cell progenitors, endocrine associated cell progenitors, skeletal system cell progenitors, connective tissue cell progenitors, musculoskeletal cell progenitors, chondrocyte progenitors, osteoblast progemtors, osteoclast progenitors, myocyte progenitors, blood cell progenitors, epidermal cell progenitors, neuron progenitors, glial cell progenitors, kidney cell progenitors, liver cell progenitors and any combination thereof.

7. The method of claim 1, wherein said host cells are adherent to a solid support.

8. The method of claim 7, wherein said solid support is selected from the group consisting of: tissue culture plastic, glass, polystyrene, polypropylene, polyethylene, dextran, nylon, amylases, natural and modified celluloses, polyacrylamides, gabbros, magnetite, soluble material, partially soluble material, insoluble material, magnetic material, and nonmagnetic material.

9. The method of claim 7, wherein said solid support has a structure selected from the group consisting of: spherical, bead-like, bead, cylindrical, test tube-like, tube-like, tube, rod-like, rod, flat, sheet-like, sheet, test strip, strip-like, strip, bead, microbead, well, plate, tissue culture plate, petri plate, microplate, microtiter plate, flask, stick, vial, and paddle.

10. The method of claim 1, wherein said library of insert polynucleotides is selected from the group consisting of: a cDNA library, a genomic library, a combinatorial polynucleotide library, a library of natural polynucleotides, a library of artificial polynucleotides, a library of polynucleotides endogenous to said host cells, a library of polynucleotides exogenous to said host cells, an antisense library, and any combination thereof.

11. The method of claim 5, wherein said cell death is the result of apoptosis.

12. The method of claim 11, wherein apoptosis is induced through expression of a apoptosis-related gene product which directly promotes apoptosis.

13. The method of claim 11, wherein apoptosis is induced through expression of an apoptosis related gene product which indirectly promotes apoptosis.

14. The method of claim 13, wherein said apoptosis related gene product comprises a death domain containing receptor expressed on the surface of said host cells, and wherein said host cells are contacted with a ligand for said death domain containing receptor.

15. The method of claim 11, wherein said host cells are adherent to a solid support.

16. The method of claim 15, wherein those cells which have undergone apoptosis are released from said support.

17. The method of claim 16, wherein said released host cells, or contents thereof, are collected by removing the liquid medium in which said host cells are cultured.

18. The method of claim 15, wherein those host cells which have undergone apoptosis are fully or partially lysed, thereby releasing their cytoplasmic contents into the liquid medium in which said host cells are cultured.

19. The method of claim 18, wherein said released host cell contents are collected by removing the liquid medium in which said host cells are cultured.

20. The method of claim 5, wherein said cell death is the result of expression of a suicide gene product.

21. The method of claim 20, wherein said suicide gene product is selected from the group consisting of a diphtheria toxin A chain polypeptide, a Pseudomonas exotoxin A chain polypeptide, a ricin A chain polypeptide, an abrin A chain polypeptide, a modeccin A chain polypeptide, and an alpha-sarcin polypeptide.

22. The method of claim 20, wherein said host cells are progenitor cells comprising a suicide gene operably associated with a tissue-restricted promoter; wherein expression of said target polynucleotide directly or indirectly induces transcription of said tissue restricted-promoter, resulting in expression of said suicide gene; and wherein expression of said suicide gene promotes death of those progenitor cells comprising said target polynucleotide.

23. The method of claim 22, wherein said host cell is a RAW cell, and wherein said suicide gene is operably associated with the TRAP promoter.

24. The method of claim 23, wherein said target polynucleotide directly or indirectly regulates osteoclast differentiation.

25. The method of claim 23, wherein said suicide gene encodes the Diphtheria toxin A subunit.

26. The method of claim 22, wherein said tissue-restricted promoter is identified by gene expression profiling of said host cells under different physical conditions in microarrays of ordered cDNA libraries.

27. The method of claim 26, wherein said expression profiling compares gene expression under different physical conditions in host cells infected with a eukaryotic virus expression vector, wherein said eukaryotic virus expression vector is the vector used to construct said library of polynucleotides.

28. The method of claim 20, wherein said host cells are non-dividing cells comprising a suicide gene operably associated with a proliferation-specific promoter; wherein expression of said target polynucleotide directly or indirectly induces transcription of said proliferation-specific promoter, resulting in expression of said suicide gene; and wherein expression of said suicide gene promotes death of those non-dividing host cells comprising said target polynucleotide.

29. The method of claim 28, wherein said proliferation-specific promoter is identified by gene expression profiling of said host cells under different physical conditions in microarrays of ordered cDNA libraries.

30. The method of claim 29, wherein said expression profiling compares gene expression under different physical conditions in host cells infected with a eukaryotic virus expression vector, wherein said eukaryotic virus expression vector is the vector used to construct said library of polynucleotides.

31. The method of claim 20, wherein said host cells are adherent to a solid support.

32. The method of claim 31, wherein those host cells expressing said suicide gene product are released from said support.

33. The method of claim 32, wherein said released host cells, or contents thereof, are collected by removing the liquid medium in which said host cells are cultured.

34. The method of claim 31, wherein those host cells expressing said suicide gene product are fully or partially lysed, thereby releasing their cytoplasmic contents into the liquid medium in which said host cells are cultured.

35. The method of claim 34, wherein said released host cell contents are collected by removing the liquid medium in which said host cells are cultured.

36. The method claim 5, wherein cell death occurs within a period selected from the group consisting of: 48 hours after expression of said insert polynucleotide, 24 hours after expression of said insert polynucleotide, and 12 hours after expression of said insert polynucleotide.

37. The method of claim 1, wherein said host cells are infected with said library at an MOI selected from the group consisting of: from about 1 to about 10, about 1 to about 5, and about 1.

38. The method of claim 1, wherein said host cells are permissive for the production of infectious viral particles of said virus.

39. The method of claim 1, wherein said vaccinia virus is attenuated.

40. The method of claim 39, wherein said attenuation is by genetic mutation.

41. The method of claim 39, wherein said attenuation is by reversible inhibition of virus replication.

42. The method of claim 39, wherein said vaccinia virus vector is derived from strain MVA.

43. The method of claim 39, wherein said vaccinia virus vector is derived from strain D4R.

44. The method of claim 1, wherein said insert polynucleotide is in operably associated with a transcriptional control sequence.

45. The method of claim 44, wherein said transcriptional control sequence functions in the cytoplasm of a vaccinia virus-infected cell.

46. The method of claim 44, wherein said transcriptional control sequence comprises a promoter.

47. The method of claim 46, wherein said promoter is constitutive.

48. The method of claim 47, wherein said promoter is a vaccinia virus p7.5 promoter.

49. The method of claim 47, wherein said promoter is a synthetic early/late promoter.

50. The method of claim 44, wherein said transcriptional control sequence comprises a transcriptional termination region.

51. The method of claim 39, wherein said vaccinia virus vector is derived from strain WR.

* * * * *